United States Patent
Kyotani et al.

(10) Patent No.: US 6,869,954 B2
(45) Date of Patent: *Mar. 22, 2005

(54) WATER-SOLUBLE PHENYLPYRIDAZINE COMPOUNDS AND COMPOSITIONS CONTAINING THE SAME

(75) Inventors: Yoshinori Kyotani, Higashiyamato (JP); Tomoyuki Koshi, Shiki (JP); Hiromichi Shigyo, Fuchu (JP); Hideo Yoshizaki, Sayama (JP); Takahiro Kitamura, Higashimurayama (JP); Shunji Takemura, Hachioji (JP); Kyoko Yasuoka, Higashiyamato (JP); Junko Totsuka, Asaka (JP); Seiichi Sato, Tokyo (JP)

(73) Assignee: Kowa Co., Ltd., Nagoya (JP)

(*) Notice: Subject to any disclaimer, the term of this patent is extended or adjusted under 35 U.S.C. 154(b) by 130 days.

This patent is subject to a terminal disclaimer.

(21) Appl. No.: 10/253,523

(22) Filed: Sep. 25, 2002

(65) Prior Publication Data

US 2003/0119838 A1 Jun. 26, 2003

Related U.S. Application Data

(60) Provisional application No. 60/324,569, filed on Sep. 26, 2001.

(51) Int. Cl.[7] .................. A61K 31/50; A61K 31/51; C07D 237/04; C07D 403/06
(52) U.S. Cl. .............. 514/247; 514/236.5; 514/252.02; 514/252.03; 544/114; 544/238; 544/239
(58) Field of Search ................... 544/238, 239, 544/114; 514/247, 252.02, 236.5, 252.03

(56) References Cited

U.S. PATENT DOCUMENTS 4,404,203 A * 9/1983 Sircar ................... 514/247
6,348,468 B1    2/2002 Ohkuchi et al.
6,403,586 B1    6/2002 Ohkuchi et al.
2003/0225081 A1 * 12/2003 Nagato et al. ........... 514/235.8

OTHER PUBLICATIONS

Livingston, Journal of Cellular Biochemistry, vol. 64, p. 19–26 (1997).*

* cited by examiner

Primary Examiner—Emily Bernhardt
(74) Attorney, Agent, or Firm—Oblon, Spivak, McClelland, Maier & Neustadt, P.C.

(57) ABSTRACT

Compounds having the formula (1):

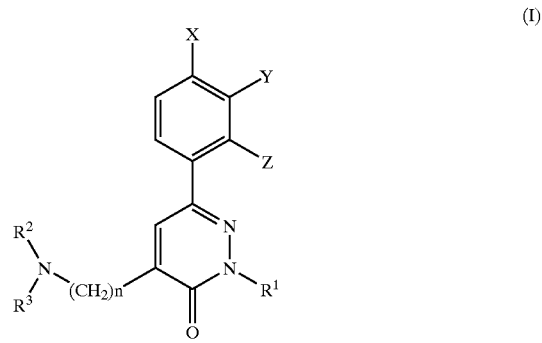

wherein $R^1$ represents an alkyl or alkenyl group, $R^2$ and $R^3$ each independently represent a hydrogen atom or an alkyl, hydroxyalkyl, dihydroxyalkyl or alkynyl group, or $R^2$ and $R^3$ may be fused together with the adjacent nitrogen atom to form a substituted or unsubstituted, nitrogen-containing, saturated heterocyclic group, X, Y and Z each independently represent a hydrogen atom, an alkyl group, a halogen atom or the like, and n stands for an integer of from 1 to 5; and also to medicinal compositions containing them. These compounds have inhibitory activity against IL-1β production, high water solubility and good oral absorbability.

4 Claims, 4 Drawing Sheets

WATER-SOLUBLE PHENYLPYRIDAZINE COMPOUNDS AND COMPOSITIONS CONTAINING THE SAME

FIELD OF THE INVENTION

This invention relates to water-soluble phenylpyridazine compounds, which exhibit excellent inhibitory activity against interleukin-1β production, have high water solubility and oral absorbability, and are useful for the prevention and treatment of immune system diseases, inflammatory diseases, and ischemic diseases, for example, and also to compositions containing them as effective ingredients therein.

DESCRIPTION OF THE BACKGROUND

In many diseases, for example, rheumatism, arthritis, osteoporosis, inflammatory colitis, immune deficiency syndrome, ichorrhemia, hepatitis, nephritis, ischemic diseases, insulin-dependent diabetes mellitus, arterial sclerosis, Parkinson's disease, Alzheimer's disease, and leukemia, for example, stimulation of interleukin-1β production, an inflammatory cytokine, is observed. This interleukin-1β serves to induce synthesis of an enzyme which is considered to take part in inflammation-like collagenase and PLA2 and, when intra-articularly injected to animals, causes multiarticular damage highly resembling rheumatoid arthritis. In a healthy body, on the other hand, the activity of interleukin-1β is controlled by interleukin-1 receptor, soluble interleukin-1 receptor and interleukin-1 receptor antagonist.

From research conducted using recombinant versions of these bioactivity-inhibiting substances, anti-interleukin-1β antibodies and anti-receptor antibodies against various disease models, interleukin-1β has been found to play an important role in the body, leading to an increasing potential of substances having interleukin-1β inhibitory activity as therapeutics for such diseases.

For example, immunosuppressors and steroids, which are used for the treatment of rheumatism, have been reported to inhibit production of interleukin-1β. Among compounds currently under development, KE298, a benzoylpropionic acid compound [*The Japanese Society of Inflammation* (11th), 1990], for example, has been reported to exhibit inhibitory activity against interleukin-1β production although it is an immunoregulator. Inhibitory activity against interleukin-1β production is also observed on a group of compounds which are called "COX-2 selective inhibitors", for example, nimesulide as a phenoxysulfonanilide compound (DE 2333643), T-614 as a phenoxybenzopyran compound (U.S. Pat. No. 4,954,518), and tenidap (hydroxyindole compound) as a dual inhibitor (COX-1/5-LO).

Moreover, interleukin-1β production inhibitory activity is not the primary action or effect of any of these compounds so the inhibitory activity against interleukin-1β production is less than the primary action thereof.

More recently, increased synthetic research has been conducted emphasizing inhibitory activity against interleukin-1β production. Production inhibitors can be classified into (1) a group of compounds which inhibit the transfer process of an inflammatory signal to a cell nucleus and (2) another group of compounds which inhibit the enzyme ICE that functions in the processing of a precursor of interleukin-1β. Known examples of compounds presumed to have the former action 1) include SB203580 [Japanese Language Laid-Open (Kokai) Publication (PCT) No. HEI 7-503017], FR167653 (*Eur. J. Pharm.*, 327, 169–175, 1997), E-5090 (EP 376288), CGP47969A (*Gastroenterology*, 109, 812–828, 1995), hydroxyindole derivatives (*Eur. J. Med. Chem.* 31, 187–198, 1996), and triarylpyrrole derivatives (WO 9705878), while known examples of compounds presumed to have the latter action 2) include VE-13,045 which is a peptide compound (*Cytokine*, 8 (5), 377–386, 1996).

None of these compounds, however, exhibits sufficient inhibitory activity against interleukin-1β production.

On the other hand, it is known that 5,6-diphenylpyridazine compounds exhibit analgesic and anti-inflammatory action (*Eur. J. Med. Chem.*, 14, 53–60, 1979). Further, 6-phenylpyridazinones have been reported to be useful as cardio-active compounds (U.S. Pat. No. 4,404,203). Nothing has been reported, however, with respect to inhibitory activity of these pyridazine compounds against interleukin-1β production.

The present inventors previously reported in WO 99/44995 that high inhibitory activity against interleukin-1β production was observed on phenylpyridazine compounds. Recently, certain phenylpyridazine compounds having inhibitory activity against interleukin-1β production have been reported (JP 7-69894 A, WO 98/41511, WO 99/10331, WO 99/10332, WO 99/25697, WO 00/50408). These reported compounds, different in chemical structure from the compounds of the present invention, however.

SUMMARY OF THE INVENTION

The compounds disclosed in WO 99/44995 exhibit strong inhibitory activity against interleukin-1β production. However, the water solubility of these compounds is so low that their formulation into pharmaceutical preparations, such as tablets, was practically impossible. In the course of a further investigation, however, the present inventors discovered that the introduction of a substituted or unsubstituted aminoalkyl group to the 4-position of 6-phenylpyridazine-3-one affords a compound useful as a preventive or therapeutic for immune system diseases, inflammatory diseases, and ischemic diseases, for example, due to its significantly improved water solubility, good oral absorbability and excellent inhibitory activity against interleukin-1β production, leading to the completion of the present invention.

Thus, in one aspect of the present invention; there is provided a phenylpyridazine compound represented by the following formula (1):

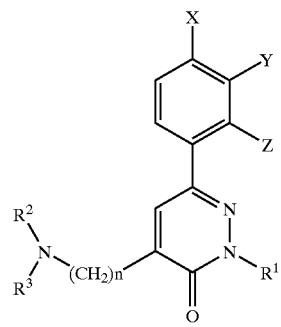

(I)

wherein:
R$^1$ represents a substituted or unsubstituted alkyl group or a substituted or unsubstituted alkenyl group;

$R^2$ and $R^3$ each independently represents a hydrogen atom or an alkyl, hydroxyalkyl, dihydroxyalkyl or alkynyl group, or $R^2$ and $R^3$ may be fused together with the adjacent nitrogen atom to form a substituted or unsubstituted, nitrogen-containing, saturated heterocyclic group;

X, Y and Z each independently represents a hydrogen or halogen atom, a substituted or unsubstituted alkyl, alkoxy, alkylthio, alkylsulfinyl or alkylsulfonyl group, or a substituted or unsubstituted aryl group; and n stands for a number of from 1 to 5;

with the proviso that $R^2$ and $R^3$ are not hydrogen atoms or the same $C_1$–$C_3$ alkyl groups at the same time when $R^1$ is a benzyl group or a $C_1$–$C_3$ alkyl group; or a salt thereof.

In another aspect of the present invention, there is also provided a pharmaceutical composition containing the phenylpyridazine compound (1) or the salt thereof as an active ingredient.

In yet a further aspect of the present invention, there is also provided a pharmaceutical composition containing the phenylpyridazine compound (1) or the salt thereof and a pharmacologically acceptable carrier.

In still a further aspect of the present invention, there is also provided a method of using the phenylpyridazine compound (1) or the salt thereof for the production of a medicine.

In a yet further aspect of the present invention, there is also provided a method for treating of a disease caused by stimulation of interleukin-1β production, which entails administering the phenylpyridazine compound (1) or the salt thereof to a mammal in need thereof.

DETAILED DESCRIPTION OF THE PREFERRED EMBODIMENTS

Figure 1:
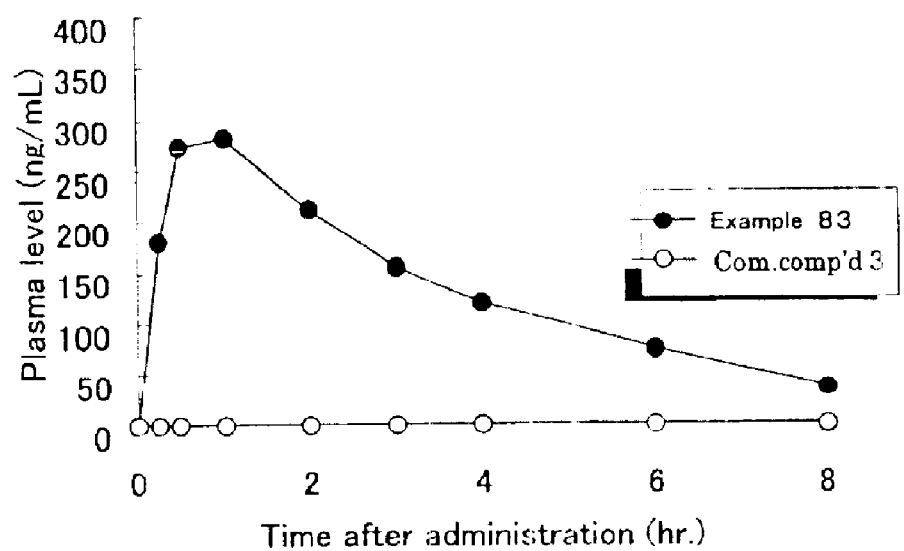
FIG. 1 is a graphic representation of the oral absorbability of a compound according to the present invention (Example 83) and a comparative compound 3.

In the above formula (1), the alkyl moieties in the alkyl, hydroxyalkyl, dihydroxyalkyl, alkoxy, alkylthio, alkylsulfinyl and alkylsulfonyl groups represent those having 1 to about 12 carbon atoms, more preferably 1 to 7 carbon atoms. These alkyl moieties may include linear, branched and cyclic alkyl groups as well as alkyl groups having cyclic structures, for example, methyl, ethyl, n-propyl, isopropyl, n-butyl, isobutyl, cyclopropyl, cyclobutyl, cyclopentyl, cyclohexyl, cyclopropylmethyl, cyclopropylethyl, cyclobutylmethyl, cyclopentylmethyl and cyclohexylmethyl.

In the above formula (1), the alkyl group represented by $R^1$ has preferably 1 to about 12 carbon atoms, more preferably 1 to 7 carbon atoms, notably 4 to 7 carbon atoms. Illustrative of such alkyl groups are linear, branched and cyclic alkyl groups as well as alkyl groups having cyclic structures. Preferred examples can include methyl, ethyl, propyl, isobutyl, cyclobutyl, cyclopentyl, cyclohexyl, cyclopropylmethyl, cyclopropylethyl, cyclobutylmethyl, cyclopentylmethyl and cyclohexylmethyl, with methyl, ethyl, isobutyl, cyclopropylmethyl and cyclopentylmethyl being particularly preferred.

The alkenyl group represented by $R^1$ preferably has 2 to about 12 carbon atoms, with 2 to 7 carbon atoms being particularly preferred. Illustrative of such alkenyl groups are linear and branched alkenyl groups, specifically vinyl, propenyl, butenyl and pentenyl.

Illustrative of group(s) which the alkyl or alkenyl group represented by $R^1$ may contain as substituent(s) are substituted or unsubstituted aryl groups and substituted or unsubstituted heteroaryl groups. Examples of the aryl groups include aryl groups having 6 to about 14 carbon atoms, specifically phenyl and naphthyl, with phenyl being particularly preferred. Examples of the heteroaryl groups, on the other hand, include 5- or 6-membered heteroaryl groups having 1 to 3 nitrogen atoms, specifically pyrrolyl, imidazolyl, pyrazolyl, pyridyl, pyrimidyl, pyrazinyl and pyridazinyl, with pyridyl being particularly preferred.

These aryl or heteroaryl groups may contain 1 to 3 substituents such as halogen atoms, alkyl groups or alkoxy groups. Examples of the halogen atoms include fluorine, chlorine, bromine and iodine, with fluorine and chlorine being particularly preferred. These alkyl and alkoxy groups preferably have 1 to 12 carbon atoms, with 1 to 7 carbon atoms being particularly preferred.

The alkyl, hydroxyalkyl and dihydroxyalkyl groups represented by $R^2$ and $R^3$ preferably have 1 to about 12 carbon atoms, with 1 to 7 carbon atoms being particularly preferred. These groups may preferably be linear or branched. Specific examples include methyl, ethyl, n-propyl, isopropyl, n-butyl, isobutyl, hydroxyethyl, hydroxypropyl, hydroxybutyl, dihydroxypropyl and dihydroxybutyl.

The alkynyl groups represented by $R^2$ and $R^3$ preferably have 3 to about 12 carbon atoms, with 3 to 7 carbon atoms being particularly preferred. Illustrative is propargyl (2-propynyl).

Illustrative of the nitrogen-containing, saturated heterocyclic group which may be formed as a result of fusing $R^2$ and $R^3$ with the adjacent nitrogen atom are 5- to 7-membered saturated heterocyclic groups, specifically pyrrolidinyl, piperidino, piperazinyl, homopiperazinyl and morpholino, with piperazinyl, piperidino and morpholino being particularly preferred.

Illustrative of group(s) which these heterocyclic groups may contain as substituent(s) are halogen atoms, alkyl groups, alkoxycarbonyl groups and aralkyl groups. Examples of the halogen atoms include fluorine, chlorine, bromine and iodine. The alkyl groups can contain 1 to about 12 carbon atoms, preferably 1 to 7 carbon atoms. Illustrative of the alkoxycarbonyl groups are $C_1$–$C_{12}$ alkyloxycarbonyl groups, with $C_1$–$C_7$ alkyloxycarbonyl groups being preferred. Illustrative of the aralkyl groups are phenyl($C_1$–$C_7$ alkyl) groups, with benzyl being particularly preferred.

Illustrative of the halogen atoms represented by X, Y and Z are fluorine, chlorine, bromine, and iodine. The alkyl groups can contain 1 to about 12 carbon atoms, with 1 to 7 carbon atoms being particularly preferred. Among these alkyl groups, linear or branched ones are particularly preferred. Illustrative of group(s) which the alkyl group may contain as substituent(s) are halogen atoms and alkoxy groups. The alkoxy, alkylthio, alkylsulfinyl and alkylsulfonyl groups can contain 1 to about 12 carbon atoms, with 1 to 7 carbon atoms being particularly preferred. Among these alkoxy, alkylthio, alkylsulfinyl and alkylsulfonyl groups, linear or branched ones are particularly preferred. Specific examples include methoxy, ethoxy, propoxy, isopropoxy, butoxy, methylthio, ethylthio, propylthio, isopropylthio, butylthio, methylsulfinyl, ethylsulfinyl, propylsulfinyl, isopropylsulfinyl, butylsulfinyl, methyl-sulfonyl, ethylsulfonyl, propylsulfonyl, isopropylsulfonyl, and butylsulfonyl. Illustrative of the aryl group are aryl groups having 6 to about 14 carbon atoms, specifically phenyl and naphthyl, with phenyl being particularly preferred. Illustrative of group(s) which the aryl group may contain as substituent(s) are halogen atoms, alkyl groups, and alkoxy groups.

n stands for a number of from 1 to 5, with 1 to 3 being more preferred, and with 1 or 3 being particularly preferred.

When $R^1$ is a benzyl group or a $C_1$–$C_3$ alkyl group, $R^2$ and $R^3$ are not hydrogen atoms or the same $C_1$–$C_3$ alkyl groups at the same time.

In the formula (1), particularly preferred as $R^1$ are isobutyl, cyclopropylmethyl, cyclopentylmethyl, cinnamyl, halogenocinnamyl, benzyl, halogenobenzyl, dihalogenobenzyl, and (halogenophenyl)propyl. Preferred as $R^2$ and $R^3$ are hydrogen, $C_{1-7}$ alkyl, $C_{1-7}$ hydroxyalkyl, and propargyl. Preferred as the heterocyclic group formed by $R^2$ and $R^3$ are piperazinyl, piperidino, pyrrolidino and morpholino, each of which may optionally be substituted by one or more $C_{1-7}$ alkyl or benzyl groups. Preferred as X are methyl, methoxy, methylhalo, and halogens. Preferred as Y are hydrogen and halogens. Preferred as Z is hydrogen. Preferred as n are 1 and 3.

As the salt of the compound (1) of the present invention, an acid addition salt is preferred. Examples of the acid addition salt include inorganic acid salts, such as the hydrochloride, sulfate, nitrate and phosphate, and organic acid salts, such as the methanesulfonate, maleate, fumarate, citrate and oxalate.

Further, the compound according to the present invention may exist in the form of solvates and a keto-enol tautomer. Such solvates and tautomer are encompassed by the present invention. Illustrative of solvates are those formed as a result of addition of solvents used upon production, for example, water and alcohols. No particular limitation is imposed on the solvents insofar as they do not adversely affect the inhibitory activity of the compound according to the present invention against interleukin-1β production. As a solvate, the hydrate is preferred.

No particular limitation is imposed on a process for the preparation of the water-soluble phenylpyridazine compound or the salt thereof according to the present invention, and any process, which has conventionally been used for the synthesis of pyridazine compounds, and their modifications may be used. The phenylpyridazine compound (1) according to the present invention can be prepared, for example, by the following preparation processes (a) to (d).

(a) Preparation process of compounds having the formula (1) in which n=1

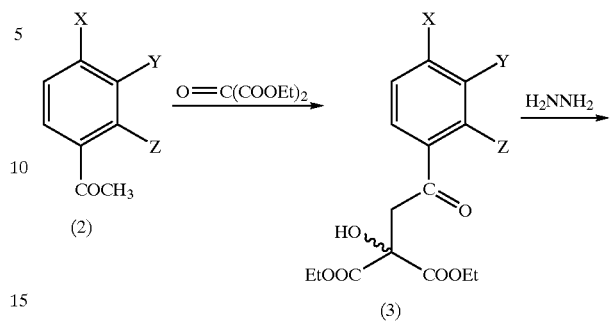

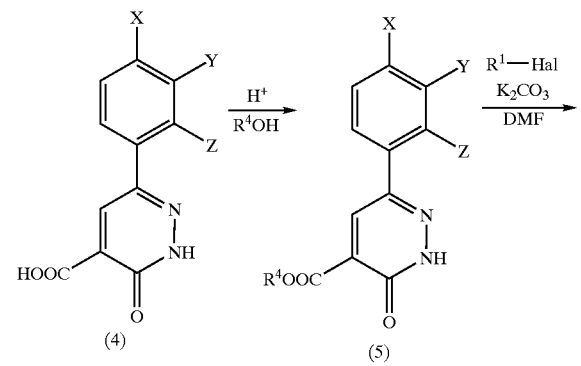

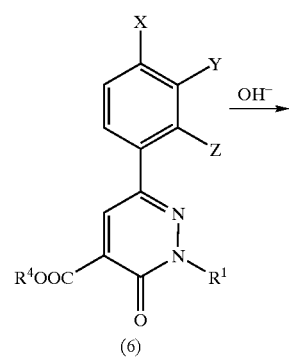

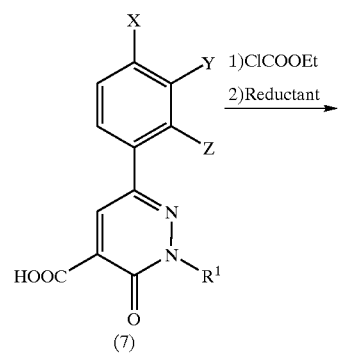

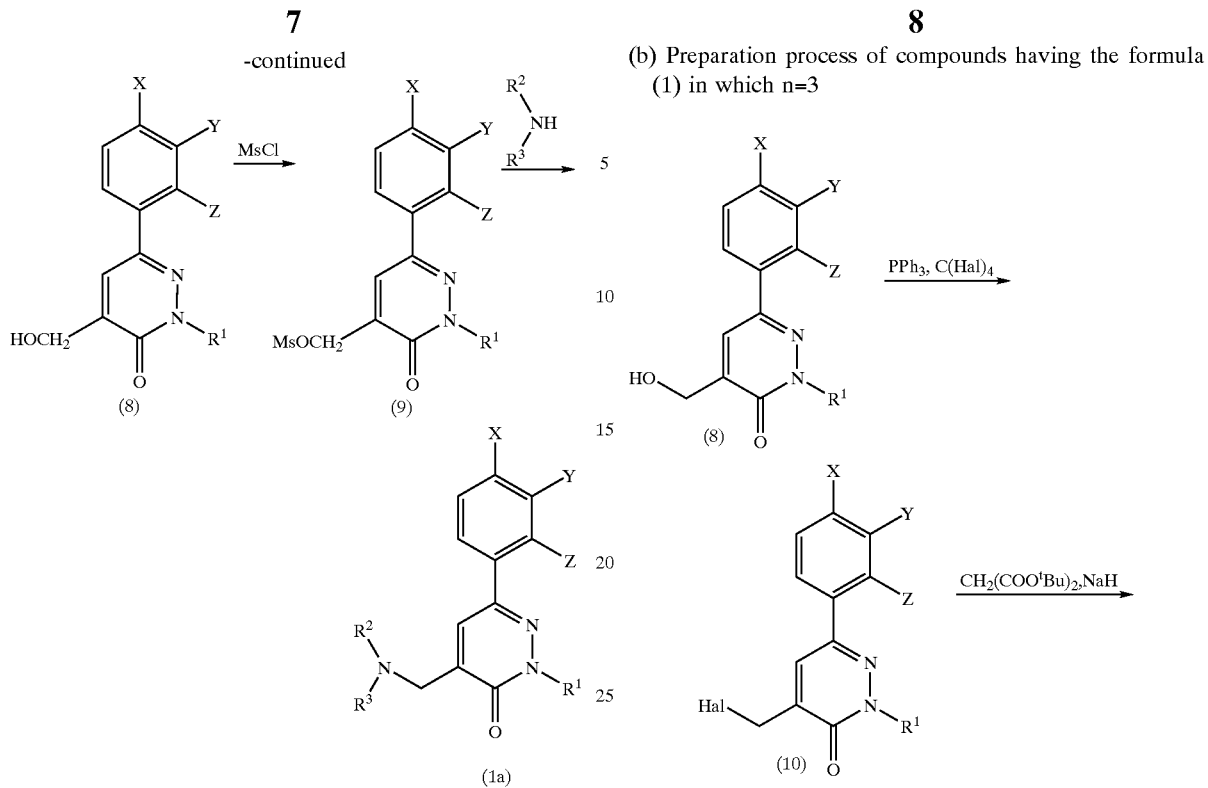

wherein $R^4$ represents an alkyl group, Hal represents a halogen atom, Ms represents a methanesulfonyl group, and $R^1$, $R^2$, $R^3$, X, Y and Z have the same meanings as described above.

A description will hereinafter be made about the individual reaction steps.

In the steps from an acetophenone (2) to a compound (5), the acetophenone (2) and diethyl ketomalonate are heated under stirring to yield a compound (3). Hydrazine is caused to act on the compound to carry out a ring-closing reaction, and the reaction product is then treated with an alkali, for example, sodium hydroxide or the like to afford a compound (4). The compound (4) is next reacted with an alcohol such as methanol to give the compound (5).

$R^1$-Hal is reacted to the compound (5) in the presence of an alkali such as potassium carbonate to provide a compound (6). The compound (6) is hydrolyzed into a compound (7). After ethyl chlorocarbonate is caused to act on the compound (7) to convert it into an acid anhydride, the acid anhydride is reduced with a reducing agent such as sodium borohydride to afford a compound (8). A reaction of methanesulfonyl chloride with the compound (8) in the presence of a base such as triethylamine provides a compound (9), a key intermediate in this reaction scheme.

A reaction of a desired amine ($R^2$ ($R^3$)NH) with the compound (9) yields the target compound (1a). It is preferred to carry out this reaction, for example, in a polar solvent such as dimethylformamide in the presence or absence of an alkali such as potassium carbonate. Incidentally, if an amino group is contained in the group $R^2$ or $R^3$ in the amine, a reaction may be carried out using a raw material protected with an appropriate protecting group for example, an alkoxycarbonyl group, followed by the removal of the protecting group.

To obtain a compound (1a) in which $R^2$ and $R^3$ are hydrogen atoms, potassium phthalimide is reacted with the compound (9), and the reaction product is reacted further with hydrazine or the like.

(b) Preparation process of compounds having the formula (1) in which n=3

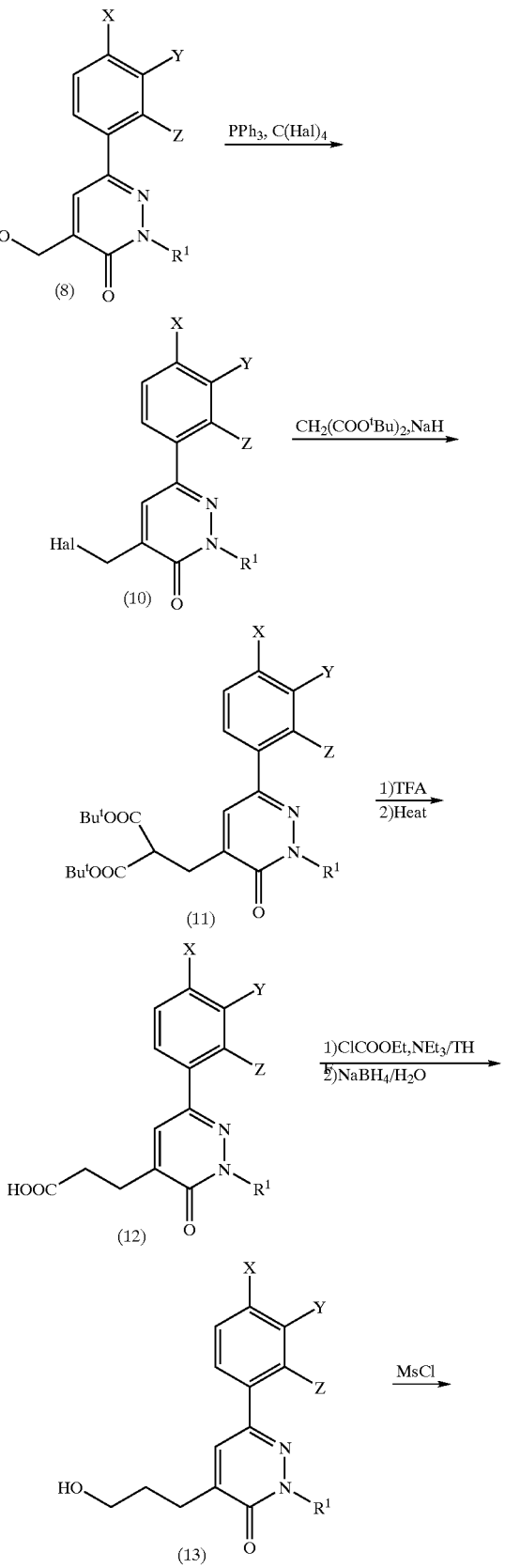

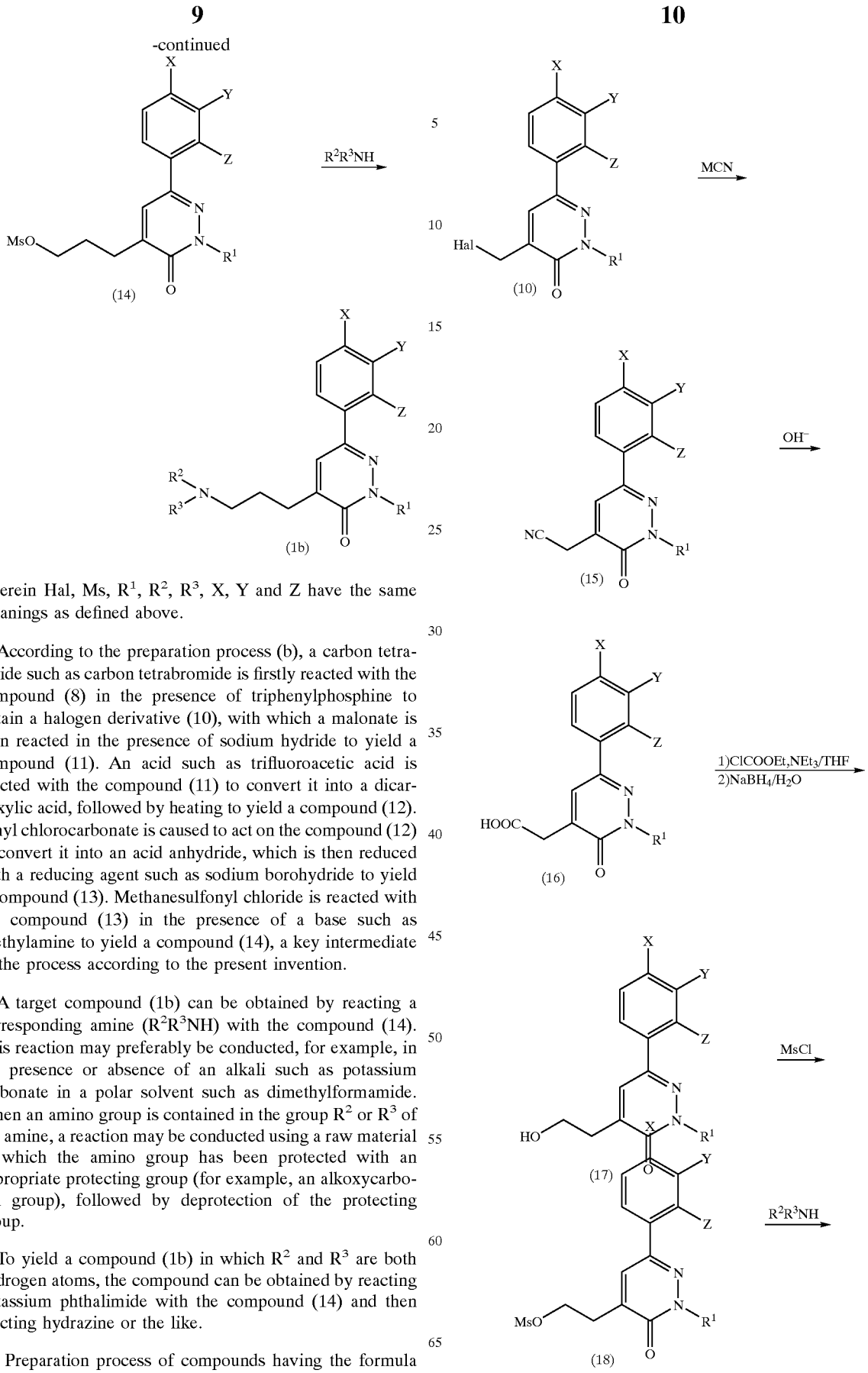

wherein Hal, Ms, $R^1$, $R^2$, $R^3$, X, Y and Z have the same meanings as defined above.

According to the preparation process (b), a carbon tetrahalide such as carbon tetrabromide is firstly reacted with the compound (8) in the presence of triphenylphosphine to obtain a halogen derivative (10), with which a malonate is then reacted in the presence of sodium hydride to yield a compound (11). An acid such as trifluoroacetic acid is reacted with the compound (11) to convert it into a dicarboxylic acid, followed by heating to yield a compound (12). Ethyl chlorocarbonate is caused to act on the compound (12) to convert it into an acid anhydride, which is then reduced with a reducing agent such as sodium borohydride to yield a compound (13). Methanesulfonyl chloride is reacted with the compound (13) in the presence of a base such as triethylamine to yield a compound (14), a key intermediate in the process according to the present invention.

A target compound (1b) can be obtained by reacting a corresponding amine ($R^2R^3NH$) with the compound (14). This reaction may preferably be conducted, for example, in the presence or absence of an alkali such as potassium carbonate in a polar solvent such as dimethylformamide. When an amino group is contained in the group $R^2$ or $R^3$ of the amine, a reaction may be conducted using a raw material in which the amino group has been protected with an appropriate protecting group (for example, an alkoxycarbonyl group), followed by deprotection of the protecting group.

To yield a compound (1b) in which $R^2$ and $R^3$ are both hydrogen atoms, the compound can be obtained by reacting potassium phthalimide with the compound (14) and then reacting hydrazine or the like.

(c) Preparation process of compounds having the formula (1) in which n=2

-continued

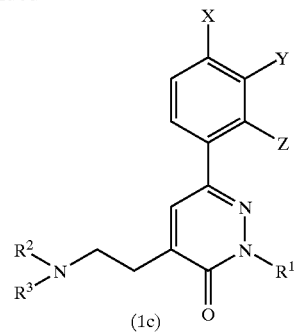

(1c)

wherein M represents a metal atom, and Hal, Ms, $R^1$, $R^2$, $R^3$, X, Hal, Ms, Y and Z have the same meanings as defined above.

According to the preparation process (c), a cyanide such as sodium cyanide is reacted with a halogen derivative (10) to convert it into a nitrile derivative (15), which is then hydrolyzed to yield a compound (16). From the compound (16), a target compound (1c) can be obtained via an alcohol derivative (17) and a mesyloxy derivative (18) by a similar procedure as in the preparation of compounds each of which contains three methylene groups.

(d) Preparation process of compounds having the formula (1) in which n=4 or 5.

These compounds can be obtained by combining the synthesis processes (b) and (c).

The salt of the compound (1) according to the present invention can be obtained by causing an organic acid or inorganic acid to act in a manner known per se in the art.

The compound (1) according to the present invention can be isolated and purified by subjecting it to purification procedures commonly employed in organic synthesis chemistry, for example, filtration, extraction, washing, drying, concentration, recrystallization, various chromatographic procedures, and/or the like. Each intermediates can be subjected to the subsequent reaction without bothering to purify it. The compound (1) may be provided as a solvate with a solvent such as a reaction solvent or recrystallization solvent, especially as the hydrate.

The compound (1) according to the present invention is excellent in water solubility, is also good in oral absorbability and has inhibitory activity against interleukin-1β production, and therefore, is useful as a preventive or therapeutic for immune system diseases, inflammatory diseases, ischemic diseases, osteoporosis, ichoremia and the like. Examples of ischemic diseases include ischemic heart diseases, ischemic encephalopathy, ischemic nephritis, and ischemic hepatitis.

The pharmaceutical composition of the present invention contains the compound (1) or the pharmaceutically acceptable salt thereof as an active ingredient. Using the active ingredient alone or together with a pharmaceutically acceptable carrier such as a solubilizer, excipient, binder or extender, it can be formed into pharmaceutical preparation forms such as tablets, capsules, granules, powders, injections and suppositories. These pharmaceutical preparations can be produced by known methods. For example, oral preparations can be produced by suitably formulating the compound (1) or the salt in combination with solubilizers such as tragacanth gum, gum arabic, sucrose esters, lecithin, olive oil, soybean oil and PEG400; excipients such as starch, mannitol and lactose; binders such as carboxymethylcellulose sodium and hydroxypropylcellulose; disintegrators such as crystalline cellulose and carboxymethylcellulose calcium; lubricants such as talc and magnesium stearate; anticaking agents such as light anhydrous silicic acid. The pharmaceutical composition according to the present invention is administered orally or parenterally.

The administered dosage of the pharmaceutical composition according to the present invention varies depending on the body weight, age, sex, conditions and the like of each patient. In general, however, it is preferred to administer to an adult in an amount of about 0.01 to 1,000 mg, preferably 0.1 to 100 mg, of the present pharmaceutical composition in terms of the compound (1) per day in 1 to 3 portions.

EXAMPLES

The present invention will now be further described by reference to the following Examples. The Examples are provided solely for purposes of illustration and are not intended to be limitative.

Example 1

Preparation of 4-(4-tert-butoxycarbonyl-1-piperazinyl)methyl-6-(3-fluoro-4-methylphenyl)-2-isobutyl-2H-pyridazin-3-one 1) Preparation of 4-(1-hydroxyethyl)-2-fluorotoluene To an ice-cold solution of 3-fluoro-4-methylbenzaldehyde (50 mg, 0.36 mmol) in THF (0.5 mL) was added dropwise a 0.93 M solution (0.47 mL) of methylmagnesium bromide (0.44 mmol) in THF. The temperature of the reaction mixture was allowed to rise back to room temperature, at which the reaction mixture was stirred for 1 hour. Then, 2 mol/L hydrochloric acid was added, and the mixture was extracted with ethyl acetate. The extract was washed with brine and dried over anhydrous sodium sulfate. The solvent was distilled off under reduced pressure to yield title compound as a pale yellow oil (55.8 mg, quantitative).

$^1$H NMR (400 MHz, CDCl$_3$) δ: 1.46 (3H, d, J=6.4 Hz), 2.26 (3H, d, J=1.8 Hz), 4.85 (1H, q, J=6.4 Hz), 6.99–7.06 (2H, m), 7.14 (1H, dd, J=7.8, 7.8 Hz).

2) Preparation of 3'-fluoro-4'-methylacetophenone

To a solution of 4-(1-hydroxyethyl)-2-fluorotoluene (55.8 mg, 0.36 mmol) in methylene chloride (1 mL) were added molecular sieve 4A (56.0 mg) and PCC 94.0 mg (0.43 mmol), and the mixture was stirred at room temperature for 1 hour. The reaction mixture was filtered through Celite, and the filtrate was concentrated under reduced pressure. The residue was purified by column chromatography on silica gel to yield the title compound as a pale yellow oil (47.5 mg, 86.0%).

$^1$H NMR (400 MHz, CDCl$_3$) δ: 2.32 (3H, d, J=1.8 Hz), 2.56 (3H, s), 7.26 (1H, dd, J=7.6, 7.6 Hz), 7.56 (1H, dd, J=1.6, 10.4 Hz), 7.62 (1H, dd, J=1.6, 7.8 Hz).

3) Preparation of ethyl 2-ethoxycarbonyl-4-(3-fluoro-4-methylphenyl)-2-hydroxy-4-oxobutanoate A mixture of 3'-fluoro-4'-methylacetophenone (4.92 g, 32.3 mmol) and diethyl ketomalonate (6.19 g, 35.6 mmol) was stirred at 120° C. for 48 hours. The temperature of the reaction mixture was allowed to drop back to room temperature, and the mixture was purified by column chromatography on silica gel [silica gel 100 g, chloroform/ethyl acetate (10/1)] to yield the title compound as yellow crystals (8.41 g, 79.3%).

Melting point: 68.7–69.0° C.

$^1$H NMR (400 MHz, CDCl$_3$) δ: 1.30 (6H, t, J=7.1 Hz), 2.34 (3H, s), 3.78 (2H, s), 4.25 (1H, s), 4.31 (4H, q, J=7.1

Hz), 7.29 (1H, dd, J=7.6 Hz), 7.59 (1H, d, J=10.2 Hz), 7.65 (1H, dd, J=1.5, 7.8 Hz).

IR (KBr) cm$^{-1}$: 3485, 1740, 1684, 1253, 856, 577.

4) Preparation of 4-carboxy-6-(3-fluoro-4-methylphenyl)-2H-pyridazin-3-one

To a solution of ethyl 2-ethoxycarbonyl-4-(3-fluoro-4-methylphenyl)-2-hydroxy-4-oxobutanoate (8.41 g, 25.8 mmol) in isopropanol (100 mL) was added hydrazine monohydrate (2.84 g, 56.8 mmol), and the mixture was heated under stirring at 100° C. for 6 hours. Then, 2 mol/L sodium hydroxide was added, and the mixture was stirred further at the same temperature for 4 hours. The reaction mixture was ice-cooled, and concentrated hydrochloric acid was added to acidify the system. The precipitate was collected by filtration, thoroughly washed with water and dried to yield the title compound as a slightly yellow crystalline powder (5.67 g, 87.7%).

Melting point: 281.3–282.0° C. (dec.)

$^1$H NMR (400 MHz, DMSO-d$_6$) δ: 2.28 (3H, d, J=1.0 Hz), 7.41 (1H, dd, J=8.1, 8.1 Hz), 7.67–7.73 (2H, m), 8.49 (1H, s), 14.09 (1H, br).

IR (KBr) cm$^{-1}$: 1736, 1641, 1441, 1125, 926, 806.

5) Preparation of 6-(3-fluoro-4-methylphenyl)-4-methoxycarbonyl-2H-pyridazin-3-one To an ice-cold suspension of 4-carboxy-6-(3-fluoro-4-methyl-phenyl)-2H-pyridazin-3-one (5.50 g, 22.2 mmol) in methanol (100 mL) was added dropwise thionyl chloride (2.72 g, 24.4 mmol), and the mixture was stirred at 80° C. for 8 hours. The temperature of the reaction mixture was allowed to drop back to room temperature, and the solvent was distilled off under reduced pressure. Water was added to the ice-cold residue. The precipitate was collected by filtration, washed with water and dried to yield the title compound as pale yellow fine-needles (5.43 g, 92.7%).

Melting point: 206.0–207.3° C.

$^1$H NMR (400 MHz, CDCl$_3$) δ: 2.33 (3H, d, J=1.7 Hz), 4.00 (3H, s), 7.29 (1H, dd, J=7.9, 7.9 Hz), 7.46–7.53 (2H, m), 8.32 (1H, s), 11.61 (1H, s).

IR (KBr) cm$^{-1}$: 1715, 1671, 1266, 1177, 1091, 812.

6) Preparation of 6-(3-fluoro-4-methylphenyl)-2-isobutyl-4-methoxycarbonyl-2H-pyridazin-3-one To a solution of 6-(3-fluoro-4-methylphenyl)-4-methoxycarbonyl-2H-pyridazin-3-one (5.28 g, 20.0 mmol) in N,N-dimethylformamide (40 mL) were added potassium carbonate (5.53 g, 40.0 mmol) and isobutyl bromide (3.29 g, 24.0 mmol), and the mixture was stirred at 80° C. for 1 hour. The temperature of the reaction mixture was allowed to drop back to room temperature. A saturated aqueous solution of sodium hydrogencarbonate was added, and the mixture was extracted with ethyl acetate. The extract was washed with brine, and dried over anhydrous sodium sulfate. The solvent was distilled off under reduced pressure. The residue was purified by column chromatography on silica gel [silica gel 100 g, chloroform/methanol (100/1→50/1)) to yield the title compound as an orange oil (5.41 g, 84.9%).

$^1$H NMR (400 MHz, CDCl$_3$) δ: 0.99 (6H, d, J=6.6 Hz), 2.32–2.42 (1H, m), 2.33 (3H, s), 3.98 (3H, s), 4.12 (2H, d, J=7.4 Hz), 7.28 (1H, dd, J=7.8, 7.8 Hz), 7.46 (1H, dd, J=1.6, 7.8 Hz), 7.50 (1H, dd, J=1.6, 10.7 Hz), 8.21 (1H, s).

7) Preparation of 4-carboxy-6-(3-fluoro-4-methylphenyl)-2-isobutyl-2H-pyridazin-3-one To a suspension of 6-(3-fluoro-4-methylphenyl)-2-isobutyl-4-methoxycarbonyl-2H-pyridazin-3-one (5.27 g, 16.6 mmol) in methanol (50 mL) was added a 2 mol/L aqueous sodium hydroxide (50 mL), and the mixture was stirred at 60° C. for 15 minutes. The temperature of the reaction mixture was allowed to drop back to room temperature, and then, water was added. After the system was acidified with concentrated hydrochloric acid, the mixture was extracted with ethyl acetate. The extract was washed with brine, and dried over anhydrous sodium sulfate. The solvent was distilled off under reduced pressure, and the residue was recrystallized from chloroform-hexane to yield the title compound as colorless fine-needles (4.73 g, 93.8%).

Melting point: 159.0–159.5° C.

$^1$H NMR (400 MHz, CDCl$_3$) δ: 1.02 (6H, d, J=6.7 Hz), 2.33–2.42 (1H, m), 2.35 (3H, d, J=1.6 Hz), 4.21 (2H, d, J=7.4 Hz), 7.32 (1H, dd, J=7.8, 7.8 Hz), 7.52 (1H, dd, J=1.8, 8.0 Hz), 7.55 (1H, dd, J=1.8, 10.6 Hz), 8.63 (1H, s), 14.13 (1H, s).

IR (KBr) cm$^{-1}$: 2960, 1742, 1633, 1574, 1425, 1101, 820.

8) Preparation of 6-(3-fluoro-4-methylphenyl)-4-hydroxymethyl-2-isobutyl-2H-pyridazin-3-one To a solution of 4-carboxy-6-(3-fluoro-4-methyl-phenyl)-2-isobutyl-2H-pyridazin-3-one (4.53 g, 14.9 mmol) in THF (40 mL) was added triethylamine (1.66 g, 16.4 mmol). To the ice-cooled mixture was added dropwise a solution of ethyl chlorocarbonate (1.78 g, 16.4 mmol) in THF (5 mL), and the mixture was stirred for 30 minutes. Triethylamine hydrochloride was filtered off. A solution of sodium borohydride (564 mg, 14.9 mmol) in water (1 mL) was added to the filtrate, and then, the mixture was stirred at room temperature for 10 minutes. Thereafter, 2 mol/L hydrochloric acid was added to the reaction mixture, and the mixture was extracted with ethyl acetate. The organic layer was washed with brine, and dried over anhydrous sodium sulfate. The solvent was distilled off under reduced pressure. The residue was purified by column chromatography on silica gel [silica gel 300 g, chloroform/methanol (100/1→50/1)) to yield the title compound as a colorless crystalline powder (1.08 g, 25.0%).

Melting point: 147.3–147.5° C.

$^1$H NMR (400 MHz, CDCl$_3$) δ: 0.99 (6H, d, J=6.6 Hz), 2.29–2.39 (1H, m), 2.32 (3H, d, J=1.8 Hz), 3.05 (1H, t, J=6.0 Hz), 4.08 (2H, d, J=7.4 Hz), 4.71 (2H, dd, J=1.2, 6.0 Hz), 7.26 (1H, dd, J=7.8 Hz), 7.46 (1H, dd, J=7.8, 7.8 Hz), 7.50 (1H, dd, J=1.8, 10.8 Hz), 7.65 (1H, s).

IR (KBr) cm$^{-1}$: 3330, 1644, 1596, 1514, 1226, 1087, 824.

9) Preparation of 6-(3-fluoro-4-methylphenyl)-2-isobutyl-4-methanesulfonyloxymethyl-2H-pyridazin-3-one To an ice-cold solution of 6-(3-fluoro-4-methyl-phenyl)-4-hydroxymethyl-2-isobutyl-2H-pyridazin-3-one (1.08 g, 3.73 mmol) in methylene chloride (20 mL) were added triethylamine (491 mg, 4.85 mmol) and methanesulfonyl chloride (513 mg, 4.48 mmol), and the mixture was stirred for 1 hour. A saturated aqueous solution of sodium hydrogencarbonate was added to the reaction mixture, and then, the mixture was extracted with ethyl acetate. The extract was washed with brine and dried over anhydrous sodium sulfate. The solvent was distilled off under reduced pressure, and the residue was recrystallized from chloroform-hexane to yield the title compound as a colorless crystalline powder (964 mg, 70.4%).

Melting point: 142.7–143.4° C.

$^1$H NMR (400 MHz, CDCl$_3$) δ: 0.99 (6H, d, J=6.8 Hz), 2.30–2.34 (1H, m), 2.33 (3H, d, J=1.8 Hz), 3.17 (3H, s), 4.08 (2H, d, J=7.4 Hz), 5.27 (2H, d, J=1.4 Hz), 7.27 (1H, dd, J=7.8, 7.8 Hz), 7.45 (1H, dd, J=1.8, 8.0 Hz), 7.50 (1H, dd, J=1.8, 10.9 Hz), 7.76 (1H, t, J=1.4 Hz).

IR (KBr) cm$^{-1}$: 3435, 2964, 1658, 1610, 1354, 1165, 875.

10) Preparation of 4-(4-tert-butoxycarbonyl-1-piperazinyl)-methyl-6-(3-fluoro-4-methylphenyl)-2-isobutyl-2H-pyridazin-3-one To a solution of 6-(3-fluoro-4-methylphenyl)-2-isobutyl-4-methanesulfonyloxymethyl-2H-pyridazin-3-one (100 mg, 0.27 mmol) in acetonitrile (1 mL) were added potassium carbonate (56.3 mg, 0.41 mmol) and tert-butyl 1-piperazinecarboxylate (60.7 mg, 0.33 mmol), and the mixture was stirred at 80° C. for 2 hours. The temperature of the reaction mixture was allowed to drop back to room temperature, and then, water was added. The mixture was extracted with chloroform. The extract was dried over anhydrous sodium sulfate. The solvent was distilled off under reduced pressure, and the residue was purified by column chromatography on silica gel [chloroform/methanol (40/1)] to yield the title compound as a yellow oil (115 mg, 92.4%).

$^1$H NMR (400 MHz, CDCl$_3$) δ: 0.98 (6H, d, J=3.4 Hz), 1.47 (9H, s), 2.28–2.40 (1H, m), 2.33 (3H, s), 2.52 (4H, t, J=4.7 Hz), 3.51 (4H, t, J=4.7 Hz), 3.58 (2H, s), 4.07 (2H, d, 4.1 Hz), 7.27 (1H, dd, J=7.6, 7.6 Hz), 7.44–7.52 (2H, m), 7.77 (1H, s).

Example 2

Preparation of 6-(3-fluoro-4-methylphenyl)-2-isobutyl-4-(1-piperazinyl)methyl-2H-pyridazin-3-one dihydrochloride To a solution of 4-(4-tert-butoxycarbonyl-1-piperazinyl)methyl-6-(3-fluoro-4-methylphenyl)-2-isobutyl-2H-pyridazin-3-one (115 mg, 0.25 mmol) in ethyl acetate (2 mL) was added a 4 mol/L solution (2 mL) of hydrochloric acid in ethyl acetate, and the mixture was stirred at 50° C. for 1 hour. The temperature of the reaction mixture was allowed to drop back to room temperature, and then, diethyl ether was added. The precipitate was collected to yield the title compound as a colorless crystalline powder (81.1 mg, 75.0%).

Melting point: 186.2–195.0° C. (dec.)

$^1$H NMR (400 MHz, DMSO-d$_6$) δ: 0.95 (6H, d, J=6.8 Hz), 2.22–2.33 (1H, m), 2.29 (3H, d, J=2.0 Hz), 3.15 (4H, br), 3.32 (4H, t, J=5.2 Hz), 3.93 (2H, s), 4.02 (2H, d, J=7.1 Hz), 7.40 (1H, dd, J=8.1, 8.1 Hz), 7.59–7.66 (2H, m), 8.21 (1H, s).

IR (KBr) cm$^{-1}$: 1656, 1610, 1425, 1306, 956.

Mass m/z: 358 (M$^+$).

Example 3

Preparation of 6-(3-fluoro-4-methylphenyl)-2-isobutyl-4-(4-methyl-1-piperazinyl)methyl-2H-pyridazin-3-one Following the procedure of Example 1(10), 6-(3-fluoro-4-methylphenyl)-2-isobutyl-4-methanesulfonyloxymethyl-2H-pyridazin-3-one and 1-methylpiperazine were reacted to yield the title compound as a yellow oil (yield: 93.4%).

$^1$H NMR (400 MHz, CDCl$_3$) δ: 0.98 (6H, d, J=6.8 Hz), 2.28–2.40 (1H, m), 2.33 (6H, s), 2.52 (4H, br), 2.62 (4H, br), 3.58 (2H, s), 4.07 (2H, d, J=7.4 Hz), 7.27 (1H, dd, J=7.9, 7.9 Hz), 7.46–7.52 (2H, m), 7.75 (1H, d, J=1.0 Hz).

Example 4

Preparation of 6-(3-fluoro-4-methylphenyl)-2-isobutyl-4-(4-methyl-1-piperazinyl)methyl-2H-pyridazin-3-one dihydrochloride To a solution of 6-(3-fluoro-4-methylphenyl)-2-isobutyl-4-(4-methyl-1-piperazinyl)methyl-2H-pyridazin-3-one (94.4 mg, 0.25 mmol) in methanol (1 mL) was added dropwise at room temperature under stirring a 4 mol/L solution (0.15 mL) of hydrochloric acid in ethyl acetate. The solvent was distilled off under reduced pressure. The residue was recrystallized from methanol-diethyl ether to yield the title compound as a colorless crystalline powder (71.9 mg, 63.7%).

Melting point: 248.5–252.0° C. (dec.)

$^1$H NMR (400 MHz, DMSO-d$_6$) δ: 0.94 (6H, d, J=6.8 Hz), 2.29 (3H, d, J=1.8 Hz), 2.22–2.33 (1H, m), 2.77 (3H, s), 3.18 (4H, br), 3.38 (4H, br), 3.91 (2H, s), 4.02 (2H, d, J=7.0 Hz), 7.40 (1H, dd, J=8.0, 8.0 Hz), 7.59–7.65 (2H, m), 8.16 (1H, s).

IR (KBr) cm$^{-1}$: 1653, 1609, 1451, 1425, 951.

Mass m/z: 372 (M$^+$).

Example 5

Preparation of 4-N,N-bis(2-hydroxyethyl)aminomethyl-6-(3-fluoro-4-methylphenyl)-2-isobutyl-2H-pyridazin-3-one Following the procedure of Example 1(10), 6-(3-fluoro-4-methylphenyl)-2-isobutyl-4-methanesulfonyloxymethyl-2H-pyridazin-3-one and diethanolamine were reacted to yield the title compound as a yellow oil (yield: 84.8%).

$^1$H NMR (400 MHz, CDCl$_3$) δ: 0.96 (6H, d, J=6.6 Hz), 2.27–2.38 (1H, m), 2.30 (3H, s), 2.70 (4H, t, J=5.0 Hz), 3.66 (4H, t, J=5.2 Hz), 3.69 (2H, s), 4.06 (2H, d, J=7.2 Hz), 7.23 (1H, dd, J=7.9, 7.9 Hz), 7.46–7.52 (2H, m), 7.79 (1H, s).

Example 6

Preparation of 4-N,N-bis(2-hydroxyethyl)aminomethyl-6-(3-fluoro-4-methylphenyl)-2-isobutyl-2H-pyridazin-3-one hydrochloride Following the procedure of Example 4, 4-N,N-bis(2-hydroxyethyl)aminomethyl-6-(3-fluoro-4-methylphenyl)-2-isobutyl-2H-pyridazin-3-one was reacted to yield the title compound as a colorless crystalline powder (yield: 85.9%).

Melting point: 159.7–160.7° C.

$^1$H NMR (400 MHz, DMSO-d$_6$) δ: 0.96 (6H, d, J=6.6 Hz), 2.20–2.34 (1H, m), 2.30 (3H, d, J=1.7 Hz), 3.35 (4H, t, J=5.1 Hz), 3.84 (4H, t, J=5.1 Hz), 4.05 (2H, d, J=7.0 Hz), 4.45 (2H, s), 7.42 (1H, dd, J=8.2, 8.2 Hz), 7.62–7.68 (2H, m), 8.47 (1H, s).

IR (KBr) cm$^{-1}$: 1663, 1613, 1427, 1087, 1052, 821.

Mass m/z: 359 (M$^+$-H$_2$O).

Example 7

Preparation of 4-dimethylaminomethyl-6-(3-fluoro-4-methylphenyl)-2-isobutyl-2H-pyridazin-3-one To 6-(3-fluoro-4-methylphenyl)-2-isobutyl-4-methanesulfonyloxymethyl-2H-pyridazin-3-one (100 mg, 0.27 mmol) was added a 40% aqueous dimethylamine (1 mL), and the mixture was stirred at 80° C. for 2 hours. The temperature of the reaction mixture was allowed to drop back to room temperature, and then, water was added. The mixture was extracted with chloroform. The extract was dried over anhydrous sodium sulfate. The solvent was distilled off under reduced pressure, and the residue was purified by column chromatography on silica gel [chloroform/methanol (40/1)] to yield the title compound as a yellow oil (69.7 mg, 80.9%).

$^1$H NMR (400 MHz, CDCl$_3$) δ: 0.98 (6H, d, J=6.8 Hz), 2.23–2.41 (1H, m), 2.31 (3H, s), 2.35 (6H, s), 3.50 (2H, d, J=1.2 Hz), 4.08 (2H, d, J=7.4 Hz), 7.26 (1H, dd, J=7.9, 7.9 Hz), 7.47–7.54 (2H, m), 7.76 (1H, d, J=1.4 Hz).

Example 8

Preparation of 4-dimethylaminomethyl-6-(3-fluoro-4-methylphenyl)-2-isobutyl-2H-pyridazin-3-one hydrochloride Following the procedure of Example 4, 4-dimethylaminomethyl-6-(3-fluoro-4-methylphenyl)-2-isobutyl-2H-pyridazin-3-one was reacted to yield the title compound as a colorless crystalline powder (yield: 85.4%).

Melting point: 246.5–248.5° C.

$^1$H NMR (400 MHz, DMSO-$d_6$) δ: 0.96 (6H, d, J=6.6 Hz), 2.23–2.34 (1H, m), 2.30 (3H, s), 2.81 (6H, s), 4.05 (2H, d, J=7.0 Hz), 4.27 (2H, s), 7.41 (1H, dd, J=8.0, 8.0 Hz), 7.22–7.68 (2H, m), 8.52 (1H, s).

IR (KBr) cm$^{-1}$: 1648, 1607, 1422, 1227, 1110, 1051.

Mass m/z: 317 (M$^+$).

Example 9

Preparation of 2-cyclopropylmethyl-6-(3-fluoro-4-methoxyphenyl)-4-methanesulfonyloxymethyl-2H-pyridazin-3-one 1) Preparation of 4-carboxy-2-cyclopropylmethyl-6-(3-fluoro-4-methoxyphenyl)-2H-pyridazin-3-one Following the procedure of Example 1(7), 2-cyclopropylmethyl-6-(3-fluoro-4-methoxyphenyl)-4-methoxycarbonyl-2H-pyridazin-3-one was reacted to yield the title compound as yellow crystals (yield: 98.9%).

Melting point: 169.1–170.7° C.

$^1$H NMR (400 MHz, CDCl$_3$) δ: 0.50–0.67 (4H, m), 1.40–1.50 (1H, m), 3.97 (3H, s), 4.23 (2H, d, J=7.3 Hz), 7.07 (1H, dd, J=8.5, 8.5 Hz), 7.57 (1H, ddd, J=1.2, 2.2, 8.5 Hz), 7.85 (1H, dd, J=2.2, 12.2 Hz), 8.63 (1H, s), 14.20 (1H, s).

IR (KBr) cm$^{-1}$: 1761, 1629, 1521, 1476, 1461.

Mass m/z: 318 (M$^+$).

2) Preparation of 2-cyclopropylmethyl-6-(3-fluoro-4-methoxyphenyl)-4-hydroxymethyl-2H-pyridazin-3-one Following the procedure of Example 1(8), 4-carboxy-2-cyclopropylmethyl-6-(3-fluoro-4-methoxyphenyl)-2H-pyridazin-3-one was reacted to yield the title compound as slightly yellow fine-needles (yield: 21.3%).

Melting point: 119.4–122.6° C.

$^1$H NMR (400 MHz, CDCl$_3$) δ: 0.45–0.60 (4H, m), 1.36–1.47 (1H, m), 3.12 (1H, t, J=6.0 Hz), 3.95 (3H, s), 4.10 (2H, d, J=7.3 Hz), 4.72 (2H, dd, J=1.2, 5.9 Hz), 7.03 (1H, dd, J=8.5, 8.5 Hz), 7.51 (1H, ddd, J=1.2, 2.2, 8.5 Hz), 7.62 (1H, dd, J=2.2, 12.4 Hz), 7.65 (1H, t, J=11.2 Hz).

IR (KBr) cm$^{-1}$: 3431, 1652, 1604, 1524.

Mass m/z: 304 (M$^+$).

3) Preparation of 2-cyclopropylmethyl-6-(3-fluoro-4-methoxyphenyl)-4-methanesulfonyloxymethyl-2H-pyridazin-3-one Following the procedure of Example 1(9), 2-cyclopropylmethyl-6-(3-fluoro-4-methoxyphenyl)-4-hydroxymethyl-2H-pyridazin-3-one was reacted to yield the title compound as slightly yellow needles (yield: 80.4%).

Melting point: 156.9–158.4° C.

$^1$H NMR (400 MHz, CDCl$_3$) δ: 0.45–0.61 (4H, m), 1.36–1.46 (1H, m), 3.18 (3H, s), 3.95 (3H, s), 4.10 (2H, d, J=7.3 Hz), 5.28 (2H, d, J=1.2 Hz), 7.03 (1H, dd, J=8.5, 8.5 Hz), 7.51 (1H, ddd, J=1.2, 2.2, 8.5 Hz), 7.62 (1H, dd, J=2.2, 12.2 Hz), 7.76 (1H, t, J=1.2 Hz).

IR (KBr) cm$^{-1}$: 1656, 1612, 1523, 1358, 1177.

Mass m/z: 382 (M$^+$).

4) Preparation of 2-cyclopropylmethyl-6-(3-fluoro-4-methoxyphenyl)-4-methylaminomethyl-2H-pyridazin-3-one A solution of 2-cyclopropylmethyl-6-(3-fluoro-4-methoxyphenyl)-4-methanesulfonyloxymethyl-2H-pyridazin-3-one (160 mg, 0.42 mmol) in 30% methylamine/ethanol (5 mL) was stirred at 80° C. for 4 hours in a sealed tube. The solvent was distilled off under reduced pressure, and the residue was purified by preparative thin-layer chromatography on silica gel [developing solvent: chloroform/methanol (10/1)] to yield title compound as a slightly yellow oil (87 mg, 65.5%).

$^1$H NMR (400 MHz, CDCl$_3$) δ: 0.45–0.59 (4H, m), 1.36–1.47 (1H, m), 1.85 (1H, br), 2.52 (3H, s), 3.80 (2H, d, J=1.2 Hz), 3.95 (3H, s), 4.10 (2H, d, J=7.3 Hz), 7.01 (1H, dd, J=8.5, 8.5 Hz), 7.52 (1H, ddd, J=1.2, 2.2, 8.5 Hz), 7.62 (1H, dd, J=2.2, 12.4 Hz), 7.66 (1H, t, J=1.2 Hz).

Mass m/z: 317 (M$^+$).

Example 10

Preparation of 2-cyclopropylmethyl-6-(3-fluoro-4-methoxyphenyl)-4-methylaminomethyl-2H-pyridazin-3-one hydrochloride Following the procedure of Example 4, 2-cyclopropylmethyl-6-(3-fluoro-4-methoxyphenyl)-4-methylaminomethyl-2H-pyridazin-3-one was reacted to yield the title compound as slightly yellow needles (yield: 93.8%).

Melting point: 220.8–224.3° C. (dec.)

$^1$H NMR (400 MHz, DMSO-$d_6$) δ: 0.44–0.54 (4H, m), 1.29–1.40 (1H, m), 2.66 (3H, s), 3.91 (3H, s), 4.05 (2H, d, J=7.3 Hz), 4.12 (2H, s), 7.33 (1H, dd, J=8.5, 8.5 Hz), 7.70–7.79 (2H, m), 8.39 (1H, s).

IR (KBr) cm$^{-1}$: 1645, 1599, 1521, 1437.

Example 11

Preparation of 2-cyclopropylmethyl-6-(3-fluoro-4-methoxyphenyl)-4-(4-methyl-1-piperazinyl)methyl-2H-pyridazin-3-one Following the procedure of Example 1(10), 2-cyclopropylmethyl-6-(3-fluoro-4-methoxyphenyl)-4-methane-sulfonyloxymethyl-2H-pyridazin-3-one and 1-methylpiperazine were reacted to yield the title compound as a yellow oil (yield: 73.8%).

$^1$H NMR (400 MHz, CDCl$_3$) δ: 0.45–0.59 (4H, m), 1.36–1.47 (1H, m), 2.33 (3H, s), 2.52 (4H, br), 2.62 (4H, br), 3.80 (2H, d, J=1.2 Hz), 3.58 (2H, d, J=1.0 Hz), 3.95 (3H, s), 4.09 (2H, d, J=7.3 Hz), 7.04 (1H, dd, J=8.5, 8.5 Hz), 7.53 (1H, ddd, J=1.2, 2.2, 8.5 Hz), 7.61 (1H, dd, J=2.2, 12.4 Hz), 7.74 (1H, t, J=1.2 Hz).

IR (Neat) cm$^{-1}$: 1652, 1608, 1520, 1456, 1440.

Mass m/z: 386 (M$^+$).

Example 12

Preparation of 2-cyclopropylmethyl-6-(3-fluoro-4-methoxyphenyl)-4-(4-methyl-1-piperazinyl)methyl-2H-pyridazin-3-one dihydrochloride Following the procedure of Example 4, 2-cyclopropylmethyl-6-(3-fluoro-4-methoxyphenyl)-4-(4-methyl-1-piperazinyl)methyl-2H-pyridazin-3-one was reacted to yield the title compound as pale yellow needles (yield: 81.0%).

Melting point: 237.4–238.4° C. (dec.)

$^1$H NMR (400 MHz, DMSO-$d_6$) δ: 0.47–0.58 (4H, m), 1.31–1.41 (1H, m), 2.33 (3H, s), 2.52 (4H, br), 2.62 (4H, br), 2.90–3.85 (10H, m), 3.91 (3H, s), 4.03 (2H, d, J=7.3 Hz), 7.30 (1H, dd, J=8.5, 8.5 Hz), 7.70–7.78 (2H, m), 8.28 (1H, brs).

IR (KBr) cm$^{-1}$: 1653, 1608, 1523, 1438.

Example 13

Preparation of 2-cyclopropylmethyl-4-dimethylamino-methyl-6-(3-fluoro-4-methoxyphenyl)-2H-pyridazin-3-one Following the procedure of Example 7, 2-cyclopropyl-methyl-6-(3-fluoro-4-methoxyphenyl)-4-methanesulfonyloxy-methyl-2H-pyridazin-3-one and dimethylamine were reacted to yield the title compound as a yellow oil (yield: 88.1%).

$^1$H NMR (400 MHz, CDCl$_3$) δ: 0.45–0.59 (4H, m), 1.37–1.48 (1H, m), 2.36 (6H, s), 3.51 (2H, s), 3.95 (3H, s), 4.10 (2H, d, J=7.3 Hz), 7.02 (1H, dd, J=8.5, 8.5 Hz), 7.53–7.57 (1H, m), 7.64 (1H, dd, J=2.2, 12.7 Hz), 7.75 (1H, s).

IR (Neat) cm$^{-1}$: 1652, 1608, 1523, 1456, 1438.

Mass m/z: 331 (M$^+$).

Example 14

Preparation of 2-cyclopropylmethyl-4-dimethylamino-methyl-6-(3-fluoro-4-methoxyphenyl)-2H-pyridazin-3-one hydrochloride Following the procedure of Example 4, 2-cyclopropyl-methyl-4-dimethylaminomethyl-6-(3-fluoro-4-methoxyphenyl)-2H-pyridazin-3-one was reacted to yield the title compound as slightly yellow needles (yield: 89.0%).

Melting point: 233.6–235.0° C. (dec.)

$^1$H NMR (400 MHz, DMSO-d$_6$) δ: 0.41–0.54 (4H, m), 1.27–1.37 (1H, m), 2.83 (6H, s), 3.92 (3H, s), 4.06 (2H, d, J=7.3 Hz), 4.30 (2H, s), 7.33 (1H, dd, J=8.8, 8.8 Hz), 7.69–7.77 (2H, m), 8.51 (1H, s).

IR (KBr) cm$^{-1}$: 1648, 1584, 1522, 1439.

Example 15

Preparation of 2-cyclopropylmethyl-6-(3-fluoro-4-methoxyphenyl)-4-N-(2-hydroxyethyl)aminomethyl-2H-pyridazin-3-one Following the procedure of Example 9 (4), 2-cyclopropylmethyl-6-(3-fluoro-4-methoxyphenyl)-4-methane-sulfonyloxymethyl-2H-pyridazin-3-one and 2-aminoethanol were reacted to yield the title compound as a yellow oil (yield: 72.1%).

$^1$H NMR (400 MHz, CDCl$_3$) δ: 0.44–0.59 (4H, m), 1.36–1.47 (1H, m), 2.86 (2H, t, J=5.1 Hz), 3.73 (2H, t, J=5.1 Hz), 3.84 (2H, d, J=1.0 Hz), 3.94 (3H, s), 4.10 (2H, d, J=7.3 Hz), 7.02 (1H, dd, J=8.5, 8.5 Hz), 7.50–7.54 (1H, m), 7.62 (1H, dd, J=2.2, 12.7 Hz), 7.67 (1H, s).

IR (Neat) cm$^{-1}$: 3411, 1651, 1605, 1523, 1439.

Mass m/z: 347 (M$^+$).

Example 16

Preparation of 2-cyclopropylmethyl-6-(3-fluoro-4-methoxyphenyl)-4-N-(2-hydroxyethyl)aminomethyl-2H-pyridazin-3-one hydrochloride Following the procedure of Example 4, 2-cyclopropyl-methyl-6-(3-fluoro-4-methoxyphenyl)-4-N-(2-hydroxyethyl)-aminomethyl-2H-pyridazin-3-one was reacted to yield the title compound as pale brown needles (yield: 79.2%).

Melting point: 166.8–169.3° C. (dec.)

$^1$H NMR (400 MHz, CDCl$_3$) δ: 0.40–0.54 (4H, m), 1.27–1.37 (1H, m), 3.13 (2H, br), 3.28 (2H, br), 3.74 (3H, s), 4.05 (2H, d, J=7.1 Hz), 4.18 (2H, s), 5.31 (1H, br), 7.33 (1H, dd, J=8.8, 8.8 Hz), 7.69–7.79 (2H, m), 8.40 (1H, s).

IR (KBr) cm$^{-1}$: 3334, 1654, 1616, 1604, 1523, 1441.

Example 17

Preparation of 4-(4-benzyl-1-piperazinyl)methyl-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-methane-sulfonyloxymethyl-2H-pyridazin-3-one and 1-benzylpiperazine were reacted to yield the title compound as a yellow oil (yield: 97.7%).

$^1$H NMR (400 MHz, CDCl$_3$) δ: 0.44–0.58 (4H, m), 1.36–1.46 (1H, m), 2.56 (4H, br), 2.62 (4H, br), 3.56 (2H, s), 3.58 (2H, d, J=1.0 Hz), 3.95 (3H, s), 4.09 (2H, d, J=7.1 Hz), 7.04 (1H, dd, J=8.5, 8.5 Hz), 7.23–7.36 (5H, m), 7.50–7.55 (1H, m), 7.61 (1H, dd, J=2.2, 12.7 Hz), 7.75 (1H, s).

IR (Neat) cm$^{-1}$: 1652, 1608, 1522, 1438, 1289, 1237.

Mass m/z: 462 (M$^+$).

Example 18

Preparation of 4-(4-benzyl-1-piperazinyl)methyl-2-cyclopropylmethyl-6-(3-fluoro-4-methoxyphenyl)-2H-pyridazin-3-one dihydrochloride Following the procedure of Example 4, 4-(4-benzyl-1-piperazinyl)methyl-2-cyclopropylmethyl-6-(3-fluoro-4-methoxyphenyl)-2H-pyridazin-3-one was reacted to yield the title compound as slightly yellow prisms (yield: 85.7%).

Melting point: 253.0–257.9° C. (dec.)

$^1$H NMR (400 MHz, DMSO-d$_6$) δ: 0.41–0.55 (4H, m), 1.27–1.38 (1H, m), 3.06–3.49 (10H, br), 3.56 (2H, s), 3.91 (3H, s), 4.02 (2H, d, J=7.3 Hz), 4.39 (2H, brs), 7.30 (1H, dd, J=8.5, 8.5 Hz), 7.44–7.48 (3H, m), 7.59–7.64 (2H, m), 7.69–7.77 (2H, m), 8.30 (1H, brs).

IR (KBr) cm$^{-1}$: 1656, 1616, 1523, 1439, 1292, 1271.

Example 19

Preparation of 4-(4-tert-butoxycarbonyl-1-piperazinyl)methyl-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-methane-sulfonyloxymethyl-2H-pyridazin-3-one and tert-butyl 1-piperazinecarboxylate were reacted to yield the title compound as a pale brown oil (yield: 98.9%).

$^1$H NMR (400 MHz, CDCl$_3$) δ: 0.44–0.59 (4H, m), 1.47 (9H, s), 1.38–1.46 (1H, m), 2.53 (4H, t, J=4.9 Hz), 3.51 (4H, t, J=4.9 Hz), 3.58 (2H, d, J=1.2 Hz), 3.95 (3H, s), 4.10 (2H, d, J=7.3 Hz), 7.03 (1H, dd, J=8.5, 8.5 Hz), 7.51 (1H, ddd, J=1.2, 2.2, 8.5 Hz), 7.61 (1H, dd, J=2.2, 12.7 Hz), 7.76 (1H, s).

IR (Neat) cm$^{-1}$: 1698, 1653, 1609, 1523, 1438, 1427.

Mass m/z: 472 (M$^+$).

Example 20

Preparation of 2-cyclopropylmethyl-6-(3-fluoro-4-methoxyphenyl)-4-(1-piperazinyl)methyl-2H-pyridazin-3-one 4-(4-tert-Butoxycarbonyl-1-piperazinyl)methyl-2-cyclopropylmethyl-6-(3-fluoro-4-methoxyphenyl)-2H- pyridazine-3-one (220 mg, 0.47 mmol) was dissolved in ice-cold trifluoroacetic acid (2 mL), and at the same temperature, the mixture was stirred for 15 minutes. Water (10 mL) was added to the reaction mixture. The mixture was alkalinized with potassium carbonate and extracted twice with chloroform (20 mL) The extracts were washed with brine (20 mL) and dried over anhydrous sodium sulfate. The solvent was distilled off. The residue was recrystallized from chloroform-hexane to yield the title compound as pale yellow prisms (120 mg, 69.2%).

Melting point: 111.5–118.0° C.

$^1$H NMR (400 MHz, CDCl$_3$) δ: 0.45–0.59 (4H, m), 1.36–1.47 (1H, m), 2.55 (4H, br), 2.96 (4H, t, J=4.9 Hz), 3.56 (2H, d, J=1.5 Hz), 3.95 (3H, s), 4.09 (2H, d, J=7.3 Hz), 7.04 (1H, dd, J=8.5, 8.5 Hz), 7.53 (1H, ddd, J=1.2, 2.2, 8.5 Hz), 7.62 (1H, dd, J=2.2, 12.7 Hz), 7.76 (1H, t, J=1.5 Hz).

IR (KBr) cm$^{-1}$: 3328, 1648, 1605, 1520, 1437.

Mass m/z: 372 (M$^+$).

Example 21

Preparation of 2-cyclopropylmethyl-6-(3-fluoro-4-methoxyphenyl)-4-(1-piperazinyl)methyl-2H-pyridazin-3-one dihydrochloride Following the procedure of Example 4, 2-cyclopropyl-methyl-6-(3-fluoro-4-methoxyphenyl)-4-(1-piperazinyl)-methyl-2H-pyridazin-3-one was reacted to yield the title compound as slightly yellow prisms (yield: 94.5%).

Melting point: 139.1–142.4° C.

$^1$H NMR (400 MHz, DMSO-d$_6$) δ: 0.42–0.56 (4H, m), 1.29–1.39 (1H, m), 3.40 (4H, br), 3.70 (4H, br), 3.91 (3H, s), 4.16 (2H, d, J=7.3 Hz), 4.16 (2H, brs), 7.31 (1H, dd, J=8.5, 8.5 Hz), 7.71–7.73 (2H, m), 8.41 (1H, brs).

IR (KBr) cm$^{-1}$: 3435, 1660, 1610, 1526, 1440, 1291.

Example 22

Preparation of 4-N,N-bis(2-hydroxyethyl) aminomethyl-2-cyclopropylmethyl-6-(3-fluoro-4-methoxyphenyl)-2H-pyridazin-3-one Following the procedure of Example 1(10), 2-cyclopropylmethyl-6-(3-fluoro 4-methoxyphenyl)-4-methane-sulfonyloxymethyl-2H-pyridazin-3-one and diethanolamine were reacted to yield the title compound as a pale brown oil (yield: 83.0%).

$^1$H NMR (400 MHz, CDCl$_3$) δ: 0.43–0.58 (4H, m), 1.35–1.46 (1H, m), 2.71 (4H, t, J=4.9 Hz), 3.67 (4H, t, J=4.9 Hz), 3.71 (2H, s), 3.85 (2H, br), 3.94 (3H, s), 4.10 (2H, d, J=7.3 Hz), 7.01 (1H, dd, J=8.5, 8.5 Hz), 7.51–7.56 (1H, m), 7.61 (1H, dd, J=2.2, 12.4 Hz), 7.73 (1H, t, J=1.5 Hz).

IR (Neat) cm$^{-1}$: 3616, 3476, 3275, 1648, 1601, 1529.

Mass m/z: 391 (M$^+$).

Example 23

Preparation of 4-N,N-bis(2-hydroxyethyl) aminomethyl-2-cyclopropylmethyl-6-(3-fluoro-4-methoxyphenyl)-2H-pyridazin-3-one hydrochloride Following the procedure of Example 4, 4-N,N-bis(2-hydroxyethyl)aminomethyl-2-cyclopropylmethyl-6-(3-fluoro-4-methoxyphenyl)-2H-pyridazin-3-one was reacted to yield the title compound as pale yellow prisms (yield: 75.9%).

Melting point: 175.2–176.8° C.

$^1$H NMR (400 MHz, DMSO-d$_6$) δ: 0.42–0.55 (4H, m), 1.28–1.39 (1H, m), 3.36 (4H, br), 3.82 (4H, br), 3.92 (3H, s), 4.06 (2H, d, J=7.3 Hz), 4.49 (2H, brs), 7.33 (1H, dd, J=8.5, 8.5 Hz), 7.71–7.79 (2H, m), 8.47 (1H, brs).

IR (KBr) cm$^{-1}$: 3162, 1652, 1604, 1531.

Example 24

Preparation of 4-aminomethyl-2-cyclopropylmethyl-6-(3-fluoro-4-methoxyphenyl)-2H-pyridazin-3-one 1) Preparation of 2-cyclopropylmethyl-6-(3-fluoro-4-methoxyphenyl)-4-phthalimidomethyl-2H-pyridazin-3-one To a solution of 2-cyclopropylmethyl-6-(3-fluoro-4-methoxyphenyl)-4-methanesulfonyloxymethyl-2H-pyridazin-3-one (220 mg, 0.57 mmol) in N,N-dimethylformamide (5 mL) was added potassium phthalimide (160 mg, 0.87 mmol), and the mixture was stirred at 80° C. for 2 hours. Water (30 mL) was added to the reaction mixture. After stirring under cooling over ice water, precipitated crystals were collected by filtration, dried in air, and recrystallized from chloroform-hexane to yield the title compound as colorless needles (202 mg, 81.0%).

Melting point: 241.7–243.6° C.

$^1$H NMR (400 MHz, CDCl$_3$) δ: 0.45–0.59 (4H, m), 1.37–1.47 (1H, m), 3.90 (3H, s), 4.10 (2H, d, J=7.1 Hz), 4.91 (2H, d, J=1.2 Hz), 6.95 (1H, dd, J=8.5, 8.5 Hz), 7.29 (1H, t, J=1.2 Hz), 7.38 (1H, ddd, J=1.2, 2.2, 8.5 Hz), 7.48 (1H, dd, J=2.2, 12.4 Hz), 7.76–7.81 (2H, m), 7.90–7.95 (2H, m).

IR (KBr) cm$^{-1}$: 1712, 1653, 1614, 1524.

Mass m/z: 433 (M$^+$).

2) Preparation of 4-aminomethyl-2-cyclopropylmethyl-6-(3-fluoro-4-methoxyphenyl)-2H-pyridazin-3-one To a solution of 2-cyclopropylmethyl-6-(3-fluoro-4-methoxypheyl)-4-phthalimidomethyl-2H-pyridazin-3-one (190 mg, 0.43 mmol) in methanol (5 mL) was added hydrazine monohydrate (110 mg, 2.20 mmol), and the mixture was heated under reflux for 2 hours. Methanol was distilled off, and chloroform (20 mL) was added to the residue. The mixture was successively washed with water (10 mL) and brine (10 mL) in this order, and was then dried over anhydrous sodium sulfate. The solvent was distilled off under reduced pressure. The residue was purified by preparative thin-layer chromatography on silica gel [developing solvent: chloroform/10% w/v solution of methanol in ammonia (20/1)] to yield the title compound as yellow crystals (130 mg, 97.8%).

$^1$H NMR (400 MHz, CDCl$_3$) δ: 0.45–0.59 (4H, m), 1.37–1.47 (1H, m), 1.51 (2H, br), 3.89 (2H, d, J=1.2 Hz), 3.95 (3H, s), 4.11 (2H, d, J=7.1 Hz), 7.02 (1H, dd, J=8.5, 8.5 Hz), 7.53 (1H, ddd, J=1.2, 2.4, 8.5 Hz), 7.63 (1H, dd, J=2.2, 12.7 Hz), 7.68 (1H, s).

IR (KBr) cm$^{-1}$: 3393, 1651, 1606, 1523, 1438, 1293.

Mass m/z: 303 (M$^+$).

Example 25

Preparation of 4-aminomethyl-2-cyclopropylmethyl-6-(3-fluoro-4-methoxyphenyl)-2H-pyridazin-3-one hydrochloride Following the procedure of Example 4, 4-aminomethyl-2-cyclopropylmethyl-6-(3-fluoro-4-methoxyphenyl)-2H-pyridazin-3-one was reacted to yield the title compound as pale yellow needles (81.0%).

Melting point: 188.2–194.2° C. (dec.)

$^1$H NMR (400 MHz, DMSO-d$_6$) δ: 0.42–0.55 (4H, m), 1.29–1.39 (1H, m), 3.92 (3H, s), 4.01 (2H, s), 4.06 (2H, d, J=7.1 Hz), 7.34 (1H, dd, J=8.5, 8.5 Hz), 7.71–7.78 (2H, m), 8.31 (1H, s).

IR (KBr) cm$^{-1}$: 3507, 3440, 1644, 1581, 1522, 1438.

Example 26

Preparation of 4-(4-tert-butoxycarbonyl-1-piperazinyl)methyl-6-(3-fluoro-4-methoxyphenyl)-2-isobutyl-2H-pyridazin-3-one Following the procedure of Example 1(10), 6-(3-fluoro-4-methoxyphenyl)-2-isobutyl-4-methane-sulfonyloxymethyl-2H-pyridazin-3-one and tert-butyl 1-piperazinecarboxylate were reacted to yield the title compound as a yellow oil (yield: 94.3%).

$^1$H NMR (400 MHz, CDCl$_3$) δ: 0.98 (6H, d, J=6.6 Hz), 1.46 (9H, s), 2.27–2.40 (1H, m), 2.52 (4H, t, J=5.2 Hz), 3.50 (4H, t, J=5.2 Hz), 3.57 (2H, s), 3.95 (3H, s), 4.06 (2H, d, J=7.4 Hz), 7.03 (1H, dd, J=8.6, 8.6 Hz), 7.51 (1H, dd, J=1.2, 8.4 Hz), 7.60 (1H, dd, J=2.2, 12.5 Hz), 7.75 (1H, s).

Example 27

Preparation of 6-(3-fluoro-4-methoxyphenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3-fluoro-4-methoxy-phenyl)-2-isobutyl-2H-pyridazin-3-one was reacted to yield the title compound as a colorless crystalline powder (yield: 58.5%).

Melting point: 163.0–177.0° C. (dec.)

$^1$H NMR (400 MHz, DMSO-d$_6$) δ: 0.94 (6H, d, J=6.8 Hz), 2.22–2.33 (1H, m), 3.17 (4H, br), 3.33 (4H, t, J=5.3 Hz), 3.92 (3H, s), 3.96 (2H, s), 4.01 (2H, d, J=7.1 Hz), 7.27 (1H, dd, J=8.9, 8.9 Hz), 7.67–7.72 (2H, m), 8.22 (1H, s).

IR (KBr) cm$^{-1}$: 1656, 1608, 1522, 1440, 1291, 1113.

Mass m/z: 374 (M$^+$).

Example 28

Preparation of 6-(3-fluoro-4-methoxyphenyl)-2-isobutyl-4-(4-methyl-1-piperazinyl)methyl-2H-pyridazin-3-one Following the procedure of Example 1(10), 6-(3-fluoro-4-methoxyphenyl)-2-isobutyl-4-methanesulfonyloxymethyl-2H-pyridazin-3-one and 1-methylpiperazine were reacted to yield the title compound as a yellow oil (yield: 80.9%).

$^1$H NMR (400 MHz, CDCl$_3$) δ: 0.98 (6H, d, J=6.8 Hz), 2.28–2.40 (1H, m), 2.34 (3H, s), 2.55 (4H, br), 2.63 (4H, br), 3.58 (2H, d, J=1.4 Hz), 3.95 (3H, s), 4.06 (2H, d, J=7.4 Hz), 7.04 (1H, dd, J=8.6, 8.6 Hz), 7.53 (1H, dd, J=1.2, 8.6 Hz), 7.61 (1H, dd, J=2.2, 12.5 Hz), 7.73 (1H, s).

Example 29

Preparation of 6-(3-fluoro-4-methoxyphenyl)-2-isobutyl-4-(4-methyl-1-piperazinyl)methyl-2H-pyridazin-3-one dihydrochloride Following the procedure of Example 4, 6-(3-fluoro-4-methoxyphenyl)-2-isobutyl-4-(4-methyl-1-piperazinyl)methyl-2H-pyridazin-3-one was reacted to yield the title compound as a colorless crystalline powder (yield: 73.3%).

Melting point: 236.9–237.0° C.

$^1$H NMR (400 MHz, DMSO-d$_6$) δ: 0.94 (6H, d, J=6.8 Hz), 2.21–2.32 (1H, m), 2.77 (3H, s), 3.14 (4H, br), 3.36 (4H, br), 3.87 (2H, s), 3.91 (3H, s), 4.00 (2H, d, J=7.1 Hz), 7.26 (1H, dd, J=8.5, 8.5 Hz), 7.66–7.71 (2H, m), 8.12 (1H, s).

IR (KBr) cm$^{-1}$: 1655, 1606, 1524, 1440, 1291, 1113, 1022.

Mass m/z: 388 (M$^+$).

Example 30

Preparation of 4-N,N-bis(2-hydroxyethyl)aminomethyl-6-(3-fluoro-4-methoxyphenyl)-2-isobutyl-2H-pyridazin-3-one Following the procedure of Example 1(10), 6-(3-fluoro-4-methoxyphenyl)-2-isobutyl-4-methanesulfonyloxymethyl-2H-pyridazin-3-one and diethanolamine were reacted to yield the title compound as a yellow oil (yield: 87.2%).

$^1$H NMR (400 MHz, CDCl$_3$) δ: 0.96 (6H, d, J=6.8 Hz), 2.27–2.39 (1H, m), 2.71 (4H, t, J=5.0 Hz), 3.67 (4H, t, J=5.0 Hz), 3.70 (2H, s), 3.93 (3H, s), 4.07 (2H, d, J=7.4 Hz), 7.01 (1H, dd, J=8.6, 8.6 Hz), 7.53 (1H, dd, J=1.4, 8.4 Hz), 7.61 (1H, dd, J=2.2, 12.5 Hz), 7.72 (1H, s).

Example 31

Preparation of 4-N,N-bis(2-hydroxyethyl)aminomethyl-6-(3-fluoro-4-methoxyphenyl)-2-isobutyl-2H-pyridazin-3-one hydrochloride Following the procedure of Example 4, 4-N,N-bis(2-hydroxyethyl)aminomethyl-6-(3-fluoro-4-methoxyphenyl)-2-isobutyl-2H-pyridazin-3-one was reacted to yield the title compound as colorless flakes (yield: 89.0%).

Melting point: 129.8–133.1° C.

$^1$H NMR (400 MHz, DMSO-d$_6$) δ: 0.95 (6H, d, J=6.8 Hz), 2.23–2.34 (1H, m), 3.34 (4H, t, J=5.1 Hz), 3.83 (4H, t, J=5.2 Hz), 3.92 (3H, s), 4.03 (2H, d, J=7.0 Hz), 4.44 (2H, s), 7.29 (1H, dd, J=8.7, 8.7 Hz), 7.69–7.75 (2H, m), 8.46 (1H, s).

IR (KBr) cm$^{-1}$: 1652, 1601, 1525, 1440, 1277.

Mass m/z: 362 (M$^+$-CH$_2$OH).

Example 32

Preparation of 4-dimethylaminomethyl-6-(3-fluoro-4-methoxyphenyl)-2-isobutyl-2H-pyridazin-3-one Following the procedure of Example 7, 6-3-(fluoro-4-methoxyphenyl)-2-isobutyl-4-methanesulfonyloxymethyl-2H-pyridazin-3-one and dimethylamine were reacted to yield the title compound as a yellow oil (yield: 88.6%).

$^1$H NMR (400 MHz, CDCl$_3$) δ: 0.98 (6H, d, J=6.8 Hz), 2.30–2.40 (1H, m), 2.36 (6H, s), 3.50 (2H, s), 3.93 (3H, s), 4.07 (2H, d, J=7.2 Hz), 7.02 (1H, dd, J=8.6, 8.6 Hz), 7.55 (1H, d, J=8.6 Hz), 7.63 (1H, dd, J=2.1, 12.5 Hz), 7.75 (1H, s).

Example 33

Preparation of 4-dimethylaminomethyl-6-(3-fluoro-4-methoxyphenyl)-2-isobutyl-2H-pyridazin-3-one hydrochloride Following the procedure of Example 4, 4-dimethylaminomethyl-6-(3-fluoro-4-methoxyphenyl)-2-isobutyl-2H-pyridazin-3-one was reacted to yield the title compound as colorless needles (yield: 81.0%).

Melting point: 212.4–212.8° C.

$^1$H NMR (400 MHz, DMSO-d$_6$) δ: 0.95 (6H, d, J=6.8 Hz), 2.23–2.33 (1H, m), 2.81 (6H, s), 3.92 (3H, s), 4.04 (2H, s,

J=7.1 Hz), 4.27 (2H, s), 7.29 (1H, dd, J=8.1, 8.1 Hz), 7.70–7.75 (2H, m), 8.51 (1H, s).

IR (KBr) cm$^{-1}$: 1652, 1607, 1522, 1439, 1292, 1112.

Mass m/z: 333 (M$^+$).

Example 34

Preparation of 4-(4-tert-butoxycarbonyl-1-piperazinyl)methyl-2-isobutyl-6-phenyl-2H-pyridazin-3-one 1) Preparation of 4-methoxycarbonyl-6-phenyl-2H-pyridazin-3-one Following the procedure of Example 1(5), 4-carboxy-6-phenyl-2H-pyridazin-3-one was reacted to yield the title compound as pale yellow crystals (yield: 98.9%).

Melting point: 202.5–206.2° C.

$^1$H NMR (400 MHz, CDCl$_3$) δ: 4.01 (3H, s), 7.45–7.54 (3H, m), 7.78–7.85 (2H, m), 8.38 (1H, s), 11.86 (1H, br).

IR (KBr) cm$^{-1}$: 1717, 1670, 1443, 1259.

Mass m/z: 230 (M$^+$).

2) Preparation of 2-isobutyl-4-methoxycarbonyl-6-phenyl-2H-pyridazin-3-one

Following the procedure of Example 1(6), 4-methoxycarbonyl-6-phenyl-2H-pyridazin-3-one was reacted to yield the title compound as a yellow oil (yield: 94.1%).

$^1$H NMR (400 MHz, CDCl$_3$) δ: 1.00 (6H, d, J=6.6 Hz), 2.33–2.44 (1H, m), 3.98 (3H, s), 4.14 (2H, d, J=7.4 Hz), 7.42–7.51 (3H, m), 7.79–7.83 (2H, m), 8.27 (1H, s).

3) Preparation of 4-carboxy-2-isobutyl-6-phenyl-2H-pyridazin-3-one

Following the procedure of Example 1(7), 2-isobutyl-4-methoxycarbonyl-6-phenyl-2H-pyridazin-3-one was reacted to yield the title compound as colorless fine-needles (yield: 82.5%).

Melting point: 120.5–121.0° C.

$^1$H NMR (400 MHz, CDCl$_3$) δ: 1.03 (6H, d, J=6.6 Hz), 2.34–2.45 (1H, m), 4.23 (2H, d, J=7.4 Hz), 7.49–7.54 (3H, m), 7.84–7.89 (2H, m), 8.69 (1H, s), 14.20 (1H, s).

IR (KBr) cm$^{-1}$: 3448, 2956, 1741, 1636, 1418, 1116.

Mass m/z: 272 (M$^+$).

4) Preparation of 4-hydroxymethyl-2-isobutyl-6-phenyl-2H-pyridazin-3-one

Following the procedure of Example 1(8), 4-carboxy-2-isobutyl-6-phenyl-2H-pyridazin-3-one was reacted to yield the title compound as colorless fine-needles (yield: 22.3%).

$^1$H NMR (400 MHz, CDCl$_3$) δ: 0.98 (6H, d, J=6.6 Hz), 2.29–2.40 (1H, m), 3.67 (1H, br), 4.08 (2H, d, J=7.4 Hz), 4.72 (2H, d, J=3.9 Hz), 7.39–7.49 (3H, m), 7.76 (1H, t, J=1.4 Hz), 7.79–7.84 (2H, m).

5) Preparation of 2-isobutyl-4-methanesulfonyloxymethyl-6-phenyl-2H-pyridazin-3-one Following the procedure of Example 1(9), 4-hydroxymethyl-2-isobutyl-6-phenyl-2H-pyridazin-3-one was reacted to yield the title compound as colorless fine-needles (yield: 68.4%).

Melting point: 129.7° C.

$^1$H NMR (400 MHz, CDCl$_3$) δ: 0.99 (6H, d, J=6.6 Hz), 2.30–2.41 (1H, m), 3.17 (3H, s), 4.10 (2H, d, J=7.2 Hz), 5.28 (2H, d, J=1.2 Hz), 7.43–7.52 (3H, m), 7.79–7.82 (3H, m).

IR (KBr) cm$^{-1}$: 3442, 2963, 1658, 1611, 1355, 1165, 872.

Mass m/z: 336 (M$^+$).

6) Preparation of 4-(4-tert-butoxycarbonyl-1-piperazinyl)-methyl-2-isobutyl-6-phenyl-2H-pyridazin-3-one Following the procedure of Example 1(10), 2-isobutyl-4-methanesulfonyloxy-6-phenyl-2H-pyridazin-3-one and tert-butyl 1-piperazinecarboxylate were reacted in N,N-dimethylformamide as a solvent to yield the title compound as a yellow oil (yield: 83.5%).

$^1$H NMR (400 MHz, CDCl$_3$) δ: 0.99 (6H, d, J=6.8 Hz), 1.47 (9H, s), 2.53 (4H, t, J=4.9 Hz), 3.50 (4H, t, J=4.9 Hz), 3.59 (2H, d, J=1.0 Hz), 4.09 (2H, d, J=7.2 Hz), 7.40–7.50 (3H, m), 7.80–7.84 (3H, m).

Example 35

Preparation of 2-isobutyl-6-phenyl-4-(1-piperazinyl)-methyl-2H-pyridazin-3-one dihydrochloride Following the procedure of Example 2, 4-(4-tert-butoxycarbonyl-1-piperazinyl)methyl-2-isobutyl-6-phenyl-2H-pyridazin-3-one was reacted to yield the title compound as a white solid (yield: 67.9%).

Melting point: 154.3–159.5° C.

$^1$H NMR (400 MHz, CDCl$_3$) δ: 0.94 (6H, d, J=6.8 Hz), 2.20–2.32 (1H, m), 2.86 (4H, br), 3.21 (4H, br), 3.71 (2H, s), 4.01 (2H, d, J=7.2 Hz), 7.42–7.53 (3H, m), 7.84–7.89 (2H, m), 7.96 (1H, s).

IR (KBr) cm$^{-1}$: 1656, 1610, 1445, 694.

Mass m/z: 326 (M$^+$).

Example 36

Preparation of 2-isobutyl-4-(4-methyl-1-piperazinyl)-methyl-6-phenyl-2H-pyridazin-3-one Following the procedure of Example 1(10), 2-isobutyl-4-methanesulfonyloxymethyl-6-phenyl-2H-pyridazin-3-one and 1-methylpiperazine were reacted to yield the title compound as a yellow oil (yield: 77.1%).

$^1$H NMR (400 MHz, CDCl$_3$) δ: 0.99 (6H, d, J=6.8 Hz), 2.30–2.40 (1H, m), 2.34 (3H, s), 2.55 (4H, br), 2.64 (4H, br), 3.59 (2H, d, J=1.4 Hz), 4.08 (2H, d, J=7.2 Hz), 7.40–7.50 (3H, m), 7.78–7.84 (3H, m).

Example 37

Preparation of 2-isobutyl-4-(4-methyl-1-piperazinyl)-methyl-6-phenyl-2H-pyridazin-3-one dihydrochloride Following the procedure of Example 4, 2-isobutyl-4-(4-methyl-1-piperazinyl)methyl-6-phenyl-2H-pyridazin-3-one was reacted to yield the title compound as a colorless crystalline powder (yield: 66.3%).

Melting point: 243.8–244.3° C.

$^1$H NMR (400 MHz, DMSO-d$_6$) δ: 0.95 (6H, d, J=6.8 Hz), 2.22–2.34 (1H, m), 2.76 (3H, s), 3.01 (4H, br), 3.30 (4H, br), 3.77 (2H, s), 4.02 (2H, d, J=7.2 Hz), 7.43–7.53 (3H, m), 7.85–7.89 (2H, m), 8.02 (1H, s).

IR (KBr) cm$^{-1}$: 2960, 1653, 1610, 1446.

Mass m/z: 340 (M$^+$).

Example 38

Preparation of 4-N,N-bis(2-hydroxyethyl)aminomethyl-2-isobutyl-6-phenyl-2H-pyridazin-3-one Following the procedure of Example 1(10), 2-isobutyl-4-methanesulfonyloxymethyl-6-phenyl-2H-pyridazin-3-one and diethanolamine were reacted to yield the title compound as a yellow oil (yield: 38.7%).

$^1$H NMR (400 MHz, CDCl$_3$) δ: 0.97 (6H, d, J=6.6 Hz), 2.29–2.40 (1H, m), 2.79 (4H, br), 3.70 (4H, br), 3.80 (2H, s), 4.09 (2H, d, J=7.4 Hz), 7.39–7.48 (3H, m), 7.81–7.87 (3H, m).

Example 39

Preparation of 4-N,N-bis(2-hydroxyethyl)aminomethyl-2-isobutyl-6-phenyl-2H-pyridazin-3-one hydrochloride Following the procedure of Example 4, 4-N,N-bis(2-hydroxyethyl)aminomethyl-2-isobutyl-6-phenyl-2H-pyridazin-3-one was reacted to yield the title compound as colorless flakes (yield: 68.4%).

Melting point: 131.6–132.0° C.

$^1$H NMR (400 MHz, DMSO-$d_6$) δ: 0.96 (6H, d, J=6.6 Hz), 2.25–2.35 (1H, m), 3.35 (4H, t, J=5.1 Hz), 3.84 (4H, t, J=5.4 Hz), 4.06 (2H, d, J=7.1 Hz), 4.47 (2H, s), 7.45–7.54 (3H, m), 7.90–7.94 (2H, m), 8.48 (1H, s).

IR (KBr) cm$^{-1}$: 1655, 1610, 1421, 1053.

Mass m/z: 314 (M$^+$-CH$_2$OH).

Example 40

Preparation of 4-dimethylaminomethyl-2-isobutyl-6-phenyl-2H-pyridazin-3-one

Following the procedure of Example 7, 2-isobutyl-4-methanesulfonyloxymethyl-6-phenyl-2H-pyridazin-3-one and dimethylamine were reacted to yield the title compound as a yellow oil (yield: 81.1%).

$^1$H NMR (400 MHz, CDCl$_3$) δ: 0.99 (6H, d, J=6.8 Hz), 2.32–2.41 (1H, m), 2.35 (6H, s), 3.51 (2H, d, J=1.2 Hz), 4.09 (2H, d, J=7.2 Hz), 7.38–7.48 (3H, m), 7.80–7.87 (3H, m).

Example 41

Preparation of 4-dimethylaminomethyl-2-isobutyl-6-phenyl-2H-pyridazin-3-one hydrochloride Following the procedure of Example 4, 4-dimethylaminomethyl-2-isobutyl-6-phenyl-2H-pyridazin-3-one was reacted to yield the title compound as pale yellow flakes (yield: 71.5%).

Melting point: 221.7–222.3° C.

$^1$H NMR (400 MHz, DMSO-$d_6$) δ: 0.96 (6H, d, J=6.8 Hz), 2.24–2.35 (1H, m), 2.82 (6H, s), 4.06 (2H, d, J=7.1 Hz), 4.29 (2H, s), 7.44–7.54 (3H, m), 7.90–7.94 (2H, m), 8.54 (1H, s).

IR (KBr) cm$^{-1}$: 1648, 1610, 1460, 1052.

Mass m/z: 285 (M$^+$).

Example 42

Preparation of 4-(4-benzyl-1-piperazinyl)methyl-2-isobutyl-6-(4-methylphenyl)-2H-pyridazin-3-one 1) Preparation of 2-isobutyl-4-methoxycarbonyl-6-(4-methylphenyl)-2H-pyridazin-3-one Following the procedure of Example 1(6), 4-methoxycarbonyl-6-(4-methylphenyl)-2H-pyridazin-3-one was reacted to yield the title compound as slightly yellow needles (yield: 91.6%).

Melting point: 67.0–70.1° C.

$^1$H NMR (400 MHz, CDCl$_3$) δ: 0.99 (6H, d, J=6.6 Hz), 2.32–2.43 (1H, m), 2.41 (3H, s), 3.98 (3H, s), 4.13 (2H, d, J=7.3 Hz), 7.28 (2H, d, J=8.3 Hz), 7.70 (2H, d, J=8.3 Hz), 8.24 (1H, s).

IR (KBr) cm$^{-1}$: 1718, 1663, 1605.

Mass m/z: 300 (M$^+$).

2) Preparation of 4-carboxy-2-isobutyl-6-(4-methylphenyl)-2H-pyridazin-3-one

Following the procedure of Example 1(7), 2-isobutyl-4-methoxycarbonyl-6-(4-methylphenyl)-2H-pyridazin-3-one was reacted to yield the title compound as slightly yellow needles (yield: 86.7%).

Melting point: 162.1–165.4° C.

$^1$H NMR (400 MHz, CDCl$_3$) δ: 1.02 (6H, d, J=6.8 Hz), 2.34–2.44 (1H, m), 2.47 (3H, s), 4.21 (2H, d, J=7.3 Hz), 7.31 (2H, d, J=8.3 Hz), 7.75 (2H, d, J=8.3 Hz), 8.66 (1H, s), 14.26 (1H, s).

IR (KBr) cm$^{-1}$: 1740, 1633, 1571, 1425.

Mass m/z: 286 (M$^+$).

3) Preparation of 4-hydroxymethyl-2-isobutyl-6-(4-methylphenyl)-2H-pyridazin-3-one Following the procedure of Example 1(8), 4-carboxy-2-isobutyl-6-(4-methylphenyl)-2H-pyridazin-3-one was reacted to yield the title compound as slightly yellow needles (yield: 46.0%).

Melting point: 121.9–123.5° C.

$^1$H NMR (400 MHz, CDCl$_3$) δ: 0.99 (6H, d, J=6.8 Hz), 2.30–2.40 (1H, m), 2.40 (3H, s), 3.22 (1H, br), 4.08 (2H, d, J=7.3 Hz), 4.71 (2H, s), 7.27 (2H, d, J=8.3 Hz), 7.77 (1H, s), 7.70 (2H, d, J=8.3 Hz).

IR (KBr) cm$^{-1}$: 3334, 1645, 1596, 1522.

Mass m/z: 272 (M$^+$).

4) Preparation of 2-isobutyl-4-methanesulfonyloxymethyl-6-(4-methylphenyl)-2H-pyridazin-3-one Following the procedure of Example 1(9), 4-hydroxymethyl-2-isobutyl-6-(4-methylphenyl)-2H-pyridazin-3-one was reacted to yield the title compound as slightly yellow needles (yield: 87.4%).

Melting point: 132.0–135.5° C.

$^1$H NMR (400 MHz, CDCl$_3$) δ: 0.99 (6H, d, J=6.6 Hz), 2.29–2.39 (1H, m), 2.41 (3H, s), 3.17 (3H, s), 4.08 (2H, d, J=7.6 Hz), 5.27 (2H, t, J=1.5 Hz), 7.27 (2H, d, J=8.3 Hz), 7.72 (2H, d, J=8.3 Hz), 7.79 (1H, t, J=1.5 Hz).

IR (KBr) cm$^{-1}$: 1656, 1609, 1355, 1166.

Mass m/z: 350 (M$^+$).

5) Preparation of 4-(4-benzyl-1-piperazinyl)methyl-2-isobutyl-6-(4-methylphenyl)-2H-pyridazin-3-one Following the procedure of Example 1(10), 2-isobutyl-4-methanesulfonyloxymethyl-6-(4-methylphenyl)-2H-pyridazin-3-one and 1-benzylpiperazine were reacted to yield the title compound as a pale yellow oil (yield: 97.7%).

$^1$H NMR (400 MHz, CDCl$_3$) δ: 0.97 (6H, d, J=6.8 Hz), 2.29–2.39 (1H, m), 2.41 (3H, s), 2.55 (4H, br), 2.61 (4H, br), 3.54 (2H, s), 3.57 (2H, d, J=1.5 Hz), 4.07 (2H, d, J=7.3 Hz), 7.22–7.36 (7H, m), 7.70 (2H, d, J=8.3 Hz), 7.77 (1H, t, J=1.5 Hz).

IR (Neat) cm$^{-1}$: 1657, 1652, 1518, 1455.

Mass m/z: 430 (M$^+$).

Example 43

Preparation of 4-(4-benzyl-1-piperazinyl)methyl-2-isobutyl-6-(4-methylphenyl)-2H-pyridazin-3-one dihydrochloride Following the procedure of Example 4, 4-(4-benzyl-1-piperazinyl)methyl-2-isobutyl-6-(4-methylphenyl)-2H-pyridazin-3-one was reacted to yield the title compound as colorless needles (yield: 91.8%).

Melting point: 253.5–260.1° C.

$^1$H NMR (400 MHz, DMSO-$d_6$) δ: 0.92 (6H, d, J=6.6 Hz), 2.18–2.28 (1H, m), 2.34 (3H, s), 3.43 (10H, br), 3.99 (2H, d, J=7.3 Hz), 4.36 (2H, brs), 7.22 (2H, d, J=8.1 Hz), 7.43–7.49 (3H, m), 7.58–7.65 (2H, m), 7.78 (2H, d, J=8.1 Hz), 8.30 (1H, brs).

IR (KBr) cm$^{-1}$: 1660, 1617, 1452.

Example 44

Preparation of 4-dimethylaminomethyl-2-isobutyl-6-(4-methylphenyl)-2H-pyridazin-3-one Following the procedure of Example 7, 2-isobutyl-4-methanesulfonyloxymethyl-6-(4-methylphenyl)-2H- pyridazin-3-one and dimethylamine were reacted to yield the title compound as a slightly yellow oil (yield: 96.6%).

$^1$H NMR (400 MHz, CDCl$_3$) δ: 0.98 (6H, d, J=6.8 Hz), 2.38–2.41 (1H, m), 2.35 (6H, s), 2.40 (3H, s), 3.50 (2H, d, J=1.5 Hz), 4.08 (2H, d, J=7.3 Hz), 7.26 (2H, d, J=8.1 Hz), 7.73 (2H, d, J=8.1 Hz), 7.78 (1H, t, J=1.5 Hz).

IR (Neat) cm$^{-1}$: 1652, 1609, 1518, 1455.

Mass m/z: 299 (M$^+$).

Example 45

Preparation of 4-dimethylaminomethyl-2-isobutyl-6-(4-methylphenyl)-2H-pyridazin-3-one hydrochloride Following the procedure of Example 4, 4-dimethylaminomethyl-2-isobutyl-6-(4-methylphenyl)-2H-pyridazin-3-one was reacted to yield the title compound as colorless needles (yield: 91.8%).

Melting point: 237.6–239.6° C.

$^1$H NMR (400 MHz, DMSO-d$_6$) δ: 0.94 (6H, d, J=6.8 Hz), 2.19–2.30 (1H, m), 2.37 (3H, s), 2.81 (6H, s), 4.02 (2H, d, J=7.0 Hz), 4.30 (2H, s), 7.34 (2H, d, J=8.1 Hz), 7.81 (2H, d, J=8.1 Hz), 8.46 (1H, s).

IR (KBr) cm$^{-1}$: 1648, 1605, 1460, 1421.

Example 46

Preparation of 4-diethylaminomethyl-2-isobutyl-6-(4-methylphenyl)-2H-pyridazin-3-one Following the procedure of Example 9 (4), 2-isobutyl-4-methanesulfonyloxymethyl-6-(4-methylphenyl)-2H-pyridazin-3-one and diethylamine were reacted to yield the title compound as a pale yellow oil (yield: 95.0%).

$^1$H NMR (400 MHz, CDCl$_3$) δ: 0.98 (6H, d, J=6.8 Hz), 1.07 (6H, t, J=7.1 Hz), 2.30–2.42 (1H, m), 2.40 (3H, s), 2.60 (4H, q, J=7.1 Hz), 3.60 (2H, d, J=1.5 Hz), 4.08 (2H, d, J=7.3 Hz), 7.26 (2H, d, J=8.1 Hz), 7.73 (2H, d, J=8.1 Hz), 7.89 (1H, t, J=1.5 Hz).

IR (Neat) cm$^{-1}$: 1652, 1609, 1518, 1465, 1455.

Mass m/z: 327 (M$^+$).

Example 47

Preparation of 4-diethylaminomethyl-2-isobutyl-6-(4-methylphenyl)-2H-pyridazin-3-one hydrochloride Following the procedure of Example 4, 4-diethylaminomethyl-2-isobutyl-6-(4-methylphenyl)-2H-pyridazin-3-one was reacted to yield the title compound as slightly yellow needles (yield: 93.8%).

Melting point: 203.9–207.0° C.

$^1$H NMR (400 MHz, DMSO-d$_6$) δ: 0.94 (6H, d, J=6.6 Hz), 1.27 (6H, t, J=7.2 Hz), 2.20–2.30 (1H, m), 2.37 (3H, s), 3.09–3.24 (4H, m), 4.03 (2H, d, J=7.1 Hz), 4.28 (2H, d, J=5.4 Hz), 7.34 (2H, d, J=8.1 Hz), 7.82 (2H, d, J=8.1 Hz), 8.55 (1H, s).

IR (KBr) cm$^{-1}$: 1652, 1610, 1523, 1481, 1468.

Example 48

Preparation of 4-N,N-bis(2-hydroxyethyl)aminomethyl-6-(4-methylphenyl)-2-isobutyl-2H-pyridazin-3-one Following the procedure of Example 1(10), 2-isobutyl-4-methanesulfonyloxymethyl-6-(4-methylphenyl)-2H-pyridazin-3-one and diethanolamine were reacted to yield the title compound as a pale yellow oil (yield: 95.0%).

$^1$H NMR (400 MHz, CDCl$_3$) δ: 0.97 (6H, d, J=6.6 Hz), 2.28–2.41 (1H, m), 2.40 (3H, s), 2.71 (4H, t, J=5.0 Hz), 3.66 (4H, t, J=5.0 Hz), 3.70 (2H, s), 3.78 (2H, br), 4.09 (2H, d, J=7.6 Hz), 7.26 (2H, d, J=8.1 Hz), 7.68 (1H, s), 7.70 (2H, d, J=8.1 Hz).

IR (Neat) cm$^{-1}$: 3392, 1645, 1600, 1520.

Mass m/z: 341 (M$^+$-H$_2$O).

Example 49

Preparation of 4-N,N-bis(2-hydroxyethyl)aminomethyl-6-(4-methylphenyl)-2-isobutyl-2H-pyridazin-3-one hydrochloride Following the procedure of Example 4, 4-N,N-bis(2-hydroxyethyl)aminomethyl-6-(4-methylphenyl)-2-isobutyl-2H-pyridazin-3-one was reacted to yield the title compound as slightly yellow needles (yield: 86.4%).

Melting point: 158.9–161.5° C.

$^1$H NMR (400 MHz, DMSO-d$_6$) δ: 0.94 (6H, d, J=6.6 Hz), 2.19–2.30 (1H, m), 2.37 (3H, s), 3.27–3.46 (4H, m), 3.77–3.85 (4H, m), 4.02 (2H, d, J=7.3 Hz), 4.50 (2H, brs), 5.35 (2H, br), 7.34 (2H, d, J=8.1 Hz), 7.81 (2H, d, J=8.1 Hz), 8.46 (1H, s).

IR (KBr) cm$^{-1}$: 3292, 1664, 1615, 1423.

Example 50

Preparation of 4-aminomethyl-2-isobutyl-6-(4-methylphenyl)-2H-pyridazin-3-one

1) Preparation of 2-isobutyl-6-(4-methylphenyl)-4-phthalimidomethyl-2H-pyridazin-3-one Following the procedure of Example 24(1), 2-isobutyl-4-methanesulfonyloxymethyl-6-(4-methylphenyl)-2H-pyridazin-3-one was reacted to yield the title compound as colorless needles (yield: 98.2%).

Melting point: 221.6–223.8° C.

$^1$H NMR (400 MHz, CDCl$_3$) δ: 0.98 (6H, d, J=6.6 Hz), 2.27–2.41 (1H, m), 2.36 (3H, s), 4.08 (2H, d, J=7.3 Hz), 4.91 (2H, d, J=1.5 Hz), 7.20 (2H, d, J=8.1 Hz), 7.32 (1H, t, J=1.5 Hz), 7.56 (2H, d, J=8.1 Hz), 7.75–7.80 (2H, m), 7.89–7.94 (2H, m).

IR (KBr) cm$^-$: 1767, 1721, 1655, 1616.

Mass m/z: 401 (M$^+$).

2) Preparation of 4-aminomethyl-2-isobutyl-6-(4-methylphenyl)-2H-pyridazin-3-one Following the procedure of Example 24(2), 2-isobutyl-6-(4-methylphenyl)-4-phthalimidomethyl-2H-pyridazin-3-one was reacted to yield the title compound as colorless prisms (yield: 98.1%).

Melting point: 74.9–77.9° C.

$^1$H NMR (400 MHz, CDCl$_3$) δ: 0.98 (6H, d, J=6.9 Hz), 1.68 (2H, br), 2.28–2.42 (1H, m), 2.40 (3H, s), 3.87 (2H, d, J=1.2 Hz), 4.07 (2H, d, J=7.3 Hz), 7.26 (2H, d, J=8.0 Hz), 7.69 (1H, t, J=1.5 Hz), 7.71 (2H, d, J=8.0 Hz).

IR (KBr) cm$^{-1}$: 3363, 3289, 1648, 1604, 1519.

Mass m/z: 271 (M$^+$).

Example 51

Preparation of 4-aminomethyl-2-isobutyl-6-(4-methyl-phenyl)-2H-pyridazin-3-one hydrochloride Following the procedure of Example 4, 4-aminomethyl-2-isobutyl-6-(4-methylphenyl)-2H-pyridazin-3-one was reacted to yield the title compound as pale yellow prisms (yield: 93.1%).

Melting point: 207.4–209.4° C. (dec.)

$^1$H NMR (400 MHz, DMSO-d$_6$) δ: 0.93 (6H, d, J=6.6 Hz), 2.19–2.30 (1H, m), 2.37 (3H, s), 4.01 (2H, d, J=7.1 Hz), 4.02 (2H, s), 7.34 (2H, d, J=8.1 Hz), 7.80 (2H, d, J=8.1 Hz), 8.26 (1H, s).

IR (KBr) cm$^{-1}$: 1655, 1616, 1520, 1467.

Example 52

Preparation of 4-N-(1,3-dihydroxypropan-2-yl) amino-methyl-2-isobutyl-6-(4-methylphenyl)-2H-pyridazin-3-one Following the procedure of Example 1(10), 2-isobutyl-4-methanesulfonyloxymethyl-6-(4-methylphenyl)-2H-pyridazin-3-one and 2-amino-1,3-propanediol were reacted to yield the title compound as colorless needles (yield: 83.7%).

Melting point: 134.1–135.2° C.

$^1$H NMR (400 MHz, CDCl$_3$) δ: 0.97 (6H, d, J=6.6 Hz), 2.29–2.39 (1H, m), 2.40 (3H, s), 2.60 (3H, br), 2.82–2.87 (1H, m), 3.64 (2H, dd, J=5.6, 11.2 Hz), 3.80 (2H, dd, J=4.5, 11.2 Hz), 3.86 (2H, d, J=1.0 Hz), 4.07 (2H, d, J=7.3 Hz), 7.26 (2H, d, J=8.1 Hz), 7.71 (2H, d, J=8.1 Hz), 7.74 (1H, s).

IR (KBr) cm$^{-1}$: 3408, 3293, 1641, 1592, 1520.

Mass m/z: 345 (M$^+$).

Example 53

Preparation of 4-N-(1,3-dihydroxypropan-2-yl) amino-methyl-2-isobutyl-6-(4-methylphenyl)-2H-pyridazin-3-one hydrochloride Following the procedure of Example 4, 4-N-(1,3-dihydroxypropan-2-yl)aminomethyl-2-isobutyl-6-(4-methylphenyl)-2H-pyridazin-3-one was reacted to yield the title compound as colorless needles (yield: 95.7%).

Melting point: 191.2–193.0° C.

$^1$H NMR (400 MHz, DMSO-d$_6$) δ: 0.93 (6H, d, J=6.6 Hz), 2.19–2.30 (1H, m), 2.37 (3H, s), 3.29 (1H, br), 3.60–3.78 (4H, m), 4.02 (2H, d, J=7.1 Hz), 4.29 (2H, s), 5.40 (2H, brs), 7.34 (2H, d, J=8.1 Hz), 7.81 (2H, d, J=8.1 Hz), 8.38 (1H, s).

IR (KBr) cm$^{-1}$: 3392, 1652, 1610.

Example 54

Preparation of 2-isobutyl-4-methylaminomethyl-6-(4-methylphenyl)-2H-pyridazin-3-one Following the procedure of Example 9 (4), 2-isobutyl-4-methanesulfonyloxymethyl-6-(4-methylphenyl)-2H-pyridazin-3-one and methylamine were reacted to yield the title compound as a slightly yellow oil (yield: 94.5%).

$^1$H NMR (400 MHz, CDCl$_3$) δ: 0.98 (6H, d, J=6.6 Hz), 1.87 (1H, br), 2.29–2.42 (1H, m), 2.40 (3H, s), 2.50 (3H, s), 3.76 (2H, d, J=1.2 Hz), 4.07 (2H, d, J=7.3 Hz), 7.26 (2H, d, J=8.1 Hz), 7.67 (1H, t, J=1.2 Hz), 7.71 (2H, d, J=8.1 Hz).

IR (Neat) cm$^{-1}$: 3317, 1652, 1607.

Mass m/z: 285 (M$^+$).

Example 55

Preparation of 2-isobutyl-4-methylaminomethyl-6-(4-methylphenyl)-2H-pyridazin-3-one hydrochloride Following the procedure of Example 4, 2-isobutyl-4-methylaminomethyl-6-(4-methylphenyl)-2H-pyridazin-3-one was reacted to yield the title compound as colorless needles (yield: 97.5%).

Melting point: 198.3–201.0° C.

$^1$H NMR (400 MHz, DMSO-d$_6$) δ: 0.94 (6H, d, J=6.8 Hz), 2.20–2.31 (1H, m), 2.37 (3H, s), 2.65 (3H, s), 4.02 (2H, d, J=7.3 Hz), 4.12 (2H, s), 7.34 (2H, d, J=8.1 Hz), 7.80 (2H, d, J=8.1 Hz), 8.35 (1H, s).

IR (KBr) cm$^{-1}$: 3085, 1652, 1612.

Example 56

Preparation of 4-N-(2-hydroxyethyl)aminomethyl-2-isobutyl-6-(4-methylphenyl)-2H-pyridazin-3-one Following the procedure of Example 9 (4), 2-isobutyl-4-methanesulfonyloxymethyl-6-(4-methylphenyl)-2H-pyridazin-3-one and 2-aminoethanol were reacted to yield the title compound as a slightly yellow oil (yield: 80.3%).

$^1$H NMR (400 MHz, CDCl$_3$) δ: 0.98 (6H, d, J=6.8 Hz), 2.20–2.38 (3H, m), 2.39 (3H, s), 2.84 (2H, t, J=5.1 Hz), 3.72 (2H, t, J=5.1 Hz), 3.82 (2H, d, J=1.2 Hz), 4.07 (2H, d, J=7.3 Hz), 7.26 (2H, d, J=8.1 Hz), 7.68 (1H, s), 7.70 (2H, d, J=8.1 Hz).

IR (Neat) cm$^{-1}$: 3429, 1652, 1601, 1519.

Mass m/z: 315 (M$^+$).

Example 57

Preparation of 4-N-(2-hydroxyethyl)aminomethyl-2-isobutyl-6-(4-methylphenyl)-2H-pyridazin-3-one hydrochloride Following the procedure of Example 4, 4-N-(2-hydroxyethyl)aminomethyl-2-isobutyl-6-(4-methylphenyl)-2H-pyridazin-3-one was reacted to yield the title compound as colorless needles (yield: 93.4%).

Melting point: 190.8–191.9° C.

$^1$H NMR (400 MHz, DMSO-d$_6$) δ: 0.94 (6H, d, J=6.6 Hz), 2.20–2.31 (1H, m), 2.37 (3H, s), 3.12 (2H, t, J=5.4 Hz), 3.70–3.76 (2H, m), 4.02 (2H, d, J=7.3 Hz), 4.18 (2H, s), 5.30 (1H, br), 7.34 (2H, d, J=8.3 Hz), 7.81 (2H, d, J=8.3 Hz), 8.36 (1H, s).

IR (KBr) cm$^{-1}$: 3491, 1652, 1611.

Example 58

Preparation of 4-(4-tert-butoxycarbonyl-1-piperazinyl)methyl-2-isobutyl-6-(4-trifluoromethylphenyl)-2H-pyridazin-3-one 1) Preparation of ethyl 2-ethoxycarbonyl-2-hydroxy-4-(4-trifluoromethylphenyl)-4-oxo-butanoate Following the procedure of Example 1(3), 4'-(trifluoromethyl)acetophenone was reacted to yield the title compound as pale yellow crystals (yield: 80.8%).

$^1$H NMR (400 MHz, CDCl$_3$) δ: 1.30 (6H, t, J=7.1 Hz), 3.85 (2H, s), 4.22 (1H, s), 4.31 (4H, q, J=7.1 Hz), 7.76 (2H, d, J=8.6 Hz), 8.07 (2H, d, J=8.6 Hz). IR (KBr) cm$^{-1}$: 3446, 1750, 1727, 1691.

Mass m/z: 343 (M$^+$-H$_2$O).

2) Preparation of 4-carboxy-6-(4-trifluoromethylphenyl)-2H-pyridazin-3-one

Following the procedure of Example 1(4), ethyl 2-ethoxycarbonyl-2-hydroxy-4-(4-trifluoromethylphenyl)-4-oxobutanoate was reacted to yield the title compound as a pale brown crystalline powder (yield: 91.4%).

3) Preparation of 4-methoxycarbonyl-6-(4-trifluoromethylphenyl)-2H-pyridazin-3-one Following the procedure of Example 1(5), 4-carboxy-6-(4-trifluoromethylphenyl)-2H-pyridazin-3-one was reacted to yield the title compound as slightly yellow crystalline powder (yield: 88.5%).

$^1$H NMR (400 MHz, CDCl$_3$) δ: 4.02 (3H, s), 7.75 (2H, d, J=8.2 Hz), 7.95 (2H, d, J=8.2 Hz), 8.39 (1H, s), 11.69 (1H, br).

IR (KBr) cm$^{-1}$: 3218, 3140, 3097, 1720, 1678, 1326.

Mass m/z: 298 (M$^+$).

4) Preparation of 2-isobutyl-4-methoxycarbonyl-6-(4-trifluoromethylphenyl)-2H-pyridazin-3-one Following the procedure of Example 1(6), 4-methoxycarbonyl-6-(4-trifluoromethylphenyl)-2H-pyridazin-3-one was reacted to yield the title compound as yellow crystals (yield: 82.2%).

$^1$H NMR (400 MHz, CDCl$_3$) δ: 1.00 (6H, d, J=6.6 Hz), 2.32–2.43 (1H, m), 3.99 (3H, s), 4.15 (2H, d, J=7.2 Hz), 7.74 (2H, d, J=8.4 Hz), 7.93 (2H, d, J=8.4 Hz), 8.12 (1H, s).

IR (Neat) cm$^{-1}$: 2961, 1746, 1670, 1327, 1115, 1068.

Mass m/z: 354 (M$^+$).

5) Preparation of 4-carboxy-2-isobutyl-6-(4-trifluoromethylphenyl)-2H-pyridazin-3-one Following the procedure of Example 1(7), 2-isobutyl-4-methoxycarbonyl-6-(4-trifluoromethylphenyl)-2H-pyridazin-3-one was reacted to yield the title compound as colorless fine-needles (yield: 91.6%).

Melting point: 184.4–185.0° C.

$^1$H NMR (400 MHz, CDCl$_3$) δ: 1.03 (6H, d, J=6.6 Hz), 2.34–2.45 (1H, m), 4.25 (2H, d, J=7.2 Hz), 7.78 (2H, d, J=8.2 Hz), 7.99 (2H, d, J=8.2 Hz), 8.70 (1H, s), 14.02 (1H, s).

IR (KBr) cm$^{-1}$: 3447, 1739, 1631, 1570, 1330, 1174, 1114, 1070, 847.

Mass m/z: 340 (M$^+$).

6) Preparation of 4-hydroxymethyl-2-isobutyl-6-(4-trifluoromethylphenyl)-2H-pyridazin-3-one Following the procedure of Example 1(8), 4-carboxy-2-isobutyl-6-(4-trifluoromethylphenyl)-2H-pyridazin-3-one was reacted to yield the title compound as colorless fine-needles (yield: 28.1%).

Melting point: 145.8–146.5° C.

$^1$H NMR (400 MHz, CDCl$_3$) δ: 0.99 (6H, d, J=6.8 Hz), 2.30–2.41 (1H, m), 2.96 (1H, t, J=5.9 Hz), 4.11 (2H, d, J=7.4 Hz), 4.74 (2H, dd, J=1.4, 5.8 Hz), 7.70–7.74 (3H, m), 7.94 (2H, d, J=8.2 Hz).

IR (KBr) cm$^{-1}$: 3339, 1646, 1596, 1328, 1131, 1070, 848.

7) Preparation of 2-isobutyl-4-methanesulfonyloxymethyl-6-(4-trifluoromethylphenyl)-2H-pyridazin-3-one Following the procedure of Example 1(9), 4-hydroxymethyl-2-isobutyl-6-(4-trifluoromethylphenyl)-2H-pyridazin-3-one was reacted to yield the title compound as colorless fine-needles (yield: 89.9%).

Melting Point: 122.9–123.8° C.

$^1$H NMR (400 MHz, CDCl$_3$) δ: 0.99 (6H, d, J=6.6 Hz), 2.29–2.40 (1H, m), 3.18 (3H, s), 4.11 (2H, d, J=7.2 Hz), 5.29 (2H, d, J=1.4 Hz), 7.73 (2H, d, J=8.2 Hz), 7.83 (1H, t, J=1.4 Hz), 7.93 (2H, d, J=8.2 Hz).

IR (KBr) cm$^{-1}$: 3447, 1659, 1613, 1359, 1329, 1169, 1123, 1071, 846.

Mass m/z: 404 (M$^+$).

8) Preparation of 4-(4-tert-butoxycarbonyl-1-piperazinyl)-methyl-2-isobutyl-6-(4-trifluoromethylphenyl)-2H-pyridazin-3-one Following the procedure of Example 1(10), 2-isobutyl-4-methanesulfonyloxymethyl-6-(4-trifluoromethylphenyl)-2H-pyridazin-3-one and tert-butyl 1-piperazinecarboxylate were reacted to yield the title compound as a yellow oil (yield: 83.5%).

$^1$H NMR (400 MHz, CDCl$_3$) δ: 0.99 (6H, d, J=6.6 Hz), 1.47 (9H, s), 2.29–2.41 (1H, m), 2.53 (4H, t, J=4.9 Hz), 3.51 (4H, t, J=4.8 Hz), 3.60 (2H, s), 4.10 (2H, d, J=7.4 Hz), 7.72 (2H, d, J=8.2 Hz), 7.84 (1H, s), 7.94 (2H, d, J=8.2 Hz).

Example 59

Preparation of 2-isobutyl-4-(1-piperazinyl)methyl-6-(4-trifluoromethylphenyl)-2H-pyridazin-3-one dihydrochloride Following the procedure of Example 2, 4-(4-tert-butoxycarbonyl-1-piperazinyl)methyl-2-isobutyl-6-(4-trifluoromethylphenyl)-2H-pyridazin-3-one was reacted to yield the title compound as a colorless crystalline powder (yield: 95.0%).

Melting point: 210.8–212.5° C.

$^1$H NMR (400 MHz, DMSO-d$_6$) δ: 0.96 (6H, d, J=6.6 Hz), 2.22–2.35 (1H, m), 3.12 (4H, br), 3.30 (4H, t, J=5.2 Hz), 3.92 (2H, s), 4.05 (2H, d, J=7.1 Hz), 7.84 (2H, d, J=8.3 Hz), 8.11 (2H, d, J=8.1 Hz), 8.25 (1H, s).

IR (KBr) cm$^{-1}$: 1656, 1608, 1328, 1125, 1069.

Mass m/z: 394 (M$^+$).

Example 60

Preparation of 2-isobutyl-4-(4-methyl-1-piperazinyl)-methyl-6-(4-trifluoromethylphenyl)-2H-pyridazin-3-one Following the procedure of Example 1(10), 2-isobutyl-4-methanesulfonyloxymethyl-6-(4-trifluoromethylphenyl)-2H-pyridazin-3-one and 1-methylpiperazine were reacted to yield the title compound as a yellow oil (yield: 81.1%).

$^1$H NMR (400 MHz, CDCl$_3$) δ: 0.99 (6H, d, J=6.6 Hz), 2.30–2.41 (1H, m), 2.33 (3H, s), 2.53 (4H, br), 2.63 (4H, br), 3.60 (2H, s), 4.10 (2H, d, J=7.2 Hz), 7.72 (2H, d, J=8.2 Hz), 7.83 (1H, s), 7.94 (2H, d, J=8.2 Hz).

Example 61

Preparation of 2-isobutyl-4-(4-methyl-1-piperazinyl)-methyl-6-(4-trifluoromethylphenyl)-2H-pyridazin-3-one dihydrochloride Following the procedure of Example 4, 2-isobutyl-4-(4-methyl-1-piperazinyl)methyl-6-(4-trifluoromethylphenyl)-2H-pyridazin-3-one was reacted to yield the title compound as colorless flakes (yield: 88.6%).

Melting point: 249.9–252.8° C.

$^1$H NMR (400 MHz, DMSO-d$_6$) δ: 0.95 (6H, d, J=6.8 Hz), 2.22–2.35 (1H, m), 2.77 (3H, s), 3.14 (4H, br), 3.35 (4H, br), 3.88 (2H, s), 4.05 (2H, d, J=7.2 Hz), 7.84 (2H, d, J=8.2 Hz), 8.10 (2H, d, J=8.0 Hz), 8.19 (1H, s).

IR (KBr) cm$^{-1}$: 2966, 1653, 1610, 1328, 1125, 1069.

Mass m/z: 408 (M$^+$).

Example 62

Preparation of 4-N,N-bis(2-hydroxyethyl) aminomethyl-2-isobutyl-6-(4-trifluoromethylphenyl)-2H-pyridazin-3-one Following the procedure of Example 1(10), 2-isobutyl-4-methanesulfonyloxymethyl-6-(4-trifluoromethylphenyl)-2H-pyridazin-3-one and diethanolamine were reacted to yield the title compound as a yellow oil (yield: 79.5%).

$^1$H NMR (400 MHz, CDCl$_3$) δ: 0.98 (6H, d, J=6.6 Hz), 2.29–2.40 (1H, m), 2.72 (4H, br), 3.67 (4H, t, J=4.2 Hz), 3.72 (2H, s), 4.10 (2H, d, J=7.4 Hz), 7.70 (2H, d, J=7.6 Hz), 7.82 (1H, s), 7.94 (2H, d, J=8.2 Hz).

Example 63

Preparation of 4-N,N-bis(2-hydroxyethyl)aminomethyl-2-isobutyl-6-(4-trifluoromethylphenyl)-2H-pyridazin-3-one hydrochloride Following the procedure of Example 4, 4-N,N-bis(2-hydroxyethyl)aminomethyl-2-isobutyl-6-(4-trifluoromethyl-phenyl)-2H-pyridazin-3-one was reacted to yield the title compound as a colorless crystalline powder (yield: 58.2%).

Melting point: 134.9–135.4° C.

$^1$H NMR (400 MHz, DMSO-$d_6$) δ: 0.97 (6H, d, J=6.6 Hz), 2.25–2.36 (1H, m), 3.34 (4H, br), 3.83 (4H, t, J=5.1 Hz), 4.07 (2H, d, J=7.0 Hz), 4.46 (2H, s), 7.86 (2H, d, J=8.2 Hz), 8.13 (2H, d, J=8.2 Hz), 8.55 (1H, s).

IR (KBr) cm$^{-1}$: 1653, 1605, 1319, 1125, 1069.

Mass m/z: 395 (M$^+$-H$_2$O).

Example 64

Preparation of 4-dimethylaminomethyl-2-isobutyl-6-(4-trifluoromethylphenyl)-2H-pyridazin-3-one Following the procedure of Example 7, 2-isobutyl-4-methanesulfonyloxymethyl-6-(4-trifluoromethylphenyl)-2H-pyridazin-3-one was reacted to yield the title compound as a yellow oil (yield: 80.7%).

$^1$H NMR (400 MHz, CDCl$_3$) δ: 0.99 (6H, d, J=6.6 Hz), 2.31–2.40 (1H, m), 2.36 (6H, s), 3.51 (2H, d, J=1.2 Hz), 4.10 (2H, d, J=7.4 Hz), 7.71 (2H, d, J=8.4 Hz), 7.83 (1H, t, J=1.4 Hz), 7.97 (2H, d, J=8.2 Hz).

Example 65

Preparation of 4-dimethylaminomethyl-2-isobutyl-6-(4-trifluoromethylphenyl)-2H-pyridazin-3-one hydrochloride Following the procedure of Example 4, 4-dimethylaminomethyl-2-isobutyl-6-(4-trifluoromethylphenyl)-2H-pyridazin-3-one was reacted to yield the title compound as pale yellow flakes (yield: 93.0%).

Melting point: 242.2–242.3° C.

$^1$H NMR (400 MHz, DMSO-$d_6$) δ: 0.97 (6H, d, J=6.6 Hz), 2.25–2.36 (1H, m), 2.83 (6H, s), 4.07 (2H, d, J=7.3 Hz), 4.30 (2H, s), 7.86 (2H, d, J=8.3 Hz), 8.14 (2H, d, J=8.0 Hz), 8.61 (1H, s).

IR (KBr) cm$^{-1}$: 2963, 1646, 1606, 1321, 1115, 1069.

Mass m/z: 353 (M$^+$).

Example 66

Preparation of 6-(4-biphenylyl)-4-(4-tert-butoxycarbonyl-1-piperazinyl)methyl-2-isobutyl-2H-pyridazin-3-one 1) Preparation of ethyl 4-(4-biphenylyl)-2-ethoxycarbonyl-2-hydroxy-4-oxobutanoate Following the procedure of Example 1(3), 4-acetyl-biphenyl was reacted to yield the title compound as colorless flakes (yield: 83.3%).

Melting point: 88.0–88.3° C.

$^1$H NMR (400 MHz, CDCl$_3$) δ: 1.31 (6H, t, J=7.1 Hz), 3.87 (2H, s), 4.32 (4H, q, 7.1 Hz), 7.41 (1H, tt, J=1.4, 7.2 Hz), 7.48 (2H, dd, J=7.2, 7.2 Hz), 7.63 (2H, d, J=7.0 Hz), 7.70 (2H, d, J=8.6 Hz), 8.04 (2H, d, J=8.6 Hz).

IR (KBr) cm$^{-1}$: 3449, 1736, 1680, 1604, 1301, 1244, 1204, 763.

2) Preparation of 6-(4-biphenylyl)-4-carboxy-2H-pyridazin-3-one

Following the procedure of Example 1(4), ethyl 4-(4-biphenylyl)-2-ethoxycarbonyl-2-hydroxy-4-oxobutanoate was reacted to yield the title compound as a yellow crystalline powder (yield: 90.2%).

Melting point: 299.7–300.8° C.

$^1$H NMR (400 MHz, DMSO-$d_6$) δ: 7.40 (1H, t, J=7.4 Hz), 7.49 (2H, dd, J=7.4, 7.4 Hz), 7.74 (2H, d, J=7.2 Hz), 7.82 (2H, d, J=8.4 Hz), 8.03 (2H, d, J=8.4 Hz), 8.54 (1H, s).

IR (KBr) cm$^{-1}$: 1753, 1652, 1590, 1446, 1201, 768.

3) Preparation of 6-(4-biphenylyl)-4-methoxycarbonyl-2H-pyridazin-3-one

Following the procedure of Example 1(5), 6-(4-biphenylyl)-4-carboxy-2H-pyridazin-3-one was reacted to yield the title compound as a pale yellow crystalline powder (yield: 90.4%).

Melting point: 277.0–277.9° C. (dec.)

$^1$H NMR (400 MHz, CDCl$_3$) δ: 4.01 (3H, s), 7.39–7.45 (3H, m), 7.64 (2H, d, J=7.2 Hz), 7.72 (2H, d, J=8.2 Hz), 7.89 (2H, d, J=8.0 Hz), 8.42 (1H, s), 10.7 (1H, s).

IR (KBr) cm$^{-1}$: 2954, 1727, 1671, 1594, 1265, 1098, 768.

4) Preparation of 6-(4-biphenylyl)-2-isobutyl-4-methoxycarbonyl-2H-pyridazin-3-one Following the procedure of Example 1(6), 6-(4-biphenylyl)-4-methoxycarbonyl-2H-pyridazin-3-one was reacted to yield the title compound as yellow crystals (yield: 62.7%).

Melting point: 186.2–195.0° C.

$^1$H NMR (400 MHz, CDCl$_3$) δ: 1.01 (6H, d, J=6.8 Hz), 2.34–2.45 (1H, m), 3.99 (3H, s), 4.16 (2H, d, J=7.4 Hz), 7.39 (1H, tt, J=1.4, 7.4 Hz), 7.48 (2H, dd, J=7.2, 7.2 Hz), 7.64 (2H, d, J=7.0 Hz), 7.71 (2H, d, J=8.6 Hz), 7.89 (2H, d, J=8.6 Hz), 8.31 (1H, s).

5) Preparation of 6-(4-biphenylyl)-4-carboxy-2-isobutyl-2H-pyridazin-3-one

Following the procedure of Example 1(7), 6-(4-biphenylyl)-2-isobutyl-4-methoxycarbonyl-2H-pyridazin-3-one was reacted to yield the title compound as a colorless crystalline powder (yield: 79.2%).

Melting point: 156.9–157.6° C.

$^1$H NMR (400 MHz, CDCl$_3$) δ: 1.04 (6H, d, J=6.6 Hz), 2.36–2.46 (1H, m), 4.24 (2H, d, J=7.4 Hz), 7.41 (1H, t, J=7.4 Hz), 7.49 (2H, dd, J=7.4, 7.4 Hz), 7.65 (2H, d, J=7.0 Hz), 7.74 (2H, d, J=8.4 Hz), 7.95 (2H, d, J=8.4 Hz), 8.73 (1H, s), 14.22 (1H, s).

IR (KBr) cm$^{-1}$: 2963, 1749, 1631, 1565, 1470, 735.

6) Preparation of 6-(4-biphenylyl)-4-hydroxymethyl-2-isobutyl-2H-pyridazin-3-one Following the procedure of Example 1(8), 6-(4-biphenylyl)-4-carboxy-2-isobutyl-2H-pyridazin-3-one was reacted to yield the title compound as a while solid (yield: 15.6%).

Melting point: 146.4–147.5° C.

$^1$H NMR (400 MHz, CDCl$_3$) δ: 1.01 (6H, d, J=6.8 Hz), 2.32–2.43 (1H, m), 3.13 (1H, t, J=6.2 Hz), 4.11 (2H, d, J=7.4 Hz), 4.74 (2H, dd, J=1.2, 6.2 Hz), 7.39 (1H, t, J=7.3 Hz), 7.48 (2H, dd, J=7.4, 7.4 Hz), 7.64 (2H, d, J=7.0 Hz), 7.70 (2H, d, J=8.6 Hz), 7.74 (1H, t, J=1.2 Hz), 7.90 (2H, d, J=8.6 Hz).

IR (KBr) cm$^{-1}$: 3431, 2961, 1647, 1596, 1077, 769.

7) Preparation of 6-(4-biphenylyl)-2-isobutyl-4-methanesulfonyloxymethyl-2H-pyridazin-3-one Following the procedure of Example 1(9), 6-(4-biphenylyl)-4-hydroxymethyl-2-isobutyl-2H-pyridazin-3-one was reacted to yield the title compound as a colorless crystalline powder (yield: 79.3%).

Melting point: 121.3–122.0° C.

$^1$H NMR (400 MHz, CDCl$_3$) δ: 1.01 (6H, d, J=6.8 Hz), 2.33–2.42 (1H, m), 3.18 (3H, s), 4.12 (2H, d, J=7.4 Hz), 5.30 (2H, d, J=1.2 Hz), 7.39 (1H, t, J=7.4 Hz), 7.48 (2H, dd, J=7.6 Hz), 7.64 (2H, d, J=7.4 Hz), 7.71 (2H, d, J=8.4 Hz), 7.85–7.91 (3H, m).

IR (KBr) cm$^{-1}$: 2964, 1658, 1610, 1354, 1165, 874, 529.

8) Preparation of 6-(4-biphenylyl)-4-(4-tert-butoxycarbonyl-1-piperazinyl)methyl-2-isobutyl-2H-pyridazin-3-one Following the procedure of Example 1(10), 6-(4-biphenylyl)-2-isobutyl-4-methanesulfonyloxymethyl-2H-pyridazin-3-one and tert-butyl 1-pipeazinecarboxylate were reacted to yield the title compound as a yellow oil (yield: 87.7%).

$^1$H NMR (400 MHz, CDCl$_3$) δ: 1.00 (6H, d, J=6.6 Hz), 1.47 (9H, s), 2.30–2.43 (1H, m), 2.54 (4H, t, J=4.9 Hz), 3.51 (4H, t, J=4.9 Hz), 3.60 (2H, d, J=1.4 Hz), 4.10 (2H, d, J=7.4 Hz), 7.38 (1H, tt, J=1.4, 7.2 Hz), 7.47 (2H, dd, J=7.4, 7.4 Hz), 7.64 (2H, d, J=7.0 Hz), 7.70 (2H, d, J=8.6 Hz), 7.85–7.92 (3H, m).

Example 67

Preparation of 6-(4-biphenylyl)-2-isobutyl-4-(1-piperazinyl)methyl-2H-pyridazin-3-one dihydrochloride Following the procedure of Example 2, 6-(4-biphenylyl)-4-(4-tert-butoxycarbonyl-1-piperazinyl)methyl-2-isobutyl-2H-pyridazin-3-one was reacted to yield the title compound as a colorless crystalline powder (yield: 51.5%).

Melting point: 226.8–228.0° C.

$^1$H NMR (400 MHz, DMSO-d$_6$) δ: 0.97 (6H, d, J=6.8 Hz), 2.25–2.36 (1H, m), 3.19 (4H, br), 3.34 (4H, t, J=5.1 Hz), 3.98 (2H, s), 4.05 (2H, d, J=7.1 Hz), 7.39 (1H, t, J=7.3 Hz), 7.49 (2H, dd, J=7.7, 7.7 Hz), 7.71 (2H, d, J=7.8 Hz), 7.79 (2H, d, J=8.3 Hz), 7.99 (2H, d, J=8.3 Hz), 8.29 (1H, s).

IR (KBr) cm$^{-1}$: 1653, 1604, 1446, 771.

Mass m/z: 402 (M$^+$).

Example 68

Preparation of 6-(4-biphenylyl)-2-isobutyl-4-(4-methyl-1-piperazinyl)methyl-2H-pyridazin-3-one Following the procedure of Example 1(10), 6-(4-biphenylyl)-2-isobutyl-4-methanesulfonyloxymethyl-2H-pyridazin-3-one and 1-methylpiperazine were reacted to yield the title compound as a yellow oil (yield: 68.2%).

$^1$H NMR (400 MHz, CDCl$_3$) δ: 1.00 (6H, d, J=6.6 Hz), 2.30–2.43 (1H, m), 2.34 (3H, s), 2.55 (4H, br), 2.65 (4H, br), 3.61 (2H, d, J=1.2 Hz), 4.10 (2H, d, J=7.2 Hz), 7.38 (1H, t, J=7.3 Hz), 7.47 (2H, dd, J=7.5, 7.5 Hz), 7.64 (2H, d, J=7.2 Hz), 7.70 (2H, d, J=8.4 Hz), 7.84 (1H, s), 7.90 (2H, d, J=8.4 Hz).

Example 69

Preparation of 6-(4-biphenylyl)-2-isobutyl-4-(4-methyl-1-piperazinyl)methyl-2H-pyridazin-3-one dihydrochloride Following the procedure of Example 4, 6-(4-biphenylyl)-2-isobutyl-4-(4-methyl-1-piperazinyl)methyl-2H-pyridazin-3-one was reacted to yield the title compound as a colorless crystalline powder (yield: 69.9%).

Melting point: 262.2–263.6° C.

$^1$H NMR (400 MHz, DMSO-d$_6$) δ: 0.97 (6H, d, J=6.6 Hz), 2.26–2.35 (1H, m), 2.77 (3H, s), 3.10 (4H, br), 3.34 (4H, br), 3.85 (2H, s), 4.04 (2H, d, J=7.1 Hz), 7.39 (1H, t, J=7.6 Hz), 7.49 (2H, dd, J=8.0, 8.0 Hz), 7.71 (2H, d, J=8.0 Hz), 7.78 (2H, d, J=8.3 Hz), 7.89 (2H, d, J=8.3 Hz), 8.13 (1H, s).

IR (KBr) cm$^{-1}$: 1652, 1607, 1465, 1050.

Mass m/z: 416 (M$^+$).

Example 70

Preparation of 6-(4-biphenylyl)-4-N,N-bis(2-hydroxy-ethyl)aminomethyl-2-isobutyl-2H-pyridazin-3-one Following the procedure of Example 1(10), 6-(4-biphenylyl)-2-isobutyl-4-methanesulfonyloxymethyl-2H-pyridazin-3-one and diethanolamine were reacted to yield the title compound as a yellow oil (yield: 62.4%).

$^1$H NMR (400 MHz, CDCl$_3$) δ: 0.99 (6H, d, J=6.6 Hz), 2.30–2.43 (1H, m), 2.73 (4H, t, J=4.8 Hz), 3.67 (4H, t, J=4.8 Hz), 3.73 (2H, s), 4.12 (2H, d, J=7.4 Hz), 7.38 (1H, t, J=7.2 Hz), 7.47 (2H, dd, J=7.2, 7.2 Hz), 7.63 (2H, d, J=7.4 Hz), 7.68 (2H, d, J=8.2 Hz), 7.79 (1H, s), 7.89 (2H, d, J=8.2 Hz).

Example 71

Preparation of 6-(4-biphenylyl)-4-N,N-bis(2-hydroxy-ethyl)aminomethyl-2-isobutyl-2H-pyridazin-3-one hydrochloride Following the procedure of Example 4, 6-(4-biphenylyl)-4-N,N-bis(2-hydroxyethyl)aminomethyl-2-isobutyl-2H-pyridazin-3-one was reacted to yield the title compound as a colorless crystalline powder (yield: 63.9%).

Melting point: 218.3–218.6° C.

$^1$H NMR (400 MHz, DMSO-d$_6$) δ: 0.98 (6H, d, J=6.8 Hz), 2.26–2.37 (1H, m), 3.36 (4H, t, J=5.1 Hz), 3.85 (4H, t, J=5.1 Hz), 4.08 (2H, d, J=7.3 Hz), 4.48 (2H, s), 7.40 (1H, tt, J=1.2, 7.3 Hz), 7.49 (2H, dd, J=7.3 Hz), 7.72 (2H, dd, J=1.2, 7.3 Hz), 7.81 (2H, d, J=8.3 Hz), 8.01 (2H, d, J=8.3 Hz), 8.52 (1H, s).

IR (KBr) cm$^{-1}$: 1654, 1607, 1053, 847, 769.

m/z (EI): 403 (M$^+$-H$_2$O).

Example 72

Preparation of 6-(4-biphenylyl)-4-dimethylaminomethyl-2-isobutyl-2H-pyridazin-3-one Following the procedure of Example 7, 6-(4-biphenylyl)-2-isobutyl-4-methanesulfonyloxymethyl-2H-pyridazin-3-one was reacted to yield the title compound as a yellow oil (yield: 87.7%).

$^1$H NMR (400 MHz, CDCl$_3$) δ: 1.00 (6H, d, J=6.6 Hz), 2.36 (6H, s), 2.29–2.43 (1H, m), 3.52 (2H, d, J=1.0 Hz), 4.10 (2H, d, J=7.2 Hz), 7.37 (1H, t, J=7.4 Hz), 7.46 (2H, dd, J=7.4, 7.4 Hz), 7.63 (2H, d, J=7.2 Hz), 7.68 (2H, d, J=8.4 Hz), 7.85 (1H, s), 7.92 (2H, d, J=8.4 Hz).

Example 73

Preparation of 6-(4-biphenylyl)-4-dimethylaminomethyl-2-isobutyl-2H-pyridazin-3-one hydrochloride Following the procedure of Example 4, 6-(4-biphenylyl)-4-dimethylaminomethyl-2-isobutyl-2H-pyridazin-3-one was reacted to yield the title compound as colorless flakes (yield: 58.2%).

Melting point: 243.9–244.1° C.

$^1$H NMR (400 MHz, DMSO-d$_6$) δ: 0.98 (6H, d, J=6.6 Hz), 2.26–2.37 (1H, m), 2.83 (6H, s), 4.03 (2H, d, J=7.1 Hz), 4.30 (2H, s), 7.39 (1H, tt, J=1.2, 7.3 Hz), 7.49 (2H, dd, J=7.3, 7.3 Hz), 7.72 (2H, dd, J=1.2, 7.1 Hz), 7.81 (2H, d, J=8.8 Hz), 8.02 (2H, d, J=8.6 Hz), 8.57 (1H, s).

IR (KBr) cm$^{-1}$: 1647, 1604, 1460, 1409, 1052.

Mass m/z: 361 (M$^+$).

Example 74

Preparation of 4-(4-tert-butoxycarbonyl-1-piperazinyl)methyl-6-(3-chloro-4-methoxyphenyl)-2-isobutyl-2H-pyridazin-3-one Following the procedure of Example 1(10), 6-(3-chloro-4-methoxyphenyl)-2-isobutyl-4-methanesulfonyloxymethyl-2H-pyridazin-3-one and tert-butyl 1-piperazinecarboxylate were reacted to yield the title compound as a yellow oil (yield: 89.0%).

$^1$H NMR (400 MHz, CDCl$_3$) δ: 0.98 (6H, d, J=6.8 Hz), 1.47 (9H, s), 2.27–2.40 (1H, m), 2.52 (4H, t, J=4.9 Hz), 3.50 (4H, t, J=5.0 Hz), 3.57 (2H, d, J=1.4 Hz), 3.96 (3H, s), 4.07 (2H, d, J=7.2 Hz), 7.00 (1H, d, J=8.6 Hz), 7.66 (1H, dd, J=2.4, 8.6 Hz), 7.74 (1H, t, J=1.3 Hz), 7.86 (1H, d, J=2.4 Hz).

Example 75

Preparation of 6-(3-chloro-4-methoxyphenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3-chloro-4-methoxy-phenyl)-2-isobutyl-2H-pyridazin-3-one was reacted to yield the title compound as a white solid (yield: 70.2%).

Melting point: 203.6–204.5° C.

$^1$H NMR (400 MHz, DMSO-d$_6$): 0.95 (6H, d, J=6.6 Hz), 2.20–2.34 (1H, m), 3.14 (4H, br), 3.31 (4H, t, J=5.2 Hz), 3.93 (5H, s), 4.01 (2H, d, J=7.0 Hz), 7.26 (1H, d, J=8.8 Hz), 7.84 (1H, dd, J=2.4, 8.6 Hz), 7.91 (1H, d, J=2.4 Hz), 8.19 (1H, s).

IR (KBr) cm$^{-1}$: 1654, 1608, 1507, 1289, 1065.

Mass m/z: 390 (M$^+$), 392 (M$^+$).

Example 76

Preparation of 6-(3-chloro-4-methoxyphenyl)-2-isobutyl-4-(4-methyl-1-piperazinyl)methyl-2H-pyridazin-3-one Following the procedure of Example 1(10), 6-(3-chloro-4-methoxyphenyl)-2-isobutyl-4-methanesulfonyloxymethyl-2H-pyridazin-3-one and 1-methylpiperazine were reacted to yield the title compound as a yellow oil (yield: 76.1%).

$^1$H NMR (400 MHz, CDCl$_3$) δ: 0.98 (6H, d, J=6.6 Hz), 2.28–2.40 (1H, m), 2.33 (3H, s), 2.53 (4H, br), 2.63 (4H, br), 3.58 (2H, d, J=1.2 Hz), 3.96 (3H, s), 4.06 (2H, d, J=7.2 Hz), 7.01 (1H, d, J=8.6 Hz), 7.67 (1H, dd, J=2.2, 8.6 Hz), 7.72 (1H, s), 7.86 (1H, d, J=2.2 Hz).

Example 77

Preparation of 6-(3-chloro-4-methoxyphenyl)-2-isobutyl-4-(4-methyl-1-piperazinyl)methyl-2H-pyridazin-3-one dihydrochloride Following the procedure of Example 4, 6-(3-chloro-4-methoxyphenyl)-2-isobutyl-4-(4-methyl-1-piperazinyl) methyl-2H-pyridazin-3-one was reacted to yield the title compound as a colorless crystalline powder (yield: 67.5%).

Melting point: 235.8–236.7° C.

$^1$H NMR (400 MHz, DMSO-d$_6$) δ: 0.94 (6H, d, J=6.6 Hz), 2.25–2.32 (1H, m), 2.77 (3H, s), 3.15 (4H, br), 3.36 (4H, br), 3.88 (2H, s), 3.93 (3H, s), 4.01 (2H, d, J=7.0 Hz), 7.26 (1H, d, J=8.6 Hz), 7.83 (1H, dd, J=2.2, 8.6 Hz), 7.91 (1H, d, J=2.2 Hz), 8.12 (1H, s).

IR (KBr) cm$^{-1}$: 1653, 1608, 1507, 1289, 1064.

Mass m/z: 404 (M$^+$), 406 (M$^+$).

Example 78

Preparation of 4-N,N-bis(2-hydroxyethyl)aminomethyl-6-(3-chloro-4-methoxyphenyl)-2-isobutyl-2H-pyridazin-3-one Following the procedure of Example 1(10), 6-(3-chloro-4-methoxyphenyl)-2-isobutyl-4-methanesulfonyloxymethyl-2H-pyridazin-3-one and diethanolamine were reacted to yield the title compound as a yellow oil (yield: 79.6%).

$^1$H NMR (400 MHz, CDCl$_3$) δ: 0.96 (6H, d, J=6.6 Hz), 2.28–2.39 (1H, m), 2.71 (4H, t, J=4.9 Hz), 3.66 (4H, t, J=4.9 Hz), 3.70 (2H, s), 3.94 (3H, s), 4.07 (2H, d, J=7.4 Hz), 6.98 (1H, d, J=8.8 Hz), 7.68 (1H, dd, J=1.8, 8.7 Hz), 7.72 (1H, s), 7.85 (1H, d, J=2.1 Hz).

Example 79

Preparation of 4-N,N-bis(2-hydroxyethyl)aminomethyl-6-(3-chloro-4-methoxyphenyl)-2-isobutyl-2H-pyridazin-3-one hydrochloride Following the procedure of Example 4, 4-N,N-bis(2-hydroxyethyl)aminomethyl-6-(3-chloro-4-methoxyphenyl)-2-isobutyl-2H-pyridazin-3-one was reacted to yield the title compound as a colorless crystalline powder (yield: 60.1%).

Melting point: 153.0–153.5° C.

$^1$H NMR (400 MHz, DMSO-d$_6$) δ: 0.95 (6H, d, J=6.6 Hz), 2.23–2.34 (1H, m), 3.34 (4H, t, J=5.1 Hz), 3.83 (4H, t, J=5.1 Hz), 3.94 (3H, s), 4.04 (2H, d, J=7.1 Hz), 4.44 (2H, s), 7.28 (1H, d, J=8.8 Hz), 7.85 (1H, dd, J=2.4, 8.6 Hz), 7.94 (1H, d, J=2.4 Hz), 8.45 (1H, s).

IR (KBr) cm$^{-1}$: 1652, 1607, 1508, 1421, 1293, 1062.

Mass m/z: 391 (M$^+$-H$_2$O).

Example 80

Preparation of 6-(3-chloro-4-methoxyphenyl)-4-dimethylaminomethyl-2-isobutyl-2H-pyridazin-3-one Following the procedure of Example 7, 6-(3-chloro-4-methoxyphenyl)-2-isobutyl-4-methanesulfonyloxymethyl-2H-pyridazin-3-one was reacted to yield the title compound as a yellow oil (yield: 84.8%).

$^1$H NMR (400 MHz, CDCl$_3$) δ: 0.98 (6H, d, J=6.6 Hz), 2.31–2.39 (1H, m), 2.35 (6H, s), 3.50 (2H, s), 3.95 (3H, s), 4.07 (2H, d, J=7.2 Hz), 6.99 (1H, d, J=8.6 Hz), 7.70 (1H, dd, J=1.4, 8.6 Hz), 7.88 (1H, d, J=1.4 Hz).

Example 81

Preparation of 6-(3-chloro-4-methoxyphenyl)-4-dimethylaminomethyl-2-isobutyl-2H-pyridazin-3-one hydrochloride Following the procedure of Example 4, 6-(3-chloro-4-methoxyphenyl)-4-dimethylaminomethyl-2-isobutyl-2H- pyridazin-3-one was reacted to yield the title compound as a white solid (yield: 69.4%).

Melting point: 213.6–214.3° C.

$^1$H NMR (400 MHz, DMSO-d$_6$) δ: 0.95 (6H, d, J=6.8 Hz), 2.22–2.34 (1H, m), 2.81 (6H, s), 3.94 (3H, s), 4.04 (2H, d, J=7.1 Hz), 4.27 (2H, s), 7.28 (1H, d, J=8.8 Hz), 7.87 (1H, dd, J=2.2, 8.8 Hz), 7.95 (1H, d, J=2.2 Hz), 8.53 (1H, s).

IR (KBr) cm$^{-1}$: 1652, 1608, 1508, 1289, 1064.

Mass m/z: 349 (M$^+$), 351 (M$^+$).

Example 82

Preparation of 6-(4-fluoro-3-methylphenyl)-2-isobutyl-4-(4-methyl-1-piperazinyl)methyl-2H-pyridazin-3-one 1) Preparation of ethyl 2-ethoxycarbonyl-4-(4-fluoro-3-methylphenyl)-2-hydroxy-4-oxobutanoate Following the procedure of Example 1(3), 5-acetyl-2-fluorotoluene was reacted to yield the title compound as pale yellow prisms (yield: 95.9%).

$^1$H NMR (400 MHz, CDCl$_3$) δ: 1.30 (6H, t, J=7.1 Hz), 2.33 (3H, d, J=1.7 Hz), 3.79 (2H, s), 4.29 (1H, s), 4.31 (4H, q, J=7.1 Hz), 7.08 (1H, dd, J=8.8, 8.8 Hz), 7.78–7.85 (2H, m).

2) Preparation of 4-carboxy-6-(4-fluoro-3-methylphenyl)-2H-pyridazin-3-one

Following the procedure of Example 1(4), ethyl 2-ethoxycarbonyl-4-(4-fluoro-3-methylphenyl)-2-hydroxy-4-oxo-butanoate was reacted to yield the title compound as a pale yellow crystalline powder (yield: 88.9%).

Melting point: 213.6–214.3° C.

$^1$H NMR (400 MHz, DMSO-d$_6$) δ: 2.51 (3H, d, J=1.7 Hz), 7.26 (1H, dd, J=9.1, 9.1 Hz), 7.77–7.81 (1H, m), 7.89 (1H, d, J=7.3 Hz), 8.49 (1H, s), 13.99 (1H, br).

3) Preparation of 6-(4-fluoro-3-methylphenyl)-4-methoxycarbonyl-2H-pyridazin-3-one Following the procedure of Example 1(5), 4-carboxy-6-(4-fluoro-3-methylphenyl)-2H-pyridazin-3-one was reacted to yield the title compound as a pale yellow crystalline powder (yield: 76.8%).

$^1$H NMR (400 MHz, CDCl$_3$) δ: 2.35 (3H, d, J=2.0 Hz), 3.99 (3H, s), 7.10 (1H, dd, J=8.9, 8.9 Hz), 7.58–7.62 (1H, m), 7.60 (1H, d, J=7.3 Hz), 8.31 (1H, s).

4) Preparation of 6-(4-fluoro-3-methylphenyl)-2-isobutyl-4-methoxycarbonyl-2H-pyridazin-3-one Following the procedure of Example 1(6), 6-(4-fluoro-3-methylphenyl)-2-methoxycarbonyl-2H-pyridazin-3-one was reacted to yield the title compound as pale yellow prisms (yield: 86.3%).

Melting point: 71.4–73.8° C.

$^1$H NMR (400 MHz, CDCl$_3$) δ: 0.99 (6H, d, J=6.8 Hz), 2.31–2.42 (1H, m), 2.35 (3H, d, J=2.0 Hz), 3.98 (3H, s), 4.12 (2H, d, J=7.3 Hz), 7.10 (1H, dd, J=8.8, 8.8 Hz), 7.57–7.65 (2H, m), 8.21 (1H, s).

5) Preparation of 4-carboxy-6-(4-fluoro-3-methylphenyl)-2-isobutyl-2H-pyridazin-3-one Following the procedure of Example 1(7), 6-(4-fluoro-3-methylphenyl)-2-isobutyl-4-methoxycarbonyl-2H-pyridazin-3-one was reacted to yield the title compound as pale yellow needles (yield: 90.0%).

Melting point: 129.3–132.1° C.

$^1$H NMR (400 MHz, CDCl$_3$) δ: 1.02 (6H, d, J=6.8 Hz), 2.33–2.44 (1H, m), 2.37 (3H, d, J=2.0 Hz), 4.21 (2H, d, J=7.3 Hz), 7.13 (1H, dd, J=8.8, 8.8 Hz), 7.64–7.71 (2H, m), 8.63 (1H, s).

IR (KBr) cm$^{-1}$: 1742, 1636, 1537, 1422.

Mass m/z: 304 (M$^+$).

6) Preparation of 6-(4-fluoro-3-methylphenyl)-4-hydroxymethyl-2-isobutyl-2H-pyridazin-3-one Following the procedure of Example 1(8), 4-carboxy-6-(4-fluoro-3-methylphenyl)-2-isobutyl-2H-pyridazin-3-one was reacted to yield the title compound as colorless needles (yield: 24.7%).

Melting point: 107.4–110.4° C.

$^1$H NMR (400 MHz, CDCl$_3$) δ: 0.99 (6H, d, J=6.6 Hz), 2.29–2.40 (1H, m), 2.35 (3H, d, J=1.7 Hz), 3.14 (1H, t, J=5.9 Hz), 4.08 (2H, d, J=7.6 Hz), 4.71 (2H, d, J=5.9 Hz), 7.08 (1H, dd, J=8.8, 8.8 Hz), 7.56–7.65 (3H, m).

IR (KBr) cm$^{-1}$: 3401, 1658, 1648, 1618, 1602, 1501.

Mass m/z: 290 (M$^+$).

7) Preparation of 6-(4-fluoro-3-methylphenyl)-2-isobutyl-4-methanesulfonyloxymethyl-2H-pyridazin-3-one Following the procedure of Example 1(9), 6-(4-fluoro-3-methylphenyl)-4-hydroxymethyl-2-isobutyl-2H-pyridazin-3-one was reacted to yield the title compound as colorless needles (yield: 91.4%).

Melting point: 114.6–117.1° C.

$^1$H NMR (400 MHz, CDCl$_3$): 0.99 (6H, d, J=6.8 Hz), 2.29–2.40 (1H, m), 2.36 (3H, s), 3.17 (3H, s), 4.08 (2H, d, J=7.6 Hz), 5.27 (2H, d, J=1.5 Hz), 7.09 (1H, dd, J=8.9, 8.9 Hz), 7.56–7.69 (2H, m), 7.75 (1H, t, J=1.5 Hz).

IR (KBr) cm$^{-1}$: 1656, 1611, 1505, 1354, 1166.

Mass m/z: 368 (M$^+$).

8) Preparation of 6-(4-fluoro-3-methylphenyl)-2-isobutyl-4-(4-methyl-1-piperazinyl)methyl-2H-pyridazin-3-one Following the procedure of Example 1(10), 6-(4-fluoro-3-methylphenyl)-2-isobutyl-4-methanesulfonyloxy-methyl-2H-pyridazin-3-one and 1-methylpiperazine were reacted to yield the title compound as a slightly yellow oil (yield: 79.1%).

$^1$H NMR (400 MHz, CDCl$_3$) δ: 0.98 (6H, d, J=6.8 Hz), 2.27–2.40 (1H, m), 2.32 (3H, s), 2.36 (3H, d, J=2.0 Hz), 2.51 (4H, br), 2.62 (4H, br), 3.58 (2H, d, J=1.5 Hz), 4.07 (2H, d, J=7.3 Hz), 7.09 (1H, dd, J=8.8, 8.8 Hz), 7.58 (1H, ddd, J=2.0, 4.9, 8.8 Hz), 7.64 (1H, dd, J=2.0, 7.3 Hz), 7.73 (1H, t, J=1.5 Hz).

IR (Neat) cm$^{-1}$: 1652, 1609, 1503.

Mass m/z: 372 (M$^+$).

Example 83

Preparation of 6-(4-fluoro-3-methylphenyl)-2-isobutyl-4-(4-methyl-1-piperazinyl)methyl-2H-pyridazin-3-one dihydrochloride Following the procedure of Example 4, 6-(4-fluoro-3-methylphenyl)-2-isobutyl-4-(4-methyl-1-piperazinyl) methyl-2H-pyridazin-3-one was reacted to yield the title compound as colorless prisms (yield: 95.9%).

Melting point: 234.8–237.4° C. (dec.)

$^1$H NMR (400 MHz, DMSO-d$_6$) δ: 0.93 (6H, d, J=6.8 Hz), 2.19–2.30 (1H, m), 2.32 (3H, d, J=2.0 Hz), 2.81 (3H, s), 2.89–3.62 (10H, brm), 4.00 (2H, d, J=7.3 Hz), 7.29 (1H, dd, J=9.0, 9.0 Hz), 7.72–7.78 (1H, m), 7.83 (1H, dd, J=2.4, 7.6 Hz), 8.31 (1H, brs).

IR (KBr) cm$^{-1}$: 1660, 1609, 1504.

Example 84

Preparation of 6-(4-fluoro-3-methylphenyl)-2-isobutyl-4-methylaminomethyl-2H-pyridazin-3-one Following the procedure of Example 9 (4), 6-(4-fluoro-3-methylphenyl)-2-isobutyl-4-methanesulfonyloxymethyl-2H-pyridazin-3-one was reacted to yield the title compound as a pale yellow oil (yield: 96.2%).

¹H NMR (400 MHz, CDCl₃) δ: 0.98 (6H, d, J=6.8 Hz), 1.65 (1H, br), 2.29–2.42 (1H, m), 2.34 (3H, d, J=1.7 Hz), 2.51 (3H, s), 3.77 (2H, d, J=1.2 Hz), 4.07 (2H, d, J=7.3 Hz), 7.07 (1H, dd, J=8.8, 8.8 Hz), 7.54–7.63 (2H, m), 7.64 (1H, t, J=1.2 Hz).

IR (Neat) cm⁻¹: 3306, 1653, 1605, 1507.

Mass m/z: 303 (M⁺).

Example 85

Preparation of 6-(4-fluoro-3-methylphenyl)-2-isobutyl-4-methylaminomethyl-2H-pyridazin-3-one hydrochloride Following the procedure of Example 4, 6-(4-fluoro-3-methylphenyl)-2-isobutyl-4-methylaminomethyl-2H-pyridazin-3-one was reacted to yield the title compound as colorless prisms (yield: 86.6%).

Melting point: 196.8–199.7° C.

¹H NMR (400 MHz, DMSO-d₆) δ: 0.93 (6H, d, J=6.8 Hz), 2.19–2.31 (1H, m), 2.32 (3H, s), 2.65 (3H, s), 4.02 (2H, d, J=7.3 Hz), 4.12 (2H, s), 7.31 (1H, dd, J=8.5, 8.5 Hz), 7.72–7.78 (1H, m), 7.80–7.85 (1H, m), 8.32 (1H, s).

IR (KBr) cm⁻¹: 2722, 1652, 1615, 1505.

Example 86

Preparation of 4-(4-benzyl-1-piperazinyl)methyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxy-methyl-2H-pyridazin-3-one and 1-benzylpiperazine were reacted to yield the title compound as a pale yellow oil (yield: 98.6%).

¹H NMR (400 MHz, CDCl₃) δ: 0.97 (6H, d, J=6.8 Hz), 2.29–2.39 (1H, m), 2.36 (3H, d, J=11.7 Hz), 2.55 (4H, br), 2.61 (4H, br), 3.55 (2H, s), 3.57 (2H, d, J=1.2 Hz), 4.06 (2H, d, J=7.6 Hz), 7.09 (1H, dd, J=8.9, 8.9 Hz), 7.23–7.34 (5H, m), 7.51 (1H, ddd, J=2.4, 4.8, 8.9 Hz), 7.63 (1H, dd, J=2.4, 7.2 Hz), 7.72 (1H, s).

IR (Neat) cm⁻¹: 1652, 1608, 1505.

Mass m/z: 448 (M⁺).

Example 87

Preparation of 4-(4-benzyl-1-piperazinyl)methyl-6-(4-fluoro-3-methylphenyl)-2-isobutyl-2H-pyridazin-3-one dihydrochloride Following the procedure of Example 4, 4-(4-benzyl-1-piperazinyl)methyl-6-(4-fluoro-3-methylphenyl)-2-isobutyl-2H-pyridazin-3-one was reacted to yield the title compound as colorless needles (yield: 95.3%).

Melting point: 259.1–263.1° C. (dec.)

¹H NMR (400 MHz, DMSO-d₆) δ: 0.93 (6H, d, J=6.6 Hz), 2.17–2.29 (1H, m), 2.32 (3H, s), 2.55 (4H, br), 3.23–3.56 (8H, brm), 4.00 (2H, d, J=7.3 Hz), 4.11 (2H, brs), 4.38 (2H, brs), 7.29 (1H, dd, J=9.0, 9.0 Hz), 7.43–7.48 (3H, m), 7.59–7.65 (2H, m), 7.72–7.77 (1H, m), 7.79–7.84 (1H, m), 8.35 (1H, brs).

IR (KBr) cm⁻¹: 1660, 1618, 1612, 1453.

Example 88

Preparation of 4-dimethylaminomethyl-6-(4-fluoro-3-methylphenyl)-2-isobutyl-2H-pyridazin-3-one Following the procedure of Example 7, 6-(4-fluoro-3-methylphenyl)-2-isobutyl-4-methanesulfonyloxymethyl-2H-pyridazin-3-one was reacted to yield the title compound as a slightly yellow oil (yield: 96.4%).

¹H NMR (400 MHz, CDCl₃) δ: 0.98 (6H, d, J=6.8 Hz), 2.28–2.39 (1H, m), 2.35 (3H, d, J=2.2 Hz), 2.56 (6H, s), 3.50 (2H, d, J=1.2 Hz), 4.07 (2H, d, J=7.3 Hz), 7.07 (1H, dd, J=8.9, 8.9 Hz), 7.59–7.67 (2H, m), 7.74 (1H, t, J=1.2 Hz).

IR (Neat) cm⁻¹: 1652, 1608, 1506.

Mass m/z: 317 (M⁺).

Example 89

Preparation of 4-dimethylaminomethyl-6-(4-fluoro-3-methylphenyl)-2-isobutyl-2H-pyridazin-3-one hydrochloride Following the procedure of Example 4, 4-dimethylaminomethyl-6-(4-fluoro-3-methylphenyl)-2-isobutyl-2H-pyridazin-3-one was reacted to yield the title compound as colorless needles (yield: 97.2%).

Melting point: 208.5–213.0° C.

¹H NMR (400 MHz, DMSO-d₆) δ: 0.94 (6H, d, J=6.6 Hz), 2.19–2.30 (1H, m), 2.32 (3H, s), 2.81 (6H, s), 4.03 (2H, d, J=7.0 Hz), 4.30 (2H, s), 7.30 (1H, dd, J=9.0, 9.0 Hz), 7.74–7.80 (1H, m), 7.85 (1H, m), 8.51 (1H, s).

IR (KBr) cm⁻¹: 1648, 1608, 1507.

Example 90

Preparation of 4-N,N'-bis(2-hydroxyethyl)aminomethyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxymethyl-2H-pyridazin-3-one and diethanolamine were reacted to yield the title compound as a slightly yellow oil (yield: 91.5%).

¹H NMR (400 MHz, CDCl₃) δ: 0.97 (6H, d, J=6.8 Hz), 2.27–2.40 (1H, m), 2.34 (3H, d, J=2.0 Hz), 2.70 (4H, t, J=5.0 Hz), 3.66 (4H, d, J=5.0 Hz), 3.69 (2H, s), 3.91 (2H, br), 4.07 (2H, d, J=7.6 Hz), 7.07 (1H, dd, J=8.9, 8.9 Hz), 7.60 (1H, ddd, J=2.2, 5.1, 8.9 Hz), 7.64 (1H, dd, J=2.2, 7.3 Hz), 7.71 (1H, s).

IR (Neat) cm⁻¹: 3391, 1654, 1371, 1505.

Mass m/z: 359 (M⁺-H₂O).

Example 91

Preparation of 4-N,N-bis(2-hydroxyethyl)aminomethyl-6-(4-fluoro-3-methylphenyl)-2-isobutyl-2H-pyridazin-3-one hydrochloride Following the procedure of Example 4, 4-N,N-bis(2-hydroxyethyl)aminomethyl-6-(4-fluoro-3-methylphenyl)-2-isobutyl-2H-pyridazin-3-one was reacted to yield the title compound as slightly yellow needles (yield: 92.4%).

Melting point: 155.1–157.3° C.

¹H NMR (400 MHz, DMSO-d₆) δ: 0.94 (6H, d, J=6.6 Hz), 2.20–2.31 (1H, m), 2.32 (3H, d, J=1.2 Hz), 3.35 (4H, br, overlapped with H₂O), 3.82 (4H, br), 4.02 (2H, d, J=7.3 Hz), 4.50 (2H, s), 5.37 (2H, br), 7.30 (1H, dd, J=9.0, 9.0 Hz), 7.78 (1H, ddd, J=2.0, 4.9, 9.0 Hz), 7.85 (1H, dd, J=2.0, 7.3 Hz), 7.71 (1H, s).

IR (KBr) cm⁻¹: 3281, 1655, 1606.

Example 92

Preparation of 6-(4-fluoro-3-methylphenyl)-2-isobutyl-4-(piperidino)methyl-2H-pyridazin-3-one 6-(4-Fluoro-3-methylphenyl)-2-isobutyl-4-methanesulfonyloxymethyl-2H-pyridazin-3-one (80 mg, 0.22 mmol)

and piperidine (55 mg, 0.65 mmol) were dissolved in ethanol (0.5 mL), and the mixture was heated at 80° C. for 1 hour under stirring. The solvent was distilled off. The residue was purified by preparative thin-layer chromatography on silica gel [developing solvent: chloroform/methanol (10/1)] to yield the title compound as a slightly yellow oil (73 mg, 94.0%).

$^1$H NMR (400 MHz, CDCl$_3$) δ: 0.98 (6H, d, J=6.9 Hz), 1.45–1.53 (2H, m), 1.61–1.68 (4H, m), 2.28–2.41 (1H, m), 2.36 (3H, d, J=2.0 Hz), 2.47–2.53 (4H, m), 3.52 (2H, d, J=1.5 Hz), 4.07 (2H, d, J=7.3 Hz), 7.08 (1H, dd, J=8.9, 8.9 Hz), 7.59 (1H, ddd, J=1.7, 4.9, 8.9 Hz), 7.65 (1H, dd, J=1.7, 7.3 Hz), 7.76 (1H, t, J=1.5 Hz).

IR (Neat) cm$^{-1}$: 1652, 1616, 1506.

Mass m/z: 357 (M$^+$).

Example 93

Preparation of 6-(4-fluoro-3-methylphenyl)-2-isobutyl-4-(piperidino)methyl-2H-pyridazin-3-one hydrochloride Following the procedure of Example 4, 6-(4-fluoro-3-methylphenyl)-2-isobutyl-4-(piperidino)methyl-2H-pyridazin-3-one was reacted to yield the title compound as slightly yellow prisms (yield: 90.7%).

$^1$H NMR (400 MHz, DMSO-d$_6$) δ: 0.94 (6H, d, J=6.6 Hz), 1.34–1.47 (1H, m), 1.64–1.73 (1H, m), 1.74–1.83 (4H, m), 2.20–2.30 (1H, m), 2.32 (3H, s), 2.95–3.02 (2H, m), 3.36–3.45 (1H, m), 4.02 (2H, d, J=7.3 Hz), 4.25 (2H, d, J=5.1 Hz), 7.30 (1H, dd, J=9.0, 9.0 Hz), 7.75–7.80 (1H, m), 7.83–7.87 (1H, m), 8.59 (1H, s).

IR (KBr) cm$^{-1}$: 2532, 1652, 1616, 1505, 1433.

Example 94

Preparation of 6-(4-fluoro-3-methylphenyl)-2-isobutyl-4-(morpholino)methyl-2H-pyridazin-3-one Following the procedure of Example 92, 6-(4-fluoro-3-methylphenyl)-2-isobutyl-4-methanesulfonyloxymethyl-2H-pyridazin-3-one and morpholine were reacted to yield the title compound as a slightly yellow oil (yield: 97.4%).

$^1$H NMR (400 MHz, CDCl$_3$) δ: 0.98 (6H, d, J=6.8 Hz), 2.28–2.41 (1H, m), 2.36 (3H, d, J=2.0 Hz), 2.58 (4H, t, J=4.6 Hz), 3.57 (2H, d, J=1.2 Hz), 3.78 (4H, t, J=4.6 Hz), 4.07 (2H, d, J=7.3 Hz), 7.09 (1H, dd, J=8.8, 8.8 Hz), 7.58 (1H, ddd, J=2.0, 4.9, 8.8 Hz), 7.64 (1H, dd, J=2.0, 7.3 Hz), 7.75 (1H, t, J=1.5 Hz).

IR (Neat) cm$^{-1}$: 1659, 1606, 1503.

Mass m/z: 359 (M$^+$).

Example 95

Preparation of 6-(4-fluoro-3-methylphenyl)-2-isobutyl-4-(morpholino)methyl-2H-pyridazin-3-one hydrochloride Following the procedure of Example 4, 6-(4-fluoro-3-methylphenyl)-2-isobutyl-4-(morpholino)methyl-2H-pyridazin-3-one was reacted to yield the title compound as colorless prisms (yield: 92.4%).

Melting point: 215.4–216.6° C.

$^1$H NMR (400 MHz, DMSO-d$_6$) δ: 0.94 (6H, d, J=6.6 Hz), 2.19–2.30 (1H, m), 2.32 (3H, s), 3.21 (2H, br), 3.79–3.98 (6H, m), 4.02 (2H, d, J=7.3 Hz), 4.33 (2H, brs), 7.30 (1H, dd, J=9.0, 9.0 Hz), 7.74–7.79 (1H, m), 7.81–7.86 (1H, m), 8.56 (1H, brs).

IR (KBr) cm$^{-1}$: 2392, 1647, 1607.

Example 96

Preparation of 4-aminomethyl-6-(4-fluoro-3-methylphenyl)-2-isobutyl-2H-pyridazin-3-one 1) Preparation of 6-(4-fluoro-3-methylphenyl)-2-isobutyl-4-phthalimidomethyl-2H-pyridazin-3-one Following the procedure of Example 24(1), 6-(4-fluoro-3-methylphenyl)-2-isobutyl-4-methanesulfonyloxy-methyl-2H-pyridazin-3-one was reacted to yield the title compound as slightly yellow needles (yield: 93.7%).

Melting point: 181.2–187.2° C.

$^1$H NMR (400 MHz, CDCl$_3$) δ: 0.98 (6H, d, J=6.6 Hz), 2.29–2.40 (1H, m), 2.30 (3H, s), 4.07 (2H, d, J=7.3 Hz), 4.91 (2H, s), 7.01 (1H, dd, J=9.0, 9.0 Hz), 7.31 (1H, s), 7.41–7.46 (1H, m), 7.50–7.53 (1H, m), 7.76–7.81 (2H, m), 7.90–7.95 (2H, m).

IR (KBr) cm$^{-1}$: 1720, 1656, 1619, 1611.

Mass m/z: 419 (M$^+$).

2) Preparation of 4-aminomethyl-6-(4-fluoro-3-methylphenyl)-2-isobutyl-2H-pyridazin-3-one Following the procedure of Example 24(2), 6-(4-fluoro-3-methylphenyl)-2-isobutyl-4-phthalimidomethyl-2H-pyridazin-3-one was reacted to yield the title compound as a slightly yellow oil (yield: 99.6%).

$^1$H NMR (400 MHz, CDCl$_3$) δ: 0.98 (6H, d, J=6.8 Hz), 1.64 (2H, br), 2.30–2.40 (1H, m), 2.35 (3H, d, J=2.0 Hz), 3.89 (2H, d, J=1.2 Hz), 4.07 (2H, d, J=7.3 Hz), 7.07 (1H, dd, J=8.8, 8.8 Hz), 7.60 (1H, ddd, J=2.1, 4.9, 8.8 Hz), 7.64 (1H, dd, J=2.1, 7.4 Hz), 7.67 (1H, t, J=1.2 Hz).

IR (Neat) cm$^{-1}$: 3372, 3301, 1655, 1605, 1504.

Mass m/z: 289 (M$^+$).

Example 97

Preparation of 4-aminomethyl-6-(4-fluoro-3-methylphenyl)-2-isobutyl-2H-pyridazin-3-one hydrochloride Following the procedure of Example 4, 4-aminomethyl-6-(4-fluoro-3-methylphenyl)-2-isobutyl-2H-pyridazin-3-one was reacted to yield the title compound as colorless needles (yield: 79.8%).

Melting point: 217.5–220.5° C. (dec.)

$^1$H NMR (400 MHz, DMSO-d$_6$) δ: 0.93 (6H, d, J=6.6 Hz), 2.20–2.30 (1H, m), 2.32 (3H, d, J=11.7 Hz), 4.01 (2H, d, J=2.2 Hz), 4.02 (2H, d, J=7.3 Hz), 7.31 (1H, dd, J=9.0, 9.0 Hz), 7.75 (1H, ddd, J=2.1, 4.9, 9.0 Hz), 7.83 (1H, dd, J=2.1, 7.4 Hz), 8.28 (1H, s).

IR (KBr) cm$^{-1}$: 2960, 2927, 2872, 1656, 1614, 1507.

Example 98

Preparation of 4-diethylaminomethyl-6-(4-fluoro-3-methylphenyl)-2-isobutyl-2H-pyridazin-3-one Following the procedure of Example 9 (4), 6-(4-fluoro-3-methylphenyl)-2-isobutyl-4-methanesulfonyloxymethyl-2H-pyridazin-3-one and diethylamine were reacted to yield the title compound as a slightly yellow oil (yield: 94.7%).

$^1$H NMR (400 MHz, CDCl$_3$) δ: 0.98 (6H, d, J=6.8 Hz), 1.07 (6H, t, J=7.1 Hz), 2.30–2.41 (1H, m), 2.35 (3H, d, J=1.5 Hz), 2.61 (4H, q, J=7.1 Hz), 3.60 (2H, d, J=1.7 Hz), 4.08 (2H, d, J=7.5 Hz), 7.08 (1H, dd, J=8.9, 8.9 Hz), 7.60 (1H, ddd, J=2.2, 4.9, 8.9 Hz), 7.65 (1H, dd, J=2.2, 7.3 Hz), 7.85 (1H, t, J=1.5 Hz).

IR (Neat) cm$^{-1}$: 1652, 1609, 1506.
Mass m/z: 345 (M$^+$).

Example 99

Preparation of 4-diethylaminomethyl-6-(4-fluoro-3-methylphenyl)-2-isobutyl-2H-pyridazin-3-one hydrochloride Following the procedure of Example 4, 4-diethylaminomethyl-6-(4-fluoro-3-methylphenyl)-2-isobutyl-2H-pyridazin-3-one was reacted to yield the title compound as slightly yellow needles (yield: 70.1%).

Melting point: 154.3–157.3° C.
$^1$H NMR (400 MHz, CDCl$_3$) δ: 0.92 (6H, d, J=6.8 Hz), 1.29 (6H, t, J=7.2 Hz), 2.20–2.30 (1H, m), 2.32 (3H, d, J=1.2 Hz), 3.09–3.25 (4H, m), 4.03 (2H, d, J=7.3 Hz), 4.28 (2H, d, J=5.6 Hz), 7.30 (1H, dd, J=9.0, 9.0 Hz), 7.80 (1H, ddd, J=2.0, 4.9, 9.0 Hz), 7.87 (1H, dd, J=2.0, 7.3 Hz), 7.85 (1H, t, J=1.5 Hz).
IR (KBr) cm$^{-1}$: 2559, 2491, 1652, 1613, 1507.

Example 100

Preparation of 4-(4-tert-butoxycarbonyl-1-piperazinyl)methyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxy-methyl-2H-pyridazin-3-one and tert-butyl 1-piperazine-carboxylate were reacted to yield the title compound as a slightly yellow oil (yield: 97.5%).

$^1$H NMR (400 MHz, CDCl$_3$) δ: 0.98 (6H, d, J=6.6 Hz), 1.46 (9H, s), 2.28–2.40 (1H, m), 2.36 (3H, d, J=1.7 Hz), 3.50 (4H, t, J=4.9 Hz), 3.58 (2H, d, J=1.0 Hz), 4.08 (2H, d, J=7.3 Hz), 7.09 (1H, dd, J=8.9, 8.9 Hz), 7.58 (1H, ddd, J=2.0, 4.9, 8.9 Hz), 7.63 (1H, dd, J=2.0, 7.3 Hz), 7.75 (1H, s).
IR (Neat) cm$^{-1}$: 1695, 1652, 1608, 1506.

Example 101

Preparation of 6-(4-fluoro-3-methylphenyl)-2-isobutyl-4-(1-piperazinyl)methyl-2H-pyridazin-3-one Following the procedure of Example 2, 4-(4-tert-butoxycarbonyl-1-piperazinyl)methyl-6-(4-fluoro-3-methyl-phenyl)-2-isobutyl-2H-pyridazin-3-one was reacted to yield the title compound as a pale yellow oil (yield: quantitative).

$^1$H NMR (400 MHz, CDCl$_3$) δ: 0.98 (6H, d, J=6.8 Hz), 1.47 (1H, br), 2.28–2.40 (1H, m), 2.36 (3H, d, J=1.7 Hz), 2.56 (4H, t, J=4.9 Hz), 2.97 (4H, t, J=4.9 Hz), 3.56 (2H, d, J=1.4 Hz), 4.07 (2H, d, J=7.3 Hz), 7.09 (1H, dd, J=8.8, 8.8 Hz), 7.58 (1H, ddd, J=2.0, 4.9, 8.8 Hz), 7.64 (1H, dd, J=2.0, 7.3 Hz), 7.75 (1H, t, J=1.4 Hz).

Example 102

Preparation of 6-(4-fluoro-3-methylphenyl)-2-isobutyl-4-(1-piperazinyl)methyl-2H-pyridazin-3-one dihydrochloride Following the procedure of Example 4, 6-(4-fluoro-3-methylphenyl)-2-isobutyl-4-(1-piperazinyl)methyl-2H-pyridazin-3-one was reacted to yield the title compound as pale yellow prisms (yield: 87.2%).

Melting point: 154.9–158.0° C.
$^1$H NMR (400 MHz, DMSO-d$_6$) δ: 0.94 (6H, d, J=6.8 Hz), 2.19–2.30 (1H, m), 2.32 (3H, d, J=1.7 Hz), 3.04 (4H, br), 3.71 (4H, br), 4.01 (2H, d, J=7.3 Hz), 7.28 (1H, dd, J=8.8, 8.8 Hz), 7.76 (1H, ddd, J=2.0, 4.9, 8.8 Hz), 7.83 (1H, dd, J=2.0, 7.3 Hz), 8.40 (1H, brs).
IR (KBr) cm$^{-1}$: 1659, 1610, 1504, 1422.

Example 103

Preparation of 4-(4-tert-butoxycarbonyl-1-piperazinyl)methyl-6-(3,4-difluorophenyl)-2-isobutyl-2H-pyridazin-3-one 1) Preparation of ethyl 4-(3,4-difluorophenyl)-2-ethoxycarbonyl-2-hydroxy-4-oxobutanoate Following the procedure of Example 1(3), 3',4'-difluoroacetophenone was reacted to yield the title compound as a pale yellow oil (yield: 81.6%).

$^1$H NMR (400 MHz, CDCl$_3$) δ: 1.30 (6H, t, J=7.1 Hz), 3.78 (2H, s), 4.22 (1H, s), 4.31 (4H, q, J=7.1 Hz), 7.24–7.30 (1H, m), 7.73–7.82 (2H, m).
IR (Neat) cm$^{-1}$: 3483, 1740, 1695, 1612.
Mass m/z: 312 (M$^+$-H$_2$O).

2) Preparation of 4-carboxy-6-(3,4-difluorophenyl)-2H-pyridazin-3-one

Following the procedure of Example 1(4), ethyl 4-(3,4-difluorophenyl)-2-ethoxycarbonyl-2-hydroxy-4-oxobutanoate was reacted to yield the title compound as a pale yellow crystalline powder (yield: 88.9%).

3) Preparation of 4-methoxycarbonyl-6-(3,4-difluoromethyl-phenyl)-2H-pyridazin-3-one Following the procedure of Example 1(5), 4-carboxy-6-(3,4-difluorophenyl)-2H-pyridazin-3-one was reacted to yield the title compound as a pale yellow crystalline powder (yield: 85.8%).

$^1$H NMR (400 MHz, CDCl$_3$) δ: 4.01 (3H, s), 7.25–7.32 (1H, m), 7.53–7.57 (1H, m), 7.67–7.73 (1H, m), 8.31 (1H, s), 11.70 (1H, br).
IR (KBr) cm$^{-1}$: 3223, 3159, 1722, 1676, 1659.
Mass m/z: 266 (M$^+$).

4) Preparation of 6-(3,4-difluorophenyl)-2-isobutyl-4-methoxycarbonyl-2H-pyridazin-3-one Following the procedure of Example 1(6), 6-(3,4-difluorophenyl)-4-methoxycarbonyl-2H-pyridazin-3-one was reacted to yield the title compound as a yellow oil (yield: quantitative).

$^1$H NMR (400 MHz, CDCl$_3$) δ: 0.99 (6H, d, J=6.8 Hz), 2.30–2.41 (1H, m), 3.98 (3H, s), 4.13 (2H, d, J=7.2 Hz), 7.23–7.30 (1H, m), 7.49–7.55 (1H, m), 7.68 (1H, ddd, J=2.2, 7.6, 11.1 Hz), 8.20 (1H, s).

5) Preparation of 4-carboxy-6-(3,4-difluorophenyl)-2-isobutyl-2H-pyridazin-3-one Following the procedure of Example 1(7), 6-(3,4-difluorophenyl)-2-isobutyl-4-methoxycarbonyl-2H-pyridazin-3-one was reacted to yield the title compound as colorless fine needles (yield: 91.4%).

Melting point: 163.4–163.7° C.
$^1$H NMR (400 MHz, CDCl$_3$) δ: 1.02 (6H, d, J=6.6 Hz), 2.33–2.43 (1H, m), 4.22 (2H, d, J=7.4 Hz), 7.27–7.35 (1H, m), 7.56–7.62 (1H, m), 7.74 (1H, ddd, J=2.4, 7.6, 11.2 Hz), 8.62 (1H, s), 14.05 (1H, s).
IR (KBr) cm$^{-1}$: 3436, 1737, 1635, 1522, 1434, 1276, 1102, 806.
Mass m/z: 308 (M$^+$).

6) Preparation of 6-(3,4-difluorophenyl)-4-hydroxymethyl-2-isobutyl-2H-pyridazin-3-one Following the procedure of Example 1(8), 4-carboxy-6-(3,4-difluorophenyl)-2-isobutyl-2H-pyridazin-3-one was reacted to yield the title compound as colorless fine-needles (yield: 25.0%).

¹H NMR (400 MHz, CDCl₃) δ: 0.99 (6H, d, J=6.8 Hz), 2.29–2.39 (1H, m), 2.96 (1H, t, J=5.9 Hz), 4.08 (2H, d, J=7.4 Hz), 4.72 (2H, dd, J=1.2, 5.8 Hz), 7.22–7.28 (1H, m), 7.51–7.55 (1H, m), 7.64–7.71 (2H, m).

7) Preparation of 6-(3,4-difluorophenyl)-2-isobutyl-4-methanesulfonyloxymethyl-2H-pyridazin-3-one Following the procedure of Example 1(9), 6-(3,4-difluorophenyl)-4-hydroxymethyl-2-isobutyl-2H-pyridazin-3-one was reacted to yield the title compound as colorless fine-needles (yield: 81.4%).

Melting point: 113.3–113.4° C.

¹H NMR (400 MHz, CDCl₃) δ: 0.99 (6H, d, J=6.6 Hz), 2.27–2.40 (1H, m), 3.18 (3H, s), 4.08 (2H, d, J=7.4 Hz), 5.28 (2H, d, J=1.6 Hz), 7.23–7.30 (1H, m), 7.50–7.54 (1H, m), 7.68 (1H, ddd, J=2.2, 7.6, 11.1 Hz), 7.75 (1H, t, J=1.4 Hz).

IR (KBr) cm⁻¹: 3447, 1656, 1613, 1522, 1354, 1167, 1049, 877.

Mass m/z: 372 (M⁺).

8) Preparation of 4-(4-tert-butoxycarbonyl-1-piperazinyl)-methyl-6-(3,4-difluorophenyl)-2-isobutyl-2H-pyridazin-3-one Following the procedure of Example 1(10), 6-(3,4-difluorophenyl)-2-isobutyl-4-methanesulfonyloxymethyl-2H-pyridazin-3-one and tert-butyl 1-piperazinecarboxylate were reacted to yield the title compound as a yellow oil (yield: 85.5%).

¹H NMR (400 MHz, CDCl₃) δ: 0.98 (6H, d, J=6.6 Hz), 1.47 (9H, s), 2.28–2.38 (1H, m), 2.52 (4H, t, J=4.7 Hz), 3.51 (4H, t, J=4.7 Hz), 3.58 (2H, s), 4.07 (2H, d, J=7.2 Hz), 7.21–7.29 (1H, m), 7.50–7.55 (1H, m), 7.64–7.71 (1H, m), 7.76 (1H, d, J=1.0 Hz).

Example 104

Preparation of 6-(3,4-difluorophenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3,4-difluorophenyl)-2-isobutyl-2H-pyridazin-3-one was reacted to yield the title compound as a white solid (yield: 72.5%).

Melting point: 182.5–186.0° C.

¹H NMR (400 MHz, DMSO-d₆) δ: 0.94 (6H, d, J=6.6 Hz), 2.22–2.33 (1H, m), 3.11 (4H, br), 3.30 (4H, t, J=5.1 Hz), 3.90 (2H, s), 4.02 (2H, d, J=7.1 Hz), 7.52 (1H, ddd, J=8.6, 8.6, 10.5 Hz), 7.73–7.78 (1H, m), 7.90 (1H, ddd, J=2.2, 8.0, 11.7 Hz), 8.20 (1H, s).

IR (KBr) cm⁻¹: 1656, 1609, 1522, 1436, 1276, 1112.

Mass m/z: 362 (M⁺).

Example 105

Preparation of 6-(3,4-difluorophenyl)-2-isobutyl-4-(4-methyl-1-piperazinyl)methyl-2H-pyridazin-3-one Following the procedure of Example 1(10), 6-(3,4-difluorophenyl)-2-isobutyl-4-methanesulfonyloxymethyl-2H-pyridazin-3-one and 1-methylpiperazine were reacted to yield the title compound as a yellow oil (yield: 79.1%).

¹H NMR (400 MHz, CDCl₃) δ: 0.98 (6H, d, J=6.8 Hz), 2.28–2.39 (1H, m), 2.34 (3H, s), 2.55 (4H, br), 2.63 (4H, br), 3.58 (2H, s), 4.07 (2H, d, J=7.2 Hz), 7.22–7.29 (1H, m), 7.50–7.57 (1H, m), 7.64–7.72 (1H, m), 7.74 (1H, s).

Example 106

Preparation of 6-(3,4-difluorophenyl)-2-isobutyl-4-(4-methyl-1-piperazinyl)methyl-2H-pyridazin-3-one dihydrochloride Following the procedure of Example 4, 6-(3,4-difluorophenyl)-2-isobutyl-4-(4-methyl-1-piperazinyl) methyl-2H-pyridazin-3-one was reacted to yield the title compound as a colorless crystalline powder (yield: 70.3%).

Melting point: 242.5–243.4° C.

¹H NMR (400 MHz, DMSO-d₆) δ: 0.94 (6H, d, J=6.8 Hz), 2.22–2.33 (1H, m), 2.77 (3H, s), 3.11 (4H, br), 3.34 (4H, br), 3.84 (2H, s), 4.02 (2H, d, J=7.1 Hz), 7.52 (1H, ddd, J=8.6, 8.6, 10.5 Hz), 7.72–7.77 (1H, m), 7.89 (1H, ddd, J=2.2, 7.9, 11.7 Hz), 8.12 (1H, s).

IR (KBr) cm⁻¹: 1652, 1607, 1522, 1435, 1278.

Mass m/z: 376 (M⁺).

Example 107

Preparation of 4-N,N-bis(2-hydroxyethyl) aminomethyl-6-(3,4-difluorophenyl)-2-isobutyl-2H-pyridazin-3-one Following the procedure of Example 1(10), 6-(3,4-difluorophenyl)-2-isobutyl-4-methanesulfonyloxymethyl-2H-pyridazin-3-one and diethanolamine were reacted to yield the title compound as a yellow oil (yield: 75.8%).

¹H NMR (400 MHz, CDCl₃) δ: 0.97 (6H, d, J=6.6 Hz), 2.25–2.38 (1H, m), 2.70 (4H, br), 3.64–3.70 (6H, m), 4.06 (2H, d, J=7.4 Hz), 7.15–7.25 (1H, m), 7.54–7.58 (1H, m), 7.67–7.73 (1H, m), 7.88 (1H, s).

Example 108

Preparation of 4-N,N-bis(2-hydroxyethyl) aminomethyl-6-(3,4-difluorophenyl)-2-isobutyl-2H-pyridazin-3-one hydrochloride Following the procedure of Example 4, 4-N,N-bis(2-hydroxyethyl)aminomethyl-6-(3,4-difluorophenyl)-2-isobutyl-2H-pyridazin-3-one was reacted to yield the title compound as a white solid (yield: 70.3%).

Melting point: 127.5–128.3° C.

¹H NMR (400 MHz, DMSO-d₆) δ: 0.95 (6H, d, J=6.8 Hz), 2.23–2.34 (1H, m), 3.35 (4H, t, J=5.1 Hz), 3.84 (4H, t, J=5.1 Hz), 4.05 (2H, d, J=7.1 Hz), 4.45 (2H, s), 7.54 (1H, ddd, J=8.6, 8.6, 10.5 Hz), 7.76–7.81 (1H, m), 7.93 (1H, ddd, J=2.2, 7.8, 12.0 Hz), 8.53 (1H, s).

IR (KBr) cm⁻¹: 1653, 1604, 1521, 1437, 1275.

Mass m/z: 363 (M⁺-H₂O).

Example 109

Preparation of 6-(3,4-difluorophenyl)-4-dimethylaminomethyl-2-isobutyl-2H-pyridazin-3-one Following the procedure of Example 7, 6-(3,4-difluorophenyl)-2-isobutyl-4-methanesulfonyloxymethyl-2H-pyridazin-3-one was reacted to yield the title compound as a yellow oil (yield: 85.5%).

¹H NMR (400 MHz, CDCl₃) δ: 0.98 (6H, d, J=6.6 Hz), 2.29–2.40 (1H, m), 2.35 (6H, s), 3.50 (2H, s), 4.07 (2H, d, J=7.4 Hz), 7.20–7.30 (1H, m), 7.53–7.60 (1H, m), 7.67–7.73 (1H, m), 7.74 (1H, s).

Example 110

Preparation of 6-(3,4-difluorophenyl)-4-dimethylaminomethyl-2-isobutyl-2H-pyridazin-3-one hydrochloride Following the procedure of Example 4, 6-(3,4-difluorophenyl)-4-dimethylaminomethyl-2-isobutyl-2H- pyridazin-3-one was reacted to yield the title compound as slightly yellow flakes (yield: 85.9%).

Melting point: 226.5–227.7° C.

$^1$H NMR (400 MHz, DMSO-d$_6$) δ: 0.96 (6H, d, J=6.8 Hz), 2.23–2.34 (1H, m), 2.81 (6H, s), 4.05 (2H, d, J=7.1 Hz), 4.28 (2H, s), 7.54 (ddd, J=8.7, 8.7, 10.5 Hz), 7.76–7.81 (1H, m), 7.93 (1H, ddd, J=2.2, 7.9, 12.0 Hz), 8.57 (1H, s).

IR (KBr) cm$^{-1}$: 1648, 1607, 1525, 1437, 1288, 1112.

Mass m/z: 321 (M$^+$).

Example 111

Preparation of 4-aminomethyl-6-(2,4-difluorophenyl)-2-isobutyl-2H-pyridazin-3-one 1) Preparation of Ethyl 4-(2,4-difluorophenyl)-2-ethoxycarbonyl-2-hydroxy-4-oxobutanoate Following the procedure of Example 1(3), 2',4'-difluoroacetophenone was reacted to yield the title compound as a pale yellow oil (yield: 76.8%).

$^1$H NMR (400 MHz, CDCl$_3$) δ: 1.30 (6H, t, J=7.1 Hz), 3.81 (2H, d, J=3.4 Hz), 4.18 (1H, s), 4.30 (4H, q, J=7.1 Hz), 6.90 (1H, ddd, J=2.4, 8.5, 10.0 Hz), 6.94–7.00 (1H, m), 7.94 (1H, ddd, J=6.6, 8.5, 8.5 Hz).

IR (Neat) cm$^{-1}$: 3491, 1743, 1692, 1612.

Mass m/z: 312 (M$^+$-H$_2$O).

2) Preparation of 4-carboxy-6-(2,4-difluorophenyl)-2H-pyridazin-3-one

Following the procedure of Example 1(4), ethyl 4-(2,4-difluorophenyl)-2-ethoxycarbonyl-2-hydroxy-4-oxobutanoate was reacted to yield the title compound as a pale yellow crystalline powder (yield: 95.2%).

3) Preparation of 6-(2,4-difluorophenyl)-4-methoxycarbonyl-2H-pyridazin-3-one

Following the procedure of Example 1(5), 4-carboxy-6-(2,4-difluorophenyl)-2H-pyridazin-3-one was reacted to yield the title compound as a pale yellow crystalline powder (yield: 81.2%).

$^1$H NMR (400 MHz, CDCl$_3$) δ: 3.99 (3H, s), 6.96 (1H, ddd, J=2.4, 8.8, 10.1 Hz), 6.99–7.04 (1H, m), 7.77 (1H, ddd, J=6.3, 8.8, 8.8 Hz), 8.30 (1H, d, J=2.0 Hz), 12.05 (1H, br).

IR (KBr) cm$^{-1}$: 3217, 3148, 1721, 1673, 1611.

Mass m/z: 266 (M$^+$).

4) Preparation of 6-(2,4-difluorophenyl)-2-isobutyl-4-methoxycarbonyl-2H-pyridazin-3-one Following the procedure of Example 1(6), 6-(2,4-difluorophenyl)-4-methoxycarbonyl-2H-pyridazin-3-one was reacted to yield the title compound as a pale yellow oil (yield: 84.8%).

$^1$H NMR (400 MHz, CDCl$_3$) δ: 0.99 (6H, d, J=6.6 Hz), 2.29–2.42 (1H, m), 3.97 (3H, s), 4.12 (2H, d, J=7.3 Hz), 6.94 (1H, ddd, J=2.4, 8.8, 11.2 Hz), 6.98–7.04 (1H, m), 7.73 (1H, ddd, J=6.3, 6.3, 8.8 Hz), 8.18 (1H, d, J=2.0 Hz).

IR (Neat) cm$^{-1}$: 1755, 1748, 1668, 1620, 1506.

Mass m/z: 322 (M$^+$).

5) Preparation of 4-carboxy-6-(2,4-difluorophenyl)-2-isobutyl-2H-pyridazin-3-one Following the procedure of Example 1(7), 6-(2,4-difluorophenyl)-2-isobutyl-4-methoxycarbonyl-2H-pyridazin-3-one was reacted to yield the title compound as slightly yellow needles (yield: 92.7%).

Melting point: 126.5–128.2° C.

$^1$H NMR (400 MHz, CDCl$_3$) δ: 1.02 (6H, d, J=6.6 Hz), 2.31–2.43 (1H, m), 4.22 (2H, d, J=7.6 Hz), 6.96–7.07 (2H, m), 7.74 (1H, ddd, J=6.3, 6.3, 8.8 Hz), 8.61 (1H, d, J=2.2 Hz), 14.02 (1H, s).

IR (KBr) cm$^{-1}$: 1739, 1636, 1618, 1573, 1465.

Mass m/z: 308 (M$^+$).

6) Preparation of 6-(2,4-difluorophenyl)-4-hydroxymethyl-2-isobutyl-2H-pyridazin-3-one Following the procedure of Example 1(8), 4-carboxy-6-(2,4-difluorophenyl)-2-isobutyl-2H-pyridazin-3-one was reacted to yield the title compound as a pale yellow oil (yield: 45.0%).

$^1$H NMR (400 MHz, CDCl$_3$) δ: 0.98 (6H, d, J=6.8 Hz), 2.27–2.40 (1H, m), 3.15 (1H, t, J=6.1 Hz), 4.08 (2H, d, J=7.3 Hz), 4.69 (2H, dd, J=1.2, 6.1 Hz), 6.93 (1H, ddd, J=2.4, 8.8, 11.2 Hz), 6.96–7.02 (1H, m), 7.61–7.63 (1H, m), 7.72 (1H, ddd, J=6.3, 6.3, 8.8 Hz).

IR (Neat) cm$^{-1}$: 3412, 1652, 1620, 1507.

Mass m/z: 294 (M$^+$).

7) Preparation of 6-(2,4-difluorophenyl)-2-isobutyl-4-methanesulfonyloxymethyl-2H-pyridazin-3-one Following the procedure of Example 1(9), 6-(2,3-difluorophenyl)-4-hydroxymethyl-2-isobutyl-2H-pyridazin-3-one was reacted to yield the title compound as colorless needles (yield: 96.3%).

Melting point: 86.7–88.6° C.

$^1$H NMR (400 MHz, CDCl$_3$) δ: 0.99 (6H, d, J=6.8 Hz), 2.26–2.39 (1H, m), 3.16 (3H, s), 4.08 (2H, d, J=7.3 Hz), 5.26 (2H, d, J=1.2 Hz), 6.94 (1H, ddd, J=2.4, 8.8, 11.2 Hz), 6.97–7.03 (1H, m), 7.71 (1H, ddd, J=6.3, 6.3, 8.8 Hz), 7.73–7.75 (1H, m).

IR (KBr) cm$^{-1}$: 1659, 1612, 1508, 1359, 1166.

Mass m/z: 372 (M$^+$).

8) Preparation of 6-(2,4-difluorophenyl)-2-isobutyl-4-phthalimidomethyl-2H-pyridazin-3-one Following the procedure of Example 24(1), 6-(2,4-difluorophenyl)-2-isobutyl-4-methanesulfonyloxymethyl-2H-pyridazin-3-one was reacted to yield the title compound as colorless needles (yield: 91.1%).

Melting point: 152.3–155.6° C.

$^1$H NMR (400 MHz, CDCl$_3$) δ: 0.98 (6H, d, J=6.6 Hz), 2.28–2.39 (1H, m), 4.07 (2H, d, J=7.3 Hz), 4.89 (2H, d, J=1.0 Hz), 6.83 (1H, ddd, J=2.4, 8.8, 11.0 Hz), 6.91–6.97 (1H, m), 7.27–7.31 (1H, m), 7.66 (1H, ddd, J=6.3, 6.3, 8.8 Hz), 7.74–7.80 (2H, m), 7.86–7.94 (2H, m).

IR (KBr) cm$^{-1}$: 1773, 1720, 1650, 1617, 1509, 1418, 1389.

Mass m/z: 423 (M$^+$).

9) Preparation of 4-aminomethyl-6-(2,4-difluorophenyl)-2-isobutyl-2H-pyridazin-3-one Following the procedure of Example 24(2), 2-isobutyl-6-(2,4-difluorophenyl)-4-phthalimidomethyl-2H-pyridazin-3-one was reacted to yield the title compound as a slightly yellow oil (yield: 98.4%).

$^1$H NMR (400 MHz, CDCl$_3$) δ: 0.98 (6H, d, J=6.8 Hz), 1.66 (2H, br), 2.24–2.41 (1H, m), 3.87 (2H, s), 4.08 (2H, d, J=7.3 Hz), 6.92 (1H, ddd, J=2.4, 8.8, 11.2 Hz), 6.97–7.02 (1H, m), 7.63 (1H, t, J=1.1 Hz), 7.71 (1H, ddd, J=6.3, 6.3, 8.8 Hz).

IR (Neat) cm$^{-1}$: 3381, 3307, 1652, 1611, 1508.

Mass m/z: 293 (M$^+$).

Example 112

Preparation of 4-aminomethyl-6-(2,4-difluorophenyl)-2-isobutyl-2H-pyridazin-3-one hydrochloride Following the procedure of Example 4, 4-aminomethyl-6-(2,4-difluorophenyl)-2-isobutyl-2H-pyridazin-3-one was reacted to yield the title compound as slightly yellow needles (yield: 94.9%).

Melting point: 161.4–163.9° C.

$^1$H NMR (400 MHz, DMSO-d$_6$) δ: 0.93 (6H, d, J=6.8 Hz), 2.18–2.34 (1H, m), 4.01 (2H, s), 4.02 (2H, d, J=7.3 Hz), 7.24–7.31 (1H, m), 7.46 (1H, ddd, J=2.4, 8.8, 11.5 Hz), 7.76 (1H, ddd, J=6.3, 6.3, 8.8 Hz), 7.95 (1H, s).

IR (KBr) cm$^{-1}$: 1652, 1616, 1597, 1509.

Example 113

Preparation of 6-(2,4-difluorophenyl)-4-dimethylaminomethyl-2-isobutyl-2H-pyridazin-3-one Following the procedure of Example 7, 6-(2,4-difluorophenyl)-2-isobutyl-4-methanesulfonyloxymethyl-2H-pyridazin-3-one was reacted to yield the title compound as a slightly yellow oil (yield: 94.1%).

$^1$H NMR (400 MHz, CDCl$_3$) δ: 0.98 (6H, d, J=6.8 Hz), 2.27–2.38 (1H, m), 2.34 (6H, s), 3.49 (2H, d, J=1.5 Hz), 4.07 (2H, d, J=7.6 Hz), 6.92 (1H, ddd, J=2.4, 8.8, 11.2 Hz), 6.95–7.01 (1H, m), 7.70 (1H, t, J=1.5 Hz), 7.71 (1H, ddd, J=6.3, 6.3, 8.8 Hz).

IR (Neat) cm$^{-1}$: 1652, 1612, 1508.

Mass m/z: 321 (M$^+$).

Example 114

Preparation of 6-(2,4-difluorophenyl)-4-dimethylaminomethyl-2-isobutyl-2H-pyridazin-3-one hydrochloride Following the procedure of Example 4, 6-(2,4-difluorophenyl)-4-dimethylaminomethyl-2-isobutyl-2H-pyridazin-3-one was reacted to yield the title compound as pale yellow prisms (yield: 89.8%).

Melting point: 170.1–173.5° C.

$^1$H NMR (400 MHz, DMSO-d$_6$) δ: 0.94 (6H, d, J=6.8 Hz), 2.18–2.29 (1H, m), 2.80 (6H, s), 4.03 (2H, d, J=7.3 Hz), 4.30 (2H, s), 7.25–7.31 (1H, m), 7.45 (1H, ddd, J=2.4, 8.8, 11.2 Hz), 7.81 (1H, ddd, J=6.3, 6.3, 8.8 Hz), 8.15 (1H, d, J=1.7 Hz), IR (KBr) cm$^{-1}$: 1648, 1612, 1523, 1510.

Example 115

Preparation of 4-diethylaminomethyl-6-(2,4-difluorophenyl)-2-isobutyl-2H-pyridazin-3-one Following the procedure of Example 9 (4), 6-(2,4-difluorophenyl)-2-isobutyl-4-methanesulfonyloxymethyl-2H-pyridazin-3-one and diethylamine were reacted to yield the title compound as a pale yellow oil (yield: quantitative).

$^1$H NMR (400 MHz, CDCl$_3$) δ: 0.98 (6H, d, J=6.8 Hz), 1.06 (6H, t, J=7.1 Hz), 2.27–2.39 (1H, m), 2.59 (4H, q, J=7.1 Hz), 3.59 (2H, d, J=1.7 Hz), 4.07 (2H, d, J=7.3 Hz), 6.92 (1H, ddd, J=2.4, 8.8, 11.2 Hz), 6.95–7.01 (1H, m), 7.72 (1H, ddd, J=6.3, 6.3, 8.8 Hz), 7.83 (1H, td, J=1.5, 2.9 Hz).

IR (Neat) cm$^{-1}$: 1656, 1613, 1508.

Mass m/z: 349 (M$^+$).

Example 116

Preparation of 4-diethylaminomethyl-6-(2,4-difluorophenyl)-2-isobutyl-2H-pyridazin-3-one hydrochloride Following the procedure of Example 4, 4-diethylaminomethyl-6-(2,4-difluorophenyl)-2-isobutyl-2H-pyridazin-3-one was reacted to yield the title compound as colorless needles (yield: 80.9%).

Melting point: 128.9–131.7° C.

$^1$H NMR (400 MHz, DMSO-d$_6$) δ: 0.94 (6H, d, J=6.8 Hz), 1.28 (6H, t, J=7.2 Hz), 2.18–2.29 (1H, m), 3.10–3.23 (4H, m), 4.03 (2H, d, J=7.3 Hz), 4.29 (2H, d, J=5.4 Hz), 7.28 (1H, ddd, J=2.2, 8.8, 8.8 Hz), 7.45 (1H, ddd, J=2.2, 8.8, 8.8 Hz), 7.81 (1H, ddd, J=6.3, 8.8, 8.8 Hz), 8.24 (1H, d, J=1.5 Hz).

Example 117

Preparation of 4-N,N-bis(2-hydroxyethyl)aminomethyl-6-(2,4-difluorophenyl)-2-isobutyl-2H-pyridazin-3-one Following the procedure of Example 1(10), 6-(2,4-difluorophenyl)-2-isobutyl-4-methanesulfonyloxymethyl-2H-pyridazin-3-one and diethanolamine were reacted to yield the title compound as a slightly yellow oil (yield: 97.6%).

$^1$H NMR (400 MHz, CDCl$_3$) δ: 0.97 (6H, d, J=6.6 Hz), 2.26–2.40 (1H, m), 2.70 (4H, t, J=5.0 Hz), 3.65 (4H, t, J=5.0 Hz), 3.70 (2H, s), 4.09 (2H, d, J=7.3 Hz), 6.92 (1H, ddd, J=2.7, 8.8, 11.2 Hz), 6.97–7.03 (1H, m), 7.63 (1H, d, J=2.4 Hz), 7.75 (1H, ddd, J=6.3, 6.3, 8.8 Hz).

IR (Neat) cm$^{-1}$: 3401, 1648, 1597, 1508.

Mass m/z: 363 (M$^+$-H$_2$O).

Example 118

Preparation of 4-N,N-bis(2-hydroxy)aminomethyl-6-(2,4-difluorophenyl)-2-isobutyl-2H-pyridazin-3-one hydrochloride Following the procedure of Example 4, 4-N,N-bis(2-hydroxy)aminomethyl-6-(2,4-difluorophenyl)-2-isobutyl-2H-pyridazin-3-one was reacted to yield the title compound as slightly yellow prisms (yield: 89.0%).

Melting point: 161.8–163.9° C.

$^1$H NMR (400 MHz, DMSO-d$_6$) δ: 0.93 (6H, d, J=6.6 Hz), 2.18–2.29 (1H, m), 3.27–3.40 (4H, br, overlapped with H$_2$O), 3.76–3.84 (4H, m), 4.03 (2H, d, J=7.3 Hz), 4.51 (2H, brs), 5.34 (2H, br), 7.24–7.31 (1H, m), 7.41–7.48 (1H, m), 7.76–7.84 (1H, m), 8.15 (1H, m).

IR (KBr) cm$^{-1}$: 3233, 3172, 1645, 1613, 1593, 1421.

Example 119

Preparation of 6-(2,4-difluorophenyl)-2-isobutyl-4-(4-methyl-1-piperazinyl)methyl-2H-pyridazin-3-one Following the procedure of Example 1(10), 6-(2,4-difluorophenyl)-2-isobutyl-4-methanesulfonyloxymethyl-2H-pyridazin-3-one and 1-methylpiperazine were reacted to yield the title compound as a pale yellow oil (yield: 94.0%).

$^1$H NMR (400 MHz, CDCl$_3$) δ: 0.97 (6H, d, J=6.6 Hz), 2.28–2.38 (1H, m), 2.31 (3H, s), 2.50 (4H, br), 2.61 (4H, br), 3.57 (2H, d, J=1.5 Hz), 4.07 (2H, d, J=7.3 Hz), 6.93 (1H, ddd, J=2.4, 8.8, 11.2 Hz), 6.96–7.02 (1H, m), 7.69–7.75 (2H, m).

IR (Neat) cm$^{-1}$: 1655, 1616, 1596, 1508.

Mass m/z: 376 (M$^+$).

Example 120

Preparation of 6-(2,4-difluorophenyl)-2-isobutyl-4-(4-methyl-1-piperazinyl)methyl-2H-pyridazin-3-one dihydrochloride Following the procedure of Example 4, 6-(2,4-difluorophenyl)-2-isobutyl-4-(4-methyl-1-piperazinyl)-methyl-2H-pyridazin-3-one was reacted to yield the title compound as colorless needles (yield: 90.4%).

Melting point: 248.1–251.7° C. (dec.).

¹H NMR (400 MHz, DMSO-d$_6$, 100° C.) δ: 0.93 (6H, d, J=6.8 Hz), 2.20–2.29 (1H, m), 2.76 (3H, s), 3.09 (4H, br, overlapped with H$_2$O), 3.27 (4H, br), 3.74 (2H, s), 4.00 (2H, d, J=7.1 Hz), 7.14–7.29 (2H, m), 7.71–7.79 (2H, m).

IR (KBr) cm$^{-1}$: 1652, 1612, 1514.

Example 121

Preparation of 4-(4-tert-butoxycarbonyl-1-piperazinyl)methyl-6-(2,4-difluorophenyl)-2-isobutyl-2H-pyridazin-3-one Following the procedure of Example 1(10), 6-(2,4-difluorophenyl)-2-isobutyl-4-methanesulfonyloxymethyl-2H-pyridazin-3-one and tert-butyl 1-piperazinecarboxylate were reacted to yield the title compound as a slightly yellow oil (yield: 97.5%).

¹H NMR (400 MHz, CDCl$_3$) δ: 0.98 (6H, d, J=6.8 Hz), 1.47 (9H, s), 2.28–2.39 (1H, m), 2.52 (4H, t, J=4.9 Hz), 3.49 (4H, t, J=4.9 Hz), 3.57 (2H, d, J=11.2 Hz), 4.07 (2H, d, J=7.3 Hz), 6.93 (1H, ddd, J=2.4, 8.8, 11.2 Hz), 6.96–7.02 (1H, m), 7.69–7.75 (2H, m).

IR (Neat) cm$^{-1}$: 1695, 1655, 1613, 1508, 1425.

Mass m/z: 462 (M$^+$).

Example 122

Preparation of 6-(2,4-difluorophenyl)-2-isobutyl-4-(1-piperazinyl)methyl-2H-pyridazin-3-one Following the procedure of Example 20, 4-(4-tert-butoxycarbonyl-1-piperazinyl)methyl-6-(2,4-difluorophenyl)-2-isobutyl-2H-pyridazin-3-one was reacted to yield the title compound as a yellow oil (yield: quantitative).

¹H NMR (400 MHz, CDCl$_3$): 0.98 (6H, d, J=6.8 Hz), 1.81 (1H, br), 2.27–2.39 (1H, m), 2.50–2.56 (4H, brm), 2.94 (4H, t, J=4.8 Hz), 3.54 (2H, d, J=1.2 Hz), 4.07 (2H, d, J=7.3 Hz), 6.93 (1H, ddd, J=2.4, 8.8, 11.2 Hz), 6.94–7.02 (1H, m), 7.69–7.76 (2H, m).

IR (Neat) cm$^{-1}$: 3314, 1655, 1613, 1508.

Mass m/z: 362 (M$^+$).

Example 123

Preparation of 6-(2,4-difluorophenyl)-2-isobutyl-4-(1-piperazinyl)methyl-2H-pyridazin-3-one dihydrochloride Following the procedure of Example 4, 6-(2,4-difluorophenyl)-2-isobutyl-4-(1-piperazinyl)methyl-2H-pyridazin-3-one was reacted to yield the title compound as a slightly yellow crystalline powder (yield: 90.8%).

Melting point: 136.3–140.9° C.

¹H NMR (400 MHz, DMSO-d$_6$) δ: 0.93 (6H, d, J=6.6 Hz), 2.20–2.30 (1H, m), 2.95 (4H, t, J=5.0 Hz), 3.02 (4H, t, J=5.0 Hz), 3.76 (2H, s), 4.00 (2H, d, J=7.3 Hz), 7.14–7.20 (1H, m), 7.26 (1H, ddd, J=2.7, 8.8, 11.2 Hz), 7.86 (1H, ddd, J=6.6, 6.6, 8.8 Hz), 7.81 (1H, s).

IR (KBr) cm$^{-1}$: 1656, 1616, 1597, 1509, 1426.

Example 124

Preparation of 2-benzyl-4-(4-tert-butoxycarbonyl-1-piperazinyl)methyl-6-(4-fluoro-3-methylphenyl)-2H-pyridazin-3-one 1) Preparation of 2-benzyl-6-(4-fluoro-3-methylphenyl)-4-methoxycarbonyl-2H-pyridazin-3-one Following the procedure of Example 1(6), 6-(4-fluoro-3-methylphenyl)-4-methoxycarbonyl-2H-pyridazin-3-one and benzyl chloride were reacted to yield the title compound as yellow needles (yield: 71.0%).

Melting point: 109.0–110.5° C.

¹H NMR (400 MHz, CDCl$_3$) δ: 2.35 (3H, d, J=1.7 Hz), 3.96 (3H, s), 5.44 (2H, s), 7.10 (1H, dd, J=8.8, 8.8 Hz), 7.28–7.37 (3H, m), 7.52 (2H, d, J=6.3 Hz), 7.57–7.64 (2H, m), 8.21 (1H, s).

IR (KBr) cm$^{-1}$: 1750, 1744, 1657, 1278, 1233, 1123.

Mass m/z: 352 (M$^+$).

2) Preparation of 2-benzyl-4-carboxy-6-(4-fluoro-3-methylphenyl)-2H-pyridazin-3-one Following the procedure of Example 1(7), 2-benzyl-6-(4-fluoro-3-methylphenyl)-4-methoxycarbonyl-2H-pyridazin-3-one was reacted to yield the title compound as a pale yellow crystalline powder (yield: 65.2%).

Melting point: 191.2–192.3° C.

¹H NMR (400 MHz, CDCl$_3$) δ: 2.37 (3H, d, J=2.0 Hz), 5.52 (2H, s), 7.13 (1H, dd, J=8.8, 8.8 Hz), 7.33–7.41 (3H, m), 7.48–7.52 (2H, m), 7.64–7.70 (2H, m), 8.62 (1H, s), 14.01 (1H, br).

IR (KBr) cm$^{-1}$: 1739, 1633, 1569, 1457, 1423, 1240.

Mass m/z: 338 (M$^+$).

3) Preparation of 2-benzyl-6-(4-fluoro-3-methylphenyl)-4-hydroxymethyl-2H-pyridazin-3-one Following the procedure of Example 1(8), 2-benzyl-4-carboxy-6-(4-fluoro-3-methylphenyl)-2H-pyridazin-3-one was reacted to yield the title compound as slightly yellow needles (yield: 28.4%).

Melting point: 119.5–120.6° C.

¹H NMR (400 MHz, CDCl$_3$) δ: 2.34 (3H, d, J=1.7 Hz), 3.01 (1H, t, J=5.9 Hz), 4.70 (2H, dd, J=1.2, 5.9 Hz), 5.41 (2H, s), 7.08 (1H, dd, J=8.8, 8.8 Hz), 7.27–7.37 (3H, m), 7.48 (1H, d, J=6.6 Hz), 7.57–7.65 (2H, m). 7.66 (1H, t, J=1.2 Hz).

IR (KBr) cm$^{-1}$: 3330, 1657, 1643, 1611, 1597, 1506, 1239.

Mass m/z: 324 (M$^+$).

4) Preparation of 2-benzyl-6-(4-fluoro-3-methylphenyl)-4-methanesulfonyloxymethyl-2H-pyridazin-3-one Following the procedure of Example 1(9), 2-benzyl-6-(4-fluoro-3-methylphenyl)-4-hydroxymethyl-2H-pyridazin-3-one was reacted to yield the title compound as slightly yellow needles (yield: 98.9%).

Melting point: 147.6–148.3° C.

¹H NMR (400 MHz, CDCl$_3$) δ: 2.35 (3H, d, J=2.0 Hz), 3.15 (3H, s), 5.26 (2H, d, J=1.2 Hz), 5.41 (2H, s), 7.09 (1H, dd, J=8.8, 8.8 Hz), 7.27–7.37 (3H, m), 7.47 (2H, d, J=6.6 Hz), 7.62 (1H, d, J=7.3 Hz), 7.57–7.60 (1H, m), 7.75 (1H, s).

IR (KBr) cm$^{-1}$: 1656, 1617, 1507, 1355, 1168, 1033, 879.

Mass m/z: 402 (M$^+$).

5) Preparation of 2-benzyl-4-(4-tert-butoxycarbonyl-1-piperazinyl)methyl-6-(4-fluoro-3-methylphenyl)-2H-pyridazin-3-one Following the procedure of Example 1(10), 2-benzyl-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 91.8%).

¹H NMR (400 MHz, CDCl$_3$) δ: 1.46 (9H, s), 2.35 (3H, d, J=1.8 Hz), 2.50 (4H, t, J=4.9 Hz), 3.49 (4H, t, J=4.9 Hz), 3.56 (2H, d, J=1.4 Hz), 5.40 (2H, s), 7.26–7.36 (4H, m), 7.49 (2H, d, J=6.6 Hz), 7.55–7.60 (1H, m), 7.63 (1H, dd, J=1.8, 7.2 Hz), 7.74 (1H, s).

Example 125

Preparation of 2-benzyl-6-(4-fluoro-3-methylphenyl)-4-(1-piperazinyl)methyl-2H-pyridazin-3-one dihydrochloride Following the procedure of Example 2, 2-benzyl-4-(4-tert-butoxycarbonyl-1-piperazinyl)methyl-6-(4-fluoro-3- methylphenyl)-2H-pyridazin-3-one was reacted to yield the title compound as a colorless crystalline powder (yield: 60.9%).

Melting point: 162.7–180.7° C. (dec.)

$^1$H NMR (400 MHz, DMSO-d$_6$) δ: 2.31 (3H, d, J=2.0 Hz), 3.09 (4H, br), 3.28 (4H, t, J=5.2 Hz), 13.89 (2H, s), 5.36 (2H, s), 7.21–7.40 (6H, m), 7.70–7.76 (1H, m), 7.79 (1H, dd, J=1.7, 7.3 Hz), 8.16 (1H, s).

IR (KBr) cm$^{-1}$: 1656, 1607, 1505, 1239, 1126, 700.

Mass m/z: 392 (M$^+$).

Example 126

Preparation of 2-benzyl-6-(4-fluoro-3-methylphenyl)-4-(4-methyl-1-piperazinyl)methyl-2H-pyridazin-3-one Following the procedure of Example 1(10), 2-benzyl-6-(4-fluoro-3-methylphenyl)-4-methanesulfonyloxymethyl-2H-pyridazin-3-one and 1-methylpiperazine were reacted to yield the title compound as a yellow oil (yield: 81.3%).

$^1$H NMR (400 MHz, CDCl$_3$) δ: 2.33 (3H, s), 2.36 (3H, d, J=1.8 Hz), 2.53 (4H, br), 2.61 (4H, br), 3.57 (2H, d, J=1.4 Hz), 5.40 (2H, s), 7.08 (1H, t, J=8.9 Hz), 7.26–7.36 (3H, m), 7.49 (2H, d, J=6.8 Hz), 7.56–7.60 (1H, m), 7.64 (1H, dd, J=1.8, 7.2 Hz), 7.73 (1H, s).

Example 127

Preparation of 2-benzyl-6-(4-fluoro-3-methylphenyl)-4-(4-methyl-1-piperazinyl)methyl-2H-pyridazin-3-one dihydrochloride Following the procedure of Example 4, 2-benzyl-6-(4-fluoro-3-methylphenyl)-4-(4-methyl-1-piperazinyl)methyl-2H-pyridazin-3-one was reacted to yield the title compound as a colorless crystalline powder (yield: 78.6%).

Melting point: 240.0–242.5° C. (dec.)

$^1$H NMR (400 MHz, DMSO-d$_6$) δ: 2.31 (3H, d, J=1.7 Hz), 2.76 (3H, s), 3.10 (4H, br), 3.33 (4H, br), 3.84 (2H, s), 5.36 (2H, s), 7.21–7.39 (6H, m), 7.69–7.74 (1H, m), 7.78 (1H, dd, J=2.1, 7.8 Hz), 8.09 (1H, s).

IR (KBr) cm$^-$: 1653, 1607, 1504, 1454, 1240, 1127.

Mass m/z: 406 (M$^+$).

Example 128

Preparation of 2-benzyl-4-N,N-bis(2-hydroxyethyl)-aminomethyl-6-(4-fluoro-3-methylphenyl)-2H-pyridazin-3-one Following the procedure of Example 1(10), 2-benzyl-6-(4-fluoro-3-methylphenyl)-4-methanesulfonyloxymethyl-2H-pyridazin-3-one and diethanolamine were reacted to yield the title compound as a yellow oil (yield: 87.6%).

$^1$H NMR (400 MHz, CDCl$_3$) δ: 2.33 (3H, s), 2.69 (4H, t, J=4.9 Hz), 3.64 (4H, t, J=5.0 Hz), 3.68 (2H, s), 5.40 (2H, s), 7.06 (1H, t, J=8.9 Hz), 7.26–7.38 (3H, m), 7.45 (2H, d, J=7.0 Hz), 7.58–7.68 (2H, m), 7.75 (1H, s).

Example 129

Preparation of 2-benzyl-4-N,N-bis(2-hydroxyethyl)-aminomethyl-6-(4-fluoro-3-methylphenyl)-2H-pyridazin-3-one hydrochloride Following the procedure of Example 4, 2-benzyl-4-N,N-bis(2-hydroxyethyl)aminomethyl-6-(4-fluoro-3-methylphenyl)-2H-pyridazin-3-one was reacted to yield the title compound as a pale yellow crystalline powder (yield: 75.9%).

Melting point: 161.7–163.0° C.

$^1$H NMR (400 MHz, DMSO-d$_6$) δ: 2.31 (2H, d, J=2.0 Hz), 3.34 (4H, t, J=5.2 Hz), 3.83 (4H, t, J=5.4 Hz), 4.47 (2H, s), 5.39 (2H, s), 7.23–7.40 (6H, m), 7.73–7.77 (1H, m), 7.82 (1H, dd, J=1.7, 7.3 Hz), 8.47 (1H, s).

IR (KBr) cm$^{-1}$: 1602, 1503, 1239, 1088.

Mass m/z: 393 (M$^+$-H$_2$O).

Example 130

Preparation of 2-benzyl-4-dimethylaminomethyl-6-(4-fluoro-3-methylphenyl)-2H-pyridazin-3-one Following the procedure of Example 7, 2-benzyl-6-(4-fluoro-3-methylphenyl)-4-methanesulfonyloxymethyl-2H-pyridazin-3-one and dimethylamine were reacted to yield the title compound as a yellow oil (yield: 92.7%).

$^1$H NMR (400 MHz, CDCl$_3$) δ: 2.34 (9H, s), 3.49 (2H, s), 5.40 (2H, s), 7.06 (1H, t, J=8.9 Hz), 7.25–7.35 (3H, m), 7.49 (2H, d, J=7.4 Hz), 7.58–7.67 (2H, m), 7.75 (1H, s).

Example 131

Preparation of 2-benzyl-4-dimethylaminomethyl-6-(4-fluoro-3-methylphenyl)-2H-pyridazin-3-one hydrochloride Following the procedure of Example 4, 2-benzyl-4-dimethylaminomethyl-6-(4-fluoro-3-methylphenyl)-2H-pyridazin-3-one was reacted to yield the title compound as colorless flakes (yield: 72.6%).

Melting point: 225.3–226.0° C.

$^1$H NMR (400 MHz, DMSO-d$_6$) δ: 2.31 (3H, d, J=2.0 Hz), 2.81 (6H, s), 4.28 (2H, s), 5.39 (2H, s), 7.21–7.41 (6H, m), 7.73–7.78 (1H, m), 7.83 (1H, dd, J=2.2, 7.6 Hz), 8.52 (1H, s).

IR (KBr) cm$^{-1}$: 1652, 1610, 1506, 1240, 1126, 702.

Mass m/z: 351 (M$^+$).

Example 132

Preparation of 4-(4-tert-butoxycarbonyl-1-piperazinyl)methyl-2-cinnamyl-6-(4-fluoro-3-methylphenyl)-2H-pyridazin-3-one 1) Preparation of 2-cinnamyl-6-(4-fluoro-3-methylphenyl)-4-methoxycarbonyl-2H-pyridazin-3-one Following the procedure of Example 1(6), 6-(3-fluoro-4-methylphenyl)-4-methoxycarbonyl-2H-pyridazin-3-one and cinnamyl bromide were reacted to yield the title compound as pale yellow needles (yield: 58.7%).

Melting point: 95.9–96.7° C.

$^1$H NMR (400 MHz, CDCl$_3$) δ: 2.35 (3H, d, J=1.7 Hz), 3.99 (3H, s), 5.04 (2H, dd, J=1.2, 6.8 Hz), 6.45 (1H, dt, J=15.9, 6.8 Hz), 6.75 (1H, d, J=15.9 Hz), 7.10 (1H, dd, J=8.9, 8.9 Hz), 7.20–7.33 (3H, m), 7.39 (2H, d, J=7.1 Hz), 7.58–7.66 (2H, m), 8.23 (1H, s).

IR (KBr) cm$^{-1}$: 1724, 1661, 1603, 1501, 1292, 1234, 1123.

Mass m/z: 378 (M$^+$).

2) Preparation of 4-carboxy-2-cinnamyl-6-(4-fluoro-3-methylphenyl)-2H-pyridazin-3-one Following the procedure of Example 1(7), 2-cinnamyl-6-(4-fluoro-3-methylphenyl)-4-methoxycarbonyl-2H-pyridazin-3-one was reacted to yield the title compound as pale yellow needles (yield: 85.1%).

Melting point: 142.8–143.6° C.

$^1$H NMR (400 MHz, CDCl$_3$) δ: 2.36 (3H, d, J=2.0 Hz), 5.12 (2H, dd, J=11.2, 6.8 Hz), 6.42 (1H, dt, J=15.9, 6.8 Hz), 6.80 (1H, d, J=15.9 Hz), 7.13 (1H, dd, J=8.8, 8.8 Hz), 7.22–7.36 (3H, m), 7.40–7.43 (2H, m), 7.65–7.72 (2H, m), 8.64 (1H, s), 14.04 (1H, br).

IR (KBr) cm$^{-1}$: 3438, 3061, 2688, 1747, 1637, 1567, 1463, 1244.

Mass m/z: 364 (M$^+$).

3) Preparation of 2-cinnamyl-6-(4-fluoro-3-methylphenyl)-4-hydroxymethyl-2H-pyridazin-3-one Following the procedure of Example 1(8), 4-carboxy-2-cinnamyl-6-(4-fluoro-3-methylphenyl)-2H-pyridazin-3-one was reacted to yield the title compound as slightly yellow needles (yield: 20.1%).

Melting point: 139.9–140.9° C.

$^1$H NMR (400 MHz, CDCl$_3$) δ: 2.34 (3H, d, J=1.5 Hz), 3.00 (1H, br), 4.73 (2H, s), 5.01 (2H, d, J=6.6 Hz), 6.44 (1H, dt, J=15.9, 6.6 Hz), 6.72 (2H, d, J=15.9 Hz), 7.08 (1H, dd, J=8.9, 8.9 Hz), 7.24 (1H, t, J=7.3 Hz), 7.30 (2H, dd, J=7.3, 7.3 Hz), 7.39 (2H, d, J=7.3 Hz), 7.58–7.62 (1H, m), 7.64 (1H, d, J=7.3 Hz), 7.67 (1H, s).

IR (KBr) cm$^{-1}$: 3393, 1655, 1648, 1602, 1505, 1451, 1238, 1077.

Mass m/z: 350 (M$^+$).

4) Preparation of 2-cinnamyl-6-(4-fluoro-3-methylphenyl)-4-methanesulfonyloxymethyl-2H-pyridazin-3-one Following the procedure of Example 1(9), 2-cinnamyl-6-(4-fluoro-3-methylphenyl)-4-hydroxymethyl-2H-pyridazin-3-one was reacted to yield the title compound as colorless needles (yield: 91.9%).

Melting point: 78.4–80.5° C.

$^1$H NMR (400 MHz, CDCl$_3$) δ: 2.35 (3H, d, J=2.0 Hz), 3.17 (3H, s), 5.10 (2H, dd, J=1.2, 6.8 Hz), 5.28 (2H, d, J=1.2 Hz), 6.42 (1H, dt, J=15.9, 6.8 Hz), 6.73 (1H, d, J=15.9 Hz), 7.09 (1H, dd, J=8.9, 8.9 Hz), 7.21–7.33 (3H, m), 7.40 (2H, d, J=8.8 Hz), 7.57–7.62 (1H, m), 7.64 (1H, d, J=8.8 Hz), 7.77 (1H, t, J=1.3 Hz).

IR (KBr) cm$^{-1}$: 1663, 1612, 1508, 1355, 1241, 1167, 988, 958, 873.

Mass m/z: 428 (M$^+$).

5) Preparation of 4-(4-tert-butoxycarbonyl-1-piperazinyl)methyl-2-cinnamyl-6-(4-fluoro-3-methylphenyl)-2H-pyridazin-3-one Following the procedure of Example 1(10), 2-cinnamyl-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 86.7%).

$^1$H NMR (400 MHz, CDCl$_3$) δ: 1.47 (9H, s), 2.35 (3H, d, J=1.6 Hz), 2.52 (4H, t, J=5.0 Hz), 3.51 (4H, t, J=4.9 Hz), 3.59 (2H, d, J=1.4 Hz), 5.00 (2H, dd, J=1.0, 6.6 Hz), 6.45 (1H, dt, J=15.8, 6.6 Hz), 6.72 (1H, d, J=15.8 Hz), 7.08 (1H, dd, J=8.9, 8.9 Hz), 7.22 (1H, t, J=7.2 Hz), 7.29 (2H, dd, J=7.0, 7.0 Hz), 7.38 (2H, d, J=7.7 Hz), 7.56–7.61 (1H, m), 7.65 (1H, dd, J=1.8, 7.2 Hz), 7.77 (1H, s).

Example 133

Preparation of 2-cinnamyl-6-(4-fluoro-3-methylphenyl)-4-(1-piperazinyl)methyl-2H-pyridazin-3-one dihydrochloride Following the procedure of Example 2, 4-(4-tert-butoxycarbonyl-1-piperazinyl)methyl-2-cinnamyl-6-(4-fluoro-3-methylphenyl)-2H-pyridazin-3-one was reacted to yield the title compound as a colorless crystalline powder (yield: 96.0%).

Melting point: 171.1–187.1° C. (dec.)

$^1$H NMR (400 MHz, DMSO-d$_6$) δ: 2.31 (3H, d, J=2.0 Hz), 3.21 (4H, t, J=4.9 Hz), 3.34 (4H, t, J=5.1 Hz), 3.99 (2H, s), 4.95 (2H, dd, J=1.3, 6.4 Hz), 6.45 (1H, dt, J=16.1, 6.3 Hz), 6.68 (1H, d, J=16.1 Hz), 7.20–7.26 (2H, m), 7.29–7.34 (2H, m), 7.41–7.45 (2H, m), 7.73–7.79 (1H, m), 7.83 (1H, dd, J=1.7, 7.3 Hz), 8.26 (1H, s).

IR (KBr) cm$^{-1}$: 1656, 1605, 1505, 1239, 962.

Mass m/z: 418 (M$^+$).

Example 134

Preparation of 2-cinnamyl-6-(4-fluoro-3-methylphenyl)-4-(4-methyl-1-piperazinyl)methyl-2H-pyridazin-3-one Following the procedure of Example 1(10), 2-cinnamyl-6-(4-fluoro-3-methylphenyl)-4-methanesulfonyloxymethyl-2H-pyridazin-3-one and 1-methylpiperazine were reacted to yield the title compound as a yellow oil (yield: 80.1%).

$^1$H NMR (400 MHz, CDCl$_3$) δ: 2.32 (3H, s), 2.35 (3H, d, J=1.8 Hz), 2.51 (4H, br), 2.62 (4H, br), 3.59 (2H, d, J=1.4 Hz), 4.99 (2H, dd, J=1.1, 6.6 Hz), 6.45 (1H, dt, J=15.8, 6.0 Hz), 6.72 (1H, d, J=15.8 Hz), 7.08 (1H, dd, J=8.9, 8.9 Hz), 7.22 (1H, tt, J=11.6, 7.2 Hz), 7.29 (2H, dd, J=7.2, 7.2 Hz), 7.39 (2H, dd, J=1.4, 7.2 Hz), 7.56–7.61 (1H, m), 7.65 (1H, dd, J=1.8, 7.2 Hz), 7.75 (1H, t, J=11.4 Hz).

Example 135

Preparation of 2-cinnamyl-6-(4-fluoro-3-methylphenyl)-4-(4-methyl-1-piperazinyl)methyl-2H-pyridazin-3-one dihydrochloride Following the procedure of Example 4, 2-cinnamyl-6-(4-fluoro-3-methylphenyl)-4-(4-methyl-1-piperazinyl)methyl-2H-pyridazin-3-one was reacted to yield the title compound as a colorless crystalline powder (yield: 66.3%).

Melting point: 236.1–237.1° C.

$^1$H NMR (400 MHz, DMSO-d$_6$) δ: 2.32 (3H, d, J=2.2 Hz), 2.76 (3H, s), 3.08 (4H, br), 3.32 (4H, br), 3.83 (2H, s), 4.94 (2H, dd, J=1.2, 6.4 Hz), 6.45 (1H, dt, J=16.1, 6.3 Hz), 6.67 (1H, d, J=15.8 Hz), 7.19–7.26 (2H, m), 7.29–7.34 (2H, m), 7.41–7.44 (2H, m), 7.71–7.76 (1H, m), 7.81 (1H, dd, J=2.2, 7.6 Hz), 8.07 (1H, s).

IR (KBr) cm$^{-1}$: 1652, 1607, 1505, 1239, 1129.

Mass m/z: 432 (M$^+$).

Example 136

Preparation of 4-N,N-bis(2-hydroxyethyl)aminomethyl-2-cinnamyl-6-(4-fluoro-3-methylphenyl)-2H-pyridazin-3-one Following the procedure of Example 1(10), 2-cinnamyl-6-(4-fluoro-3-methylphenyl)-4-methanesulfonyloxymethyl-2H-pyridazin-3-one and diethanolamine were reacted to yield the title compound as a yellow oil (yield: 83.7%).

$^1$H NMR (400 MHz, CDCl$_3$) δ: 2.32 (3H, s), 2.69 (4H, t, J=4.9 Hz), 3.65 (4H, d, J=4.9 Hz), 3.69 (2H, s), 4.98 (2H, d, J=6.6 Hz), 6.41 (1H, dt, J=15.8, 6.5 Hz), 6.68 (1H, d, J=15.8 Hz), 7.05 (1H, dd, J=8.9, 8.9 Hz), 7.21 (1H, t, J=7.2 Hz), 7.28 (2H, dd, J=7.2, 7.2 Hz), 7.37 (2H, d, J=7.6 Hz), 7.58–7.63 (1H, m), 7.66 (1H, dd, J=1.8, 7.2 Hz), 7.81 (1H, s).

Example 137

Preparation of 4-N,N-bis(2-hydroxyethyl)aminomethyl-2-cinnamyl-6-(4-fluoro-3-methylphenyl)-2H-pyridazin-3-one hydrochloride Following the procedure of Example 4, 4-N,N-bis(2-hydroxyethyl)aminomethyl-2-cinnamyl-6-(4-fluoro-3- methyl-phenyl)-2H-pyridazin-3-one was reacted to yield the title compound as a colorless crystalline powder (yield: 63.2%).

Melting point: 112.5–113.2° C.

¹H NMR (400 MHz, DMSO-d₆) δ: 2.32 (3H, d, J=1.9 Hz), 3.35 (4H, t, J=5.1 Hz), 3.84 (4H, t, J=5.1 Hz), 4.46 (2H, s), 4.98 (2H, dd, J=1.5, 6.1 Hz), 6.45 (1H, dt, J=15.8, 6.1 Hz), 6.69 (1H, d, J=16.0 Hz), 7.21–7.27 (2H, m), 7.29–7.34 (2H, m), 7.41–7.44 (2H, m), 7.757.80 (1H, m), 7.85 (1H, dd, J=2.0, 7.3 Hz), 8.47 (1H, s).

IR (KBr) cm⁻¹: 1652, 1604, 1505, 1241, 971.

Mass m/z: 419 (M⁺-H₂O).

Example 138

Preparation of 2-cinnamyl-4-dimethylaminomethyl-6-(4-fluoro-3-methylphenyl)-2H-pyridazin-3-one Following the procedure of Example 7, 2-cinnamyl-6-(4-fluoro-3-methylphenyl)-4-methanesulfonyloxymethyl-2H-pyridazin-3-one and dimethylamine were reacted to yield the title compound as a yellow oil (yield: 90.9%).

¹H NMR (400 MHz, CDCl₃) δ: 2.34 (3H, d, J=2.0 Hz), 2.36 (6H, s), 3.51 (2H, d, J=1.4 Hz), 5.00 (2H, dd, J=1.3, 6.8 Hz), 6.46 (1H, dt, J=15.8, 6.6 Hz), 6.72 (1H, d, J=15.8 Hz), 7.07 (1H, dd, J=8.9, 8.9 Hz), 7.22 (1H, tt, J=1.4, 7.2 Hz), 7.29 (2H, dd, J=7.2, 7.2 Hz), 7.39 (2H, dd, J=1.6, 7.0 Hz), 7.60–7.65 (1H, m), 7.67 (1H, dd, J=2.2, 7.2 Hz), 7.76 (1H, s).

Example 139

Preparation of 2-cinnamyl-4-dimethylaminomethyl-6-(4-fluoro-3-methylphenyl)-2H-pyridazin-3-one hydrochloride Following the procedure of Example 4, 2-cinnamyl-4-dimethylaminomethyl-6-(4-fluoro-3-methylphenyl)-2H-pyridazin-3-one was reacted to yield the title compound as a colorless crystalline powder (yield: 81.1%).

Melting point: 183.6–184.5° C.

¹H NMR (400 MHz, DMSO-d₆) δ: 2.32 (3H, d, J=2.0 Hz), 2.83 (6H, s), 4.29 (2H, s), 4.98 (2H, dd, J=11.3, 6.4 Hz), 6.46 (1H, dt, J=16.1, 6.3 Hz), 6.69 (1H, d, J=16.1 Hz), 7.22–7.27 (2H, m), 7.297.35 (2H, m), 7.41–7.44 (2H, m), 7.76–7.81 (1H, m), 7.86 (1H, dd, J=2.2, 7.3 Hz), 8.50 (1H, s).

IR (KBr) cm⁻¹: 1652, 1607, 1505, 1240, 965.

Mass m/z: 377 (M⁺).

Example 140

Preparation of 4-(4-tert-butoxycarbonyl-1-piperazinyl)methyl-2-(4-chlorocinnamyl)-6-(4-fluoro-3-methylphenyl)-2H-pyridazin-3-one 1) Preparation of 2-(4-chlorocinnamyl)-6-(4-fluoro-3-methylphenyl)-4-methoxycarbonyl-2H-pyridazin-3-one Following the procedure of Example 1(6), 6-(3-fluoro-4-methylphenyl)-4-methoxycarbonyl-2H-pyridazin-3-one and 4-chlorocinnamyl chloride were reacted to yield the title compound as yellow needles (yield: 71.7%).

Melting point: 137.8–138.8° C.

¹H NMR (400 MHz, CDCl₃) δ: 2.35 (3H, d, J=1.7 Hz), 3.99 (3H, s), 5.03 (2H, d, J=6.6 Hz), 6.43 (1H, dt, J=15.6, 6.6 Hz), 6.70 (1H, d, J=15.6 Hz), 7.10 (1H, d, J=8.8 Hz), 7.27 (2H, d, J=8.8 Hz), 7.31 (2H, d, J=8.8 Hz), 7.58–7.63 (1H, m), 7.64 (1H, dd, J=2.1, 7.0 Hz), 8.24 (1H, s).

IR (KBr) cm⁻¹: 1724, 1709, 1667, 1506, 1291, 1236, 1126, 831.

Mass m/z: 412 (M⁺), 414 (M⁺).

2) Preparation of 4-carboxy-2-(4-chlorocinnamyl)-6-(4-fluoro-3-methylphenyl)-2H-pyridazin-3-one Following the procedure of Example 1(7), 2-(4-chlorocinnamyl)-6-(4-fluoro-3-methylphenyl)-4-methoxycarbonyl-2H-pyridazin-3-one was reacted to yield the title compound as a yellow crystalline powder (yield: 86.2%).

Melting point: 186.0–186.6° C.

¹H NMR (400 MHz, CDCl₃) δ: 2.36 (3H, d, J=2.0 Hz), 5.11 (2H, dd, J=1.2, 6.8 Hz), 6.39 (1H, dt, J=15.9, 6.8 Hz), 6.75 (1H, d, J=15.6 Hz), 7.13 (1H, dd, J=8.8, 8.8 Hz), 7.29 (2H, d, J=8.5 Hz), 7.33 (2H, d, J=8.5 Hz), 7.65–7.71 (2H, m), 8.64 (1H, s), 13.98 (1H, br).

IR (KBr) cm⁻¹: 3471, 1738, 1631, 1566, 1490, 1467, 1403, 1242, 812, 802.

Mass m/z: 398 (M⁺), 400 (M⁺).

3) Preparation of 2-(4-chlorocinnamyl)-6-(4-fluoro-3-methylphenyl)-4-hydroxymethyl-2H-pyridazin-3-one Following the procedure of Example 1(8), 4-carboxy-2-(4-chlorocinnamyl)-6-(4-fluoro-3-methylphenyl)-2H-pyridazin-3-one was reacted to yield the title compound as slightly yellow needles (yield: 17.2%).

Melting point: 131.8–133.1° C.

¹H NMR (400 MHz, CDCl₃) δ: 2.34 (3H, d, J=2.0 Hz), 4.73 (2H, d, J=1.2 Hz), 4.99 (2H, dd, J=1.0, 6.6 Hz), 6.40 (1H, dt, J=15.9, 6.6 Hz), 6.75 (1H, d, J=15.9 Hz), 7.08 (1H, dd, J=8.9, 8.9 Hz), 7.26 (2H, d, J=8.8 Hz), 7.31 (2H, d, J=8.8 Hz), 7.57–7.62 (1H, m), 7.64 (1H, dd, J=2.2, 7.3 Hz), 7.69 (1H, t, J=1.2 Hz).

IR (KBr) cm⁻¹: 3359, 1653, 1598, 1506, 1492, 1240, 1091, 1076.

Mass m/z: 384 (M⁺), 386 (M⁺).

4) Preparation of 2-(4-chlorocinnamyl)-6-(4-fluoro-3-methylphenyl)-4-methanesulfonyloxymethyl-2H-pyridazin-3-one Following the procedure of Example 1(9), 2-(4-chlorocinnamyl)-6-(4-fluoro-3-methylphenyl)-4-hydroxymethyl-2H-pyridazin-3-one was reacted to yield the title compound as colorless needles (yield: 94.9%).

Melting point: 117.8–119.5° C.

¹H NMR (400 MHz, CDCl₃) δ: 2.35 (3H, d, J=2.0 Hz), 3.17 (3H, s), 4.99 (2H, dd, J=1.2, 6.6 Hz), 5.28 (2H, d, J=1.2 Hz), 6.38 (1H, dt, J=15.9, 6.6 Hz), 6.75 (1H, d, J=15.9 Hz), 7.10 (1H, dd, J=8.8, 8.8 Hz), 7.27 (2H, d, J=8.5 Hz), 7.32 (2H, d, J=8.5. Hz), 7.57–7.65 (2H, m), 7.78 (1H, t, J=1.3 Hz).

IR (KBr) cm⁻¹: 1663, 1619, 1506, 1492, 1346, 1240, 1172, 960, 830.

Mass m/z: 462 (M⁺), 464 (M⁺).

5) Preparation of 4-(4-tert-butoxycarbonyl-1-piperazinyl)-methyl-2-(4-chlorocinnamyl)-6-(4-fluoro-3-methylphenyl)-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 87.9%).

¹H NMR (400 MHz, CDCl₃) δ: 1.47 (9H, s), 2.35 (3H, d, J=1.6 Hz), 2.52 (4H, t, J=4.9 Hz), 3.50 (4H, t, J=5.0 Hz), 3.59 (2H, d, J=1.2 Hz), 4.99 (2H, dd, J=1.0, 6.6 Hz), 6.42 (1H, dt, J=15.8, 6.6 Hz), 6.67 (1H, d, J=16.0 Hz), 7.09 (1H, dd, J=8.9, 8.9 Hz), 7.25 (2H, d, J=8.8 Hz), 7.31 (2H, d, J=8.6 Hz), 7.55–7.61 (1H, m), 7.64 (1H, dd, J=2.0, 7.2 Hz), 7.77 (1H, s).

Example 141

Preparation of 2-(4-chlorocinnamyl)-6-(4-fluoro-3-methylphenyl)-4-(1-piperazinyl)methyl-2H-pyridazin-3-one dihydrochloride Following the procedure of Example 2, 4-(4-tert-butoxycarbonyl-1-piperazinyl)methyl-2-(4- chlorocinnamyl)-6-(4-fluoro-3-methylphenyl)-2H-pyridazin-3-one was reacted to yield the title compound as a pale brown crystalline powder (yield: 84.7%).

Melting point: 186.7–197.0° C. (dec.)

$^1$H NMR (400 MHz, DMSO-d$_6$) δ: 2.31 (3H, d, J=2.0 Hz), 3.15 (4H, br), 3.31 (4H, t, J=5.2 Hz), 3.94 (2H, s), 4.95 (2H, dd, J=11.3, 6.3 Hz), 6.47 (1H, dt, J=15.9, 6.1 Hz), 6.66 (1H, d, J=15.9 Hz), 7.22 (1H, dd, J=9.0, 9.0 Hz), 7.34 (2H, d, J=8.6 Hz), 7.45 (2H, d, J=8.6 Hz), 7.73–7.78 (1H, m), 7.82 (1H, dd, J=1.9, 7.6 Hz), 8.21 (1H, s).

IR (KBr) cm$^{-1}$: 1656, 1606, 1240, 1090, 964.

Mass m/z: 452 (M$^+$), 454 (M$^+$).

Example 142

Preparation of 2-(4-chlorocinnamyl)-6-(4-fluoro-3-methylphenyl)-4-(4-methyl-1-piperazinyl)methyl-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and 1-methylpiperazine were reacted to yield the title compound as a yellow oil (yield: 71.8%).

$^1$H NMR (400 MHz, CDCl$_3$) δ: 2.32 (3H, s), 2.35 (3H, s), 2.51 (4H, br), 2.62 (4H, br), 3.59 (2H, s), 4.99 (2H, d, J=6.6 Hz), 6.42 (1H, dt, J=15.8, 6.4 Hz), 6.66 (1H, d, J=15.9 Hz), 7.09 (1H, dd, J=8.9, 8.9 Hz), 7.24 (2H, d, J=8.6 Hz), 7.30 (2H, d, J=8.6 Hz), 7.56–7.62 (1H, m), 7.65 (1H, dd, J=1.8, 7.2 Hz), 7.76 (1H, s).

Example 143

Preparation of 2-(4-chlorocinnamyl)-6-(4-fluoro-3-methylphenyl)-4-(4-methyl-1-piperazinyl)methyl-2H-pyridazin-3-one dihydrochloride Following the procedure of Example 4, 2-(4-chlorocinnamyl)-6-(4-fluoro-3-methylphenyl)-4-(4-methyl-1-piperazinyl)methyl-2H-pyridazin-3-one was reacted to yield the title compound as a colorless crystalline powder (yield: 80.4%).

Melting point: 229.7–243.3° C. (dec.)

$^1$H NMR (400 MHz, DMSO-d$_6$) δ: 2.31 (3H, d, J=1.8 Hz), 2.76 (3H, s), 3.09 (4H, br), 3.33 (4H, br), 3.83 (2H, s), 4.94 (2H, dd, J=1.2, 6.0 Hz), 6.42 (1H, dt, J=16.0, 6.2 Hz), 6.65 (1H, d, J=16.0 Hz), 7.22 (1H, dd, J=9.1, 9.1 Hz), 7.34 (2H, d, J=8.6 Hz), 7.45 (2H, d, J=8.6 Hz), 7.71–7.76 (1H, m), 7.80 (1H, dd, J=2.2, 7.0 Hz), 8.08 (1H, s).

IR (KBr) cm$^{-1}$: 1652, 1608, 1492, 1239, 1130.

Mass m/z: 466 (M$^+$), 468 (M$^+$).

Example 144

Preparation of 4-N,N-bis(2-hydroxyethyl)aminomethyl-2-(4-chlorocinnamyl)-6-(4-fluoro-3-methylphenyl)-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and diethanolamine were reacted to yield the title compound as a yellow oil (yield: 76.6%).

$^1$H NMR (400 MHz, CDCl$_3$) δ: 2.33 (3H, s), 2.70 (4H, t, J=4.5 Hz), 3.66 (4H, t, J=4.9 Hz), 3.70 (2H, s), 4.98 (2H, d, J=6.6 Hz), 6.36 (1H, dt, J=15.8, 6.5 Hz), 6.63 (1H, d, J=15.8 Hz), 7.06 (1H, dd, J=8.6, 8.6 Hz), 7.24 (2H, d, J=8.6 Hz), 7.30 (2H, d, J=8.2 Hz), 7.58–7.63 (1H, m), 7.65 (1H, dd, J=1.8, 7.2 Hz), 7.78 (1H, s).

Example 145

Preparation of 4-N,N-bis(2-hydroxyethyl)aminomethyl-2-(4-chlorocinnamyl)-6-(4-fluoro-3-methylphenyl)-2H-pyridazin-3-one hydrochloride Following the procedure of Example 4, 4-N,N-bis(2-hydroxyethyl)aminomethyl-2-(4-chlorocinnamyl)-6-(4-fluoro-3-methylphenyl)-2H-pyridazin-3-one was reacted to yield the title compound as a colorless crystalline powder (yield: 76.1%).

Melting point: 151.9–153.4° C.

$^1$H NMR (400 MHz, DMSO-d$_6$): 2.32 (3H, d, J=1.7 Hz), 3.35 (4H, t, J=5.1 Hz), 3.83 (4H, t, J=5.4 Hz), 4.46 (2H, s), 4.97 (2H, dd, J=1.2, 6.1 Hz), 6.48 (1H, dt, J=15.9, 6.2 Hz), 6.67 (1H, d, J=15.9 Hz), 7.24 (1H, dd, J=9.1, 9.1 Hz), 7.35 (2H, d, J=8.8 Hz), 7.45 (2H, d, J=8.6 Hz), 7.75–7.80 (1H, m), 7.85 (1H, dd, J=1.7, 7.9 Hz), 8.48 (1H, s).

IR (KBr) cm$^{-1}$: 1652, 1604, 1492, 1240, 1090, 968.

Mass m/z: 440 (M$^+$), 442 (M$^+$).

Example 146

Preparation of 2-(4-chlorocinnamyl)-4-dimethylamino-methyl-6-(4-fluoro-3-methylphenyl)-2H-pyridazin-3-one Following the procedure of Example 7, 2-(4-chlorocinnamyl)-6-(4-fluoro-3-methylphenyl)-4-methanesulfonyloxymethyl-2H-pyridazin-3-one was reacted to yield the title compound as a yellow oil (yield: 84.6%).

$^1$H NMR (400 MHz, CDCl$_3$) δ: 2.33 (3H, d, J=1.6 Hz), 2.36 (6H, s), 3.52 (2H, d, J=1.2 Hz), 4.99 (2H, dd, J=1.0, 6.6 Hz), 6.43 (1H, dt, J=15.8, 6.6 Hz), 6.66 (1H, d, J=15.8 Hz), 7.07 (1H, dd, J=8.9, 8.9 Hz), 7.24 (2H, d, J=8.6 Hz), 7.30 (2H, d, J=8.6 Hz), 7.60–7.68 (2H, m), 7.77 (1H, s).

Example 147

Preparation of 2-(4-chlorocinnamyl)-4-dimethylamino-methyl-6-(4-fluoro-3-methylphenyl)-2H-pyridazin-3-one hydrochloride Following the procedure of Example 4, 2-(4-chlorocinnamyl)-4-dimethylaminomethyl-6-(4-fluoro-3-methylphenyl)-2H-pyridazin-3-one was reacted to yield the title compound as a colorless crystalline powder (yield: 34.4%).

Melting point: 201.3–201.9° C.

$^1$H NMR (400 MHz, DMSO-d$_6$) δ: 2.32 (3H, d, J=1.7 Hz), 2.83 (6H, s), 4.28 (2H, s), 4.98 (2H, dd, J=1.3, 6.1 Hz), 6.48 (1H, dt, J=16.1, 6.1 Hz), 6.67 (1H, d, J=16.1 Hz), 7.24 (1H, dd, J=9.3, 9.3 Hz), 7.35 (2H, d, J=8.6 Hz), 7.45 (2H, d, J=8.6 Hz), 7.75–7.80 (1H, m), 7.85 (1H, dd, J=2.3, 7.6 Hz), 8.47 (1H, s).

IR (KBr) cm$^{-1}$: 1652, 1608, 1491, 1239, 968.

Mass m/z: 411 (M$^+$), 413 (M$^+$).

Example 148

Preparation of 2-cyclopropylmethyl-4-(4-methyl-1-piperazinyl)methyl-6-[4-(methylthio)phenyl]-2H-pyridazin-3-one 1) Preparation of 4-carboxy-2-cyclopropylmethyl-6-[4-(methylthio)phenyl]-2H-pyridazin-3-one Following the procedure of Example 1(7), 2-cyclopropylmethyl-4-methoxycarbonyl-6-[4-

(methylthio)-phenyl]-2H-pyridazin-3-one was reacted to yield the title compound as a yellow crystalline powder (yield: 98.2%).

$^1$H NMR (400 MHz, CDCl$_3$): 0.50–0.66 (4H, m), 1.40–1.53 (1H, m), 2.54 (3H, s), 4.24 (2H, d, J=7.4 Hz), 7.34 (2H, d, J=8.6 Hz), 7.78 (2H, d, J=8.6 Hz), 8.66 (1H, s), 14.22 (1H, s).

IR (KBr) cm$^{-1}$: 3430, 1752, 1631, 1472, 1452, 1403, 1093, 825.

Mass m/z: 316 (M$^+$).

2) Preparation of 2-cyclopropylmethyl-4-hydroxymethyl-6-[4-(methylthio)-phenyl]-2H-pyridazin-3-one Following the procedure of Example 1(8), 4-carboxy-2-cyclopropylmethyl-6-[4-(methylthio)phenyl]-2H-pyridazin-3-one was reacted to yield the title compound as a pale yellow crystalline powder (yield: 22.6%).

$^1$H NMR (400 MHz, CDCl$_3$) δ: 0.45–0.60 (4H, m), 1.37–1.46 (1H, m), 2.53 (3H, s), 3.09 (1H, t, J=6.1 Hz), 4.11 (2H, d, J=7.2 Hz), 4.72 (2H, d, J=6.0 Hz), 7.32 (2H, d, J=8.6 Hz), 7.67 (1H, s), 7.74 (2H, d, J=8.6 Hz).

IR (KBr) cm$^{-1}$: 3393, 1657, 1602, 1514, 1095, 822.

Mass m/z: 302 (M$^+$).

3) Preparation of 2-cyclopropylmethyl-4-methanesulfonyloxy-methyl-6-[4-(m ethylthio)phenyl]-2H-pyridazin-3-one Following the procedure of Example 1(9), 2-cyclopropylmethyl-4-hydroxymethyl-6-[4-(methylthio)phenyl]-2H-pyridazin-3-one was reacted to yield the title compound as pale yellow fine-needles (yield: 78.6%).

$^1$H NMR (400 MHz, CDCl$_3$) δ: 0.45–1.61 (4H, m), 1.37–1.47 (1H, m), 2.53 (3H, s), 3.17 (3H, s), 4.11 (2H, d, J=7.2 Hz), 5.28 (2H, s), 7.33 (2H, d, J=8.4 Hz), 7.74 (2H, d, J=8.4 Hz), 7.79 (1H, s).

IR (KBr) cm$^{-1}$: 3446, 1652, 1607, 1359, 1178, 1024, 829.

Mass m/z: 380 (M$^+$).

4) Preparation of 2-cyclopropylmethyl-4-(4-methyl-1-piperazinyl)methyl-6-[4-(methylthio)phenyl]-2H-pyridazin-3-one Following the procedure of Example 1(10), 2-cyclopropylmethyl-4-methanesulfonyloxymethyl-6-[4-(methylthio)phenyl]-2H-pyridazin-3-one and 1-methylpiperazine were reacted to yield the title compound as a yellow oil (yield: 85.7%).

$^1$H NMR (400 MHz, CDCl$_3$) δ: 0.44–0.58 (4H, m), 1.36–1.48 (1H, m), 2.33 (3H, s), 2.53 (3H, s), 2.47–2.66 (8H, m), 3.59 (2H, s), 4.10 (2H, d, J=7.3 Hz), 7.33 (2H, d, J=8.3 Hz), 7.75 (2H, d, J=8.3 Hz), 7.78 (1H, s).

Example 149

Preparation of 2-cyclopropylmethyl-4-(4-methyl-1-piperazinyl)methyl-6-[4-(methylthio)phenyl]-2H-pyridazin-3-one dihydrochloride Following the procedure of Example 4, 2-cyclopropylmethyl-4-(4-methyl-1-piperazinyl)methyl-6-[4-(methylthio)-phenyl]-2H-pyridazin-3-one was reacted to yield the title compound as a colorless crystalline powder (yield: 69.1%).

Melting point: 234.6–239.2° C.

$^1$H NMR (400 MHz, DMSO-d$_6$) δ: 0.40–0.45 (2H, m), 0.50–0.56 (2H, m), 1.30–1.40 (1H, m), 2.53 (3H, s), 2.77 (3H, s), 2.97 (4H, br), 3.28 (4H, br), 3.72 (2H, s), 4.05 (2H, d, J=7.1 Hz), 7.39 (2H, d, J=8.6 Hz), 7.82 (2H, d, J=8.3 Hz), 7.96 (1H, s).

IR (KBr) cm$^{-1}$: 3438, 1651, 1606, 1402, 1095.

Mass m/z: 384 (M$^+$).

Example 150

Preparation of 4-N,N-bis(2-hydroxyethyl)aminomethyl-2-cyclopropylmethyl-6-[4-(methylthio)phenyl]-2H-pyridazin-3-one Following the procedure of Example 1(10), 2-cyclopropylmethyl-4-methanesulfonyloxymethyl-6-[4-(methylthio)phenyl]-2H-pyridazin-3-one and diethanolamine were reacted to yield the title compound as a yellow oil (yield: 78.9%).

$^1$H NMR (400 MHz, CDCl$_3$) δ: 0.44–0.59 (4H, m), 1.36–1.45 (1H, m), 2.53 (3H, s), 2.73 (4H, br), 3.67 (4H, t, J=4.9 Hz), 3.73 (2H, s), 4.13 (2H, d, J=7.3 Hz), 7.32 (2H, d, J=8.3 Hz), 7.70 (1H, s), 7.74 (2H, d, J=8.3 Hz).

Example 151

Preparation of 4-N,N-bis(2-hydroxyethyl)aminomethyl-2-cyclopropylmethyl-6-[4-(methylthio)phenyl]-2H-pyridazin-3-one hydrochloride Following the procedure of Example 4, 4-N,N-bis(2-hydroxyethyl)aminomethyl-2-cyclopropylmethyl-6-[4-(methylthio)phenyl]-2H-pyridazin-3-one was reacted to yield the title compound as a slightly yellow solid (yield: 75.1%).

Melting point: 169.2–171.7° C.

$^1$H NMR (400 MHz, DMSO-d$_6$) δ: 0.42–0.46 (2H, m), 0.52–0.57 (2H, m), 1.30–1.40 (1H, m), 2.53 (3H, s), 3.31 (4H, br), 3.81 (4H, t, J=5.3 Hz), 4.42 (2H, s), 7.41 (2H, d, J=8.8 Hz), 7.85 (2H, d, J=9.0 Hz), 8.37 (1H, s).

IR (KBr) cm$^{-1}$: 3242, 1652, 1604, 1420, 1094, 1059, 823.

Mass m/z: 358 (M$^+$-CH$_2$OH).

Example 152

Preparation of 2-cyclopropylmethyl-4-dimethylamino-methyl-6-[4-(methylthio)phenyl]-2H-pyridazin-3-one Following the procedure of Example 7, 2-cyclopropylmethyl-4-methanesulfonyloxymethyl-6-[4-(methylthio)phenyl]-2H-pyridazin-3-one was reacted to yield the title compound as a yellow oil (yield: 98.6%).

$^1$H NMR (400 MHz, CDCl$_3$) δ: 0.44–0.58 (4H, m), 1.36–1.48 (1H, m), 2.35 (6H, s), 3.51 (2H, s), 4.51 (2H, d, J=7.3 Hz), 7.31 (2H, d, J=8.3 Hz), 7.77 (2H, d, J=7.8 Hz), 7.78 (1H, s).

Example 153

Preparation of 2-cyclopropylmethyl-4-dimethylamino-methyl-6-[4-(methylthio)phenyl]-2H-pyridazin-3-one hydrochloride Following the procedure of Example 4, 2-cyclopropylmethyl-4-dimethylaminomethyl-6-[4-(methylthio)phenyl]-2H-pyridazin-3-one was reacted to yield the title compound as a pale yellow crystalline powder (yield: 75.5%).

Melting point: 230.2–232.3° C.

$^1$H NMR (400 MHz, DMSO-d$_6$) δ: 0.42–0.46 (2H, m), 0.52–0.58 (2H, m), 1.31–1.40 (1H, m), 2.53 (3H, s), 2.82 (6H, s), 4.09 (2H, d, J=7.1 Hz), 4.25 (2H, s), 7.41 (2H, d, J=8.6 Hz), 7.84 (2H, d, J=8.5 Hz), 8.34 (1H, s).

IR (KBr) cm$^{-1}$: 3435, 1646, 1604, 1402, 1093, 829.

Mass m/z: 329 (M$^+$).

Example 154

Preparation of 4-(4-tert-butoxycarbonyl-1-piperazinyl)methyl-2-isobutyl-6-[4-(methylthio)-phenyl]-2H-pyridazin-3-one 1) Preparation of 4-carboxy-2-isobutyl-6-[4-(methylthio)-phenyl]-2H-pyridazin-3-one To a solution of 4-methoxycarbonyl-6-[4-(methylthio)-phenyl]-2H-pyridazin-3-one (8.00 g, 29.0 mmol) in N,N-dimethylformamide (80 mL) were added potassium carbonate (8.02 g, 58.0 mmol) and isobutyl bromide (4.76 g, 34.8 mmol), and the mixture was stirred at 80° C. for 2 hours. The temperature of the reaction mixture was allowed to drop back to room temperature, and a saturated aqueous solution of sodium hydrogencarbonate was added. The mixture was then extracted with ethyl acetate. The extract was washed with brine, and dried over anhydrous sodium sulfate. The solvent was distilled off. Following the procedure of Example 1(7), the residue was reacted to yield the title compound as a yellow solid [yield: 65.1% (2 steps)].

$^1$H NMR (400 MHz, CDCl$_3$) δ: 1.01 (6H, d, J=6.6 Hz), 2.33–2.46 (1H, m), 2.54 (3H, s), 4.21 (2H, d, J=7.4 Hz), 7.34 (2H, d, J=8.4 Hz), 7.80 (2H, d, J=8.4 Hz), 8.68 (1H, s), 12.72 (1H, s).

Mass m/z: 318 (M$^+$).

2) Preparation of 4-hydroxymethyl-2-isobutyl-6-[4-(methylthio)phenyl]-2H-pyridazin-3-one Following the procedure of Example 1(8), 4-carboxy-2-isobutyl-6-[4-(methylthio)phenyl]-2H-pyridazin-3-one was reacted to yield the title compound as a yellow oil (yield: 35.3%).

$^1$H NMR (400 MHz, CDCl$_3$) δ: 0.98 (6H, d, J=6.6 Hz), 2.27–2.39 (1H, m), 2.53 (3H, s), 4.08 (2H, d, J=7.4 Hz), 4.71 (2H, d, J=5.9 Hz), 7.26 (2H, d, J=8.4 Hz), 7.66 (1H, s), 7.73 (2H, d, J=8.6 Hz).

3) Preparation of 2-isobutyl-4-methanesulfonyloxymethyl-6-[4-(methylthio)phenyl]-2H-pyridazin-3-one Following the procedure of Example 1(9), 4-hydroxymethyl-2-isobutyl-6-[4-(methylthio)phenyl]-2H-pyridazin-3-one was reacted to yield the title compound as a pale yellow crystalline powder (yield: 73.2%).

$^1$H NMR (400 MHz, CDCl$_3$) δ: 0.99 (6H, d, J=6.6 Hz), 2.28–2.40 (1H, m), 2.53 (3H, s), 3.17 (3H, s), 4.08 (2H, d, J=7.4 Hz), 5.27 (2H, d, J=1.2 Hz), 7.32 (2H, d, J=8.4 Hz), 7.73 (2H, d, J=8.4 Hz), 7.75 (1H, d, J=1.4 Hz).

Mass m/z: 382 (M$^+$).

4) Preparation of 4-(4-tert-butoxycarbonyl-1-piperazinyl)-methyl-2-isobutyl-6-[4-(methylthio)phenyl]-2H-pyridazin-3-one Following the procedure of Example 1(10), 2-isobutyl-6-4-methanesulfonyloxymethyl-6-[4-(methylthio)phenyl]-2H-pyridazin-3-one and tert-butyl 1-piperazinecarboxylate were reacted to yield the title compound as a yellow oil (yield: 88.0%).

$^1$H NMR (400 MHz, CDCl$_3$): 0.98 (6H, d, J=6.6 Hz), 1.47 (9H, s), 2.28–2.40 (1H, m), 2.50–2.55 (4H, m), 2.53 (3H, s), 3.50 (4H, t, J=4.8 Hz), 3.58 (2H, s), 4.07 (2H, d, J=7.4 Hz), 7.32 (2H, d, J=8.4 Hz), 7.73 (2H, d, J=8.6 Hz), 7.78 (1H, s).

Example 155

Preparation of 2-isobutyl-6-[4-(methylthio)phenyl]-4-(1-piperazinyl)methyl-2H-pyridazin-3-one dihydrochloride Following the procedure of Example 2, 4-(4-tert-butoxycarbonyl-1-piperazinyl)methyl-2-isobutyl-6-[4-(methylthio)phenyl]-2H-pyridazin-3-one was reacted to yield the title compound as a yellow crystalline powder (yield: 70.5%).

Melting point: 248.5–253.7° C. (dec.).

$^1$H NMR (400 MHz, DMSO-d$_6$) δ: 0.95 (6H, d, J=6.6 Hz), 2.21–2.33 (1H, m), 2.52 (3H, s), 3.10 (4H, t, J=4.8 Hz), 3.30 (4H, t, J=5.2 Hz), 3.90 (2H, s), 4.01 (2H, d, J=7.3 Hz), 7.39 (2H, d, J=8.3 Hz), 7.83 (2H, d, J=8.3 Hz), 8.15 (1H, s).

IR (KBr) cm-1: 2961, 2442, 1640, 1596, 1511, 1433, 1406, 1089, 912.

Mass m/z: 372 (M$^+$).

Example 156

Preparation of 2-isobutyl-4-(4-methyl-1-piperazinyl)-methyl-6-[4-(methylthio)phenyl]-2H-pyridazin-3-one Following the procedure of Example 1(10), 2-isobutyl-4-methanesulfonyloxymethyl-6-[4-(methylthio)phenyl]-2H-pyridazin-3-one and 1-methylpiperazine were reacted to yield the title compound as a yellow oil (yield: 68.3%).

$^1$H NMR (400 MHz, CDCl$_3$): 0.98 (6H, d, J=6.6 Hz), 2.29–2.39 (1H, m), 2.32 (3H, s), 2.51 (4H, br), 2.53 (3H, s), 2.62 (4H, br), 3.58 (2H, d, J=1.4 Hz), 4.07 (2H, d, J=7.4 Hz), 7.33 (2H, d, J=8.6 Hz), 7.74 (2H, d, J=6.8 Hz), 7.76 (1H, s).

Example 157

Preparation of 2-isobutyl-4-(4-methyl-1-piperazinyl)-methyl-6-[4-(methylthio)phenyl]-2H-pyridazin-3-one dihydrochloride Following the procedure of Example 4, 2-isobutyl-4-(4-methyl-1-piperazinyl)methyl-6-[4-(methylthio)phenyl]-2H-pyridazin-3-one was reacted to yield the title compound as a colorless crystalline powder (yield: 86.4%).

Melting point: 242.6–243.7° C.

$^1$H NMR (400 MHz, DMSO-d$_6$) δ: 0.94 (6H, d, J=6.6 Hz), 2.21–2.33 (1H, m), 2.52 (3H, s), 2.76 (3H, s), 3.09 (4H, br), 3.33 (4H, br), 3.83 (2H, s), 4.01 (2H, d, J=7.1 Hz), 7.39 (2H, d, J=8.6 Hz), 7.82 (2H, d, J=8.5 Hz), 8.07 (1H, s).

IR (KBr) cm$^{-1}$: 3432, 2957, 2437, 1652, 1607, 1090, 953.

Mass m/z: 386 (M$^+$).

Example 158

Preparation of 4-N,N-bis(2-hydroxyethyl) aminomethyl-2-isobutyl-6-[4-(methylthio)phenyl]-2H-pyridazin-3-one Following the procedure of Example 1(10), 2-isobutyl-4-methanesulfonyloxymethyl-6-[4-(methylthio)phenyl]-2H-pyridazin-3-one and diethanolamine were reacted to yield the title compound as a yellow oil (yield: 71.2%).

$^1$H NMR (400 MHz, CDCl$_3$) δ: 0.96 (6H, d, J=6.6 Hz), 2.27–2.39 (1H, m), 2.51 (3H, s), 2.71 (4H, t, J=5.1 Hz), 3.66 (4H, t, J=5.1 Hz), 3.70 (2H, s), 4.08 (2H, d, J=7.2 Hz), 7.30 (2H, d, J=8.6 Hz), 7.71–7.76 (3H, m).

Example 159

Preparation of 4-N,N-bis(2-hydroxyethyl) aminomethyl-2-isobutyl-6-[4-(methylthio)phenyl]-2H-pyridazin-3-one oxalate To a solution of 4-N,N-bis(2-hydroxyethyl)amino-methyl-2-isobutyl-6-[4-(methylthio)phenyl]-2H-pyridazin-3-one (69.7 mg, 0.18 mmol) in methanol (1 mL) was added at room temperature oxalic acid dihydrate (22.4 mg, 0.18 mmol). The solvent was distilled off. The residue was recrystallized from chloroform-diethyl ether to obtain the title compound as a white solid (59.5 mg, 69.4%).

Melting point: 116.4–118.1° C.

$^1$H NMR (400 MHz, DMSO-d$_6$) δ: 0.94 (6H, d, J=6.6 Hz), 2.20–2.33 (1H, m), 2.52 (3H, s), 2.91 (4H, t, J=5.8 Hz), 3.61

(4H, t, J=5.6 Hz), 3.94 (2H, s), 4.01 (2H, d, J=7.3 Hz), 7.39 (2H, d, J=8.6 Hz), 7.81 (2H, d, J=8.6 Hz), 8.14 (1H, s).

IR (KBr) cm$^{-1}$: 3344, 2927, 1659, 1611, 1402, 1049, 721.

Mass m/z: 360 (M$^+$-CH$_2$OH).

Example 160

Preparation of 4-dimethylaminomethyl-2-isobutyl-6-[4-(methylthio)phenyl]-2H-pyridazin-3-one Following the procedure of Example 7, 2-isobutyl-4-methanesulfonyloxymethyl-6-[4-(methylthio)phenyl]-2H-pyridazin-3-one was reacted to yield the title compound as a yellow oil (yield: 73.9%).

$^1$H NMR (400 MHz, CDCl$_3$) δ: 0.98 (6H, d, J=6.6 Hz), 2.29–2.41 (1H, m), 2.36 (6H, s), 2.52 (3H, s), 3.52 (2H, d, J=1.2 Hz), 4.07 (2H, d, J=7.4 Hz), 7.31 (2H, d, J=8.6 Hz), 7.77 (2H, d, J=8.4 Hz), 7.79 (1H, s).

Example 161

Preparation of 4-dimethylaminomethyl-2-isobutyl-6-[4-(methylthio)phenyl]-2H-pyridazin-3-one hydrochloride Following the procedure of Example 4, 4-dimethylaminomethyl-2-isobutyl-6-[4-(methylthio)phenyl]-2H-pyridazin-3-one was reacted to yield the title compound as a colorless crystalline powder (yield: 82.3%).

Melting point: 216.8–218.4° C.

$^1$H NMR (400 MHz, DMSO-d$_6$) δ: 0.96 (6H, d, J=6.8 Hz), 2.23–2.36 (1H, m), 2.53 (3H, s), 2.82 (6H, s), 4.05 (2H, d, J=7.1 Hz), 4.27 (2H, s), 7.41 (2H, d, J=8.3 Hz), 7.84 (2H, d, J=8.3 Hz), 8.42 (1H, s).

IR (KBr) cm$^{-1}$: 3485, 1740, 1684, 1253, 856, 577.

Mass m/z: 331 (M$^+$).

Example 162

Preparation of 2-isobutyl-6-[4-(methylthio)phenyl]-4-propargylaminomethyl-2H-pyridazin-3-one Following the procedure of Example 1(10), 2-isobutyl-4-methanesulfonyloxymethyl-6-[4-(methylthio)phenyl]-2H-pyridazin-3-one and propargylamine were reacted to yield the title compound as a yellow oil (yield: 52.2%).

$^1$H NMR (400 MHz, CDCl$_3$) δ: 0.98 (6H, d, J=6.6 Hz), 2.26 (1H, t, J=2.3 Hz), 2.29–2.40 (1H, m), 2.52 (3H, s), 3.51 (2H, d, J=2.4 Hz), 3.90 (2H, s), 4.07 (2H, d, J=7.4 Hz), 7.31 (2H, d, J=8.4 Hz), 7.70 (1H, s), 7.73 (2H, d, J=8.4 Hz).

Example 163

Preparation of 2-isobutyl-6-[4-(methylthio)phenyl]-4-propargylaminomethyl-2H-pyridazin-3-one hydrochloride Following the procedure of Example 4, 2-isobutyl-6-[4-(methylthio)phenyl]-4-propargylaminomethyl-2H-pyridazin-3-one was reacted to yield the title compound as a white solid (yield: 73.6%).

Melting point: 197.5–198.4° C.

$^1$H NMR (400 MHz, DMSO-d$_6$) δ: 0.96 (6H, d, J=6.6 Hz), 2.23–2.36 (1H, m), 2.53 (3H, s), 3.48 (1H, t, J=2.4 Hz), 3.95 (2H, d, J=2.4 Hz), 4.03 (2H, d, J=7.1 Hz), 4.17 (2H, s), 7.41 (2H, d, J=8.3 Hz), 7.82 (2H, d, J=8.6 Hz), 8.28 (1H, s).

IR (KBr) cm$^{-1}$: 3447, 3207, 2958, 2122, 1651, 1607, 1441, 1093.

Mass m/z: 341 (M$^+$).

Example 164

Preparation of 2-cyclopropylmethyl-4-(4-methyl-1-piperazinyl)methyl-6-[4-(methylsulfinyl)phenyl]-2H-pyridazin-3-one 1) Preparation of 2-cyclopropylmethyl-4-methanesulfonyloxy-methyl-6-[4-(methylthio)phenyl]-2H-pyridazin-3-one To a solution of 2-cyclopropylmethyl-4-methanesulfonyloxymethyl-6-[4-(methylthio)phenyl]-2H-pyridazin-3-one (300 mg, 0.79 mmol) in methylene chloride (10 mL) was added dropwise at −20° C. a solution of 3-chloroperbenzoic acid (204 mg, 1.12 mmol) in methylene chloride (2 mL), and at the same temperature, the mixture was stirred for 30 minutes. A 10% aqueous sodium hydrogensulfite was added to the reaction mixture, and then, the mixture was extracted with chloroform. The extract was successively washed with a saturated aqueous sodium hydrogencarbonate and brine, and was then dried over anhydrous sodium sulfate. The solvent was distilled off under reduced pressure. The residue was recrystallized from chloroform-hexane to yield the title compound as a colorless crystalline powder (139 mg, 44.5%).

$^1$H NMR (400 MHz, CDCl$_3$) δ: 0.48–0.63 (4H, m), 1.37–1.46 (1H, m), 2.77 (3H, s), 3.18 (3H, s), 4.14 (2H, d, J=7.3 Hz), 5.30 (2H, d, J=1.4 Hz), 7.76 (2H, d, J=8.6 Hz), 7.84 (1H, t, J=1.4 Hz), 7.98 (2H, d, J=8.8 Hz).

Mass m/z: 396 (M$^+$).

2) Preparation of 2-cyclopropylmethyl-4-(4-methyl-1-piperazinyl)methyl-6-[4-(methylsulfinyl)phenyl]-2H-pyridazin-3-one Following the procedure of Example 1(10), 2-cyclopropyl-4-methanesulfonyloxymethyl-6-[4-(methylsulfinyl)phenyl]-2H-pyridazin-3-one and 1-methylpiperazine were reacted to yield the title compound as a yellow oil (yield: 60.6%).

$^1$H NMR (400 MHz, CDCl$_3$) δ: 0.46–0.60 (4H, m), 1.37–1.49 (1H, m), 2.34 (3H, s), 2.54 (4H, br), 2.64 (4H, br), 2.78 (3H, s), 3.61 (2H, s), 4.13 (2H, d, J=7.2 Hz), 7.75 (2H, d, J=8.2 Hz), 7.84 (1H, s), 7.99 (2H, d, J=8.2 Hz).

Example 165

Preparation of 2-cyclopropylmethyl-4-(4-methyl-1-piperazinyl)methyl-6-[4-(methylsulfinyl)phenyl]-2H-pyridazin-3-one dihydrochloride Following the procedure of Example 4, 2-cyclopropylmethyl-4-(4-methyl-1-piperazinyl)methyl-6-[4-(methylsulfinyl)phenyl]-2H-pyridazin-3-one was reacted to yield the title compound as a colorless crystalline powder (yield: 64.3%).

Melting point: 80° C. (dec.)

$^1$H NMR (400 MHz, DMSO-d$_6$) δ: 0.41–0.57 (4H, m), 1.30–1.41 (1H, m), 2.76 (3H, s), 2.77 (3H, s), 3.01 (4H, br), 3.31 (4H, br), 3.77 (2H, s), 4.08 (2H, d, J=6.8 Hz), 7.80 (2H, d, J=8.3 Hz), 8.05–8.09 (3H, m).

IR (KBr) cm$^{-1}$: 3430, 3005, 1652, 1607, 1458, 1401, 1010, 838.

Mass m/z: 400 (M$^+$).

Example 166

Preparation of 2-isobutyl-4-(4-methyl-1-piperazinyl)-methyl-6-[4-(methylsulfinyl)phenyl]-2H-pyridazin-3-one 1) Preparation of 2-isobutyl-4-methanesulfonyloxymethyl-6-[4-(methylsulfinyl)phenyl]-2H-pyridazin-3-one Following the procedure of Example 164 (1), 2-isobutyl-4-methanesulfonyloxymethyl-6-[4-(methylthio)-phenyl]-2H-pyridazin-3-one was reacted to yield the title compound as a colorless crystalline powder (yield: 54.3%).

$^1$H NMR (400 MHz, CDCl$_3$) δ: 1.00 (6H, d, J=6.8 Hz), 2.29–2.41 (1H, m), 2.77 (3H, s), 3.18 (3H, s), 4.11 (2H, d, J=7.3 Hz), 5.29 (2H, d, J=1.5 Hz), 7.76 (2H, d, J=8.8 Hz), 7.83 (1H, t, J=1.2 Hz), 7.98 (2H, d, J=8.6 Hz).

Mass m/z: 398 (M$^+$).

2) Preparation of 2-isobutyl-4-(4-methyl-1-piperazinyl)-methyl-6-[4-(methylsulfinyl)phenyl]-2H-pyridazin-3-one Following the procedure of Example 1(10), 2-isobutyl-4-methanesulfonyloxymethyl-6-[4-(methylsulfinyl)phenyl]-2H-pyridazin-3-one and 1-methylpiperazine were reacted to yield the title compound as a yellow oil (yield: 61.8%).

$^1$H NMR (400 MHz, CDCl$_3$) δ: 0.99 (6H, d, J=6.6 Hz), 2.30–2.41 (1H, m), 2.34 (3H, s), 2.54 (4H, br), 2.64 (4H, br), 2.77 (3H, s), 3.60 (2H, s), 4.10 (2H, d, J=7.4 Hz), 7.75 (2H, d, J=8.2 Hz), 7.82 (1H, s), 7.99 (2H, d, J=8.2 Hz).

Example 167

Preparation of 2-isobutyl-4-(4-methyl-1-piperazinyl)-methyl-6-[4-(methylsulfinyl)phenyl]-2H-pyridazin-3-one dihydrochloride Following the procedure of Example 4, 2-isobutyl-4-(4-methyl-1-piperazinyl)methyl-6-[4-(methylsulfinyl)-phenyl]-2H-pyridazin-3-one was reacted to yield the title compound as a colorless crystalline powder (yield: 76.1%).

Melting point: 224.5–229.1° C. (dec.)

$^1$H NMR (400 MHz, DMSO-d$_6$) δ: 0.96 (6H, d, J=6.6 Hz), 2.22–2.35 (1H, m), 2.76 (3H, s), 2.77 (3H, s), 3.14 (4H, br), 3.35 (4H, br), 3.87 (2H, s), 4.04 (2H, d, J=7.1 Hz), 7.80 (2H, d, J=8.3 Hz), 8.07 (2H, d, J=8.3 Hz), 8.18 (1H, s).

IR (KBr) cm$^{-1}$: 3426, 2960, 1656, 1608, 1459, 1400, 1044, 1011.

Mass m/z: 402 (M$^+$).

Example 168

Preparation of 4-dimethylaminomethyl-2-isobutyl-6-[4-(methylsulfinyl)phenyl]-2H-pyridazin-3-one Following the procedure of Example 7, 2-isobutyl-4-methanesulfonyloxymethyl-6-[4-(methylsulfinyl)phenyl]-2H-pyridazin-3-one was reacted to yield the title compound as a yellow oil (yield: 46.2%).

$^1$H NMR (400 MHz, CDCl$_3$) δ: 0.99 (6H, d, J=6.8 Hz), 2.30–2.43 (1H, m), 2.38 (6H, s), 2.76 (3H, s), 3.54 (2H, s), 4.10 (2H, d, J=7.4 Hz), 7.74 (2H, d, J=8.2 Hz), 7.87 (1H, s), 8.02 (2H, d, J=8.2 Hz).

Example 169

Preparation of 4-dimethylaminomethyl-2-isobutyl-6-[4-(methylsulfinyl)phenyl]-2H-pyridazin-3-one hydrochloride Following the procedure of Example 4, 4-dimethylaminomethyl-2-isobutyl-6-[4-(methylsulfinyl)-phenyl]-2H-pyridazin-3-one was reacted to yield the title compound as a colorless crystalline powder (yield: 77.4%).

Melting point: 204.2–206.0° C.

$^1$H NMR (400 MHz, DMSO-d$_6$) δ: 0.97 (6H, d, J=6.6 Hz), 2.24–2.36 (1H, m), 2.78 (3H, s), 2.83 (6H, s), 4.07 (2H, d, J=7.1 Hz), 4.28 (2H, s), 7.82 (2H, d, J=8.3 Hz), 8.09 (2H, d, J=8.3 Hz), 8.49 (1H, s).

IR (KBr) cm$^{-1}$: 3438, 2961, 1652, 1607, 1467, 1400, 1047.

Mass m/z: 347 (M$^+$).

Example 170

Preparation of 2-cyclopropylmethyl-4-(4-methyl-1-piperazinyl)methyl-6-[4-(methylsulfonyl)phenyl]-2H-pyridazin-3-one 1) Preparation of 2-cyclopropylmethyl-4-methanesulfonyloxy-methyl-6-[4-(methylsulfonyl)phenyl]-2H-pyridazin-3-one To a solution of 2-cyclopropylmethyl-4-methanesulfonyloxymethyl-6-[4-(methylthio)phenyl]-2H-pyridazin-3-one (226 mg, 0.59 mmol) in methylene chloride (10 mL) was added dropwise at −20° C. a solution of 3-chloroperbenzoic acid (410 mg, 2.38 mmol) in methylene chloride (2 mL), and at the same temperature, the mixture was stirred for 30 minutes. A 10% aqueous sodium hydrogensulfite was added to the reaction mixture, and then, the mixture was extracted with chloroform. The extract was successively washed with a saturated aqueous sodium hydrogencarbonate and brine, and was then dried over anhydrous sodium sulfate. The solvent was distilled off under reduced pressure. The residue was recrystallized from chloroform-hexane to yield the title compound as a colorless crystalline powder (209 mg, 85.3%).

$^1$H NMR (400 MHz, CDCl$_3$):

0.46–0.63 (4H, m), 1.37–1.46 (1H, m), 3.10 (3H, s), 3.18 (3H, s), 4.20 (2H, d, J=7.3 Hz), 5.31 (2H, d, J=1.2 Hz), 7.86 (1H, t, J=1.2 Hz), 8.02 (2H, d, J=8.8 Hz), 8.06 (2H, d, J=9.0 Hz).

Mass m/z: 412 (M$^+$).

2) Preparation of 2-cyclopropylmethyl-4-(4-methyl-1-piperazinyl)methyl-6-[4-(methylsulfonyl)phenyl]-2H-pyridazin-3-one Following the procedure of Example 1(10), 2-cyclopropyl-4-methanesulfonyloxymethyl-6-[4-(methylsulfonyl)phenyl]-2H-pyridazin-3-one and 1-methylpiperazine were reacted to yield the title compound as a yellow oil (yield: 80.9%).

$^1$H NMR (400 MHz, CDCl$_3$) δ: 0.46–0.61 (4H, m), 1.38–1.48 (1H, m), 2.34 (3H, s), 2.54 (4H, br), 2.64 (4H, br), 3.10 (3H, s), 3.61 (2H, d, J=1.2 Hz), 4.13 (2H, d, J=7.1 Hz), 7.85 (1H, t, J=1.2 Hz), 8.03 (2H, d, J=9.0 Hz), 8.05 (2H, d, J=9.0 Hz).

Example 171

Preparation of 2-cyclopropylmethyl-4-(4-methyl-1-piperazinyl)methyl-6-[4-(methylsulfonyl)phenyl]-2H-pyridazin-3-one dihydrochloride Following the procedure of Example 4, 2-cyclopropyl-methyl-4-(4-methyl-1-piperazinyl)methyl-6-[4-(methylsulfonyl)phenyl]-2H-pyridazin-3-one was reacted to yield the title compound as a colorless crystalline powder (yield: 76.8%).

Melting point: 209.0–211.4° C.

$^1$H NMR (400 MHz, DMSO-d$_6$) δ: 0.41–0.46 (2H, m), 0.52–0.57 (2H, m), 1.31–1.41 (1H, m), 2.77 (3H, s), 3.04 (4H, br), 3.21 (3H, s), 3.31 (4H, br), 3.80 (2H, s), 4.09 (2H, d, J=7.1 Hz), 8.04 (2H, d, J=8.3 Hz), 8.12 (1H, s), 8.14 (2H, d, J=8.3 Hz).

IR (KBr) cm$^{-1}$: 3434, 3012, 1652, 1596, 1458, 1402, 1302, 1150.

Mass m/z: 416 (M$^+$).

Example 172

Preparation of 2-cyclopropylmethyl-4-dimethylamino-methyl-6-[4-(methylsulfonyl)phenyl]-2H-pyridazin-3-one Following the procedure of Example 1(10), 2-cyclopropylmethyl-4-methanesulfonyloxymethyl-6-[4-(methyl-sulfonyl)phenyl]-2H-pyridazin-3-one and dimethylamine were reacted to yield the title compound as a yellow oil (yield: 65.6%).

$^1$H NMR (400 MHz, CDCl$_3$) δ: 0.45–0.62 (4H, m), 1.39–1.49 (1H, m), 2.38 (6H, s), 3.09 (3H, s), 3.55 (2H, s), 4.14 (2H, d, J=7.2 Hz), 7.89 (1H, s), 8.02 (2H, d, J=8.4 Hz), 8.06 (2H, d, J=8.6 Hz).

Example 173

Preparation of 2-cyclopropylmethyl-4-dimethylamino-methyl-6-[4-(methylsulfonyl)phenyl]-2H-pyridazin-3-one hydrochloride Following the procedure of Example 4, 2-cyclopropyl-methyl-4-dimethylaminomethyl-6-[4-(methylsulfonyl)phenyl]-2H-pyridazin-3-one was reacted to yield the title compound as a colorless crystalline powder (yield: 63.4%).

Melting point: 239.5–240.7° C.

$^1$H NMR (400 MHz, DMSO-d$_6$) δ: 0.43–0.59 (4H, m), 1.33–1.43 (1H, m), 2.83 (6H, s), 3.23 (3H, s), 4.13 (2H, d, J=7.1 Hz), 4.29 (2H, s), 8.06 (2H, d, J=7.8 Hz), 8.17 (2H, d, J=8.3 Hz), 8.57 (1H, s).

IR (KBr) cm$^{-1}$: 3447, 2674, 1646, 1608, 1596, 1306, 1150, 777.

Mass m/z: 361 (M$^+$).

Example 174

Preparation of 4-(4-tert-butoxycarbonyl-1-piperazinyl)methyl-2-isobutyl-6-[4-(methyl-sulfonyl)phenyl]-2H-pyridazin-3-one 1) Preparation of 2-isobutyl-4-methanesulfonyloxymethyl-6-[4-(methylsulfonyl)phenyl]-2H-pyridazin-3-one Following the procedure of Example 170 (1), 2-isobutyl-4-methanesulfonyloxymethyl-6-[4-(methylthio)-phenyl]-2H-pyridazin-3-one was reacted to yield the title compound as a colorless crystalline powder (yield: 97.8%).

$^1$H NMR (400 MHz, CDCl$_3$) δ: 0.99 (6H, d, J=6.6 Hz), 2.29–2.41 (1H, m), 3.10 (3H, s), 3.18 (3H, s), 4.12 (2H, d, J=7.3 Hz), 5.29 (2H, d, J=1.2 Hz), 7.85 (1H, t, J=1.4 Hz), 8.02 (2H, d, J=8.8 Hz), 8.05 (2H, d, J=8.8 Hz).

Mass m/z: 414 (M$^+$).

2) Preparation of 4-(4-tert-butoxycarbonyl-1-piperazinyl)-methyl-2-isobutyl-6-[4-(methylsulfonyl)phenyl]-2H-pyridazin-3-one Following the procedure of Example 1(10), 2-isobutyl-4-methanesulfonyloxymethyl-6-[4-(methylsulfonyl)phenyl]-2H-pyridazin-3-one and tert-butyl 1-piperazinecarboxylate were reacted to yield the title compound as a yellow oil (yield: 75.9%).

$^1$H NMR (400 MHz, CDCl$_3$) δ: 0.99 (6H, d, J=6.6 Hz), 1.47 (9H, s), 2.29–2.41 (1H, m), 2.54 (4H, br), 3.09 (3H, s), 3.51 (4H, br), 3.60 (2H, s), 4.11 (2H, d, J=7.2 Hz), 7.86 (1H, s), 8.02 (2H, d, J=8.8 Hz), 8.05 (2H, d, J=8.8 Hz).

Example 175

Preparation of 2-isobutyl-6-[4-(methylsulfonyl)-phenyl]-4-(1-piperazinyl)methyl-2H-pyridazin-3-one dihydrochloride Following the procedure of Example 2, 4-(4-tert-butoxycarbonyl-1-piperazinyl)methyl-2-isobutyl-6-[4-(methylsulfonyl)phenyl]-2H-pyridazin-3-one was reacted to yield the title compound as a colorless crystalline powder (yield: 88.2%).

Melting point: 222.4–224.2° C.

$^1$H NMR (400 MHz, DMSO-d$_6$) δ: 0.96 (6H, d, J=6.8 Hz), 2.22–2.35 (1H, m), 3.06 (4H, br), 3.21 (3H, s), 3.28 (4H, t, J=5.2 Hz), 3.87 (2H, s), 4.05 (2H, d, J=7.1 Hz), 8.04 (2H, d, J=8.6 Hz), 8.14 (2H, d, J=8.3 Hz), 8.22 (1H, s).

IR (KBr) cm$^{-1}$: 3421, 2957, 1656, 1611, 1597, 1305, 1149, 961.

Mass m/z: 404 (M$^+$).

Example 176

Preparation of 2-isobutyl-4-(4-methyl-1-piperazinyl)-methyl-6-[4-(methylsulfonyl)phenyl]-2H-pyridazin-3-one Following the procedure of Example 1(10), 2-isobutyl-4-methanesulfonyloxymethyl-6-[4-(methylsulfonyl)phenyl]-2H-pyridazin-3-one and 1-methylpiperazine were reacted to yield the title compound as a yellow oil (yield: 88.5%).

$^1$H NMR (400 MHz, CDCl$_3$) δ: 0.99 (6H, d, J=6.8 Hz), 2.28–2.40 (1H, m), 2.37 (3H, s), 2.53 (4H, br), 2.63 (4H, br), 3.10 (3H, s), 3.60 (2H, s), 4.10 (2H, d, J=7.3 Hz), 7.84 (1H, s), 8.02 (2H, d, J=9.0 Hz), 8.05 (2H, d, J=8.8 Hz).

Example 177

Preparation of 2-isobutyl-4-(4-methyl-1-piperazinyl)-methyl-6-[4-(methylsulfonyl)phenyl]-2H-pyridazin-3-one dihydrochloride Following the procedure of Example 4, 2-isobutyl-4-(4-methyl-1-piperazinyl)methyl-6-[4-(methylsulfonyl)-phenyl]-2H-pyridazin-3-one was reacted to yield the title compound as a colorless crystalline powder (yield: 62.0%).

Melting point: 224.5–228.0° C.

$^1$H NMR (400 MHz, DMSO-d$_6$) δ: 0.95 (6H, d, J=6.8 Hz), 2.23–2.35 (1H, m), 2.76 (3H, s), 3.08 (4H, br), 3.21 (3H, s), 3.32 (4H, br), 3.83 (2H, s), 4.05 (2H, d, J=7.1 Hz), 8.04 (2H, d, J=8.3 Hz), 8.13 (2H, d, J=8.5 Hz), 8.15 (1H, s).

IR (KBr) cm$^{-1}$: 3447, 2958, 1652, 1610, 1596, 1319, 1152, 955.

Mass m/z: 418 (M$^+$).

Example 178

Preparation of 4-N,N-bis(2-hydroxyethyl)aminomethyl-2-isobutyl-6-[4-(methylsulfonyl)phenyl]-2H-pyridazin-3-one Following the procedure of Example 1(10), 2-isobutyl-4-methanesulfonyloxymethyl-6-[phenyl]-2H-pyridazin-3-one and diethanolamine were reacted to yield the title compound as a yellow oil (yield: 51.1%).

$^1$H NMR (400 MHz, CDCl$_3$) δ: 0.98 (6H, d, J=6.6 Hz), 2.28–2.40 (1H, m), 2.73 (4H, t, J=4.8 Hz), 3.08 (3H, s), 3.68 (4H, t, J=4.9 Hz), 3.73 (2H, s), 4.11 (2H, d, J=7.4 Hz), 7.93,(1H, s), 8.00 (2H, d, J=8.6 Hz), 8.05 (2H, d, J=8.8 Hz).

Mass m/z: 392 (M$^+$-CH$_2$OH).

Example 179

Preparation of 4-dimethylaminomethyl-2-isobutyl-6-[4-(methylsulfonyl)phenyl]-2H-pyridazin-3-one Following the procedure of Example 7, 2-isobutyl-4-methanesulfonyloxymethyl-6-[4-(methylsulfonyl)phenyl]-

2H-pyridazin-3-one was reacted to yield the title compound as a yellow oil (yield: 82.1%).

$^{1}$H NMR (400 MHz, CDCl$_3$) δ: 0.99 (6H, d, J=6.6 Hz), 2.30–2.41 (1H, m), 2.37 (6H, s), 3.09 (3H, s), 3.52 (2H, s), 4.11 (2H, d, J=7.2 Hz), 7.86 (1H, s), 8.02 (2H, d, J=8.8 Hz), 8.05 (2H, d, J=8.8 Hz).

Example 180

Preparation of 4-dimethylaminomethyl-2-isobutyl-6-[4-(methylsulfonyl)phenyl]-2H-pyridazin-3-one hydrochloride Following the procedure of Example 4, 4-dimethylaminomethyl-2-isobutyl-6-[4-(methylsulfonyl)-phenyl]-2H-pyridazin-3-one was reacted to yield the title compound as a colorless crystalline powder (yield: 58.6%).

Melting point: 221.4–223.3° C.

$^{1}$H NMR (400 MHz, DMSO-d$_6$) δ: 0.97 (6H, d, J=6.6 Hz), 2.25–2.36 (1H, m), 2.82 (6H, s), 3.22 (3H, s), 4.08 (2H, d, J=7.3 Hz), 4.28 (2H, s), 8.06 (2H, d, J=8.3 Hz), 8.15 (2H, d, J=8.5 Hz), 8.55 (1H, s).

IR (KBr) cm$^{-1}$: 3447, 2963, 1653, 1609, 1597, 1307, 1152, 777.

Mass m/z: 363 (M$^+$).

Example 181

Preparation of 2-cyclopropylmethyl-6-(3-fluoro-4-methoxyphenyl)-4-pyrrolidinomethyl-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and pyrrolidine were reacted to yield the title compound as a yellow oil (yield: 75.9%).

$^{1}$H NMR (400 MHz, CDCl$_3$) δ: 0.44–0.61 (4H, m), 1.42 (1H, m), 1.85–2.00 (4H, m), 2.70–3.00 (4H, m), 3.83 (2H, brs), 3.94 (3H, s), 4.10 (2H, d, J=7.3 Hz), 7.03 (1H, dd, J=8.5, 8.5 Hz), 7.60 (1H, d, J=8.5 Hz), 7.65 (1H, dd, J=8.5, 2.0 Hz), 8.00 (1H, brs).

IR (Neat) cm$^{-1}$: 1652, 1608, 1523, 1438, 1286, 758.

Mass m/z: 357 (M$^+$).

Example 182

Preparation of 2-cyclopentylmethyl-6-(3-fluoro-4-methoxyphenyl)-4-(4-methyl-1-piperazinyl)methyl-2H-pyridazin-3-one 1) Preparation of 2-cyclopentylmethyl-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and cyclopentylmethyl bromide {*J. Org. Chem.*, 36, 3103 (1971)} were reacted to yield the title compound as yellow needles (yield: 72.0%).

Melting point: 56–66° C.

$^{1}$H NMR (400 MHz, CDCl$_3$) δ: 1.30–1.45 (2H, m), 1.53–1.65 (2H, m), 1.65–1.80 (4H, m), 2.57 (1H, m), 3.95 (3H, s), 3.98 (3H, s), 4.24 (2H, d, J=7.8 Hz), 7.03 (1H, dd, J=8.5, 8.5 Hz), 7.50 (1H, d, J=8.8 Hz), 7.61 (1H, d, J=10.2 Hz), 8.19 (1H, s).

2) Preparation of 4-carboxy-2-cyclopentylmethyl-6-(3-fluoro-4-methoxyphenyl)-2H-pyridazin-3-one Following the procedure of Example 1(7), 2-cyclopentylmethyl-6-(3-fluoro-4-methoxyphenyl)-4-methoxycarbonyl-2H-pyridazin-3-one was reacted to yield the title compound as a yellow powder (yield: 71.1%).

Melting point: 159–161° C.

$^{1}$H NMR (400 MHz, CDCl$_3$) δ: 1.33–1.45 (2H, m), 1.58–1.65 (2H, m), 1.68–1.82 (4H, m), 2.57 (1H, m), 3.97 (3H, s), 4.32 (2H, d, J=7.6 Hz), 7.06 (1H, dd, J=8.5, 8.5 Hz), 7.56 (1H, d, J=8.5 Hz), 7.68 (1H, dd, J=12.2, 2.0 Hz), 8.61 (1H, s).

3) Preparation of 2-cyclopentylmethyl-6-(3-fluoro-4-methoxyphenyl)-4-hydroxymethyl-2H-pyridazin-3-one Following the procedure of Example 1(8), 4-carboxy-2-cyclopentylmethyl-6-(3-fluoro-4-methoxyphenyl)-2H-pyridazin-3-one was reacted to yield the title compound as a yellow powder (yield: 47.3%).

Melting point: 130–133° C.

$^{1}$H NMR (400 MHz, CDCl$_3$) δ: 1.30–1.42 (2H, m), 1.50–1.62 (2H, m), 1.62–1.80 (4H, m), 2.54 (1H, m), 3.95 (3H, s), 4.19 (2H, d, J=7.6 Hz), 4.71 (2H, s), 7.02 (1H, dd, J=8.5, 8.5 Hz), 7.51 (1H, d, J=8.5 Hz), 7.62 (1H, dd, J=12.8, 1.5 Hz), 7.63 (1H, s).

4) Preparation of 2-cyclopentylmethyl-6-(3-fluoro-4-methoxyphenyl)-4-methanesulfonyloxymethyl-2H-pyridazin-3-one Following the procedure of Example 1(9), 2-cyclopentylmethyl-6-(3-fluoro-4-methoxyphenyl)-4-hydroxymethyl-2H-pyridazin-3-one was reacted to yield the title compound as a yellow powder (yield: 75.3%).

Melting point: 108–116° C.

$^{1}$H NMR (400 MHz, CDCl$_3$) δ: 1.25–1.32 (2H, m), 1.32–1.45 (2H, m), 1.65–1.77 (4H, m), 2.54 (1H, m), 3.17 (3H, s), 3.95 (3H, s), 4.19 (2H, d, J=7.6 Hz), 5.27 (2H, s), 7.03 (1H, dd, J=8.5, 8.5 Hz), 7.50 (1H, d, J=8.5 Hz), 7.62 (1H, dd, J=12.2, 2.2 Hz), 7.74 (1H, s).

5) Preparation of 2-cyclopentylmethyl-6-(3-fluoro-4-methoxyphenyl)-4-(4-methyl-1-piperazinyl)methyl-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and 1-methylpiperazine were reacted to yield the title compound as a yellow oil (yield: 61.4%).

$^{1}$H NMR (400 MHz, CDCl$_3$) δ: 1.32–1.42 (2H, m), 1.50–1.60 (2H, m), 1.65–1.80 (4H, m), 2.38, 2.40 (each s, 3H in total), 2.54 (1H, m), 2.60–2.75 (8H, m), 3.59 (2H, s), 3.95 (3H, s), 4.18 (2H, d, J=7.6 Hz), 7.04 (1H, dd, J=8.5, 8.5 Hz), 7.54 (1H, d, J=8.5 Hz), 7.61 (1H, dd, J=8.5, 2.2 Hz), 7.72 (1H, s).

IR (Neat) cm$^{-1}$: 1652, 1608, 1523, 1439, 1286, 760.

Mass m/z: 414 (M$^+$).

Example 183

Preparation of 2-cyclopentylmethyl-6-(3-fluoro-4-methoxyphenyl)-4-(4-methyl-1-piperazinyl)methyl-2H-pyridazin-3-one dihydrochloride Following the procedure of Example 4, 2-cyclopentylmethyl-6-(3-fluoro-4-methoxyphenyl)-4-(4-methyl-1-piperazinyl)methyl-2H-pyridazin-3-one was reacted to yield the title compound as a pale brown crystalline powder (yield: 59.6%).

Melting point: 234–236° C. (dec.)

$^{1}$H NMR (400 MHz, DMSO-d$_6$) δ: 1.28–1.40 (2H, m), 1.48–1.56 (2H, m), 1.60–1.73 (4H, m), 2.46 (1H, m), 2.82 (3H, s), 3.50–3.75 (10H, m), 3.91 (3H, s), 4.10 (2H, d, J=7.6 Hz), 7.31 (1H, dd, J=8.8, 8.8 Hz), 7.68–7.76 (2H, m), 8.25 (1H, s).

IR (KBr) cm$^{-1}$: 1652, 1606, 1523, 1439, 1292, 764.

Example 184

Preparation of 4-N,N-bis(2-hydroxyethyl)aminomethyl-2-cyclopentylmethyl-6-(3-fluoro-4-methoxyphenyl)-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and diethanolamine were reacted to yield the title compound as a yellow oil (yield: 54.9%).

$^1$H NMR (400 MHz, CDCl$_3$) δ: 1.30–1.45 (2H, m), 1.50–1.62 (2H, m), 1.62–1.80 (4H, m), 2.53 (1H, m), 2.75–2.90 (4H, m), 3.70–3.75 (4H, m), 3.80–3.85 (2H, m), 3.94 (3H, s), 4.20 (2H, d, J=7.6 Hz), 7.02 (1H, dd, J=8.5, 8.5 Hz), 7.56 (1H, d, J=8.5 Hz), 7.63 (1H, dd, J=8.5, 2.0 Hz), 7.65 (1H, m).

IR (Neat) cm$^{-1}$: 1648, 1598, 1523, 1439, 1267, 728.

Mass m/z: 383 (M$^+$−2H$_2$O).

Example 185

Preparation of 2-cyclopentylmethyl-4-dimethylaminomethyl-6-(3-fluoro-4-methoxyphenyl)-2H-pyridazin-3-one Following the procedure of Example 7, 2-cyclopentylmethyl-6-(3-fluoro-4-methoxyphenyl)-4-methanesulfonyloxymethyl-2H-pyridazin-3-one and dimethylamine were reacted to yield the title compound as a yellow oil (yield: 63.7%).

$^1$H NMR (400 MHz, CDCl$_3$) δ: 1.30–1.45 (2H, m), 1.50–1.63 (2H, m), 1.63–1.80 (4H, m), 2.43 (6H, s), 2.55 (1H, m), 3.61 (2H, s), 3.94 (3H, s), 4.19 (2H, d, J=7.6 Hz), 7.20 (1H, dd, J=8.5, 8.5 Hz), 7.58 (1H, d, J=8.5 Hz), 7.65 (1H, dd, J=8.5, 2.2 Hz), 7.91 (1H, brs).

IR (Neat) cm$^{-1}$: 1652, 1608, 1523, 1438, 1288, 762.

Mass m/z: 359 (M$^+$).

Example 186

Preparation of 2-cyclopentylmethyl-6-(3-fluoro-4-methoxyphenyl)-4-(1-piperazinyl)methyl-2H-pyridazin-3-one 1) Preparation of 4-(4-tert-butoxycarbonyl-1-piperazinyl)methyl-2-cyclopentylmethyl-6-(3-fluoro-4-methoxyphenyl)-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and tert-butyl 1-piperazinecarboxylate were reacted to yield the title compound as a yellow oil (yield: 78.8%).

$^1$H NMR (400 MHz, CDCl$_3$) δ: 1.35–1.43 (2H, m), 1.47 (9H, s), 1.55–1.60 (2H, m), 1.65–1.75 (4H, m), 2.45–2.60 (5H, m), 3.45–3.55 (4H, m), 3.95 (3H, s), 4.18 (2H, d, J=7.6 Hz), 7.03 (1H, dd, J=8.5, 8.5 Hz), 7.52 (1H, m), 7.62 (1H, d, J=12.4 Hz), 7.74 (1H, m).

2) Preparation of 2-cyclopentylmethyl-6-(3-fluoro-4-methoxyphenyl)-4-(1-piperazinyl)methyl-2H-pyridazin-3-one Following the procedure of Example 20, 4-(4-tert-butoxycarbonyl-1-piperazinyl)methyl-2-cyclopentylmethyl-6-(3-fluoro-4-methoxyphenyl)-2H-pyridazin-3-one was reacted to yield the title compound as a yellow oil (yield: 88.0%).

$^1$H NMR (400 MHz, CDCl$_3$) δ: 1.33–1.43 (2H, m), 1.50–1.62 (2H, m), 1.62–1.80 (4H, m), 2.55 (1H, m), 2.57–2.63 (4H, m), 3.00–3.02 (4H, m), 3.56 (2H, brs), 3.95 (3H, s), 4.18 (2H, d, J=7.6 Hz), 7.04 (1H, dd, J=8.5, 8.5 Hz), 7.52 (1H, d, J=8.5 Hz), 7.62 (1H, dd, J=8.5, 2.2 Hz), 7.73 (1H, s).

IR (Neat) cm$^{-1}$: 1652, 1608, 1523, 1439, 1287, 761.

Mass m/z: 400 (M$^+$).

Example 187

Preparation of 4-aminomethyl-2-cyclopentylmethyl-6-(3-fluoro-4-methoxyphenyl)-2H-pyridazin-3-one Following the procedure of Example 24(1), 2-cyclopentylmethyl-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24(2) to yield the title compound as a yellow oil (yield: 53.7%).

$^1$H NMR (400 MHz, CDCl$_3$) δ: 1.30–1.45 (2H, m), 1.50–1.63 (2H, m), 1.63–1.80 (4H, m), 2.54 (1H, m), 3.91 (2H, s), 3.93 (3H, s), 4.17 (2H, d, J=7.6 Hz), 7.01 (1H, dd, J=8.5, 8.5 Hz), 7.52 (1H, d, J=8.5 Hz), 7.62 (1H, dd, J=8.5, 2.2 Hz), 7.71 (1H, brs).

IR (Neat) cm$^{-1}$: 3376, 1649, 1606, 1523, 1439, 1285, 761.

Mass m/z: 331 (M$^+$).

Example 188

Preparation of 4-aminomethyl-2-cyclopentylmethyl-6-(3-fluoro-4-methoxyphenyl)-2H-pyridazin-3-one hydrochloride Following the procedure of Example 4, 4-aminomethyl-2-cyclopentylmethyl-6-(3-fluoro-4-methoxyphenyl)-2H-pyridazin-3-one was reacted to yield the title compound as a slightly-yellow crystalline powder (yield: 59.0%). Melting point: 193–196° C.

$^1$H NMR (400 MHz, DMSO-d$_6$) δ: 1.29–1.40 (2H, m), 1.45–1.57 (2H, m), 1.60–1.70 (4H, m), 2.45 (1H, m), 3.91 (3H, s), 4.00 (2H, s), 4.12 (2H, d, J=7.6 Hz), 7.34 (1H, dd, J=8.5, 8.5 Hz), 7.69–7.72 (2H, m), 8.47 (1H, brs).

IR (KBr) cm$^{-1}$: 3436, 1656, 1617, 1521, 1438, 1295, 763.

Example 189

Preparation of 2-(4-fluorobenzyl)-6-(3-fluoro-4-methoxyphenyl)-4-(4-methyl-1-piperazinyl)methyl-2H-pyridazin-3-one 1) Preparation of 2-(4-fluorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-fluorobenzyl chloride were reacted to yield the title compound as a slightly-yellow crystalline powder (yield: 86.6%).

$^1$H NMR (400 MHz, CDCl$_3$) δ: 3.95 (3H, s), 3.97 (3H, s), 5.39 (2H, s), 7.00–7.06 (3H, m), 7.48–7.63 (4H, m), 8.19 (1H, s).

2) Preparation of 4-carboxy-2-(4-fluorobenzyl)-6-(3-fluoro-4-methoxyphenyl)-2H-pyridazin-3-one Following the procedure of Example 1(7), 2-(4-fluorobenzyl)-6-(3-fluoro-4-methoxyphenyl)-4-methoxycarbonyl-2H-pyridazin-3-one was reacted to yield the title compound as a yellow powder (yield: 97.7%).

Melting point: 222–224° C.

$^1$H NMR (400 MHz, CDCl$_3$) δ: 3.97 (3H, s), 5.47 (2H, s), 7.03–7.10 (3H, m), 7.49–7.56 (3H, m), 7.67 (1H, dd, J=12.1, 2.2 Hz), 8.60 (1H, s).

3) Preparation of 2-(4-fluorobenzyl)-6-(3-fluoro-4-methoxyphenyl)-4-hydroxymethyl-2H-pyridazin-3-one Following the procedure of Example 1(8), 4-carboxy-2-(4-fluorobenzyl)-6-(3-fluoro-4-methoxyphenyl)-2H-pyridazin-3-one was reacted to yield the title compound as a yellow powder (yield: 27.0%).

Melting point: 127–130° C.

$^1$H NMR (400 MHz, CDCl$_3$) δ: 3.95 (3H, s), 4.79 (2H, d, J=1.5 Hz), 5.36 (2H, s), 6.98–7.05 (3H, m), 7.46–7.52 (3H, m), 7.61 (1H, dd, J=12.2, 2.2 Hz), 7.65 (1H, s).

4) Preparation of 2-(4-fluorobenzyl)-6-(3-fluoro-4-methoxyphenyl)-4-methanesulfonyloxymethyl-2H-pyridazin-3-one Following the procedure of Example 1(9), 2-(4-fluorobenzyl)-6-(3-fluoro-4-methoxyphenyl)-4-hydroxymethyl-2H-pyridazin-3-one was reacted to yield the title compound as a pale yellow powder (yield: 49.4%).

Melting point: 125–133° C.

$^1$H NMR (400 MHz, CDCl$_3$) δ: 3.15 (3H, s), 3.95 (3H, s), 5.25 (2H, d, J=1.2 Hz), 5.35 (2H, s), 7.00–7.06 (3H, m), 7.45–7.55 (3H, m), 7.61 (1H, dd, J=12.4, 2.2 Hz), 7.74 (1H, s).

5) Preparation of 2-(4-fluorobenzyl)-6-(3-fluoro-4-methoxyphenyl)-4-(4-methyl-1-piperazinyl)methyl-2H-pyridazin-3-one Following the procedure of Example 1(10), 2-(4-fluorobenzyl)-6-(3-fluoro-4-methoxyphenyl)-4-methanesulfonyloxymethyl-2H-pyridazin-3-one and 1-methylpiprazine were reacted to yield the title compound as a slightly-brown crystalline powder (yield: 45.8%).

Melting point: 112–113° C.

$^1$H NMR (400 MHz, CDCl$_3$) δ: 2.39 (3H, s), 2.60–2.90 (8H, m), 3.60 (2H, s), 3.95 (3H, s), 5.34 (2H, s), 6.99–7.06 (3H, m), 7.47–7.51 (3H, m), 7.59 (1H, dd, J=12.4, 2.0 Hz), 7.71 (1H, s).

IR (KBr) cm$^{-1}$: 1651, 1608, 1518, 1439, 1289, 764.

Mass m/z: 440 (M$^+$).

Example 190

Preparation of 4-dimethylaminomethyl-2-(4-fluorobenzyl)-6-(3-fluoro-4-methoxyphenyl)-2H-pyridazin-3-one Following the procedure of Example 7, 2-(4-fluorobenzyl)-6-(3-fluoro-4-methoxyphenyl)-4-methanesulfonyloxymethyl-2H-pyridazin-3-one and dimethylamine were reacted to yield the title compound as a slightly-yellow crystalline powder (yield: 60.8%).

Melting point: 127–129° C.

$^1$H NMR (400 MHz, CDCl$_3$): 2.41 (6H, s), 3.58 (2H, s), 3.94 (3H, s), 5.35 (2H, s), 6.98–7.05 (3H, m), 7.46–7.52 (2H, m), 7.56 (1H, d, J=8.8 Hz), 7.64 (1H, dd, J=12.4, 2.2 Hz), 7.90 (1H, brs).

IR (KBr) cm$^{-1}$: 1652, 1612, 1519, 1439, 1291, 763.

Mass m/z: 385 (M$^+$).

Example 191

Preparation of 4-N,N-bis(2-hydroxyethyl)aminomethyl-2-(4-fluorobenzyl)-6-(3-fluoro-4-methoxyphenyl)-2H-pyridazin-3-one Following the procedure of Example 1(10), 2-(4-fluorobenzyl)-6-(3-fluoro-4-methoxyphenyl)-4-methanesulfonyloxymethyl-2H-pyridazin-3-one and diethanolamine were reacted to yield the title compound as a yellow oil (yield: 66.1%).

$^1$H NMR (400 MHz, CDCl$_3$) δ: 2.70–2.92 (4H, m), 3.70–3.85 (6H, m), 3.93 (3H, s), 5.35 (2H, s), 6.99–7.04 (3H, m), 7.45–7.50 (2H, m), 7.55 (1H, d, J=8.3 Hz), 7.63 (1H, dd, J=12.4, 2.0 Hz), 7.90 (1H, m).

IR (Neat) cm$^{-1}$: 1652, 1606, 1520, 1435, 1281, 762.

Mass m/z: 385 (M$^+$-CH$_2$OH).

Example 192

Preparation of 2-(4-fluorobenzyl)-6-(3-fluoro-4-methoxyphenyl)-4-(1-piperazinyl)methyl-2H-pyridazin-3-one 1) Preparation of 4-(4-tert-butoxycarbonyl-1-piperazinyl)methyl-2-(4-fluorobenzyl)-6-(3-fluoro-4-methoxyphenyl)-2H-pyridazin-3-one Following the procedure of Example 1(10), 2-(4-fluorobenzyl)-6-(3-fluoro-4-methoxyphenyl)-4-methanesulfonyloxymethyl-2H-pyridazin-3-one and tert-butyl 1-piperazinecarboxylate were reacted to yield the title compound as a yellow oil (yield: 78.8%).

$^1$H NMR (400 MHz, CDCl$_3$) δ: 1.46 (9H, s), 1.55–1.65 (4H, m), 3.40–3.60 (4H, m), 3.95 (3H, s), 5.34 (2H, s), 6.96–7.05 (3H, m), 7.47–7.50 (3H, m), 7.41 (1H, d, J=12.4 Hz), 7.74 (1H, brs).

2) Preparation of 2-(4-fluorobenzyl)-6-(3-fluoro-4-methoxyphenyl)-4-(1-piperazinyl)methyl-2H-pyridazin-3-one Following the procedure of Example 20, 4-(4-tert-butoxycarbonyl-1-piperazinyl)methyl-2-(4-fluorobenzyl)-6-(3-fluoro-4-methoxyphenyl)-2H-pyridazin-3-one was reacted to yield the title compound as a pale yellow crystalline powder (yield: 63.4%).

Melting point: 142–143° C.

$^1$H NMR (400 MHz, CDCl$_3$) δ: 2.50–2.60 (4H, m), 2.96–3.02 (4H, m), 3.54 (2H, d, J=11.2 Hz), 3.95 (3H, s), 5.34 (2H, s), 6.98–7.06 (3H, m), 7.46–7.53 (3H, m), 7.61 (1H, dd, J=12.5, 2.2 Hz), 7.74 (1H, br.s).

IR (KBr) cm$^{-1}$: 1652, 1609, 1523, 1437, 1290, 762.

Mass m/z: 426 (M$^+$).

Example 193

Preparation of 2-(4-fluorobenzyl)-6-(3-fluoro-4-methoxyphenyl)-4-(1-piperazinyl)methyl-2H-pyridazin-3-one dihydrochloride Following the procedure of Example 4, 2-(4-fluorobenzyl)-6-(3-fluoro-4-methoxyphenyl)-4-(1-piperazinyl)methyl-2H-pyridazin-3-one was reacted to yield the title compound as a colorless crystalline powder (yield: 76.9%).

Melting point: 153–156° C.

$^1$H NMR (400 MHz, DMSO-d$_6$) δ: 3.30–3.75 (10H, m), 3.90 (3H, s), 5.33 (2H, s), 7.15–7.21 (2H, m), 7.30 (1H, m), 7.43–7.49 (2H, m), 7.69–7.78 (3H, m).

IR (KBr) cm$^{-1}$: 1660, 1609, 1524, 1439, 1292, 766.

Example 194

Preparation of 4-aminomethyl-2-(4-fluorobenzyl)-6-(3-fluoro-4-methoxyphenyl)-2H-pyridazin-3-one Following the procedure of Example 24(1), 2-(4-fluorobenzyl)-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24(2) to yield the title compound as a pale brown crystalline powder (yield: 50.4%).

Melting point: 145–149° C.

$^1$H NMR (400 MHz, CDCl$_3$) δ: 3.92 (3H, s), 3.94 (2H, s), 5.31 (2H, s), 6.95–7.03 (3H, m), 7.40–7.52 (3H, m), 7.60 (1H, dd, J=12.5, 2.2 Hz), 7.75 (1H, brs).

IR (KBr) cm$^{-1}$: 3391, 1648, 1606, 1519, 1437, 1292, 761.

Mass m/z: 357 (M$^+$).

Example 195

Preparation of 4-aminomethyl-2-(4-fluorobenzyl)-6-(3-fluoro-4-methoxyphenyl)-2H-pyridazin-3-one hydrochloride Following the procedure of Example 4, 4-aminomethyl-2-(4-fluorobenzyl)-6-(3-fluoro-4-methoxyphenyl)-2H-pyridazin-3-one was reacted to yield the title compound as a slightly-yellow crystalline powder (yield: 72.5%).

Melting point: 210–214° C.

$^1$H NMR (400 MHz, DMSO-d$_6$) δ: 3.91 (3H, s), 4.01 (2H, s), 5.35 (2H, s), 7.16–7.21 (2H, m), 7.34 (1H, dd, J=8.8, 8.8 Hz), 7.45–7.49 (2H, m), 7.68–7.78 (2H, m), 8.29 (1H, s).

IR (KBr) cm$^{-1}$: 3429, 1653, 1612, 1522, 1439, 1292, 764.

Example 196

Preparation of 6-(3-fluoro-4-methoxyphenyl)-2-[3-(4-fluorophenyl)propyl]-4-(4-methyl-1-piperazinyl)methyl-2H-pyridazin-3-one 1) Preparation of 6-(3-fluoro-4-methoxyphenyl)-2-[3-(4-fluorophenyl)propyl]-4-methoxycarbonyl-2H-pyridazin-3-one Following the procedure of Example 1(6), 6-(3-fluoro-4-methoxyphenyl)-4-methoxycarbonyl-2H-pyridazin-3-one and the mesylate derivative of 3-(4-fluorophenyl)-1-propanol {J. Med. Chem., 19, 461 (1976)} were reacted to yield the title compound as a yellow oil (yield: 90.1%). The mesylate derivative was prepared in accordance with the procedure of Example 1(9).

$^1$H NMR (400 MHz, CDCl$_3$) δ: 2.16–2.26 (2H, m), 2.71 (2H, t, J=7.3 Hz), 3.95 (3H, s), 3.98 (3H, s), 4.32 (2H, t, J=7.3 Hz), 6.93–7.06 (3H, m), 7.14–7.18 (2H, m), 7.49 (1H, m), 7.60 (1H, dd, J=13.2, 2.2 Hz), 8.17 (1H, s).

2) Preparation of 4-carboxy-6-(3-fluoro-4-methoxyphenyl)-2-[3-(4-fluorophenyl)propyl]-2H-pyridazin-3-one Following the procedure of Example 1(7), 6-(3-fluoro-4-methoxyphenyl)-2-[3-(4-fluorophenyl)propyl]-4-methoxycarbonyl-2H-pyridazin-3-one was reacted to yield the title compound as a yellow powder (yield: 89.2%).

Melting point: 185–187° C.

$^1$H NMR (400 MHz, CDCl$_3$) δ: 2.20–2.30 (2H, m), 2.74 (2H, t, J=7.3 Hz), 3.97 (3H, s), 4.40 (2H, t, J=7.3 Hz), 6.94–7.17 (5H, m), 7.55 (1H, d, J=8.5 Hz), 7.66 (1H, dd, J=12.2, 2.2 Hz), 8.58 (1H, s).

3) Preparation of 6-(3-fluoro-4-methoxyphenyl)-2-[3-(4-fluorophenyl)propyl]-4-hydroxymethyl-2H-pyridazin-3-one Following the procedure of Example 1(8), 4-carboxy-6-(3-fluoro-4-methoxyphenyl)-2-[3-(4-fluorophenyl)propyl]-2H-pyridazin-3-one was reacted to yield the title compound as a yellow powder (yield: 37.0%).

Melting point: 130–133° C.

$^1$H NMR (400 MHz, CDCl$_3$) δ: 2.15–2.22 (2H, m), 2.71 (2H, t, J=7.3 Hz), 3.95 (3H, s), 4.27 (2H, t, J=7.3 Hz), 4.70 (2H, d, J=1.2 Hz), 6.93–7.06 (3H, m), 7.14–7.18 (2H, m), 7.50 (1H, d, J=8.8 Hz), 7.61 (1H, dd, J=12.7, 2.2 Hz), 7.63 (1H, s).

4) Preparation of 6-(3-fluoro-4-methoxyphenyl)-2-[3-(4-fluorophenyl)propyl]-4-methanesulfonyloxymethyl-2H-pyridazin-3-one Following the procedure of Example 1(9), 6-(3-fluoro-4-methoxyphenyl)-2-[3-(4-fluorophenyl)propyl]-4-hydroxymethyl-2H-pyridazin-3-one was reacted to yield the title compound as a yellow powder (yield: 92.3%).

Melting point: 112–116° C.

$^1$H NMR (400 MHz, CDCl$_3$) δ: 2.15–2.25 (2H, m), 2.71 (2H, t, J=7.3 Hz), 3.17 (3H, s), 3.95 (3H, s), 4.27 (2H, t, J=7.3 Hz), 5.25 (2H, d, J=1.2 Hz), 6.93–7.05 (3H, m), 7.14–7.18 (2H, m), 7.49 (1H, d, J=8.5 Hz), 7.61 (1H, dd, J=13.4, 2.0 Hz), 7.72 (1H, s).

5) Preparation of 6-(3-fluoro-4-methoxyphenyl)-2-[3-(4-fluorophenyl)propyl]-4-(4-methyl-1-piperazinyl)methyl-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and 1-methylpiperazine were reacted to yield the title compound as a yellow oil (yield: 79.3%).

$^1$H NMR (400 MHz, CDCl$_3$) δ: 2.15–2.25 (2H, m), 2.41 (3H, s), 2.60–2.75 (10H, m), 3.58 (2H, s), 3.75 (3H, s), 4.27 (2H, t, J=7.3 Hz), 6.92–7.06 (3H, m), 7.14–7.18 (2H, m), 7.51 (1H, d, J=8.5 Hz), 7.60 (1H, dd, J=12.4, 2.0 Hz), 7.69 (1H, s).

IR (Neat) cm$^{-1}$: 1652, 1608, 1511, 1439, 1284, 758.

Mass m/z: 468 (M$^+$).

Example 197

Preparation of 4-dimethylaminomethyl-6-(3-fluoro-4-methoxyphenyl)-2-[3-(4-fluorophenyl)propyl]-2H-pyridazin-3-one Following the procedure of Example 7, 6-(3-fluoro-4-methoxyphenyl)-2-[3-(4-fluorophenyl)propyl]-4-methanesulfonyloxymethyl-2H-pyridazin-3-one and dimethylamine were reacted to yield the title compound as a pale yellow crystalline powder (yield: 61.8%).

Melting point: 97–100° C.

$^1$H NMR (400 MHz, CDCl$_3$) δ: 2.15–2.25 (2H, m), 2.43 (6H, s), 2.71 (2H, t, J=7.3 Hz), 3.60 (2H, s), 3.94 (3H, s), 4.27 (2H, t, J=7.3 Hz), 6.93–7.05 (3H, m), 7.15–7.18 (2H, m), 7.57 (1H, d, J=8.5 Hz), 7.64 (1H, dd, J=12.6, 2.2 Hz), 7.90 (1H, brs).

IR (KBr) cm$^{-1}$: 1653, 1611, 1510, 1436, 1296, 763.

Mass m/z: 413 (M$^+$).

Example 198

Preparation of 4-N,N-bis(2-hydroxyethyl)aminomethyl-6-(3-fluoro-4-methoxyphenyl)-2-[3-(4-fluorophenyl)propyl]-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and diethanolamine were reacted to yield the title compound as a yellow oil (yield: 67.3%).

$^1$H NMR (400 MHz, CDCl$_3$) 2.14–2.22 (2H, m), 2.70 (2H, t, J=7.6 Hz), 2.75–2.95 (4H, m), 3.70–3.80 (6H, m), 3.94 (3H, s), 4.28 (2H, t, J=7.6 Hz), 6.93–7.05 (3H, m), 7.15–7.18 (2H, m), 7.56 (1H, m), 7.63 (1H, m), 7.85 (1H, m).

IR (Neat) cm$^{-1}$: 1645, 1601, 1510, 1439, 1277, 763.

Mass m/z: 473 (M$^+$).

Example 199

Preparation of 6-(3-fluoro-4-methoxyphenyl)-2-[3-(4-fluorophenyl)propyl]-4-(1-piperazinyl)methyl-2H-pyridazin-3-one 1) Preparation of 4-(4-tert-butoxycarbonyl-1-piperazinyl)methyl-6-(3-fluoro-4-methoxyphenyl)-2-[3-(4-fluorophenyl)propyl]-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and tert-butyl 1-piperazinecarboxylate were reacted to yield the title compound as a yellow oil (yield: 72.6%).

$^1$H NMR (400 MHz, CDCl$_3$) δ: 1.40 (9H, s), 2.07–2.16 (2H, m), 2.40–2.50 (4H, m), 2.63 (2H, t, J=7.6 Hz), 3.36–3.46 (4H, m), 3.48 (2H, brs), 3.88 (3H, s), 4.20 (2H, t, J=7.6 Hz), 6.84–6.98 (3H, m), 7.07–7.11 (2H, m), 7.43 (1H, d, J=8.1 Hz), 7.53 (1H, d, J=12.4 Hz), 7.65 (1H, brs).

2) Preparation of 6-(3-fluoro-4-methoxyphenyl)-2-[3-(4-fluorophenyl)propyl]-4-(1-piperazinyl)methyl-2H-pyridazin-3-one Following the procedure of Example 20, 4-(4-tert-butoxycarbonyl-1-piperazinyl)methyl-6-(3-fluoro-4-methoxyphenyl)-2-[3-(4-fluorophenyl)propyl]-2H-pyridazin-3-one was reacted to yield the title compound as a yellow oil (yield: 97.2%).

$^1$H NMR (400 MHz, CDCl$_3$) δ: 2.12–2.22 (2H, m), 2.50–2.60 (4H, m), 2.71 (2H, t, J=7.3 Hz), 2.92–3.02 (4H, m), 3.53 (2H, s), 3.95 (3H, s), 4.27 (2H, t, J=7.3 Hz), 6.91–7.06 (3H, m), 7.15–7.18 (2H, m), 7.51 (1H, d, J=8.8 Hz), 7.61 (1H, dd, J=12.5, 2.2 Hz), 7.73 (1H, s).

IR (Neat) cm$^{-1}$: 1650, 1607, 1510, 1439, 1275, 758.

Mass m/z: 454 (M$^+$).

Example 200

Preparation of 4-aminomethyl-6-(3-fluoro-4-methoxyphenyl)-2-[3-(4-fluorophenyl)propyl]-2H-pyridazin-3-one Following the procedure of Example 24(1), 6-(3-fluoro-4-methoxyphenyl)-2-[3-(4-fluorophenyl)propyl]-4-methanesulfonyloxymethyl-2H-pyridazin-3-one was reacted to a crude product. Without purification, the crude product was reacted in accordance with the procedure of Example 24(2) to yield the title compound as a pale yellow crystalline powder (yield: 41.7%).

Melting point: 82–84° C.

$^1$H NMR (400 MHz, CDCl$_3$) δ: 2.12–2.22 (2H, m), 2.70 (2H, t, J=7.6 Hz), 3.89 (2H, s), 3.94 (3H, s), 4.27 (2H, t, J=7.6 Hz), 6.93–7.04 (3H, m), 7.15–7.18 (2H, m), 7.51 (1H, d, J=7.3 Hz), 7.61 (1H, dd, J=12.4, 2.0 Hz), 7.67 (1H, s).

IR (KBr) cm$^{-1}$: 3366, 1651, 1605, 1509, 1436, 1273, 764.

Mass m/z: 385 (M$^+$).

Example 201

Preparation of 4-aminomethyl-6-(3-fluoro-4-methoxyphenyl)-2-[3-(4-fluorophenyl)propyl]-2H-pyridazin-3-one hydrochloride Following the procedure of Example 4, 4-aminomethyl-6-(3-fluoro-4-methoxyphenyl)-2-[3-(4-fluorophenyl)propyl]-2H-pyridazin-3-one was reacted to yield the title compound as a slightly-yellow crystalline powder (yield: 73.1%).

Melting point: 160–165° C.

$^1$H NMR (400 MHz, DMSO-d$_6$) δ: 2.05–2.15 (2H, m), 2.66 (2H, t, J=7.3 Hz), 3.92 (3H, s), 3.99 (2H, s), 4.19 (2H, t, J=7.3 Hz), 7.05–7.12 (2H, m), 7.23–7.30 (2H, m), 7.34 (1H, dd, J=8.8, 8.8 Hz), 7.66–7.76 (2H, m), 8.25 (1H, s).

IR (KBr) cm$^{-1}$: 3430, 1652, 1515, 1436, 1269, 763.

Example 202

Preparation of 2-(4-chlorobenzyl)-6-(3-fluoro-4-methoxyphenyl)-4-(4-methyl-1-piperazinyl)methyl-2H-pyridazin-3-one 1) Preparation of 2-(4-chlorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-chlorobenzyl chloride were reacted to yield the title compound as yellow needles (yield: 97.6%).

Melting point: 170.5–171.1° C.

$^1$H NMR (400 MHz, CDCl$_3$) δ: 3.95 (3H, s), 3.99 (3H, s), 5.38 ((2H, s), 7.03 (1H, dd, J=8.5, 8.5 Hz), 7.31 (2H, d, J=8.5 Hz), 7.47 (2H, d, J=8.5 Hz), 7.49 (1H, m), 7.60 (1H, dd, J=12.2, 2.2 Hz), 8.20 (1H, s).

IR (KBr) cm$^{-1}$: 1723, 1670, 1526, 1271, 1128.

Mass m/z: 402 (M$^+$), 404 ((M$^+$).

2) Preparation of 4-carboxy-2-(4-chlorobenzyl)-6-(3-fluoro-4-methoxyphenyl)-2H-pyridazin-3-one Following the procedure of Example 1(7), 2-(4-chlorobenzyl)-6-(3-fluoro-4-methoxyphenyl)-4-methoxycarbonyl-2H-pyridazin-3-one was reacted to yield the title compound as a pale yellow crystalline powder (yield: 96.0%).

Melting point: 228.3–229.1° C.

$^1$H NMR (400 MHz, CDCl$_3$) δ: 3.97 (3H, s), 5.46 (2H, s), 7.07 (1H, dd, J=8.5, 8.5 Hz), 7.35 (2H, d, J=8.3 Hz), 7.46 (2H, d, J=8.3 Hz), 7.55 (1H, d, J=8.4 Hz), 7.67 (1H, dd, J=12.2, 2.2 Hz), 8.61 (1H, s).

IR (KBr) cm$^{-1}$: 1745, 1635, 1456, 1447, 1431, 1298, 1273.

Mass m/z: 388 (M$^+$), 390 (M$^+$).

3) Preparation of 2-(4-chlorobenzyl)-6-(3-fluoro-4-methoxyphenyl)-4-hydroxymethyl-2H-pyridazin-3-one Following the procedure of Example 1(8), 4-carboxy-2-(4-chlorobenzyl)-6-(3-fluoro-4-methoxyphenyl)-2-H-pyridazin-3-one was reacted to yield the title compound as pale yellow needles (yield: 20.4%).

Melting point: 164.6–165.3° C.

$^1$H NMR (400 MHz, CDCl$_3$) δ: 3.94 (3H, s), 4.69 (2H, s), 5.34 (2H, s), 7.01 (1H, dd, J=8.5, 8.5 Hz), 7.30 (2H, d, J=8.5 Hz), 7.42 (2H, d, J=8.5 Hz), 7.50 (1H, m), 7.63 (1H, dd, J=12.4, 2.2 Hz), 7.67 (1H, s).

IR (KBr) cm$^{-1}$: 3373, 1653, 1610, 1527, 1291, 1135.

Mass m/z: 374 (M$^+$), 376 (M$^+$).

4) Preparation of 2-(4-chlorobenzyl)-6-(3-fluoro-4-methoxyphenyl)-4-methanesulfonyloxymethyl-2H-pyridazin-3-one Following the procedure of Example 1(9), 2-(4-chlorobenzyl)-6-(3-fluoro-4-methoxyphenyl)-4-hydroxymethyl-2H-pyridazin-3-one was reacted to yield the title compound as pale yellow needles (yield: 81.6%).

Melting point: 156.5–157.4° C.

$^1$H NMR (400 MHz, CDCl$_3$) δ: 3.15 (3H, s), 3.95 (3H, s), 5.22 (2H, d, J=1.5 Hz), 5.35 (2H, s), 7.03 (1H, dd, J=8.5, 8.5 Hz), 7.31 (2H, d, J=8.5 Hz), 7.42 (2H, d, J=8.5 Hz), 7.49 (1H, m), 7.61 (1H, dd, J=12.2, 2.2 Hz), 7.75 (1H, s).

IR (KBr) cm$^{-1}$: 1658, 1616, 1358, 1183, 1017.

5) Preparation of 2-(4-chlorobenzyl)-6-(3-fluoro-4-methoxyphenyl)-4-(4-methyl-1-piperazinyl)methyl-2H-pyridazin-3-one Following the procedure of Example 1(10), 2-(4-chlorobenzyl)-6-(3-fluoro-4-methoxyphenyl)-4-methanesulfonyloxymethyl-2H-pyridazin-3-one and 1-methylpiperazine were reacted to yield the title compound as pale brown prisms (yield: 39.5%).

Melting point: 128.7–130.2° C.

$^1$H NMR (400 MHz, CDCl$_3$) δ: 2.33 (3H, s), 2.52 (4H, brs), 2.60 (4H, brs), 3.55 (2H, s), 3.95 (3H, s), 5.34 (2H, s), 7.04 (1H, dd, J=8.5, 8.5 Hz), 7.30 (2H, d, J=8.5 Hz), 7.43 (2H, d, J=8.5 Hz), 7.51 (1H, m), 7.60 (1H, dd, J=12.4, 2.0 Hz), 7.73 (1H, s).

IR (KBr) cm$^{-1}$: 1652, 1607, 1524, 1516, 1438, 1288, 1135.

Example 203

Preparation of 2-(4-chlorobenzyl)-4-dimethylaminomethyl-6-(3-fluoro-4-methoxyphenyl)-2H-pyridazin-3-one Following the procedure of Example 7, 2-(4-chlorobenzyl)-6-(3-fluoro-4-methoxyphenyl)-4-methanesulfonyloxymethyl-2H-pyridazin-3-one and dimethylamine were reacted to yield the title compound as a slightly-yellow crystalline powder (yield: 74.7%).

Melting point: 95.3–96.7° C.

$^1$H NMR (400 MHz, CDCl$_3$) δ: 2.33 (6H, s), 3.47 (2H, d, J=1.2 Hz), 3.94 (3H, s), 5.34 (2H, s), 7.01 (1H, dd, J=8.5, 8.5 Hz), 7.30 (2H, d, J=8.5 Hz), 7.44 (2H, d, J=8.5 Hz), 7.53 (1H, ddd, J=8.5, 2.0, 1.2 Hz), 7.62 (1H, dd, J=12.4, 2.2 Hz), 7.74 (1H, s).

IR (KBr) cm$^{-1}$: 1652, 1609, 1524, 1515, 1436, 1289, 1264, 1017.

Mass m/z: 401 (M$^+$), 403 (M$^+$).

Example 204

Preparation of 2-(4-chlorobenzyl)-4-dimethylaminomethyl-6-(3-fluoro-4-methoxyphenyl)-2H-pyridazin-3-one hydrochloride Following the procedure of Example 4, 2-(4-chlorobenzyl)-4-dimethylaminomethyl-6-(3-fluoro-4-methoxyphenyl)-2H-pyridazin-3-one was reacted to yield the title compound as a slightly-yellow crystalline powder (yield: 59.7%).

Melting point: 193.4–194.7° C.

$^1$H NMR (400 MHz, CD$_3$OD) δ: 2.96 (6H, s), 3.94 (3H, s), 4.33 (2H, s), 5.43 (2H, s), 7.22 (1H, dd, J=8.5, 8.5 Hz), 7.36 (2H, d, J=8.5 Hz), 7.46 (2H, d, J=8.5 Hz), 7.67–7.72 (2H, m), 8.20 (1H, s).

IR (KBr) cm$^{-1}$: 1655, 1616, 1529, 1327, 1279.

Example 205

Preparation of 4-aminomethyl-2-(4-chlorobenzyl)-6-(3-fluoro-4-methoxyphenyl)-2H-pyridazin-3-one 1) Preparation of 2-(4-chlorobenzyl)-6-(3-fluoro-4-methoxyphenyl)-4-phthalimidomethyl-2H-pyridazin-3-one Following the procedure of Example 24(1), 2-(4-chlorobenzyl)-6-(3-fluoro-4-methoxyphenyl)-4-methanesulfonyloxymethyl-2H-pyridazin-3-one was reacted to yield the title compound as slightly-yellow needles (yield: 75.4%).

Melting point: 212.5–213.9° C.

$^1$H NMR (400 MHz, CDCl$_3$): 3.90 (3H, s), 4.88 (2H, d, J=0.73 Hz), 5.35 (2H, s), 6.95 (1H, dd, J=8.5, 8.5 Hz), 7.29 (1H, s), 7.31 (2H, d, J=8.5 Hz), 7.36 (1H, m), 7.44 (2H, d, J=8.5 Hz), 7.47 (1H, dd, J=12.2, 2.0 Hz), 7.76–7.81 (2H, m), 7.89–7.94 (2H, m).

IR (KBr) cm$^{-1}$: 1773, 1713, 1651, 1610, 1522, 1439, 1419, 1393, 1300.

Mass m/z: 503 (M$^+$), 505 (M$^+$).

2) Preparation of 4-aminomethyl-2-(4-chlorobenzyl)-6-(3-fluoro-4-methoxyphenyl)-2H-pyridazin-3-one Following the procedure of Example 24(2), 2-(4-chlorobenzyl)-6-(3-fluoro-4-methoxyphenyl)-4-phthalimidomethyl-2H-pyridazin-3-one was reacted to yield the title compound as slightly-yellow needles (yield: 48.8%).

Melting point: 128.5–131.4° C.

$^1$H NMR (400 MHz, CDCl$_3$) δ: 3.88 (2H, s), 3.94 (3H, s), 5.34 (2H, s), 7.02 (1H, dd, J=8.5, 8.5 Hz), 7.30 (2H, d, J=8.5 Hz), 7.43 (2H, d, J=8.5 Hz), 7.51 (1H, ddd, J=8.5, 2.2, 1.2 Hz), 7.61 (1H, dd, J=12.4, 2.2 Hz), 7.69 (1H, t, J=1.2 Hz).

IR (KBr) cm$^{-1}$: 3392, 1615, 1604, 1520, 1434, 1292, 1133, 1018.

Mass m/z: 373 (M$^+$), 375 ((M$^+$).

Example 206

Preparation of 4-aminomethyl-2-(4-chlorobenzyl)-6-(3-fluoro-4-methoxyphenyl)-2H-pyridazin-3-one hydrochloride Following the procedure of Example 4, 4-aminomethyl-2-(4-chlorobenzyl)-6-(3-fluoro-4-methoxyphenyl)-2H-pyridazin-3-one was reacted to yield the title compound as a slightly-yellow crystalline powder (yield: 66.0%).

Melting point: 202.0–205.5° C.

$^1$H NMR (400 MHz, CD$_3$OD) δ: 3.94 (3H, s), 4.13 (2H, s), 5.41 (2H, s), 7.21 (1H, dd, J=8.8, 8.8 Hz), 7.35 (2H, d, J=8.5 Hz), 7.46 (2H, d, J=8.5 Hz), 7.65–7.71 (2H, m), 8.08 (1H, s).

IR (KBr) cm$^{-1}$: 2940, 1655, 1616, 1526, 1439, 1292.

Example 207

Preparation of 2-(3,4-difluorobenzyl)-6-(3-fluoro-4-methoxyphenyl)-4-(4-methyl-1-piperazinyl)methyl-2H-pyridazin-3-one 1) Preparation of 2-(3,4-difluorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 3,4-difluorobenzyl bromide were reacted to yield the title compound as a yellow crystalline powder (yield: 92.1%).

Melting point: 144–148° C.

$^1$H NMR (400 MHz, CDCl$_3$) δ: 3.96 (3H, s), 3.97 (3H, s), 5.35 (2H, s), 7.04 (1H, dd, J=8.5, 8.5 Hz), 7.12 (1H, m), 7.28 (1H, m), 7.36 (1H, m), 7.50 (1H, m), 7.60 (1H, dd, J=12.2, 1.5 Hz), 8.21 (1H, s).

IR (KBr) cm$^{-1}$: 1756, 1656, 1609, 1518, 1439, 1239, 1293, 1278, 1204.

Mass m/z: 404 (M$^+$).

2) Preparation of 4-carboxy-2-(3,4-difluorobenzyl)-6-(3-fluoro-4-methoxyphenyl)-2H-pyridazin-3-one Following the procedure of Example 1(7), 2-(3,4-difluorobenzyl)-6-(3-fluoro-4-methoxyphenyl)-4-methoxycarbonyl-2H-pyridazin-3-one was reacted to yield the title compound as a yellow crystalline powder (yield: 97.6%).

Melting point: 196.4–197.0° C.

$^1$H NMR (400 MHz, CDCl$_3$) δ: 3.97 (3H, s), 5.44 (2H, s), 7.07 (1H, dd, J=8.5, 8.5 Hz), 7.17 (1H, m), 7.27 (1H, m), 7.36 (1H, ddd, J=8.1, 8.1, 2.2 Hz), 7.56 (1H, m), 7.66 (1H, dd, J=12.2, 2.2 Hz), 8.61 (1H, s), 13.83 (1H, s).

IR (KBr) cm$^{-1}$: 1757, 1636, 1567, 1518, 1463, 1440, 1284.

Mass m/z: 390 (M$^+$).

3) Preparation of 2-(3,4-difluorobenzyl)-6-(3-fluoro-4-methoxyphenyl)-4-hydroxymethyl-2H-pyridazin-3-one Following the procedure of Example 1(8), 4-carboxy-2-(3,4-difluorobenzyl)-6-(3-fluoro-4-methoxyphenyl)-2H-pyridazin-3-one was reacted to yield the title compound as slightly-yellow neeldes (yield: 7.7%).

Melting point: 154.1–155.5° C.

$^1$H NMR (400 MHz, CDCl$_3$) δ: 2.85 (1H, t, J=5.6 Hz), 3.95 (3H, s), 4.71 (2H, d, J=5.6 Hz), 5.33 (2H, s), 7.03 (1H, dd, J=8.5, 8.5 Hz), 7.12 (1H, m), 7.23 (1H, m), 7.31 (1H, ddd, J=11.0, 7.6, 2.2 Hz), 7.51 (1H, ddd, J=8.5, 2.2, 1.2 Hz), 7.61 (1H, dd, J=12.4, 2.2 Hz), 7.68 (1H, t, J=1.2 Hz).

IR (KBr) cm$^{-1}$: 3390, 1648, 1602, 1518, 1440, 1285, 1141.

Mass m/z: 376 (M$^+$).

4) Preparation of 2-(3,4-difluorobenzyl)-6-(3-fluoro-4-methoxyphenyl)-4-methanesulfonyloxymethyl-2H-pyridazin-3-one Following the procedure of Example 1(9), 2-(3,4-difluorobenzyl)-6-(3-fluoro-4-methoxyphenyl)-4-hydroxymethyl-2H-pyridazin-3-one was reacted to yield the title compound as slightly-yellow neeldes (yield: 91.5%).

Melting point: 145.6–146.6° C.

$^1$H NMR (400 MHz, CDCl$_3$) δ: 3.16 (3H, s), 3.96 (3H, s), 5.26 (2H, d, J=1.2 Hz), 5.32 (2H, s), 7.04 (1H, dd, J=8.58.5 Hz), 7.13 (1H, m), 7.23 (1H, m), 7.32 (1H, m), 7.50 (1H, m), 7.61 (1H, dd, J=12.4, 2.2 Hz), 7.76 (1H, t, J=1.2 Hz).

IR (KBr) cm$^{-1}$: 1656, 1612, 1522, 1440, 1352, 1277, 1163.

Mass m/z: 454 (M$^+$).

5) Preparation of 2-(3,4-difluorobenzyl)-6-(3-fluoro-4-methoxyphenyl)-4-(4-methyl-1-piperazinyl)methyl-2H-pyridazin-3-one Following the procedure of Example 1(10), 2-(3,4-difluorobenzyl)-6-(3-fluoro-4-methoxyphenyl)-4-methanesulfonyloxymethyl-2H-pyridazin-3-one and 1-methylpiperazine were reacted to yield the title compound as slightly-yellow neeldes (yield: 55.0%).

Melting point: 135.4–136.0° C.

$^1$H NMR (400 MHz, CDCl$_3$): 2.33 (3H, s), 2.51 (4H, brs), 2.62 (4H, brs), 3.56 (2H, d, J=11.5 Hz), 3.95 (3H, s), 5.31 (2H, s), 7.04 (1H, dd, J=8.5, 8.5 Hz), 7.11 (1H, m), 7.23 (1H, m), 7.32 (1H, ddd, J=11.0, 7.6, 2.0 Hz), 7.52 (1H, ddd, J=8.5, 2.2, 1.2 Hz), 7.59 (1H, dd, J=12.2, 2.2 Hz), 7.74 (1H, t, J=1.2 Hz).

IR (KBr) cm$^{-1}$: 1652, 1608, 1522, 1437, 1291, 1273, 1139.

Mass m/z: 458 (M$^+$).

Example 208

Preparation of 2-(3,4-difluorobenzyl)-4-dimethylaminomethyl-6-(3-fluoro-4-methoxyphenyl)-2H-pyridazin-3-one Following the procedure of Example 7, 2-(3,4-difluorobenzyl)-6-(3-fluoro-4-methoxyphenyl)-4-methanesulfonyloxymethyl-2H-pyridazin-3-one and dimethylamine were reacted to yield the title compound as slightly-yellow needles (yield: 77.1%).

Melting point: 129.9–130.4° C.

$^1$H NMR (400 MHz, CDCl$_3$) δ: 2.35 (6H, s), 3.49 (2H, s), 3.95 (3H, s), 5.32 (2H, s), 7.02 (1H, dd, J=8.5, 8.5 Hz), 7.11 (1H, m), 7.24 (1H, m), 7.32 (1H, ddd, J=11.0, 7.6, 2.2 Hz), 7.54 (1H, ddd, J=8.5, 2.2, 1.2 Hz), 7.62 (1H, dd, J=12.4, 2.2 Hz), 7.77 (1H, s).

IR (KBr) cm$^{-1}$: 1653, 1610, 1519, 1437, 1291, 1283, 1267, 1138, 1114.

Mass m/z: 403 (M$^+$).

Example 209

Preparation of 2-(4-chlorocinnamyl)-6-(3-fluoro-4-methoxyphenyl)-4-(4-methyl-1-piperazinyl)methyl-2H-pyridazin-3-one 1) Preparation of 2-(4-chlorocinnamyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-chlorocinnamyl chloride were reacted to yield the title compound as a pale yellow crystalline powder (yield: 51.1%).

Melting point: 117–119° C.

$^1$H NMR (400 MHz, CDCl$_3$) δ: 3.95 (3H, s), 3.98 (3H, s), 5.02 (2H, dd, J=6.8, 1.2 Hz), 6.43 (1H, dt, J=15.9, 6.8 Hz), 6.70 (1H, d, J=15.9 Hz), 7.03 (1H, dd, J=8.5, 8.5 Hz), 7.25 (2H, d, J=8.8 Hz), 7.31 (2H, d, J=8.8 Hz), 7.50 (1H, dt, J=8.5, 2.2 Hz), 7.62 (1H, dd, J=12.2, 2.2 Hz), 8.22 (1H, s).

IR (KBr) cm$^{-1}$: 1724, 1709, 1667, 1506, 1291, 1236, 1126, 831.

Mass m/z: 412 (M$^+$), 414 (M$^+$).

2) Preparation of 4-carboxy-2-(4-chlorocinnamyl)-6-(3-fluoro-4-methoxyphenyl)-2H-pyridazin-3-one Following the procedure of Example 1(7), 2-(4-chlorocinnamyl)-6-(3-fluoro-4-methoxyphenyl)-4-methoxycarbonyl-2H-pyridazin-3-one was reacted to yield the title compound as a pale yellow crystalline powder (yield: 98.2%).

Melting point: 217.2–218.5° C.

$^1$H NMR (400 MHz, CDCl$_3$) δ: 3.97 (3H, s), 5.10 (2H, d, J=6.8 Hz), 6.39 (1H, dt, J=15.9, 6.8 Hz), 6.75 (1H, d, J=15.9 Hz), 7.06 (1H, dd, J=8.5, 8.5 Hz), 7.30 (2H, d, J=8.5 Hz), 7.34 (2H, d, J=8.5 Hz), 7.57 (1H, m), 7.69 (1H, dd, J=12.2, 2.2 Hz), 8.63 (1H, s), 13.99 (1H, s).

IR (KBr) cm$^{-1}$: 3059, 1744, 1629, 1523, 1480, 1438, 1426, 1296, 1272.

Mass m/z: 414 (M$^+$), 416 (M$^+$).

3) Preparation of 2-(4-chlorocinnamyl)-6-(3-fluoro-4-methoxyphenyl)-4-hydroxymethyl-2H-pyridazin-3-one Following the procedure of Example 1(8), 4-carboxy-2-(4-chlorocinnamyl)-6-(3-fluoro-4-methoxyphenyl)-2H-pyridazin-3-one was reacted to yield the title compound as pale yellow crystals (yield: 17.0%).

Melting point: 158.2–160.5° C.

$^1$H NMR (400 MHz, CDCl$_3$) δ: 2.95 (1H, t, J=5.9 Hz), 3.94 (3H, s), 4.73 (2H, dd, J=5.9, 1.2 Hz), 4.98 (2H, dd, J=6.6, 1.2 Hz), 6.40 (1H, dt, J=15.9, 6.6 Hz), 6.67 (1H, d, J=15.9 Hz), 7.02 (1H, dd, J=8.5, 8.5 Hz), 7.27 (2H, d, J=8.5 Hz), 7.32 (2H, d, J=8.5 Hz), 7.51 (1H, ddd, J=8.8, 2.2, 1.2 Hz), 7.63 (1H, dd, J=12.4, 2.2 Hz), 7.67 (1H, t, J=1.2 Hz).

IR (KBr) cm$^{-1}$: 3392, 1648, 1603, 1523, 1440, 1284, 1273, 1140.

Mass m/z: 400 (M$^+$), 402 (M$^+$).

4) Preparation of 2-(4-chlorocinnamyl)-6-(3-fluoro-4-methoxyphenyl)-4-methanesulfonyloxymethyl-2H-pyridazin-3-one Following the procedure of Example 1(9), 2-(4-chlorocinnamyl)-6-(3-fluoro-4-methoxyphenyl)-4-hydroxymethyl-2H-pyridazin-3-one was reacted to yield the title compound as pale yellow neeldes (yield: 90.7%).

Melting point: 135.8–136.4° C.

$^1$H NMR (400 MHz, CDCl$_3$) δ: 3.17 (3H, s), 3.95 (3H, s), 4.98 (2H, dd, J=6.6, 0.98 Hz), 5.28 (2H, d, J=1.5 Hz), 6.39 (1H, dt, J=15.9, 6.6 Hz), 6.67 (1H, d, J=15.9 Hz), 7.03 (1H, dd, J=8.5, 8.5 Hz), 7.27 (2H, d, J=8.5 Hz), 7.32 (2H, d, J=8.5 Hz), 7.50 (1H, m), 7.62 (1H, dd, J=12.2, 2.2 Hz), 7.77 (1H, t, J=1.2 Hz).

IR (KBr) cm$^{-1}$: 1660, 1615, 1523, 1436, 1360, 1335, 1287, 1273, 1179.

Mass m/z: 478 (M$^+$), 480 (M$^+$).

5) Preparation of 2-(4-chlorocinnamyl)-6-(3-fluoro-4-methoxyphenyl)-4-(4-methyl-1-piperazinyl)methyl-2H-pyridazin-3-one Following the procedure of Example 1(10), 2-(4-chlorocinnamyl)-6-(3-fluoro-4-methoxyphenyl)-4- methanesulfonyloxymethyl-2H-pyridazin-3-one and 1-methylpiperazine were reacted to yield the title compound as pale brown neeldes (yield: 66.3%).

Melting point: 123.9–125.5° C.

$^1$H NMR (400 MHz, CDCl$_3$) δ: 2.33 (3H, s), 2.52 (4H, brs), 2.62 (4H, brs), 3.58 (2H, d, J=1.2 Hz), 3.95 (3H, s), 4.98 (2H, dd, J=6.8, 1.2 Hz), 6.41 (1H, dt, J=15.9, 6.8 Hz), 6.66 (1H, d, J=15.9 Hz), 7.04 (1H, dd, J=8.5, 8.5 Hz), 7.26 (2H, d, J=8.5 Hz), 7.32 (2H, d, J=8.5 Hz), 7.53 (1H, ddd, J=8.5, 2.0, 1.2 Hz), 7.62 (1H, dd, J=12.4, 2.2 Hz), 7.75 (1H, t, J=1.2 Hz).

IR (KBr) cm$^{-1}$: 1647, 1606, 1522, 1439, 1282, 1270.

Mass m/z: 482 (M$^+$), 484 (M$^+$).

Example 210

Preparation of 2-(4-chlorocinnamyl)-6-(3-fluoro-4-methoxyphenyl)-4-[4-(2-hydroxyethyl)-1-piperazinyl]methyl-2H-pyridazin-3-one Following the procedure of Example 1(10), 2-(4-chlorocinnamyl)-6-(3-fluoro-4-methoxyphenyl)-4-methanesulfonyloxymethyl-2H-pyridazin-3-one and 1-piperazineethanol were reacted to yield the title compound as slightly-yellow needles (yield: 65.1%).

Melting point: 133.1–134.9° C.

$^1$H NMR (400 MHz, CDCl$_3$) δ: 2.57–2.62 (11H, m), 3.58 (2H, d, J=1.2 Hz), 3.63 (2H, t, J=5.4 Hz), 3.94 (3H, s), 4.97 (2H, d, J=6.6 Hz), 6.41 (1H, dt, J=15.9, 6.6 Hz), 6.67 (1H, d, J=15.9 Hz), 7.03 (1H, dd, J=8.5, 8.5 Hz), 7.26 (2H, d, J=8.5 Hz), 7.32 (2H, d, J=8.5 Hz), 7.53 (1H, m), 7.61 (1H, dd, J=12.4, 2.2 Hz), 7.75 (1H, s).

IR (KBr) cm$^{-1}$: 3451, 1647, 1605, 1523, 1438, 1285, 1274, 1137.

Mass m/z: 478 (M$^+$), 480 (M$^+$).

Example 211

Preparation of 2-cyclopropylmethyl-6-(3-fluoro-4-methoxyphenyl)-4-[3-(4-methyl-1-piperazinyl)propyl]-2H-pyridazin-3-one 1) Preparation of 4-bromomethyl-2-cyclopropylmethyl-6-(3-fluoro-4-methoxyphenyl)-2H-pyridazin-3-one 2-Cyclopropyl-methyl-6-(3-fluoro-4-methoxyphenyl)-4-hydroxymethyl-2H-pyridazin-3-one (185 mg, 0.61 mmol), carbon tetrabromide (404 mg, 1.2 mmol) and pyridine (48 mg, 0.61 mmol) were dissolved in tetrahydrofuran (3 mL), and under ice-cold stirring, a solution of triphenylphosphine (319 mg, 1.2 mmol) in tetrahydrofuran (3 mL) was added. Under ice cooling, the mixture was stirred for 1 hour, and further stirred overnight at room temperature. Insoluble materials were filtered off, the solvent was distilled off under reduced pressure, and the residue was isolated and purified by column chromatography on silica gel (hexane/ethyl acetate=2/1) to yield the title compound as a yellow powder (yield: 155 mg, 69.5%).

$^1$H NMR (400 MHz, CDCl$_3$) δ: 0.45–0.60 (4H, m), 1.58 (1H, m), 3.95 (3H, s), 4.12 (2H, d, J=7.3 Hz), 4.49 (2H, s), 7.03 (1H, dd, J=8.5, 8.5 Hz), 7.50 (1H, m), 7.60 (1H, dd, J=13.4, 2.2 Hz), 7.77 (1H, s).

2) Preparation of 2-cyclopropylmethyl-4-[2,2-di(tert-butoxycarbonyl)ethyl]-6-(3-fluoro-4-methoxyphenyl)-2H-pyridazin-3-one After 55% sodium hydride (322 mg, 7.38 mmol) was added to a solution of di-tert-butyl malonate (970 mg, 4.48 mmol) in N,N-dimethylformamide (10 mL), 4-bromomethyl-2-cyclopropylmethyl-6-(3-fluoro-4-methoxyphenyl)-2H-pyridazin-3-one (1.8 g, 4.90 mmol) was added under ice-cold stirring. The reaction mixture was stirred at room temperature for 1 hour, poured into water, and extracted with ethyl acetate. The extract was washed with brine and dried over anhydrous sodium sulfate. The solvent was distilled off under reduced pressure. The residue was isolated and purified by column chromatography on silica gel (hexane/ethyl acetate=3/1) to yield the title compound as a yellow powder (yield: 1.39 mg, 61.8%).

$^1$H NMR (400 MHz, CDCl$_3$) δ: 0.44–0.50 (2H, m), 0.50–0.58 (2H, m), 1.41 (18H, s), 1.56 (1H, m), 3.12 (2H, d, J=7.8 Hz), 3.87 (1H, t, J=7.8 Hz), 3.94 (3H, s), 4.09 (2H, d, J=7.8 Hz), 7.01 (1H, dd, J=8.5, 8.5 Hz), 7.43 (1H, d, J=8.5 Hz), 7.50 (1H, s), 7.57 (1H, dd, J=12.4, 2.2 Hz).

3) Preparation of 4-(2-carboxyethyl)-2-cyclopropylmethyl-6-(3-fluoro-4-methoxyphenyl)-2H-pyridazin-3-one Trifluoroacetic acid (21 mL) was added to 2-cyclopropylmethyl-4-[2,2-di(tert-butoxycarbonyl)ethyl]-6-(3-fluoro-4-methoxyphenyl)-2H-pyridazin-3-one (1.39 g, 2.77 mmol), and the mixture was stirred at room temperature for 30 minutes. The solvent was distilled off under reduced pressure, and toluene was added further, followed by azeotropic boiling. The residue was heated at 190 to 200° C. for 30 minutes under a nitrogen atmosphere to yield the title compound as a pale brown powder (yield: 907 mg, 94.7%).

$^1$H NMR (400 MHz, CDCl$_3$): 0.45–0.50 (2H, m), 0.50–0.60 (2H, m), 1.41 (1H, m), 2.80 (2H, t, J=7.1 Hz), 2.97 (2H, t, J=7.1 Hz), 3.94 (3H, s), 4.10 (2H, d, J=7.3 Hz), 7.02 (1H, dd, J=8.5, 8.5 Hz), 7.47 (1H, d, J=8.5 Hz), 7.55 (1H, s), 7.59 (1H, dd, J=12.4, 2.2 Hz).

4) Preparation of 2-cyclopropylmethyl-6-(3-fluoro-4-methoxyphenyl)-4-(3-hydroxypropyl)-2H-pyridazin-3-one Following the procedure of Example 1(8), 4-(2-carboxyethyl)-2-cyclopropylmethyl-6-(3-fluoro-4-methoxyphenyl)-2H-pyridazin-3-one was reacted to yield the title compound as a brown oil (yield: 82.9%).

$^1$H NMR (400 MHz, CDCl$_3$) δ: 0.44–0.52 (2H, m), 0.52–0.60 (2H, m), 1.42 (1H, m), 1.88–1.94 (2H, m), 2.81 (2H, t, J=6.1 Hz), 3.63 (2H, t, J=5.9 Hz), 3.95 (3H, s), 4.12 (2H, d, J=7.3 Hz), 7.02 (1H, dd, J=8.5, 8.5 Hz), 7.50 (1H, m), 7.52 (1H, s), 7.60 (1H, dd, J=12.4, 2.2 Hz).

5) Preparation of 2-cyclopropylmethyl-6-(3-fluoro-4-methoxyphenyl)-4-(3-methanesulfonyloxypropyl)-2H-pyridazin-3-one Following the procedure of Example 1(9), 2-cyclopropylmethyl-6-(3-fluoro-4-methoxyphenyl)-4-(3-hydroxypropyl)-2H-pyridazin-3-one was reacted to yield the title compound as a pale brown powder (yield: 82.0%).

$^1$H NMR (400 MHz, CDCl$_3$) δ: 0.44–0.51 (2H, m), 0.51–0.60 (2H, m), 1.41 (1H, m), 2.13–2.21 (2H, m), 2.80 (2H, t, J=7.1 Hz), 3.04 (3H, s), 3.94 (3H, s), 4.09 (2H, d, J=7.3 Hz), 4.31 (2H, t, J=6.1 Hz), 7.02 (1H, dd, J=8.5, 8.5 Hz), 7.49 (1H, d, J=8.5 Hz), 7.53 (1H, s), 7.61 (1H, dd, J=12.4, 2.2 Hz).

6) Preparation of 2-cyclopropylmethyl-6-(3-fluoro-4-methoxyphenyl)-4-[3-(4-methyl-1-piperazinyl)propyl]-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and 1-methylpiperazine were reacted to yield the title compound as a yellow oil (yield: 62.0%).

$^1$H NMR (400 MHz, CDCl$_3$) δ: 0.44–0.50 (2H, m), 0.50–0.60 (2H, m), 1.41 (1H, m), 1.90–2.00 (2H, m), 2.45 (3H, s), 2.50–3.00 (12H, m), 3.94 (3H, s), 4.08 (2H, d, J=7.3 Hz), 7.02 (1H, dd, J=8.5, 8.5 Hz), 7.48 (1H, s), 7.50 (1H, d, J=8.5 Hz), 7.70 (1H, dd, J=12.3, 2.0 Hz).

IR (Neat) cm$^{-1}$: 1648, 1607, 1524, 1286, 1122, 1022, 755. Mass m/z: 414 (M$^+$).

Example 212

Preparation of 2-cyclopropylmethyl-4-(3-dimethylaminopropyl)-6-(3-fluoro-4-methoxyphenyl)-2H-pyridazin-3-one Following the procedure of Example 7, 2-cyclopropylmethyl-6-(3-fluoro-4-methoxyphenyl)-4-(3-methanesulfonyloxypropyl)-2H-pyridazin-3-one and dimethylamine were reacted to yield the title compound as a yellow powder (yield: 64.7%).

$^1$H NMR (400 MHz, CDCl$_3$) δ: 0.44–0.50 (2H, m), 0.53–0.60 (2H, m), 1.40 (1H, m), 2.24–2.35 (2H, m), 2.75–2.80 (2H, m), 2.79 (6H, s), 3.03 (2H, t, J=7.3 Hz), 3.94 (3H, s), 4.08 (2H, d, J=7.1 Hz), 7.04 (1H, dd, J=8.5, 8.5 Hz), 7.57 (1H, d, J=8.5 Hz), 7.65 (1H, dd, J=12.4, 2.2 Hz), 7.72 (1H, s).

IR (Neat) cm$^{-1}$: 1649, 1608, 1524, 1288, 1122, 1022, 761. Mass m/z: 359 (M$^+$).

Example 213

Preparation of 2-cyclopropylmethyl-6-(3-fluoro-4-methoxyphenyl)-4-[3-(1-piperazinyl)propyl]-2H-pyridazin-3-one 1) Preparation of 2-cyclopropylmethyl-4-[3-(4-tert-butoxycarbonyl-1-piperazinyl)propyl]-6-(3-fluoro-4-methoxyphenyl)-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and tert-butyl 1-piperazinecarboxylate were reacted to yield the title compound as a yellow oil (yield: 76.9%).

$^1$H NMR (400 MHz, CDCl$_3$) δ: 0.44–0.50 (2H, m), 0.52–0.60 (2H, m), 1.44 (1H, m), 1.46 (9H, s), 2.00–2.40 (2H, m), 2.50–2.80 (6H, m), 3.50–3.75 (6H, m), 3.94 (3H, s), 4.08 (2H, d, J=7.1 Hz), 7.02 (1H, dd, J=8.5, 8.5 Hz), 7.47–7.65 (3H, m).

2) Preparation of 2-cyclopropylmethyl-6-(3-fluoro-4-methoxyphenyl)-4-[3-(1-piperazinyl)propyl]-2H-pyridazin-3-one Following the procedure of Example 20, 2-cyclopropylmethyl-4-[3-(4-tert-butoxycarbonyl-1-piperazinyl)propyl]-6-(3-fluoro-4-methoxyphenyl)-2H-pyridazin-3-one was reacted to yield the title compound as a yellow oil (yield: 78.9%).

$^1$H NMR (400 MHz, CDCl$_3$) δ: 0.43–0.50 (2H, m), 0.50–0.59 (2H, m), 1.42 (1H, m), 1.82–1.92 (2H, m), 2.40–2.50 (6H, m), 2.68 (2H, t, J=7.6 Hz), 2.93–2.95 (4H, m), 3.94 (3H, s), 4.08 (2H, d, J=7.3 Hz), 7.01 (1H, dd, J=8.5, 8.5 Hz), 7.45 (1H, s), 7.48 (1H, d, J=8.5 Hz), 7.59 (1H, dd, J=11.4, 2.0 Hz).

IR (Neat) cm$^{-1}$: 1648, 1607, 1523, 1288, 1122, 1023, 760. Mass m/z: 400 (M$^+$).

Example 214

Preparation of 2-cyclopropylmethyl-6-(3-fluoro-4-methoxyphenyl)-4-[3-(1-piperazinyl)propyl]-2H-pyridazin-3-one dihydrochloride Following the procedure of Example 4, 2-cyclopropylmethyl-6-(3-fluoro-4-methoxyphenyl)-4-[3-(1-piperazinyl)propyl]-2H-pyridazin-3-one was reacted to yield the title compound as a slightly-yellow crystalline powder (yield: 83.1%).

Melting point: 174–178° C.

$^1$H NMR (400 MHz, DMSO-d$_6$) δ: 0.39–0.45 (2H, m), 0.45–0.55 (2H, m), 1.32 (1H, m), 2.00–2.25 (2H, m), 2.62–2.66 (2H, m), 3.20–3.85 (10H, m), 3.90 (3H, s), 4.01 (2H, d, J=7.1 Hz), 7.28 (1H, dd, J=8.8, 8.8 Hz), 7.72–7.80 (2H, m), 7.96 (1H, s).

IR (KBr) cm$^{-1}$: 1647, 1604, 1523, 1297, 1123, 1020, 762.

Example 215

Preparation of 4-[3-[N,N-bis(2-hydroxyethyl)amino]propyl]-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and diethanolamine were reacted to yield the title compound as a yellow oil (yield: 13.1%).

$^1$H NMR (400 MHz, CDCl$_3$) δ: 0.44–0.50 (2H, m), 0.50–0.60 (2H, m), 1.41 (1H, m), 2.10–2.20 (2H, m), 2.76 (2H, t, J=7.3 Hz), 3.00–3.15 (6H, m), 3.87–3.92 (4H, m), 3.94 (3H, s), 4.08 (2H, d, J=7.3 Hz), 7.02 (1H, dd, J=8.5, 8.5 Hz), 7.53 (1H, d, J=8.5 Hz), 7.60 (1H, s), 7.62 (1H, dd, J=12.4, 2.2 Hz).

IR (Neat) cm$^{-1}$: 1645, 1602, 1524, 1288, 1123, 1024, 756. Mass m/z: 400 (M$^+$-CH$_2$OH).

Example 216

Preparation of 4-(3-aminopropyl)-2-cyclopropylmethyl-6-(3-fluoro-4-methoxyphenyl)-2H-pyridazin-3-one Following the procedure of Example 24(1), 2-cyclopropylmethyl-6-(3-fluoro-4-methoxyphenyl)-4-(3-methanesulfonyloxypropyl)-2H-pyridazin-3-one was reacted to yield a crude product. Without purification, the crude product was reacted further in accordance with the procedure of Example 24(2) to yield the title compound as a yellow oil (yield: 67.8%).

$^1$H NMR (400 MHz, CDCl$_3$) δ: 0.44–0.50 (2H, m), 0.50–0.60 (2H, m), 1.41 (1H, m), 1.84–1.96 (2H, m), 2.67–2.80 (4H, m), 2.87 (2H, t, J=6.1 Hz), 3.94 (3H, s), 4.08 (2H, d, J=7.3 Hz), 7.01 (1H, dd, J=8.5, 8.5 Hz), 7.49 (1H, d, J=8.5 Hz), 7.50 (1H, s), 7.59 (1H, dd, J=12.4, 2.2 Hz).

IR (Neat) cm$^{-1}$: 3370, 1648, 1606, 1523, 1289, 1122, 1023, 760.

Mass m/z: 331 (M$^+$).

Example 217

Preparation of 4-(3-aminopropyl)-2-cyclopropylmethyl-6-(3-fluoro-4-methoxyphenyl)-2H-pyridazin-3-one hydrochloride Following the procedure of Example 4, 4-(3-aminopropyl)-2-cyclopropylmethyl-6-(3-fluoro-4-methoxyphenyl)-2H-pyridazin-3-one was reacted to yield the title compound as a slightly-yellow crystalline powder (yield: 70.6%).

Melting point: 183–185° C.

$^1$H NMR (400 MHz, DMSO-d$_6$) δ: 0.40–0.45 (2H, m), 0.45–0.55 (2H, m), 1.32 (1H, m), 1.88–1.93 (2H, m), 2.64 (2H, t, J=7.3 Hz), 2.78–2.88 (2H, m), 3.90 (3H, s), 4.00 (2H, d, J=7.3 Hz), 7.28 (1H, dd, J=8.5, 8.5 Hz), 7.70–7.78 (2H, m), 7.96 (1H, s).

IR (KBr) cm$^{-1}$: 3437, 1648, 1608, 1526, 1273, 1122, 1021, 762.

Experiment 1
Inhibitory Activity against Interleukin-1β Production

HL-60 cells were cultured for 4 days until confluence on RPMI 1640 medium with 10% fetal bovine serum (FBS) added thereto. The medium was centrifuged. The supernatant was discarded, and the cells were then suspended at 1×10$^6$ cells/mL on RPMI 1640 medium with 3% FBS, and lipopolysaccharide was added to give a final concentration of 10 μg/mL. The culture was inoculated at 1 mL/well to a 24-well plate. A sample compound was added at 1 μL/well, followed by culturing for 3 days. Three days later, the amount of interleukin-1β in each culture was determined by ELISA. Each IC$_{50}$ value was determined by a comparison in yield with a control to which no test sample was added. Results on some representative compounds are shown in Table 1.

TABLE 1

(I)

[Structure: phenyl substituted with X, Y, Z attached to pyridazinone with R¹ on N, and (CH₂)ₙ-N(R²)(R³) substituent]

CyprCH₂: Cyclopropylmethyl

| Example No. | X | Y | Z | n | R¹ | R²(R³)N— | Salt | Inhibitory activity against IL-1β production IC50 (μM) |
|---|---|---|---|---|---|---|---|---|
| 8 | Me | F | H | 1 | iso-Bu | Me₂N— | HCl | 3.45 |
| 14 | MeO | F | H | 1 | CyprCH₂ | Me₂N— | HCl | 3.61 |
| 18 | MeO | F | H | 1 | CyprCH₂ | Bn—N(piperazine)N— | 2HCl | 5.40 |
| 21 | MeO | F | H | 1 | CyprCH₂ | H—N(piperazine)N— | 2HCl | 1.01 |
| 23 | MeO | F | H | 1 | CyprCH₂ | (HOCH₂CH₂)₂N— | HCl | 0.33 |
| 25 | MeO | F | H | 1 | CyprCH₂ | H₂N— | HCl | 2.74 |
| 45 | Me | H | H | 1 | iso-Bu | Me₂N— | HCl | 6.21 |
| 47 | Me | H | H | 1 | iso-Bu | Et₂N— | HCl | 5.20 |
| 49 | Me | H | H | 1 | iso-Bu | (HOCH₂CH₂)₂N— | HCl | 3.53 |
| 83 | F | Me | H | 1 | iso-Bu | Me—N(piperazine)N— | 2HCl | 0.27 |
| 89 | F | Me | H | 1 | iso-Bu | Me₂N— | HCl | 5.50 |
| 108 | F | F | H | 1 | iso-Bu | (HOCH₂CH₂)₂N— | HCl | 3.44 |
| 143 | F | Me | H | 1 | 4-Cl-C₆H₄-CH=CH-CH₂- | Me—N(piperazine)N— | 2HCl | 8.55 |
| 149 | MeS | H | H | 1 | CyprCH₂ | Me—N(piperazine)N— | 2HCl | 1.63 |
| 153 | MeS | H | H | 1 | CyprCH₂ | Me₂N— | HCl | 0.58 |

TABLE 1-continued

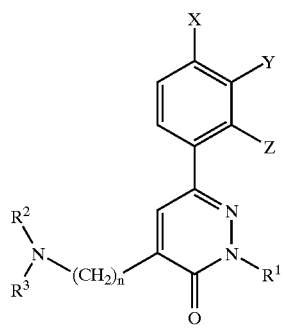

(I)

CyprCH₂: Cyclopropylmethyl

| Example No. | X | Y | Z | n | R¹ | R²(R³)N— | Salt | Inhibitory activity against IL-1β production IC50 ($\mu$M) |
|---|---|---|---|---|---|---|---|---|
| 161 | MeS | H | H | 1 | iso-Bu | Me₂N— | HCl | 2.78 |
| 163 | MeS | H | H | 1 | iso-Bu | HN—CH₂—C≡CH | HCl | 2.78 |
| 213 | MeO | F | H | 3 | CyprCH₂ | H—N(piperazine)N— | free | 0.24 |
| 216 | MeO | F | H | 3 | CyprCH₂ | H₂N— | free | 1.14 |
| 189 | MeO | F | H | 1 | F-C₆H₄-CH₂ | MeN(piperazine)N— | free | 0.87 |
| 192 | MeO | F | H | 1 | F-C₆H₄-CH₂ | H—N(piperazine)N— | free | 0.64 |

Experiment 2 (Water Solubility Test)

Testing method

Each sample compound was weighed in the amount shown in Table 2, to which purified water was added in 0.05 mL aliquots. The solubility (%) of the compound was determined based on the amount of water required for its dissolution.

Results

As is shown in Table 2, the compounds of the present invention showed water solubility significantly improved over the comparative compounds.

TABLE 2

| Example No. | Weighed amount (mg) | Amount of added water (mL) | Solubility (%) |
|---|---|---|---|
| 14 | 2.048 | 0.25 | 0.8 |
| 18 | 1.048 | 0.1 | 1 |
| 21 | 10.47 | 0.05 | >20 |
| 23 | 10.82 | 0.1 | 10 |
| 25 | 1.025 | 0.25 | 0.4 |
| 45 | 10.37 | 0.25 | 4 |
| 47 | 10.47 | 0.05 | >20 |

TABLE 2-continued

| Example No. | Weighed amount (mg) | Amount of added water (mL) | Solubility (%) |
|---|---|---|---|
| 89 | 10.57 | 0.05 | >20 |
| 108 | 9.75 | 0.045 | >20 |
| 149 | 3.09 | 0.03 | >10 |
| 153 | 2.95 | 0.6 | 0.5 |
| 214 | 5.061 | 0.05 | 10 |
| 193 | 5.032 | 0.1 | 5 |
| 217 | 5.061 | 0.05 | 10 |
| 195 | 5.072 | 2.2 | 0.2 |
| 188 | 2.008 | 2.5 | 0.08 |
| 206 | 2.042 | 3.5 | 0.06 |
| Comparative Compound 1 | 0.677 | 100 (insoluble) | <0.001 |
| Comparative Compound 2 | 0.742 | 100 (insoluble) | <0.001 |
| Comparative Compound 3 | 0.740 | 100 (insoluble) | <0.001 |
| Comparative Compound 4 | 0.95 | 100 (insoluble) | <0.001 |

TABLE 2-continued

| Example No. | Weighed amount (mg) | Amount of added water (mL) | Solubility (%) |
|---|---|---|---|

Comp comp'd 1 (structure: 4-methoxyphenyl-pyridazinone with EtO-C(O)-NH substituent and N-cinnamyl-4-Cl)

Comp comp'd 2 (structure: 4-methoxyphenyl-pyridazinone with MeNH-C(O)- substituent and N-isobutyl)

Comp comp'd 3 (structure: 3-fluoro-4-methoxyphenyl-pyridazinone with MeNH-C(O)- substituent and N-cyclopropylmethyl)

Comp. comp'd 4 (structure: 4-methoxyphenyl-pyridazinone with HO-C(O)- substituent and N-cinnamyl-4-Cl)

Experiment 3 (Oral Absorbability Test on Rats)

The compound of Example 83 and the comparative compound 3 were suspended at 2 mg/mL with a 0.5% MC solution in mortars, respectively, and were orally administered to male SD rats at 10 mg/5 mL/kg. Upon elapsed time of 0.25, 0.5, 1, 2, 4, 6 and 8 hours after the administration, blood samples were collected and then centrifuged to provide plasma samples. The plasma levels of the respective compounds were determined by HPLC. As is shown in FIG. 1, no substantial absorption was observed on the comparative compound 3, but good absorption was observed on the compound of Example 83 equipped with increased water solubility. The compound of Example 83 is, therefore, useful as an orally dosable medicine.

Experiment 4 (Oral Absorbability Test on Rats and Mice)

Figure 2:
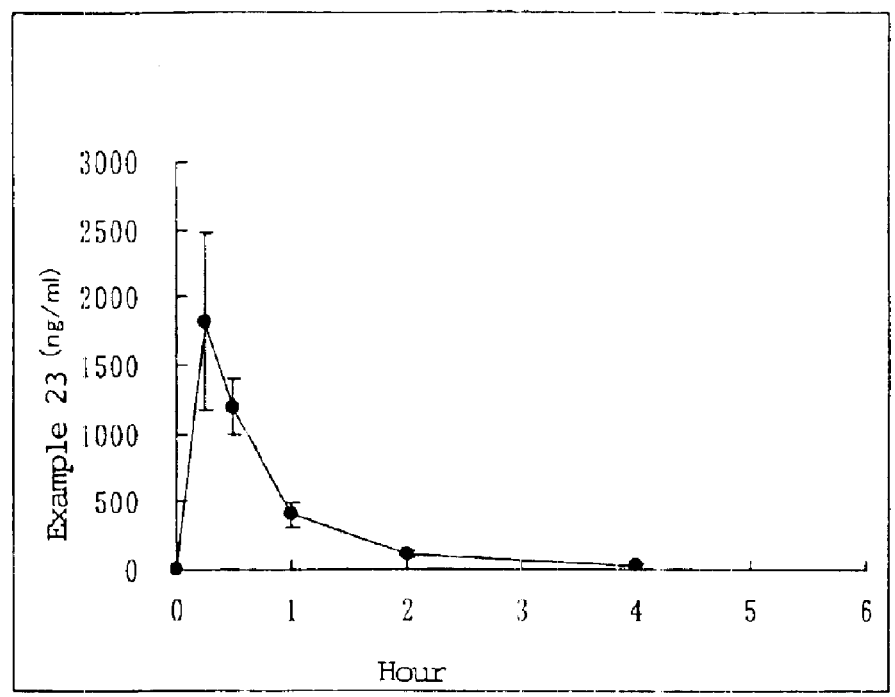
FIG. 2 is graphic representations of the oral absorbability of another compound according to the present invention (Example 23)
Figure 2:
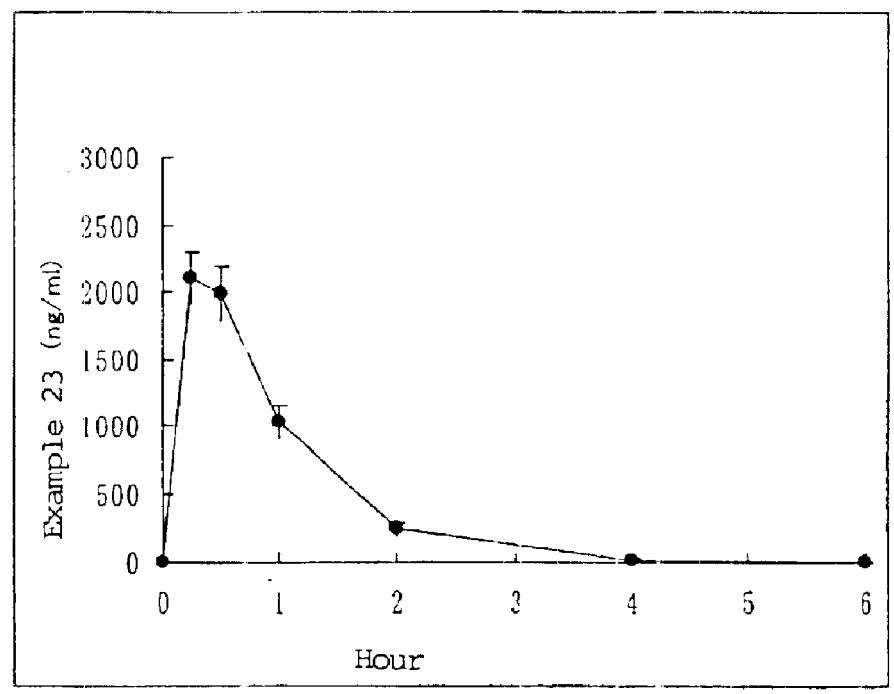
Figure 3:
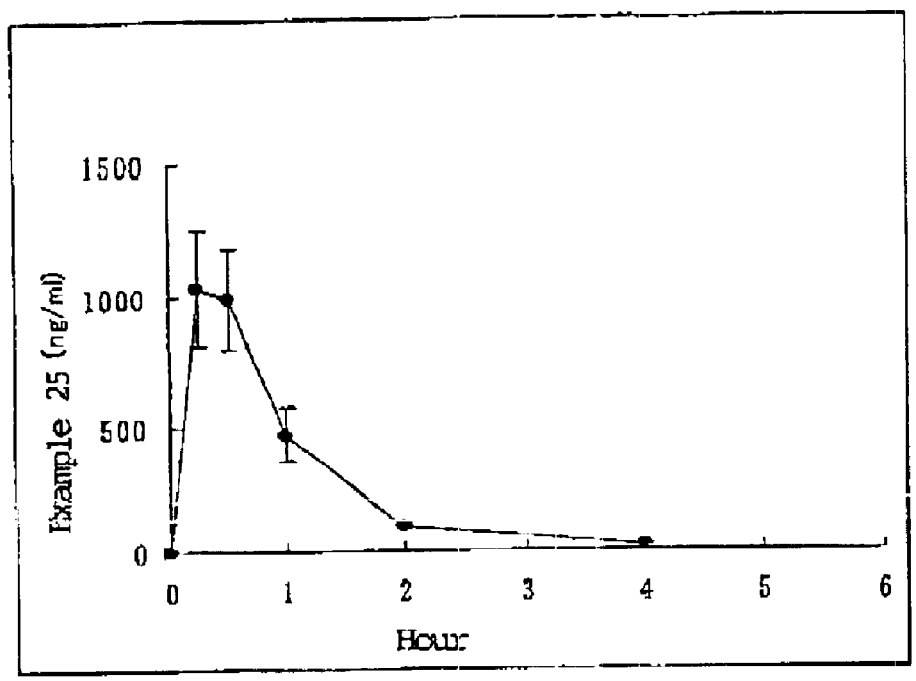
FIG. 3 is graphic representations of the oral absorbability of a further compound according to the present invention (Example 25)
Figure 3:
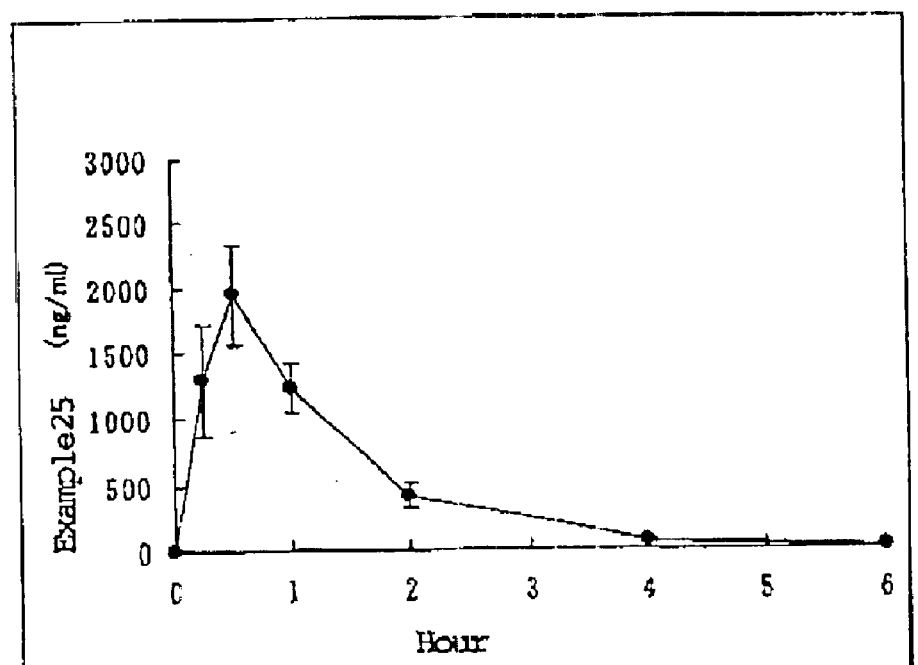
Figure 4:
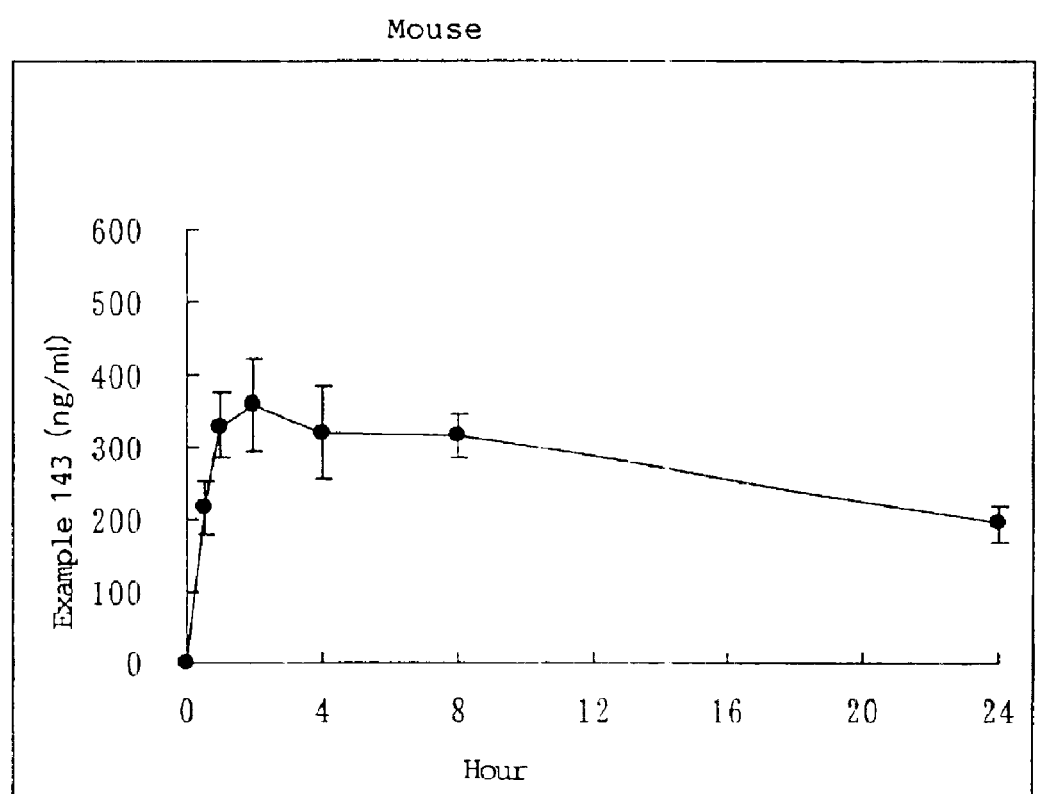
FIG. 4 is graphic representations of the oral absorbability of a still further compound according to the present invention (Example 143).

In a similar manner as in Experiment 3, test compounds of Examples 23, 25 and 143 were orally administered to mice and rats to test their oral absorbability. As is shown in FIGS. 2 to 4, good absorbability was observed on the compounds of Examples 23, 25 and 143 so that they are useful as orally dosable medicines.

Having described the present invention, it will now be apparent to one of ordinary skill in the art that many changes and modifications may be made to the above-described embodiments without departing from the spirit and the scope of the present invention.

What is claimed is:

1. A phenylpyridazine compound, or a salt thereof, wherein the phenylpyridazine compound is selected from the group consisting of 4-dimethylaminomethyl-6-(3-fluoro-4-methylphenyl)-2-isobutyl-2H-pyridazin-3-one, 2-cyclopropylmethyl-4-dimethylamino-methyl-6-(3-fluoro-4-methoxyphenyl)-2H-pyridazin-3-one, 2-cyclopropylmethyl-6-(3-fluoro-4-methoxyphenyl)-4-(4-benzyl-1-piperazinyl)methyl-2H-pyridazin-3-one, 2-cyclopropyl-methyl-6-(3-fluoro-4-methoxyphenyl)-4-(1-piperazinyl)-methyl-2H-pyridazin-3-one, 4-N,N-bis(2-hydroxyethyl)amino-methyl-2-cyclopropylmethyl-6-(3-fluoro-4-methoxyphenyl)-2H-pyridazin-3-one, 4-aminomethyl-2-cyclopropylmethyl-6-(3-fluoro-4-methoxyphenyl)-2H-pyridazin-3-one, 4-dimethyl-aminomethyl-2-isobutyl-6-(4-methylphenyl)-2H-pyridazin-3-one, 4-diethylaminomethyl-2-isobutyl-6-(4-methylphenyl)-2H-pyridazin-3-one, 4-N,N-bis(2-hydroxyethyl)aminomethyl-6-(4-methylphenyl)-2-isobutyl-2H-pyridazin-3-one, 6-(4-fluoro-3-methylphenyl)-2-isobutyl-4-(4-methyl-1-piperazinyl)methyl-2H-pyridazin-3-one, 4-dimethylaminomethyl-6-(4-fluoro-3-methylphenyl)-2-isobutyl-2H-pyridazin-3-one, 4-N,N-bis(2-hydroxyethyl)aminomethyl-6-(3,4-difluorophenyl)-2-isobutyl-2H-pyridazin-3-one, 2-(4-chlorocinnamyl)-6-(4-fluoro-3-methylphenyl)-4-(4-methyl-1-piperazinyl)methyl-2H-pyridazin-3-one, 2-cyclopropylmethyl-4-(4-methyl-1-piperazinyl)methyl-6-[4-(methylthio)phenyl]-2H-pyridazin-3-one, 4-N,N-bis(2-hydroxyethyl)aminomethyl-2-cyclopropyl-methyl-6-[4-(methylthio)phenyl]-2H-pyridazin-3-one, 2-cyclopropylmethyl-4-dimethylaminomethyl-6-[4-(methylthio)-phenyl]-2H-pyridazin-3-one, 2-isobutyl-6-[4-(methylthio)-phenyl]-4-propargylaminomethyl-2H-pyridazin-3-one, 4-dimethylaminomethyl-2-isobutyl-6-[4-(methylthio)-phenyl]-2H-pyridazin-3-one, 2-(4-chlorobenzyl)-4-dimethylaminomethyl-6-(3-fluoro-4-methoxyphenyl)-2H-pyridazin-3-one,
2-cyclopentylmethyl-6-(3-fluoro-4-methoxyphenyl)-4-(4-methyl-1-piperazinyl)methyl-2H-pyridazin-3-one,
2-cyclopentylmethyl-4-dimethylaminomethyl-6-(3-fluoro-4-methoxyphenyl)-2H-pyridazin-3-one,
2-cyclopentylmethyl-6-(3-fluoro-4-methoxyphenyl)-4-(1-piperazinyl)methyl-2H-pyridazin-3-one,
4-aminomethyl-2-cyclopentylmethyl-6-(3-fluoro-4-methoxyphenyl)-2H-pyridazin-3-one,
2-(4-fluorobenzyl)-6-(3-fluoro-4-methoxyphenyl)-4-(4-methyl-1-piperazinyl)methyl-2H-pyridazin-3-one,
4-dimethylaminomethyl-2-(4-fluorobenzyl)-6-(3-fluoro-4-methoxyphenyl)-2H-pyridazin-3-one,
2-(4-fluorobenzyl)-6-(3-fluoro-4-methoxyphenyl)-4-(1-piperazinyl)methyl-2H-pyridazin-3-one,
4-aminomethyl-2-(4-fluorobenzyl)-6-(3-fluoro-4-methoxyphenyl)-2H-pyridazin-3-one,
4-aminomethyl-2-(4-chlorobenzyl)-6-(3-fluoro-4-methoxyphenyl)-2H-pyridazin-3-one,
2-(3,4-difluorobenzyl)-6-(3-fluoro-4-methoxyphenyl)-4-(4-methyl-1-piperazinyl)methyl-2H-pyridazin-3-one,
2-(3,4-difluorobenzyl)-4-dimethylaminomethyl-6-(3-fluoro-4-methoxyphenyl)-2H-pyridazin-3-one,
6-(3-fluoro-4-methoxyphenyl)-2-[3-(4-fluorophenyl)propyl]-4-(4-methyl-1-piperazinyl)methyl-2H-pyridazin-3-one,
4-dimethylaminomethyl-6-(3-fluoro-4-methoxyphenyl)-2-[3-(4-fluorophenyl)propyl]-2H-pyridazin-3-one,
4-N,N-bis(2-hydroxyethyl)aminomethyl-6-(3-fluoro-4-methoxyphenyl)-2-[3-(4-fluorophenyl)propyl]-2H-pyridazin-3-one,
6-(3-fluoro-4-methoxyphenyl)-2-[3-(4-fluorophenyl)propyl]-4-(1-piperazinyl)methyl-2H-pyridazin-3-one,
4-aminomethyl-6-(3-fluoro-4-methoxyphenyl)-2-[3-(4-fluorophenyl)propyl]-2H-pyridazin-3-one,
2-(4-chlorocinnamyl)-6-(3-fluoro-4-methoxyphenyl)-4-[4-(2-hydroxyethyl)-1-piperazinyl]methyl-2H-pyridazin-3-one,
2-(4-chlorocinnamyl)-6-(3-fluoro-4-methoxyphenyl)-4-(4-methyl-1-piperazinyl)methyl-2H-pyridazin-3-one,
2-cyclopropylmethyl-6-(3-fluoro-4-methoxyphenyl)-4-[3-(4-methyl-1-piperazinyl)propyl]-2H-pyridazin-3-one,
2-cyclopropylmethyl-4-(3-dimethylaminopropyl)-6-(3-fluoro-4-methoxyphenyl)-2H-pyridazin-3-one,
2-cyclopropylmethyl-6-(3-fluoro-4-methoxyphenyl)-4-[3-(1-piperazinyl)propyl]-2H-pyridazin-3-one or
4-(3-aminopropyl)-2-cyclopropylmethyl-6-(3-fluoro-4-methoxyphenyl)-2H-pyridazin-3-one.

2. A pharmaceutical composition comprising at least one of the phenylpyridazine compound, or a salt thereof, of claim 1 and a pharmaceutically-acceptable carrier.

3. A The pharmaceutical composition of claim 2, wherein the pharmaceutical composition is in a form suitable for oral administration.

4. The pharmaceutical composition of claim 3, wherein the form suitable for oral administration is a tablet.

* * * * *

UNITED STATES PATENT AND TRADEMARK OFFICE
CERTIFICATE OF CORRECTION

PATENT NO. : 6,869,954 B2
DATED : March 22, 2005
INVENTOR(S) : Yoshinori Kyotani et al.

It is certified that error appears in the above-identified patent and that said Letters Patent is hereby corrected as shown below:

Column 100,
Line 20, "or" should read -- and --.

Signed and Sealed this

Twenty-eighth Day of June, 2005

JON W. DUDAS
*Director of the United States Patent and Trademark Office*